US011866498B2

(12) United States Patent
Ellerman et al.

(10) Patent No.: US 11,866,498 B2
(45) Date of Patent: Jan. 9, 2024

(54) BISPECIFIC ANTIGEN-BINDING MOLECULES AND METHODS OF USE

(71) Applicant: Genentech, Inc., South San Francisco, CA (US)

(72) Inventors: Diego Ellerman, San Francisco, CA (US); Teemu T. Junttila, San Mateo, CA (US); Twyla Noelle Lombana, San Francisco, CA (US); Dionysos Slaga, Richmond, CA (US); Christoph Spiess, Mountain View, CA (US)

(73) Assignee: Genentech, Inc., South San Francisco, CA (US)

( * ) Notice: Subject to any disclaimer, the term of this patent is extended or adjusted under 35 U.S.C. 154(b) by 338 days.

(21) Appl. No.: 16/271,410

(22) Filed: Feb. 8, 2019

(65) Prior Publication Data

US 2019/0270814 A1   Sep. 5, 2019

Related U.S. Application Data

(60) Provisional application No. 62/628,088, filed on Feb. 8, 2018.

(51) Int. Cl.

| | | |
|---|---|---|
| *C07K 16/28* | (2006.01) | |
| *A61P 35/00* | (2006.01) | |
| *C07K 16/32* | (2006.01) | |
| *A61K 39/395* | (2006.01) | |
| *A61K 47/65* | (2017.01) | |
| *A61K 9/00* | (2006.01) | |
| *C07K 16/46* | (2006.01) | |
| *C07K 16/10* | (2006.01) | |
| *A61P 35/02* | (2006.01) | |

(52) U.S. Cl.
CPC ........ *C07K 16/2809* (2013.01); *A61K 9/0019* (2013.01); *A61K 39/3955* (2013.01); *A61K 47/65* (2017.08); *A61P 35/00* (2018.01); *A61P 35/02* (2018.01); *C07K 16/1063* (2013.01); *C07K 16/2803* (2013.01); *C07K 16/2818* (2013.01); *C07K 16/32* (2013.01); *C07K 16/468* (2013.01)

(58) Field of Classification Search
CPC ............ C07K 16/2809; C07K 16/2818; C07K 16/32; A61K 47/65; A61K 9/0019; A61P 35/00
See application file for complete search history.

(56) References Cited

U.S. PATENT DOCUMENTS

| | | |
|---|---|---|
| 5,500,362 A | 3/1996 | Robinson et al. |
| 5,571,894 A | 11/1996 | Wels et al. |
| 5,587,458 A | 12/1996 | King et al. |
| 5,591,828 A | 1/1997 | Bosslet et al. |
| 5,624,821 A | 4/1997 | Winter et al. |
| 5,648,260 A | 7/1997 | Winter et al. |
| 5,677,171 A | 10/1997 | Hudziak et al. |
| 5,731,168 A | 3/1998 | Carter et al. |
| 5,821,337 A | 10/1998 | Carter et al. |
| 5,869,046 A | 2/1999 | Presta et al. |
| 6,194,551 B1 | 2/2001 | Idusogie et al. |
| 6,248,516 B1 | 6/2001 | Winter et al. |
| 6,455,043 B1 | 9/2002 | Grillo-Lopez |
| 6,602,684 B1 | 8/2003 | Umana et al. |
| 6,733,752 B1 | 5/2004 | Greene et al. |
| 6,737,056 B1 | 5/2004 | Presta |
| 6,809,185 B1 | 10/2004 | Schoonjans et al. |
| 7,332,581 B2 | 2/2008 | Presta |
| 7,371,826 B2 | 5/2008 | Presta |
| 7,435,797 B2 | 10/2008 | Lowman et al. |
| 7,612,181 B2 | 11/2009 | Wu et al. |
| 7,682,612 B1 | 3/2010 | White et al. |
| 7,695,936 B2 | 4/2010 | Carter et al. |
| 7,799,900 B2 | 9/2010 | Adams et al. |
| 8,219,149 B2 | 7/2012 | Lafata et al. |
| 8,227,577 B2 | 7/2012 | Klein et al. |
| 8,242,247 B2 | 8/2012 | Klein et al. |
| 8,258,268 B2 | 9/2012 | Wu et al. |
| 8,562,992 B2 | 10/2013 | Adams et al. |
| 8,703,132 B2 | 4/2014 | Imhof-Jung et al. |

(Continued)

FOREIGN PATENT DOCUMENTS

| | | |
|---|---|---|
| CN | 101675077 A | 3/2010 |
| EP | 0404097 B1 | 9/1996 |

(Continued)

OTHER PUBLICATIONS

Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*

(Continued)

*Primary Examiner* — Meera Natarajan
*Assistant Examiner* — Cheom-Gil Cheong
(74) *Attorney, Agent, or Firm* — Clark & Elbing LLP; Karen L. Elbing

(57) ABSTRACT

The present invention provides bispecific antigen-binding molecules having a monovalent arm specific to a first target antigen (e.g., a T cell antigen, such as CD3) and a bivalent arm specific for a second target antigen (e.g., a tumor antigen, such as HER2). Bispecific antigen-binding molecules are useful in the treatment of disorders, such as cancer (e.g., HER2-positive cancer). The invention also features methods of producing bispecific antigen-binding molecules, methods of treating disorders using bispecific antigen-binding molecules, and compositions including bispecific antigen-binding molecules.

24 Claims, 42 Drawing Sheets

Specification includes a Sequence Listing.

(56) References Cited

U.S. PATENT DOCUMENTS

| | | |
|---|---|---|
| 8,709,421 B2 | 4/2014 | Heiss et al. |
| 8,722,859 B2 | 5/2014 | Miller et al. |
| 8,796,424 B2 | 8/2014 | Croasdale et al. |
| 8,969,526 B2 | 3/2015 | Baehner et al. |
| 9,011,864 B2 | 4/2015 | Schulz et al. |
| 9,017,676 B2 | 4/2015 | Lindhofer |
| 9,068,008 B2 | 6/2015 | Mossner et al. |
| 9,266,938 B2 | 2/2016 | Ast et al. |
| 9,266,967 B2 | 2/2016 | Klein et al. |
| 9,308,257 B2 | 4/2016 | Sharma, Sr. et al. |
| 9,315,567 B2 | 4/2016 | Chang et al. |
| 9,382,323 B2 | 7/2016 | Brinkmann et al. |
| 9,447,159 B2 | 9/2016 | Ast et al. |
| 9,493,563 B2 | 11/2016 | Blein et al. |
| 9,526,797 B2 | 12/2016 | Gerdes et al. |
| 9,587,021 B2 | 3/2017 | Huang et al. |
| 9,657,102 B2 | 5/2017 | Smith et al. |
| 9,714,294 B2 | 7/2017 | De Goeij et al. |
| 10,000,576 B1* | 6/2018 | Weisser ............. C07K 16/3015 |
| 10,105,391 B2* | 10/2018 | Wu .................. C07K 14/70578 |
| 10,561,686 B2* | 2/2020 | Xiao .................... C07K 14/705 |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0095243 A1 | 5/2005 | Chan et al. |
| 2005/0123546 A1 | 6/2005 | Umana et al. |
| 2007/0111281 A1 | 5/2007 | Sondermann et al. |
| 2008/0241152 A1 | 10/2008 | Alitalo et al. |
| 2009/0252683 A1 | 10/2009 | Kischel et al. |
| 2010/0015133 A1 | 1/2010 | Igawa et al. |
| 2010/0150918 A1 | 6/2010 | Kufer et al. |
| 2010/0316645 A1 | 12/2010 | Imhof-Jung et al. |
| 2010/0331527 A1 | 12/2010 | Davis et al. |
| 2011/0020322 A1 | 1/2011 | Wilkins et al. |
| 2011/0293613 A1 | 12/2011 | Brinkmann et al. |
| 2012/0225071 A1 | 9/2012 | Klein et al. |
| 2012/0244577 A1 | 9/2012 | Dixit et al. |
| 2012/0251531 A1 | 10/2012 | Baehner et al. |
| 2012/0276125 A1 | 11/2012 | Ast et al. |
| 2013/0022601 A1 | 1/2013 | Brinkmann et al. |
| 2013/0058936 A1 | 3/2013 | Bruenker et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0129723 A1 | 5/2013 | Blankenship et al. |
| 2013/0150558 A1 | 6/2013 | Williams et al. |
| 2013/0165638 A1 | 6/2013 | Hsu et al. |
| 2013/0171095 A1 | 7/2013 | Bernett et al. |
| 2013/0287774 A1 | 10/2013 | Zugmaier et al. |
| 2014/0088295 A1 | 3/2014 | Smith et al. |
| 2014/0112914 A1 | 4/2014 | Nezu et al. |
| 2014/0154254 A1 | 6/2014 | Kannan et al. |
| 2014/0170148 A1 | 6/2014 | De Goeij et al. |
| 2014/0170149 A1 | 6/2014 | Neijssen et al. |
| 2014/0187753 A1 | 7/2014 | Blein et al. |
| 2014/0242079 A1 | 8/2014 | Bacac et al. |
| 2014/0242080 A1 | 8/2014 | Jaeger et al. |
| 2014/0288275 A1 | 9/2014 | Moore et al. |
| 2014/0294823 A1 | 10/2014 | Moore et al. |
| 2014/0294833 A1 | 10/2014 | Desjarlais et al. |
| 2014/0302064 A1 | 10/2014 | Moore |
| 2014/0322217 A1 | 10/2014 | Moore et al. |
| 2014/0363426 A1 | 12/2014 | Moore et al. |
| 2014/0370013 A1 | 12/2014 | Desjarlais et al. |
| 2014/0377270 A1 | 12/2014 | Moore et al. |
| 2015/0098900 A1 | 4/2015 | Ebens et al. |
| 2015/0133640 A1 | 5/2015 | Blein et al. |
| 2015/0166661 A1 | 6/2015 | Chen et al. |
| 2015/0266966 A1 | 9/2015 | Smith et al. |
| 2015/0274845 A1 | 10/2015 | Bruenker et al. |
| 2015/0284475 A1 | 10/2015 | Zhou et al. |
| 2015/0315296 A1 | 11/2015 | Schaefer et al. |
| 2015/0368351 A1 | 12/2015 | Vu et al. |
| 2015/0376287 A1 | 12/2015 | Vu et al. |
| 2016/0000916 A1 | 1/2016 | Crotts et al. |
| 2016/0017058 A1 | 1/2016 | Kim et al. |
| 2016/0075785 A1 | 3/2016 | Ast et al. |
| 2016/0090416 A1 | 3/2016 | Gunde et al. |
| 2016/0130347 A1 | 5/2016 | Bruenker et al. |
| 2016/0145339 A1 | 5/2016 | Zhou et al. |
| 2016/0145354 A1 | 5/2016 | Bacac et al. |
| 2016/0159906 A1 | 6/2016 | Sun et al. |
| 2016/0175397 A1 | 6/2016 | Umana et al. |
| 2016/0208017 A1 | 7/2016 | Ast et al. |
| 2016/0208019 A1 | 7/2016 | Bacac et al. |
| 2016/0263240 A1 | 9/2016 | Ast et al. |
| 2016/0297881 A1 | 10/2016 | Vu et al. |
| 2016/0368985 A1 | 12/2016 | Hotzel et al. |
| 2016/0368994 A1 | 12/2016 | Kelley et al. |
| 2017/0008971 A1 | 1/2017 | Dennis et al. |
| 2017/0022274 A1 | 1/2017 | Chang et al. |
| 2017/0029529 A1 | 2/2017 | Croasdale et al. |
| 2017/0096485 A1 | 4/2017 | Bacac et al. |
| 2017/0096495 A1 | 4/2017 | Bacac et al. |
| 2017/0114146 A1 | 4/2017 | Klein et al. |
| 2017/0158773 A1 | 6/2017 | Adams et al. |
| 2017/0174786 A1 | 6/2017 | Bacac et al. |
| 2017/0190783 A1 | 7/2017 | Bacac et al. |
| 2017/0204194 A1 | 7/2017 | Chen et al. |
| 2017/0209573 A1 | 7/2017 | Bacac et al. |
| 2017/0224818 A1 | 8/2017 | Lindhofer et al. |
| 2017/0253670 A1 | 9/2017 | Klein et al. |
| 2017/0267783 A1 | 9/2017 | Nezu et al. |
| 2017/0306018 A1 | 10/2017 | Vu et al. |
| 2017/0306036 A1 | 10/2017 | Vu et al. |
| 2017/0306044 A1 | 10/2017 | Vu et al. |
| 2017/0327579 A1 | 11/2017 | Vu et al. |
| 2017/0327580 A1 | 11/2017 | Vu et al. |
| 2018/0057593 A1 | 3/2018 | Dennis |
| 2018/0094056 A1 | 4/2018 | Mathieu et al. |
| 2018/0134798 A1 | 5/2018 | Chu et al. |
| 2020/0339686 A1* | 10/2020 | Sato .................... C07K 16/2809 |

FOREIGN PATENT DOCUMENTS

| | | |
|---|---|---|
| EP | 1870459 A1 | 12/2007 |
| EP | 1870459 A4 | 9/2010 |
| EP | 2482212 A1 | 8/2012 |
| EP | 2578230 A1 | 4/2013 |
| EP | 2647707 A1 | 10/2013 |
| EP | 2647707 A4 | 4/2014 |
| EP | 2789630 A1 | 10/2014 |
| EP | 1870459 B1 | 6/2016 |
| JP | 2008-291036 A | 12/2008 |
| JP | 2009-539413 A | 11/2009 |
| JP | 2010-524435 A | 7/2010 |
| JP | 2013-515509 A | 5/2013 |
| JP | 2013-528569 A | 7/2013 |
| JP | 2013-529084 A | 7/2013 |
| JP | 2013-543384 A | 12/2013 |
| JP | 2014-514314 A | 6/2014 |
| JP | 2015-509952 A | 4/2015 |
| JP | 2017-503480 A | 2/2017 |
| JP | 2017-527522 A | 9/2017 |
| RU | 2017105849 A | 8/2018 |
| WO | WO-91/03493 A1 | 3/1991 |
| WO | WO-93/16185 A2 | 8/1993 |
| WO | WO-94/04679 A1 | 3/1994 |
| WO | WO-94/29351 A2 | 12/1994 |
| WO | WO-96/01126 A1 | 1/1996 |
| WO | WO-96/27011 A1 | 9/1996 |
| WO | WO-96/40210 A1 | 12/1996 |
| WO | WO-97/30087 A1 | 8/1997 |
| WO | WO-98/50431 A2 | 11/1998 |
| WO | WO-98/58964 A1 | 12/1998 |
| WO | WO-98/50431 A3 | 1/1999 |
| WO | WO-99/22764 A1 | 5/1999 |
| WO | WO-99/51642 A1 | 10/1999 |

(56) References Cited

FOREIGN PATENT DOCUMENTS

| WO | WO-00/61739 | A1 | 10/2000 |
|---|---|---|---|
| WO | WO-01/29246 | A1 | 4/2001 |
| WO | WO-02/09573 | A2 | 2/2002 |
| WO | WO-02/31140 | A1 | 4/2002 |
| WO | WO-03/011878 | A2 | 2/2003 |
| WO | WO-03/084570 | A1 | 10/2003 |
| WO | WO-03/085107 | A1 | 10/2003 |
| WO | WO-03/085119 | A1 | 10/2003 |
| WO | WO-03/087131 | A2 | 10/2003 |
| WO | WO-2004/056312 | A2 | 7/2004 |
| WO | WO-2004/106380 | A2 | 12/2004 |
| WO | WO-2005/035586 | A1 | 4/2005 |
| WO | WO-2005/035778 | A1 | 4/2005 |
| WO | WO-2005/044859 | A2 | 5/2005 |
| WO | WO-2005/053742 | A1 | 6/2005 |
| WO | WO-2005/100402 | A1 | 10/2005 |
| WO | WO-2006/029879 | A2 | 3/2006 |
| WO | WO-2006/082515 | A2 | 8/2006 |
| WO | WO-2007/024715 | A2 | 3/2007 |
| WO | WO-2007/042261 | A2 | 4/2007 |
| WO | WO-2007/075270 | A2 | 7/2007 |
| WO | WO-2007/110205 | A2 | 10/2007 |
| WO | WO-2007/146968 | A2 | 12/2007 |
| WO | WO-2007/147901 | A1 | 12/2007 |
| WO | WO-2008/077546 | A1 | 7/2008 |
| WO | WO-2007/024715 | A3 | 10/2008 |
| WO | WO-2008/119566 | A2 | 10/2008 |
| WO | WO-2008/119567 | A2 | 10/2008 |
| WO | WO-2007/024715 | A9 | 4/2009 |
| WO | WO-2009/070642 | A1 | 6/2009 |
| WO | WO-2009/080251 | A1 | 7/2009 |
| WO | WO-2009/080252 | A1 | 7/2009 |
| WO | WO-2009/080253 | A1 | 7/2009 |
| WO | WO-2009/080254 | A1 | 7/2009 |
| WO | WO-2009/089004 | A1 | 7/2009 |
| WO | WO-2009/106321 | A1 | 9/2009 |
| WO | WO-2010/077643 | A1 | 7/2010 |
| WO | WO-2010/081173 | A2 | 7/2010 |
| WO | WO-2010/114940 | A1 | 10/2010 |
| WO | WO-2010/115589 | A1 | 10/2010 |
| WO | WO-2010/129304 | A2 | 11/2010 |
| WO | WO-2010/136172 | A1 | 12/2010 |
| WO | WO-2010/145792 | A1 | 12/2010 |
| WO | WO-2010/145793 | A1 | 12/2010 |
| WO | WO-2010/129304 | A3 | 2/2011 |
| WO | WO-2011/028952 | A1 | 3/2011 |
| WO | WO-2011/090754 | A1 | 7/2011 |
| WO | WO-2011/090762 | A1 | 7/2011 |
| WO | WO-2011/121110 | A1 | 10/2011 |
| WO | WO-2011/131746 | A2 | 10/2011 |
| WO | WO-2011/143545 | A1 | 11/2011 |
| WO | WO-2012/045703 | A1 | 4/2012 |
| WO | WO-2012/058768 | A1 | 5/2012 |
| WO | WO-2012/058768 | A8 | 6/2012 |
| WO | WO-2012/073985 | A1 | 6/2012 |
| WO | WO-2012/075581 | A1 | 6/2012 |
| WO | WO-2012/123949 | A1 | 9/2012 |
| WO | WO-2012/130831 | A1 | 10/2012 |
| WO | WO-2012/143524 | A2 | 10/2012 |
| WO | WO-2012/158818 | A2 | 11/2012 |
| WO | WO-2012/162067 | A2 | 11/2012 |
| WO | WO-2013/026831 | A1 | 2/2013 |
| WO | WO-2013/026833 | A1 | 2/2013 |
| WO | WO-2013/026837 | A1 | 2/2013 |
| WO | WO-2013/096291 | A2 | 6/2013 |
| WO | WO-2013/128194 | A1 | 9/2013 |
| WO | WO-2013/157953 | A1 | 10/2013 |
| WO | WO-2013/157954 | A1 | 10/2013 |
| WO | WO-2013/163631 | A2 | 10/2013 |
| WO | WO-2013/192546 | A1 | 12/2013 |
| WO | WO-2013/192550 | A2 | 12/2013 |
| WO | WO-2014012085 | A2 | 1/2014 |
| WO | WO-2014/022540 | A1 | 2/2014 |
| WO | WO-2014/028560 | A2 | 2/2014 |
| WO | WO-2014/047231 | A1 | 3/2014 |
| WO | WO-2014/028560 | A3 | 5/2014 |
| WO | WO-2014/081955 | A1 | 5/2014 |
| WO | WO-2014/083178 | A1 | 6/2014 |
| WO | WO-2014/108483 | A1 | 7/2014 |
| WO | WO-2014/122143 | A1 | 8/2014 |
| WO | WO-2014/122144 | A1 | 8/2014 |
| WO | WO-2014/122251 | A2 | 8/2014 |
| WO | WO-2014/141152 | A2 | 9/2014 |
| WO | WO-2014/144722 | A2 | 9/2014 |
| WO | WO-2014/153002 | A1 | 9/2014 |
| WO | WO-2014/107599 | A2 | 10/2014 |
| WO | WO-2014/122251 | A3 | 10/2014 |
| WO | WO-2014/167022 | A1 | 10/2014 |
| WO | WO-2014170063 | A1 | 10/2014 |
| WO | WO-2014/141152 | A3 | 12/2014 |
| WO | WO-2014/191113 | A1 | 12/2014 |
| WO | WO-2014/191113 | A8 | 12/2014 |
| WO | WO-2014/193973 | A2 | 12/2014 |
| WO | WO-2015/006749 | A2 | 1/2015 |
| WO | WO-2015/013671 | A1 | 1/2015 |
| WO | WO-2015018527 | A1 | 2/2015 |
| WO | WO-2015/077891 | A1 | 6/2015 |
| WO | WO-2015/095392 | A1 | 6/2015 |
| WO | WO-2015/134411 | A1 | 9/2015 |
| WO | WO-2015/143079 | A1 | 9/2015 |
| WO | WO-2015/150447 | A1 | 10/2015 |
| WO | WO-2015/184207 | A1 | 12/2015 |
| WO | WO-2015184203 | A1 | 12/2015 |
| WO | WO-2016/014942 | A1 | 1/2016 |
| WO | WO-2016/019969 | A1 | 2/2016 |
| WO | WO-2016/020065 | A1 | 2/2016 |
| WO | WO-2016/020332 | A1 | 2/2016 |
| WO | WO-2016/036678 | A1 | 3/2016 |
| WO | WO-2016/055592 | A1 | 4/2016 |
| WO | WO-2016/055593 | A1 | 4/2016 |
| WO | WO-2016/079081 | A1 | 5/2016 |
| WO | WO-2016/079177 | A1 | 5/2016 |
| WO | WO-2016/081490 | A1 | 5/2016 |
| WO | WO-2016/087531 | A1 | 6/2016 |
| WO | WO-2016/110576 | A1 | 7/2016 |
| WO | WO-2016135239 | A1 | 9/2016 |
| WO | WO-2016/179003 | A1 | 11/2016 |
| WO | WO-2016/191750 | A1 | 12/2016 |
| WO | WO-2016/201300 | A1 | 12/2016 |
| WO | WO-2016/204966 | A1 | 12/2016 |
| WO | WO-2016/205520 | A1 | 12/2016 |
| WO | WO-2016/205531 | A2 | 12/2016 |
| WO | WO-2017/021450 | A1 | 2/2017 |
| WO | WO-2017/132279 | A1 | 8/2017 |
| WO | WO-2018/093821 | A1 | 5/2018 |

OTHER PUBLICATIONS

Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*
Stieglmaier et al., "Utilizing the BiTE (bispeicfic T-cell enganger) platform for immunotherapy of cancer," Expert Opin Biol Ther. 15(8): 1093-1099 (2015).
Office Action for Vietnamese Patent Application No. 1-2020-04907, dated Oct. 6, 2020 (3 pages).
Anderson et al., "G19.4(alpha CD3) x B43(alpha CD19) monoclonal antibody heteroconjugate triggers CD19 antigen-specific lysis of t(4;11) acute lymphoblastic leukemia cells by activated CD3 antigen-positive cytotoxic T cells," Blood. 80(11): 2826-34 (1992).
Atwell et al., "Stable heterodimers from remodeling the domain interface of a homodimer using a phage display library," J Mol Biol. 270(1):26-35 (1997).
Baeuerle et al., "Bispecific T-cell engaging antibodies for cancer therapy," Cancer Res. 69(12):4941-4 (2009).
Booy et al., "Monoclonal and bispecific antibodies as novel therapeutics," Arch Immunol Ther Exp (Warsz). 54(2):85-101 (2006).
Bortoletto et al., "Optimizing anti-CD3 affinity for effective T cell targeting against tumor cells," Eur J Immunol. 32(11):3102-7 (2002).

(56) References Cited

OTHER PUBLICATIONS

Bosch et al., "MCSP/CD3-bispecific single-chain antibody construct engages CD4+ and CD8+ T cells for lysis of MCSP-expressing human uveal melanoma cells," AACR 101st Annual Meeting. Apr. 17-21, Washington, DC. 70(8 Suppl) Abstract 5621 (2010).

Bostrom et al., "High affinity antigen recognition of the dual specific variants of herceptin is entropy-driven in spite of structural plasticity," PLoS One. 6(4): e17887 (2011) (12 pages).

Brekke et al., "Human IgG isotype-specific amino acid residues affecting complement-mediated cell lysis and phagocytosis," Eur J Immunol. 24(10):2542-7 (1994).

Brown et al., "Tolerance to single, but not multiple, amino acid replacements in antibody VH CDR2: a means of minimizing B cell wastage from somatic hypermutation?" J Immunol. 156(9):3285-91 (1996).

Brüggemann et al., "Comparison of the effector functions of human immunoglobulins using a matched set of chimeric antibodies," J Exp Med. 166(5):1351-61 (1987).

Carter et al., "Humanization of an anti-p185HER2 antibody for human cancer therapy," Proc Natl Acad Sci U S A. 89(10):4285-4289 (1992).

Carter, "Bispecific human IgG by design," J Immunol Methods. 248(1-2):7-15 (2001).

Chan et al., "Variable region domain exchange in human IgGs promotes antibody complex formation with accompanying structural changes and altered effector functions," Mol Immunol. 41(5):527-38 (2004).

Clark et al., "Affinity enhancement of an in vivo matured therapeutic antibody using structure-based computational design," Protein Sci. 15(5):949-60 (2006).

Clynes et al., "Fc receptors are required in passive and active immunity to melanoma," Proc Natl Acad Sci U S A. 95(2):652-6 (1998).

Cragg et al., "Antibody specificity controls in vivo effector mechanisms of anti-CD20 reagents," Blood. 103(7):2738-43 (2004).

Donaldson et al., "Design and development of masked therapeutic antibodies to limit off-target effects: application to anti-EGFR antibodies," Cancer Biol Ther. 8(22): 2145-50 (2009) (7 pages).

Drebin et al., "Down-modulation of an oncogene protein product and reversion of the transformed phenotype by monoclonal antibodies," Cell. 41(3):695-706 (1985).

Duncan et al., "The binding site for C1q on IgG," Nature. 332(6166): 738-40 (1988).

Edelman et al., "The covalent structure of an entire gammaG immunoglobulin molecule," Proc Natl Acad Sci U S A. 63(1):78-85 (1969).

Gerstner et al., "Sequence plasticity in the antigen-binding site of a therapeutic anti-HER2 antibody," J Mol Biol. 321(5):851-62 (2002).

Guyer et al., "Immunoglobulin binding by mouse intestinal epithelial cell receptors," J Immunol. 117(2):587-93 (1976).

Harris et al., "Identification of multiple sources of charge heterogeneity in a recombinant antibody," J Chromatogr B Biomed Sci Appl. 752(2):233-45 (2001).

Hellström et al., "Antitumor effects of L6, an IgG2a antibody that reacts with most human carcinomas," Proc Natl Acad Sci U S A. 83(18):7059-63 (1986).

Hellström et al., "Strong antitumor activities of IgG3 antibodies to a human melanoma-associated ganglioside," Proc Natl Acad Sci U S A. 82(5):1499-502 (1985).

Holliger et al., "Diabodies': small bivalent and bispecific antibody fragments," Proc Natl Acad Sci U S A. 90(14):6444-8 (1993).

Holliger et al., "Specific killing of lymphoma cells by cytotoxic T-cells mediated by a bispecific diabody," Protein Eng. 9(3):299-305 (1996).

Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).

Hosseini et al., "Systems pharmacology modeling of anti-CD20/CD3 T-cell dependent bispecific antibody and its application to clinical trial design," American Conference on Pharmacometrics 7; Oct. 25; Bellevue, WA. (2016) (1 page).

Huang et al., "In vivo deamidation characterization of monoclonal antibody by LC/MS/MS," Anal Chem. 77(5):1432-9 (2005).

Hudson et al., "Engineered antibodies," Nat Med. 9(1):129-34 (2003).

Idusogie et al., "Mapping of the C1q binding site on rituxan, a chimeric antibody with a human IgG1 Fc," J Immunol. 164(8):4178-84 (2000).

Igawa et al., "VH/VL interface engineering to promote selective expression and inhibit conformational isomerization of thrombopoietin receptor agonist single-chain diabody," Protein Eng Des Sel. 23(8):667-77 (2010) (11 pages).

Jager et al., "The trifunctional antibody ertumaxomab destroys tumor cells that express low levels of human epidermal growth factor receptor 2," Cancer Res. 69(10):4270-6 (2009).

Junttila et al., "Antitumor efficacy of a bispecific antibody that targets HER2 and activates T cells," Cancer Res. 74(19):5561-71 (2014).

Kanda et al., "Comparison of cell lines for stable production of fucose-negative antibodies with enhanced ADCC," Biotechnol Bioeng. 94(4):680-8 (2006).

Kegg Drug Database Accession No. D03257, "Drug: Trastuzumab," <https://www.genome.jp/dbget-bin/www_bget?dr:D03257>, retrieved on Jan. 8, 2019 (2 pages).

Kelley et al., "Antigen binding thermodynamics and antiproliferative effects of chimeric and humanized anti-p185HER2 antibody Fab fragments," Biochemistry. 31(24):5434-41 (1992).

Kelley et al., "Thermodynamic analysis of an antibody functional epitope," Biochemistry. 32(27):6828-35 (1993).

Kiewe et al., "Phase I trial of the trifunctional anti-HER2 x anti-CD3 antibody ertumaxomab in metastatic breast cancer," 2005 ASCO Annual Meeting Proceedings. J Clin Oncol. 23(16S):Abstract 2530 (2005).

Kiewe et al., "Phase I trial of the trifunctional anti-HER2 x anti-CD3 antibody ertumaxomab in metastatic breast cancer," Clin Cancer Res. 12(10):3085-91 (2006).

Kim et al., "Localization of the site of the murine IgG1 molecule that is involved in binding to the murine intestinal Fc receptor," Eur J Immunol. 24(10):2429-34 (1994).

Kipriyanov et al., "Bispecific tandem diabody for tumor therapy with improved antigen binding and pharmacokinetics," J Mol Biol. 293(1):41-56 (1999).

Klein et al., "Progress in overcoming the chain association issue in bispecific heterodimeric IgG antibodies," MAbs. 4(6):653-63 (2012).

Kontermann, "Dual targeting strategies with bispecific antibodies," MAbs. 4(2):182-97 (2012).

Law et al., "Expression and characterization of recombinant soluble human CD3 molecules: presentation of antigenic epitopes defined on the native TCR-CD3 complex," Int Immunol. 14(4): 389-400 (2002).

Leabman et al., "Effects of altered FcgammaR binding on antibody pharmacokinetics in cynomolgus monkeys," MAbs. 5(6):896-903 (2013).

Li, "Successful QSP modeling in drug development starts with the right questions," American Conference on Pharmacometrics 8, Oct. 16, Fort Lauderdale, FL. (2017) (20 pages).

Lippow et al., "Computational design of antibody affinity improvement beyond in vivo maturation," available in PMC Jan. 7, 2010, published in final edited form as: Nat Biotechnol. 25(10):1171-6 (2007) (14 pages).

Liu et al., "Improvement in soluble expression levels of a diabody by exchanging expression vectors," Protein Expr Purif. 62(1):15-20 (2008) (6 pages).

Lum et al., "Targeting T cells with bispecific antibodies for cancer therapy," available in PMC Oct. 8, 2013, published in final edited form as: BioDrugs. 25(6):365-79 (2011) (24 pages).

Merchant et al., "An efficient route to human bispecific IgG," Nat Biotechnol. 16(7):677-81 (1998).

(56) References Cited

OTHER PUBLICATIONS

Metz et al., "Bispecific antibody derivatives with restricted binding functionalities that are activated by proteolytic processing," Protein Eng Des Sel. 25(10):571-80 (2012).

Miller et al., "Design, construction, and in vitro analyses of multivalent antibodies," J Immunol. 170(9):4854-61 (2003).

Moore et al., "A novel bispecific antibody format enables simultaneous bivalent and monovalent co-engagement of distinct target antigens," MAbs. 3(6):546-57 (2011).

Moore et al., "Application of dual affinity retargeting molecules to achieve optimal redirected T-cell killing of B-cell lymphoma," Blood. 117(17):4542-51 (2011) (11 pages).

Nagorsen et al., "Immunomodulatory therapy of cancer with T cell-engaging BiTE antibody blinatumomab," Exp Cell Res. 317(9):1255-60 (2011).

Okazaki et al., "Fucose depletion from human IgG1 oligosaccharide enhances binding enthalpy and association rate between IgG1 and FcgammaRIIIa," J Mol Biol. 336(5):1239-49 (2004).

Oshimi et al., "Increased lysis of patient CD10-positive leukemic cells by T cells coated with anti-CD3 Fab' antibody cross-linked to anti-CD10 Fab' antibody," Blood. 77(5):1044-9 (1991).

Pessano et al., "The T3/T cell receptor complex: antigenic distinction between the two 20-kd T3 (T3-delta and T3-epsilon) subunits," EMBO J. 4(2):337-44 (1985).

Petkova et al., "Enhanced half-life of genetically engineered human IgG1 antibodies in a humanized FcRn mouse model: potential application in humorally mediated autoimmune disease," Int Immunol. 18(12): 1759-69 (2006).

Ravetch et al., "Fc receptors," Annu Rev Immunol. 9:457-92 (1991).

Ridgway et al., "'Knobs-into-holes' engineering of antibody CH3 domains for heavy chain heterodimerization," Protein Eng. 9(7):617-21 (1996).

Riedle et al., "In vivo activation and expansion of T cells by a bi-specific antibody abolishes metastasis formation of human melanoma cells in SCID mice," Int J Cancer. 75(6):908-18 (1998).

Ripka et al., "Two Chinese hamster ovary glycosylation mutants affected in the conversion of GDP-mannose to GDP-fucose," Arch Biochem Biophys. 249(2):533-45 (1986).

Schaefer et al., "Immunoglobulin domain crossover as a generic approach for the production of bispecific IgG antibodies," Proc Natl Acad Sci U S A. 108(27):11187-92 (2011).

Seimetz et al., "Development and approval of the trifunctional antibody catumaxomab (anti-EpCAM x anti-CD3) as a targeted cancer immunotherapy," Cancer Treat Rev. 36(6):458-67 (2010).

Shalaby et al., "Bispecific HER2 x CD3 antibodies enhance T-cell cytotoxicity in vitro and localize to HER2-overexpressing xenografts in nude mice," Clin Immunol Immunopathol. 74(2):185-92 (1995).

Shen et al., "Preparation and characterization for bispecific antibodies of anti-CD3 x anti-idiotype to B cell lymphocytic leukemia," J Tongji Med Univ. 19(3):166-9 (1999) (4 pages).

Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem. 276(9):6591-604 (2001).

Sondermann et al., "The 3.2-A crystal structure of the human IgG1 Fc fragment-Fc gammaRIII complex," Nature. 406(6793):267-73 (2000).

Spiess et al., "Bispecific antibodies with natural architecture produced by co-culture of bacteria expressing two distinct half-antibodies," Nat Biotechnol. 31(8):753-8 (2013) (7 pages).

Stubenrauch et al., "Impact of molecular processing in the hinge region of therapeutic IgG4 antibodies on disposition profiles in cynomolgus monkeys," Drug Metab Dispos. 38(1):84-91 (2010).

Sun et al., "Anti-CD20/CD3 T cell-dependent bispecific antibody for the treatment of B cell malignancies," Sci Transl Med. 7(287):287ra70 (2015) (11 pages).

Torisu-Itakura et al., "Redirected lysis of human melanoma cells by a MCSP/CD3-bispecific BiTE antibody that engages patient-derived T cells," J Immunother. 34(8):597-605 (2011).

Tutt et al., "Trispecific F(ab')3 derivatives that use cooperative signaling via the TCR/CD3 complex and CD2 to activate and redirect resting cytotoxic T cells," J Immunol. 147(1):60-9 (1991).

Westin et al., "Safety and activity of PD1 blockade by pidilizumab in combination with rituximab in patients with relapsed follicular lymphoma: a single group, open-label, phase 2 trial," Lancet Oncol. 15(1):69-77 (2014).

Wolf et al., "BiTEs: bispecific antibody constructs with unique anti-tumor activity," Drug Discov Today. 10(18):1237-44 (2005).

Wright et al., "Effect of glycosylation on antibody function: implications for genetic engineering," Trends Biotechnol. 15(1):26-32 (1997).

Yamane-Ohnuki et al., "Establishment of FUT8 knockout Chinese hamster ovary cells: an ideal host cell line for producing completely defucosylated antibodies with enhanced antibody- dependent cellular cytotoxicity," Biotechnol Bioeng. 87(5):614-22 (2004).

Yan et al., "Succinimide formation at Asn 55 in the complementarity determining region of a recombinant monoclonal antibody IgG1 heavy chain," J Pharm Sci. 98(10):2509-21 (2009).

Yang et al., "Improving Trastuzumab's Stability Profile by Removing the Two Degradation Hotspots," J Pharm Sci. 104(6):1960-70 (2015).

Zhu et al., "Engineering high affinity humanized anti-p185HER2/anti-CD3 bispecific F(ab')2 for efficient lysis of p185HER2 overexpressing tumor cells," Int J Cancer. 62(3):319-24 (1995).

Zhu et al., "Identification of heavy chain residues in a humanized anti-CD3 antibody important for efficient antigen binding and T cell activation," J Immunol. 155(4):1903-10 (1995).

International Search Report and Written Opinion for International Application No. PCT/US2019/017251, dated Apr. 17, 2019 (13 pages).

Brack et al., "A Bispecific HER2-Targeting FynomAb with Superior Antitumor Activity and Novel Mode of Action," Mol Cancer Ther. 13(8): 2030-39 (2014) (11 pages).

Brinkmann et al., "The making of bispecific anitbodies," MAbs. 9(2): 182-212 (2017).

Choi et al., "Bispecific antibodies engage T cells for antitumor immunotherapy," Expert Opin Biol Ther. 11(7): 843-53 (2011).

Desnoyers et al., "Tumor-Specific Activation of an EGFR-Targeting Probody Enhances Therapeutic Index," Sci. Transl. Med. 5(207):207ra144 (2013) (10 pages).

Diefenbach et al., "An individualized risk mitigation approach for safety: experience from the mosunetuzumab (CD20/CD3 bispecific antibody) development program in relation to neurotoxicity risk," 61st ASH Annual Meeting & Exposition, Dec. 7-10, Orlando, Florida, Poster P-4728 (2019) (1 page).

Drent et al., "A Rational Strategy for Reducing On-Target Off-Tumor Effects of CD38-Chimeric Antigen Receptors by Affinity Optimization," Mol Ther. 25(8): 1946-58 (2017).

Haile et al., "Soluble CD80 Restores T Cell Activation and Overcomes Tumor Cell Programmed Death Ligand 1-Mediated Immune Suppression," J Immunol. 191(5):2829-36 (2013) (9 pages).

Hosseini et al., "Abstract B043: Systems pharmacology modeling of anti-CD20/CD3 T-cell dependent bispecific antibody and its application to clinical trial design," Proceedings of the Second CRI-CIMT-EATI-AACR International Cancer Immunotherapy Conference: Translating Science into Survival; Sep. 25-28; New York, NY. Cancer Immunol Res. 4(11 Suppl):Abstract nr B043 (2016) (4 pages).

Huang et al., "Structual chemistry and therapeutic intervention of protein-protein interactions in immune response, human immunodeficiency virus entry and apoptosis," Pharmacology & Therapeutics. 86(3):201-215 (2000).

Kortt et al., "Dimeric and trimeric antibodies: high avidity scFvs for cancer targeting," Biomol Eng. 18:95-108 (2001) (15 pages).

Lee et al., "Current concepts in the diagnosis and management of cytokine release syndrome," Blood. 124(2):188-95 (2014) (18 pages).

Li et al., "Exposure-response analyses indicate a promising benefit/risk profile of mosunetuzumab in relapsed and refractory non-Hodgkin lymphoma," 61st ASH Annual Meeting & Exposition, Dec. 7-10, 2019, Orlando, Florida. Poster P-1285 (2019).

(56) References Cited

OTHER PUBLICATIONS

Liu et al., "Affinity-Tuned ErbB2 or EGFR Chimeric Antigen Receptor T Cells Exhibit an Increased Therapeutic Index against Tumors in Mice," Cancer Res. 75(17): 3596-607 (2015) (13 pages).

Liu et al., "Heteroantibody duplexes target cells for lysis by cytotoxic T lymphocytes," Proc Natl Acad Sci U S A. 82(24):8648-52 (1985).

Milne et al., "Systematic Analysis of Immune Infiltrates in High-Grade Serous Ovarian Cancer Reveals CD20, FoxP3 and TIA-1 as Positive Prognostic Factors," PLoS One. 4(7):e6412 (2009) (14 pages).

Nishimoto et al., "Toxicity, pharmacokinetics, and dose-finding study of repetitive treatment with the humanized anti-interleukin 6 receptor antibody MRA in rheumatoid arthritis. Phase I/II clinical study," J Rheumatol. 30(7):1426-35 (2003).

Paino et al., "Reply to 'Response to "CD20 Positive Cells Are Undetectable in the Majority of Multiple Myeloma Cell Lines and Are Not Associated With a Cancer Stem Cell Phenotype,"'" Haematologica. 97(7):1110-1114 (2012) (1 page).

Roosnek et al., "Triggering T Cells by Otherwise Inert Hybrid Anti-CD3/Antitumor Antibodies Requires Encounter with the Specific Target Cell," J Exp Med. 170(1):297-302 (1989) (6 pages).

Shi et al., "Margin-Infiltrating CD20+ B Cells Display an Atypical Memory Phenotype and Correlate with Favorable Prognosis in Hepatocellular Carcinoma," Clinical Cancer Research. 19(21):5994-6003 (2013).

Somasundaram et al., "Will Engineered T Cells Expressing CD20 scFv Eradicate Melanoma?" Mol Ther. 19(4):638-40 (2011).

Stein et al., "Effect of a Monoclonal Antibody to PCSK9 on LDL Cholesterol," N Engl J Med. 366:1108-18 (2012).

Stein et al., "Novel and Emerging Drugs for Acute Myeloid Leukemia," available in PMC May 22, 2015, published in final edited form as: Curr Cancer Drug Targets. 12(5):522-530 (2012) (19 pages).

Spiess et al., "Alternative molecular formats and therapeutic applications for bispecific antibodies," Mol immunol. 67:95-106 (2015).

Weidle et al., "The Intriguing Options of Multispecific Antibody Formats for Treatment of Cancer," Cancer Genomics & Proteomics. 10:1-18 (2013) (18 pages).

Wells et al., "Reaching for high-hanging fruit in drug discovery at protein-protein interfaces," Nature. 450 (7172):1001-9(2007).

Wuellner et al., "Bispecific CD3/HER2 Targeting FynomAb Induces Redirected T Cell-Mediated Cytolysis with High Potency and Enhanced Tumor Selectivity," Antibodies. 4(4): 426-440 (2015) (15 pages).

Slaga et al., "Avidity-based binding to HER2 results in selective killing of HER2-overexpressing cells by anti-HER2/CD3," Sci Transl Med. 10(463). pii: eaat5775 (2018) (12 pages).

Genentech, "A Phase I Study of BTRC4017A in Participants With Locally Advanced or Metastatic HER2-Expressing Cancers," ClinicalTrials.gov, <https://clinicaltrials.gov/ct2/show/NCT03448042?term=BTRC4017A&draw=2&rank=1>, dated Feb. 27, 2018, retrieved on Nov. 2, 2021 (7 pages).

Sen et al., "Use of anti-CD3x anti-HER2/neu bispecific antibody for redirecting cytotoxicity of activated T cells toward HER2/neu+ tumors," J Hematother Stem Cell Res. 10(2):247-60 (2001).

Notice of Reasons for Rejection for Japanese Application No. 2020-542329, dated Feb. 21, 2023 (10 pages).

Office Action for Russian Application No. 2021127020, dated Sep. 26, 2022 (11 pages).

\* cited by examiner

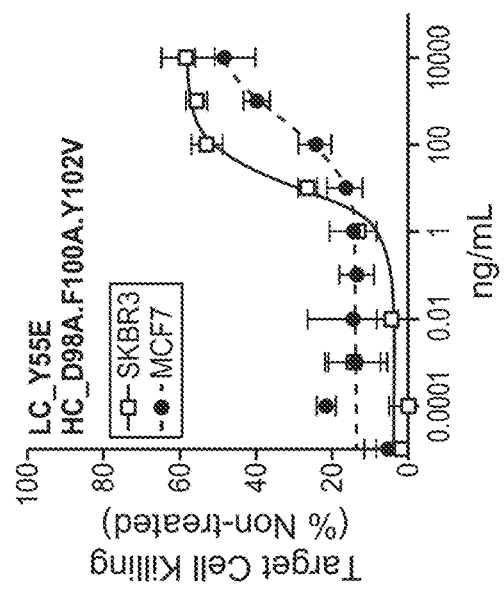
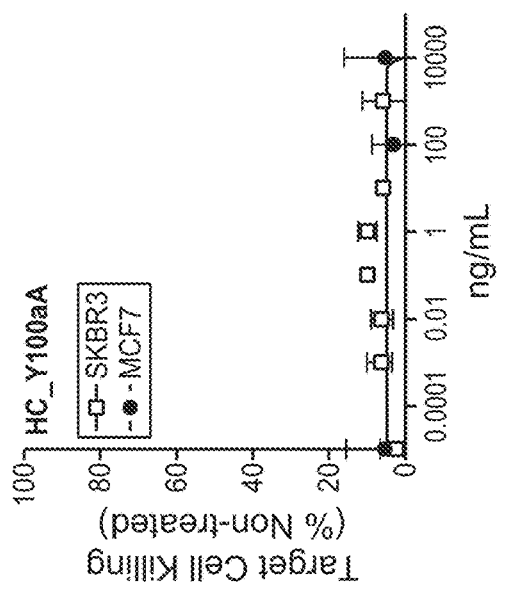
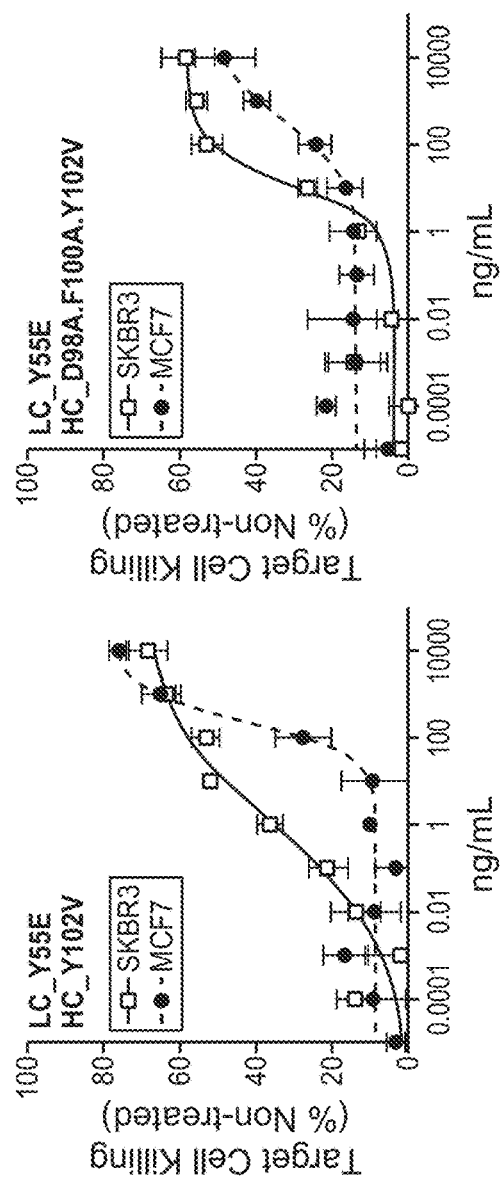
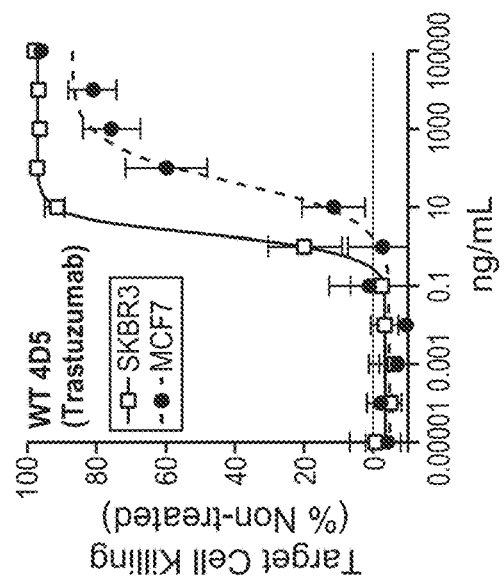
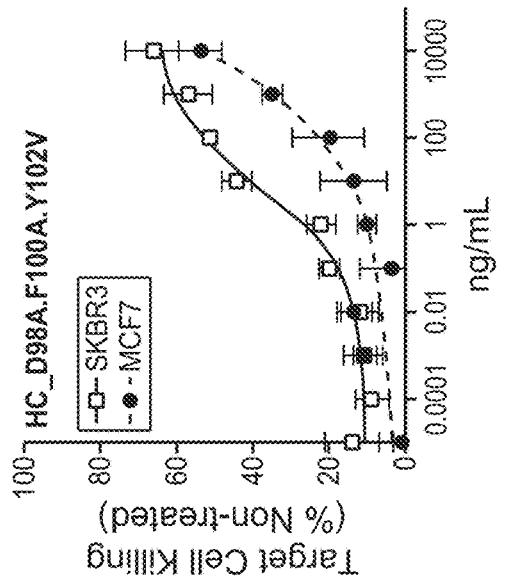

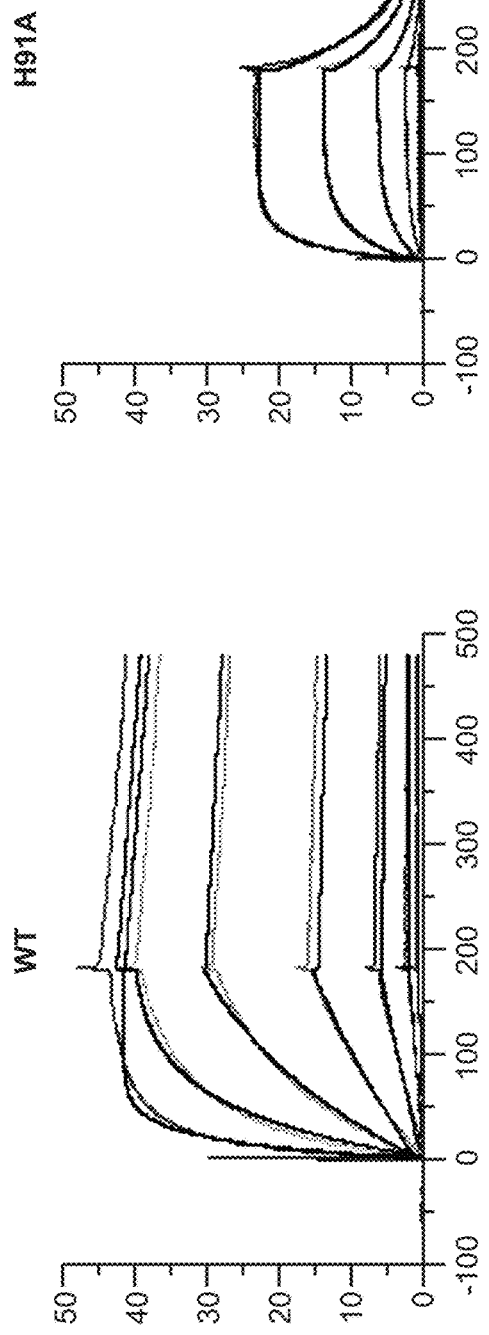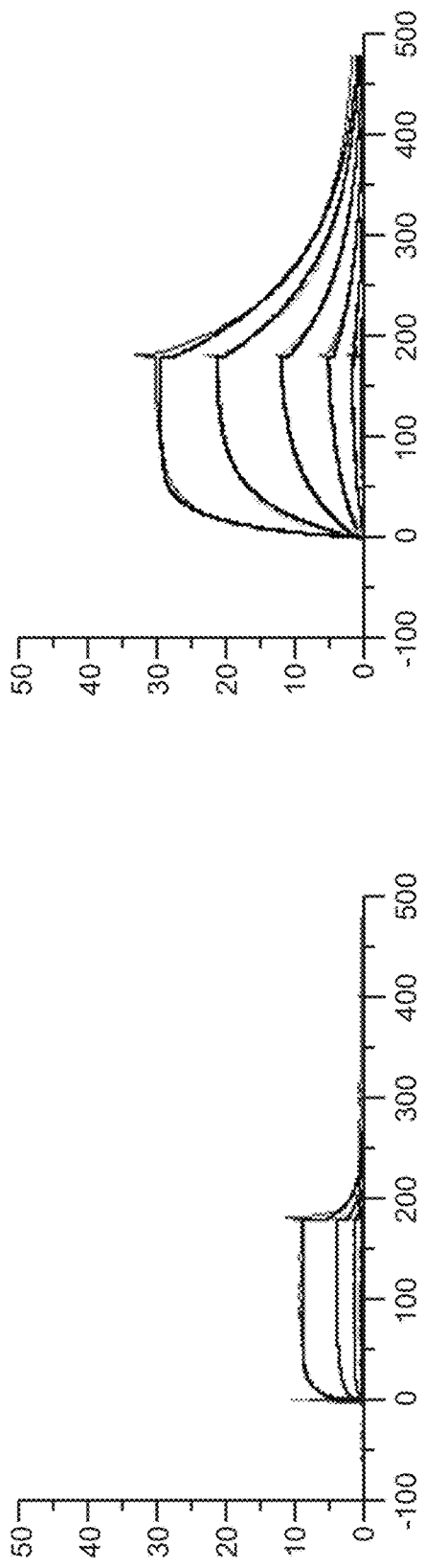

SEQUENCE LISTING

```
<160> NUMBER OF SEQ ID NOS: 98

<210> SEQ ID NO 1
<211> LENGTH: 5
<212> TYPE: PRT
<213> ORGANISM: Artificial Sequence
<220> FEATURE:
```

<223> OTHER INFORMATION: Synthetic Construct

<400> SEQUENCE: 1

Asn Tyr Tyr Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Trp Ile Tyr Pro Gly Asp Gly Asn Thr Lys Tyr Asn Glu Lys Phe Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Asp Ser Tyr Ser Asn Tyr Tyr Phe Asp Tyr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic Construct

<400> SEQUENCE: 4

Lys Ser Ser Gln Ser Leu Leu Asn Ser Arg Thr Arg Lys Asn Tyr Leu
1               5                   10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Trp Ala Ser Thr Arg Glu Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Thr Gln Ser Phe Ile Leu Arg Thr
1               5

<210> SEQ ID NO 7
<211> LENGTH: 119

```
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115

<210> SEQ ID NO 8
<211> LENGTH: 112
<212> TYPE: PRT
<213> ORGANISM: Artificial Sequence
<220> FEATURE:
<223> OTHER INFORMATION: Synthetic Construct

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

<210> SEQ ID NO 9
<211> LENGTH: 119
<212> TYPE: PRT
<213> ORGANISM: Artificial Sequence
<220> FEATURE:
<223> OTHER INFORMATION: Synthetic Construct

<400> SEQUENCE: 9

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asn Tyr
            20                  25                  30

Tyr Ile His Trp Val Lys Gln Arg Pro Gly Gln Gly Leu Glu Trp Ile
```

```
              35                  40                  45
Gly Trp Ile Tyr Pro Gly Asp Gly Asn Thr Lys Tyr Asn Glu Lys Phe
 50                  55                  60

Lys Gly Lys Ala Thr Leu Thr Ala Asp Thr Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asp Ser Tyr Ser Asn Tyr Tyr Phe Asp Tyr Trp Gly Gln Gly
                100                 105                 110

Thr Thr Leu Thr Val Ser Ser
        115
```

<210> SEQ ID NO 10
<211> LENGTH: 112
<212> TYPE: PRT
<213> ORGANISM: Artificial Sequence
<220> FEATURE:
<223> OTHER INFORMATION: Synthetic Construct

<400> SEQUENCE: 10

```
Asp Ile Val Met Thr Gln Ser Pro Ser Ser Leu Ala Val Ser Ala Gly
 1               5                  10                  15

Glu Lys Val Thr Met Ser Cys Lys Ser Ser Gln Ser Leu Leu Asn Ser
                 20                  25                  30

Arg Thr Arg Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Thr Gln
                 85                  90                  95

Ser Phe Ile Leu Arg Thr Phe Gly Gly Gly Thr Lys Leu Glu Ile Lys
                100                 105                 110
```

<210> SEQ ID NO 11
<211> LENGTH: 5
<212> TYPE: PRT
<213> ORGANISM: Artificial Sequence
<220> FEATURE:
<223> OTHER INFORMATION: Synthetic Construct

<400> SEQUENCE: 11

```
Asp Thr Tyr Ile His
 1               5
```

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Asn or Glu

<400> SEQUENCE: 12

```
Arg Ile Tyr Pro Thr Xaa Gly Tyr Thr Arg Tyr Ala Asp Ser Val Lys
 1               5                  10                  15

Gly
```

```
<210> SEQ ID NO 13
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Asp, Ala, or Thr
<220> FEATURE:
<221> NAME/KEY: MISC_FEATURE
<222> LOCATION: (6)..(6)
<223> OTHER INFORMATION: Xaa is Phe or Ala
<220> FEATURE:
<221> NAME/KEY: MISC_FEATURE
<222> LOCATION: (11)..(11)
<223> OTHER INFORMATION: Xaa is Tyr or Val

<400> SEQUENCE: 13

Trp Gly Gly Xaa Gly Xaa Tyr Ala Met Asp Xaa
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Asn, Ser, or Ala

<400> SEQUENCE: 14

Arg Ala Ser Gln Asp Val Xaa Thr Ala Val Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Tyr or Glu

<400> SEQUENCE: 15

Ser Ala Ser Phe Leu Xaa Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is His or Ala

<400> SEQUENCE: 16

Gln Gln Xaa Tyr Thr Thr Pro Pro Thr
1               5

<210> SEQ ID NO 17
```

```
<211> LENGTH: 120
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (55)..(55)
<223> OTHER INFORMATION: Xaa is Asn or Glu
<220> FEATURE:
<221> NAME/KEY: MISC_FEATURE
<222> LOCATION: (102)..(102)
<223> OTHER INFORMATION: Xaa is Asp, Ala, or Thr
<220> FEATURE:
<221> NAME/KEY: MISC_FEATURE
<222> LOCATION: (104)..(104)
<223> OTHER INFORMATION: Xaa is Phe or Ala
<220> FEATURE:
<221> NAME/KEY: MISC_FEATURE
<222> LOCATION: (109)..(109)
<223> OTHER INFORMATION: Xaa is Tyr or Val

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Xaa Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Xaa Gly Xaa Tyr Ala Met Asp Xaa Trp Gly Gln
            100                 105                 110

Gly Thr Leu Val Thr Val Ser Ser
        115                 120

<210> SEQ ID NO 18
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (30)..(30)
<223> OTHER INFORMATION: Xaa is Asn, Ser, or Ala
<220> FEATURE:
<221> NAME/KEY: MISC_FEATURE
<222> LOCATION: (55)..(55)
<223> OTHER INFORMATION: Xaa is Tyr or Glu
<220> FEATURE:
<221> NAME/KEY: MISC_FEATURE
<222> LOCATION: (91)..(91)
<223> OTHER INFORMATION: Xaa is His or Ala

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Xaa Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Xaa Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Xaa Tyr Thr Thr Pro Pro
                85                  90                  95

Thr Phe Gly Gln Gly Thr Lys Val Glu Ile Lys
                100                 105

<210> SEQ ID NO 19
<211> LENGTH: 17
<212> TYPE: PRT
<213> ORGANISM: Artificial Sequence
<220> FEATURE:
<223> OTHER INFORMATION: Synthetic Construct

<400> SEQUENCE: 19

Arg Ile Tyr Pro Thr Asn Gly Tyr Thr Arg Tyr Ala Asp Ser Val Lys
1               5                   10                  15
Gly

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Trp Gly Gly Asp Gly Phe Tyr Ala Met Asp Tyr
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic Construct

<400> SEQUENCE: 21

Arg Ala Ser Gln Asp Val Asn Thr Ala Val Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic Construct

<400> SEQUENCE: 22

Ser Ala Ser Phe Leu Tyr Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Gln Gln His Tyr Thr Thr Pro Pro Thr
1               5
```

<210> SEQ ID NO 24
<211> LENGTH: 120
<212> TYPE: PRT
<213> ORGANISM: Artificial Sequence
<220> FEATURE:
<223> OTHER INFORMATION: Synthetic Construct

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 25
<211> LENGTH: 107
<212> TYPE: PRT
<213> ORGANISM: Artificial Sequence
<220> FEATURE:
<223> OTHER INFORMATION: Synthetic Construct

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

```
Gln Gln Ala Tyr Thr Thr Pro Pro Thr
1               5
```

<210> SEQ ID NO 27
<211> LENGTH: 107
<212> TYPE: PRT
<213> ORGANISM: Artificial Sequence
<220> FEATURE:
<223> OTHER INFORMATION: Synthetic Construct

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Thr Thr Pro Pro
                85                  90                  95

Thr Phe Gly Gln Gly Thr Lys Val Glu Ile Lys
            100                 105
```

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

```
Trp Gly Gly Asp Gly Phe Tyr Ala Met Asp Val
1               5                   10
```

<210> SEQ ID NO 29
<211> LENGTH: 7
<212> TYPE: PRT
<213> ORGANISM: Artificial Sequence
<220> FEATURE:
<223> OTHER INFORMATION: Synthetic Construct

<400> SEQUENCE: 29

```
Ser Ala Ser Phe Leu Glu Ser
1               5
```

<210> SEQ ID NO 30
<211> LENGTH: 120
<212> TYPE: PRT
<213> ORGANISM: Artificial Sequence
<220> FEATURE:
<223> OTHER INFORMATION: Synthetic Construct

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
```

```
                65                  70                  75                  80
Leu Gln Met Asn Ser Leu Arg Ala Glu Asp Thr Ala Val Tyr Tyr Cys
                    85                  90                  95

Ser Arg Trp Gly Gly Asp Gly Phe Tyr Ala Met Asp Val Trp Gly Gln
                100                 105                 110

Gly Thr Leu Val Thr Val Ser Ser
        115                 120

<210> SEQ ID NO 31
<211> LENGTH: 107
<212> TYPE: PRT
<213> ORGANISM: Artificial Sequence
<220> FEATURE:
<223> OTHER INFORMATION: Synthetic Construct

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
                100                 105

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Trp Gly Gly Ala Gly Ala Tyr Ala Met Asp Val
1               5                   10

<210> SEQ ID NO 33
<211> LENGTH: 120
<212> TYPE: PRT
<213> ORGANISM: Artificial Sequence
<220> FEATURE:
<223> OTHER INFORMATION: Synthetic Construct

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                 85                  90                  95

Ser Arg Trp Gly Gly Ala Gly Ala Tyr Ala Met Asp Val Trp Gly Gln
            100                 105                 110

Gly Thr Leu Val Thr Val Ser Ser
        115                 120

<210> SEQ ID NO 34
<211> LENGTH: 11
<212> TYPE: PRT
<213> ORGANISM: Artificial Sequence
<220> FEATURE:
<223> OTHER INFORMATION: Synthetic Construct

<400> SEQUENCE: 34

Trp Gly Gly Thr Gly Ala Tyr Ala Met Asp Val
1               5                   10

<210> SEQ ID NO 35
<211> LENGTH: 120
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                 85                  90                  95

Ser Arg Trp Gly Gly Thr Gly Ala Tyr Ala Met Asp Val Trp Gly Gln
            100                 105                 110

Gly Thr Leu Val Thr Val Ser Ser
        115                 120

<210> SEQ ID NO 36
<211> LENGTH: 17
<212> TYPE: PRT
<213> ORGANISM: Artificial Sequence
<220> FEATURE:
<223> OTHER INFORMATION: Synthetic Construct

<400> SEQUENCE: 36

Arg Ile Tyr Pro Thr Glu Gly Tyr Thr Arg Tyr Ala Asp Ser Val Lys
1               5                   10                  15

Gly

<210> SEQ ID NO 37
<211> LENGTH: 11
<212> TYPE: PRT
<213> ORGANISM: Artificial Sequence
<220> FEATURE:
<223> OTHER INFORMATION: Synthetic Construct
```

<400> SEQUENCE: 37

Trp Gly Gly Thr Gly Phe Tyr Ala Met Asp Tyr
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic Construct

<400> SEQUENCE: 38

Arg Ala Ser Gln Asp Val Ser Thr Ala Val Ala
1               5                   10

<210> SEQ ID NO 39
<211> LENGTH: 120
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser Ser
        115                 120

<210> SEQ ID NO 40
<211> LENGTH: 107
<212> TYPE: PRT
<213> ORGANISM: Artificial Sequence
<220> FEATURE:
<223> OTHER INFORMATION: Synthetic Construct

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro

```
                    85                  90                  95

Thr Phe Gly Gln Gly Thr Lys Val Glu Ile Lys
                   100                 105

<210> SEQ ID NO 41
<211> LENGTH: 120
<212> TYPE: PRT
<213> ORGANISM: Artificial Sequence
<220> FEATURE:
<223> OTHER INFORMATION: Synthetic Construct

<400> SEQUENCE: 41

Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Glu Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
                100                 105                 110

Gly Thr Leu Val Thr Val Ser Ser
            115                 120

<210> SEQ ID NO 42
<211> LENGTH: 107
<212> TYPE: PRT
<213> ORGANISM: Artificial Sequence
<220> FEATURE:
<223> OTHER INFORMATION: Synthetic Construct

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Thr Thr Pro Pro
                85                  90                  95

Thr Phe Gly Gln Gly Thr Lys Val Glu Ile Lys
                100                 105

<210> SEQ ID NO 43
<211> LENGTH: 11
<212> TYPE: PRT
<213> ORGANISM: Artificial Sequence
<220> FEATURE:
<223> OTHER INFORMATION: Synthetic Construct

<400> SEQUENCE: 43
```

```
Trp Gly Gly Thr Gly Phe Tyr Ala Met Asp Val
1               5                   10
```

<210> SEQ ID NO 44
<211> LENGTH: 120
<212> TYPE: PRT
<213> ORGANISM: Artificial Sequence
<220> FEATURE:
<223> OTHER INFORMATION: Synthetic Construct

<400> SEQUENCE: 44

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Glu Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Val Trp Gly Gln
                100                 105                 110

Gly Thr Leu Val Thr Val Ser Ser
            115                 120
```

<210> SEQ ID NO 45
<211> LENGTH: 107
<212> TYPE: PRT
<213> ORGANISM: Artificial Sequence
<220> FEATURE:
<223> OTHER INFORMATION: Synthetic Construct

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Glu Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
                100                 105
```

<210> SEQ ID NO 46
<211> LENGTH: 120
<212> TYPE: PRT
<213> ORGANISM: Artificial Sequence
<220> FEATURE:
<223> OTHER INFORMATION: Synthetic Construct

<400> SEQUENCE: 46

-continued

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Ala Tyr Ala Met Asp Val Trp Gly Gln
            100                 105                 110

Gly Thr Leu Val Thr Val Ser Ser
            115                 120

<210> SEQ ID NO 47
<211> LENGTH: 120
<212> TYPE: PRT
<213> ORGANISM: Artificial Sequence
<220> FEATURE:
<223> OTHER INFORMATION: Synthetic Construct

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Ala Gly Ala Tyr Ala Met Asp Val Trp Gly Gln
            100                 105                 110

Gly Thr Leu Val Thr Val Ser Ser
            115                 120

<210> SEQ ID NO 48
<211> LENGTH: 107
<212> TYPE: PRT
<213> ORGANISM: Artificial Sequence
<220> FEATURE:
<223> OTHER INFORMATION: Synthetic Construct

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
    50                  55                  60

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Tyr Thr Thr Pro Pro
                 85                  90                  95

Thr Phe Gly Gln Gly Thr Lys Val Glu Ile Lys
            100                 105

<210> SEQ ID NO 49
<211> LENGTH: 107
<212> TYPE: PRT
<213> ORGANISM: Artificial Sequence
<220> FEATURE:
<223> OTHER INFORMATION: Synthetic Construct

<400> SEQUENCE: 49

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Glu Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Tyr Thr Thr Pro Pro
                 85                  90                  95

Thr Phe Gly Gln Gly Thr Lys Val Glu Ile Lys
            100                 105

<210> SEQ ID NO 50
<211> LENGTH: 5
<212> TYPE: PRT
<213> ORGANISM: Artificial Sequence
<220> FEATURE:
<223> OTHER INFORMATION: Synthetic Construct

<400> SEQUENCE: 50

Asp Lys Thr His Thr
 1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic Construct

<400> SEQUENCE: 51

Gly Gly Gly Gly Ser Gly Gly
 1               5

<210> SEQ ID NO 52
<211> LENGTH: 12
<212> TYPE: PRT
<213> ORGANISM: Artificial Sequence
<220> FEATURE:
<223> OTHER INFORMATION: Synthetic Construct

<400> SEQUENCE: 52

Asp Lys Thr His Thr Gly Gly Gly Gly Ser Gly Gly
 1               5                  10
```

```
<210> SEQ ID NO 53
<211> LENGTH: 11
<212> TYPE: PRT
<213> ORGANISM: Artificial Sequence
<220> FEATURE:
<223> OTHER INFORMATION: Synthetic Construct

<400> SEQUENCE: 53

Arg Ala Ser Gln Asp Val Ala Thr Ala Val Ala
1               5                   10

<210> SEQ ID NO 54
<211> LENGTH: 107
<212> TYPE: PRT
<213> ORGANISM: Artificial Sequence
<220> FEATURE:
<223> OTHER INFORMATION: Synthetic Construct

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ala Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Thr Thr Pro Pro
                85                  90                  95

Thr Phe Gly Gln Gly Thr Lys Val Glu Ile Lys
            100                 105

<210> SEQ ID NO 55
<211> LENGTH: 678
<212> TYPE: PRT
<213> ORGANISM: Artificial Sequence
<220> FEATURE:
<223> OTHER INFORMATION: Synthetic Construct

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
                245                 250                 255

Ile Lys Asp Thr Tyr Ile His Trp Val Arg Gln Ala Pro Gly Lys Gly
            260                 265                 270

Leu Glu Trp Val Ala Arg Ile Tyr Pro Thr Asn Gly Tyr Thr Arg Tyr
            275                 280                 285

Ala Asp Ser Val Lys Gly Arg Phe Thr Ile Ser Ala Asp Thr Ser Lys
290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
                325                 330                 335

Tyr Trp Gly Gln Gly Thr Leu Val Thr Val Ser Ser Ala Ser Thr Lys
            340                 345                 350

Gly Pro Ser Val Phe Pro Leu Ala Pro Ser Ser Lys Ser Thr Ser Gly
            355                 360                 365

Gly Thr Ala Ala Leu Gly Cys Leu Val Lys Asp Tyr Phe Pro Glu Pro
370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Lys Val Glu Pro
            435                 440                 445

Lys Ser Cys Asp Lys Thr His Thr Cys Pro Pro Cys Pro Ala Pro Glu
450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Gly
            515                 520                 525

Ser Thr Tyr Arg Val Val Ser Val Leu Thr Val Leu His Gln Asp Trp
530                 535                 540

Leu Asn Gly Lys Glu Tyr Lys Cys Lys Val Ser Asn Lys Ala Leu Pro
```

```
                545                 550                 555                 560
Ala Pro Ile Glu Lys Thr Ile Ser Lys Ala Lys Gly Gln Pro Arg Glu
                    565                 570                 575

Pro Gln Val Tyr Thr Leu Pro Pro Ser Arg Glu Glu Met Thr Lys Asn
                    580                 585                 590

Gln Val Ser Leu Trp Cys Leu Val Lys Gly Phe Tyr Pro Ser Asp Ile
                    595                 600                 605

Ala Val Glu Trp Glu Ser Asn Gly Gln Pro Glu Asn Asn Tyr Lys Thr
                    610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                    645                 650                 655

Ser Val Met His Glu Ala Leu His Asn His Tyr Thr Gln Lys Ser Leu
                    660                 665                 670

Ser Leu Ser Pro Gly Lys
                    675

<210> SEQ ID NO 56
<211> LENGTH: 685
<212> TYPE: PRT
<213> ORGANISM: Artificial Sequence
<220> FEATURE:
<223> OTHER INFORMATION: Synthetic Construct

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Gly Gly Gly Gly Ser Gly Gly Glu Val Gln Leu Val
```

-continued

```
               225                 230                 235                 240
        Glu Ser Gly Gly Gly Leu Val Gln Pro Gly Gly Ser Leu Arg Leu Ser
                            245                 250                 255
        Cys Ala Ala Ser Gly Phe Asn Ile Lys Asp Thr Tyr Ile His Trp Val
                        260                 265                 270
        Arg Gln Ala Pro Gly Lys Gly Leu Glu Trp Val Ala Arg Ile Tyr Pro
                    275                 280                 285
        Thr Asn Gly Tyr Thr Arg Tyr Ala Asp Ser Val Lys Gly Arg Phe Thr
                290                 295                 300
        Ile Ser Ala Asp Thr Ser Lys Asn Thr Ala Tyr Leu Gln Met Asn Ser
        305                 310                 315                 320
        Leu Arg Ala Glu Asp Thr Ala Val Tyr Tyr Cys Ser Arg Trp Gly Gly
                        325                 330                 335
        Asp Gly Phe Tyr Ala Met Asp Tyr Trp Gly Gln Gly Thr Leu Val Thr
                        340                 345                 350
        Val Ser Ser Ala Ser Thr Lys Gly Pro Ser Val Phe Pro Leu Ala Pro
                    355                 360                 365
        Ser Ser Lys Ser Thr Ser Gly Gly Thr Ala Ala Leu Gly Cys Leu Val
                370                 375                 380
        Lys Asp Tyr Phe Pro Glu Pro Val Thr Val Ser Trp Asn Ser Gly Ala
        385                 390                 395                 400
        Leu Thr Ser Gly Val His Thr Phe Pro Ala Val Leu Gln Ser Ser Gly
                        405                 410                 415
        Leu Tyr Ser Leu Ser Ser Val Val Thr Val Pro Ser Ser Ser Leu Gly
                    420                 425                 430
        Thr Gln Thr Tyr Ile Cys Asn Val Asn His Lys Pro Ser Asn Thr Lys
                435                 440                 445
        Val Asp Lys Lys Val Glu Pro Lys Ser Cys Asp Lys Thr His Thr Cys
                450                 455                 460
        Pro Pro Cys Pro Ala Pro Glu Leu Leu Gly Gly Pro Ser Val Phe Leu
        465                 470                 475                 480
        Phe Pro Pro Lys Pro Lys Asp Thr Leu Met Ile Ser Arg Thr Pro Glu
                        485                 490                 495
        Val Thr Cys Val Val Val Asp Val Ser His Glu Asp Pro Glu Val Lys
                    500                 505                 510
        Phe Asn Trp Tyr Val Asp Gly Val Glu Val His Asn Ala Lys Thr Lys
                515                 520                 525
        Pro Arg Glu Glu Gln Tyr Gly Ser Thr Tyr Arg Val Val Ser Val Leu
                530                 535                 540
        Thr Val Leu His Gln Asp Trp Leu Asn Gly Lys Glu Tyr Lys Cys Lys
        545                 550                 555                 560
        Val Ser Asn Lys Ala Leu Pro Ala Pro Ile Glu Lys Thr Ile Ser Lys
                        565                 570                 575
        Ala Lys Gly Gln Pro Arg Glu Pro Gln Val Tyr Thr Leu Pro Pro Ser
                    580                 585                 590
        Arg Glu Glu Met Thr Lys Asn Gln Val Ser Leu Trp Cys Leu Val Lys
                595                 600                 605
        Gly Phe Tyr Pro Ser Asp Ile Ala Val Glu Trp Glu Ser Asn Gly Gln
                610                 615                 620
        Pro Glu Asn Asn Tyr Lys Thr Thr Pro Pro Val Leu Asp Ser Asp Gly
        625                 630                 635                 640
        Ser Phe Phe Leu Tyr Ser Lys Leu Thr Val Asp Lys Ser Arg Trp Gln
                        645                 650                 655
```

Gln Gly Asn Val Phe Ser Cys Ser Val Met His Glu Ala Leu His Asn
              660                 665                 670

His Tyr Thr Gln Lys Ser Leu Ser Leu Ser Pro Gly Lys
          675                 680                 685

<210> SEQ ID NO 57
<211> LENGTH: 678
<212> TYPE: PRT
<213> ORGANISM: Artificial Sequence
<220> FEATURE:
<223> OTHER INFORMATION: Synthetic Construct

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
                245                 250                 255

Ile Lys Asp Thr Tyr Ile His Trp Val Arg Gln Ala Pro Gly Lys Gly
            260                 265                 270

Leu Glu Trp Val Ala Arg Ile Tyr Pro Thr Asn Gly Tyr Thr Arg Tyr
        275                 280                 285

Ala Asp Ser Val Lys Gly Arg Phe Thr Ile Ser Ala Asp Thr Ser Lys
    290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
                325                 330                 335

Tyr Trp Gly Gln Gly Thr Leu Val Thr Val Ser Ser Ala Ser Thr Lys
            340                 345                 350

Gly Pro Ser Val Phe Pro Leu Ala Pro Ser Ser Lys Ser Thr Ser Gly
            355                 360                 365

Gly Thr Ala Ala Leu Gly Cys Leu Val Lys Asp Tyr Phe Pro Glu Pro
370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
            405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Lys Val Glu Pro
            435                 440                 445

Lys Ser Cys Asp Lys Thr His Thr Cys Pro Pro Cys Pro Ala Pro Glu
450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
            485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Gly
            515                 520                 525

Ser Thr Tyr Arg Val Val Ser Val Leu Thr Val Leu His Gln Asp Trp
530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
            565                 570                 575

Pro Gln Val Tyr Thr Leu Pro Pro Ser Arg Glu Glu Met Thr Lys Asn
            580                 585                 590

Gln Val Ser Leu Trp Cys Leu Val Lys Gly Phe Tyr Pro Ser Asp Ile
            595                 600                 605

Ala Val Glu Trp Glu Ser Asn Gly Gln Pro Glu Asn Asn Tyr Lys Thr
610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
            645                 650                 655

Ser Val Met His Glu Ala Leu His Asn His Tyr Thr Gln Lys Ser Leu
            660                 665                 670

Ser Leu Ser Pro Gly Lys
            675

<210> SEQ ID NO 58
<211> LENGTH: 685
<212> TYPE: PRT
<213> ORGANISM: Artificial Sequence
<220> FEATURE:
<223> OTHER INFORMATION: Synthetic Construct

<400> SEQUENCE: 58

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
            260                 265                 270

Arg Gln Ala Pro Gly Lys Gly Leu Glu Trp Val Ala Arg Ile Tyr Pro
        275                 280                 285

Thr Asn Gly Tyr Thr Arg Tyr Ala Asp Ser Val Lys Gly Arg Phe Thr
290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
                325                 330                 335

Asp Gly Phe Tyr Ala Met Asp Tyr Trp Gly Gln Gly Thr Leu Val Thr
            340                 345                 350

Val Ser Ser Ala Ser Thr Lys Gly Pro Ser Val Phe Pro Leu Ala Pro
        355                 360                 365

Ser Ser Lys Ser Thr Ser Gly Gly Thr Ala Ala Leu Gly Cys Leu Val
370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
            420                 425                 430
```

Thr Gln Thr Tyr Ile Cys Asn Val Asn His Lys Pro Ser Asn Thr Lys
            435                 440                 445

Val Asp Lys Lys Val Glu Pro Lys Ser Cys Asp Lys Thr His Thr Cys
450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
            500                 505                 510

Phe Asn Trp Tyr Val Asp Gly Val Glu Val His Asn Ala Lys Thr Lys
        515                 520                 525

Pro Arg Glu Glu Gln Tyr Gly Ser Thr Tyr Arg Val Val Ser Val Leu
    530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590

Arg Glu Glu Met Thr Lys Asn Gln Val Ser Leu Trp Cys Leu Val Lys
        595                 600                 605

Gly Phe Tyr Pro Ser Asp Ile Ala Val Glu Trp Glu Ser Asn Gly Gln
    610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
        675                 680                 685

<210> SEQ ID NO 59
<211> LENGTH: 678
<212> TYPE: PRT
<213> ORGANISM: Artificial Sequence
<220> FEATURE:
<223> OTHER INFORMATION: Synthetic Construct

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Val Trp Gly Gln
            100                 105                 110

```
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
                245                 250                 255

Ile Lys Asp Thr Tyr Ile His Trp Val Arg Gln Ala Pro Gly Lys Gly
            260                 265                 270

Leu Glu Trp Val Ala Arg Ile Tyr Pro Thr Asn Gly Tyr Thr Arg Tyr
        275                 280                 285

Ala Asp Ser Val Lys Gly Arg Phe Thr Ile Ser Ala Asp Thr Ser Lys
    290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
                325                 330                 335

Tyr Trp Gly Gln Gly Thr Leu Val Thr Val Ser Ser Ala Ser Thr Lys
            340                 345                 350

Gly Pro Ser Val Phe Pro Leu Ala Pro Ser Ser Lys Ser Thr Ser Gly
        355                 360                 365

Gly Thr Ala Ala Leu Gly Cys Leu Val Lys Asp Tyr Phe Pro Glu Pro
    370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Lys Val Glu Pro
        435                 440                 445

Lys Ser Cys Asp Lys Thr His Thr Cys Pro Pro Cys Pro Ala Pro Glu
    450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Gly
        515                 520                 525

Ser Thr Tyr Arg Val Val Ser Val Leu Thr Val Leu His Gln Asp Trp
```

```
                530                 535                 540
Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Glu Glu Met Thr Lys Asn
                580                 585                 590

Gln Val Ser Leu Trp Cys Leu Val Lys Gly Phe Tyr Pro Ser Asp Ile
                595                 600                 605

Ala Val Glu Trp Glu Ser Asn Gly Gln Pro Glu Asn Asn Tyr Lys Thr
                610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
                660                 665                 670

Ser Leu Ser Pro Gly Lys
                675

<210> SEQ ID NO 60
<211> LENGTH: 685
<212> TYPE: PRT
<213> ORGANISM: Artificial Sequence
<220> FEATURE:
<223> OTHER INFORMATION: Synthetic Construct

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
                35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Val Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
```

-continued

```
            210                 215                 220
Lys Thr His Thr Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
                260                 265                 270

Arg Gln Ala Pro Gly Lys Gly Leu Glu Trp Val Ala Arg Ile Tyr Pro
                275                 280                 285

Thr Asn Gly Tyr Thr Arg Tyr Ala Asp Ser Val Lys Gly Arg Phe Thr
                290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
                325                 330                 335

Asp Gly Phe Tyr Ala Met Asp Tyr Trp Gly Gln Gly Thr Leu Val Thr
                340                 345                 350

Val Ser Ser Ala Ser Thr Lys Gly Pro Ser Val Phe Pro Leu Ala Pro
                355                 360                 365

Ser Ser Lys Ser Thr Ser Gly Gly Thr Ala Ala Leu Gly Cys Leu Val
370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
                420                 425                 430

Thr Gln Thr Tyr Ile Cys Asn Val Asn His Lys Pro Ser Asn Thr Lys
                435                 440                 445

Val Asp Lys Lys Val Glu Pro Lys Ser Cys Asp Lys Thr His Thr Cys
450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
                500                 505                 510

Phe Asn Trp Tyr Val Asp Gly Val Glu Val His Asn Ala Lys Thr Lys
                515                 520                 525

Pro Arg Glu Glu Gln Tyr Gly Ser Thr Tyr Arg Val Val Ser Val Leu
530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
                580                 585                 590

Arg Glu Glu Met Thr Lys Asn Gln Val Ser Leu Trp Cys Leu Val Lys
                595                 600                 605

Gly Phe Tyr Pro Ser Asp Ile Ala Val Glu Trp Glu Ser Asn Gly Gln
                610                 615                 620

Pro Glu Asn Asn Tyr Lys Thr Thr Pro Val Leu Asp Ser Asp Gly
625                 630                 635                 640
```

Ser Phe Phe Leu Tyr Ser Lys Leu Thr Val Asp Lys Ser Arg Trp Gln
            645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
            675                 680                 685

<210> SEQ ID NO 61
<211> LENGTH: 678
<212> TYPE: PRT
<213> ORGANISM: Artificial Sequence
<220> FEATURE:
<223> OTHER INFORMATION: Synthetic Construct

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Ala Gly Ala Tyr Ala Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
                245                 250                 255

Ile Lys Asp Thr Tyr Ile His Trp Val Arg Gln Ala Pro Gly Lys Gly
            260                 265                 270

Leu Glu Trp Val Ala Arg Ile Tyr Pro Thr Asn Gly Tyr Thr Arg Tyr
        275                 280                 285

Ala Asp Ser Val Lys Gly Arg Phe Thr Ile Ser Ala Asp Thr Ser Lys
    290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
                325                 330                 335

Tyr Trp Gly Gln Gly Thr Leu Val Thr Val Ser Ser Ala Ser Thr Lys
            340                 345                 350

Gly Pro Ser Val Phe Pro Leu Ala Pro Ser Ser Lys Ser Thr Ser Gly
        355                 360                 365

Gly Thr Ala Ala Leu Gly Cys Leu Val Lys Asp Tyr Phe Pro Glu Pro
    370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Lys Val Glu Pro
        435                 440                 445

Lys Ser Cys Asp Lys Thr His Thr Cys Pro Pro Cys Pro Ala Pro Glu
    450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Gly
        515                 520                 525

Ser Thr Tyr Arg Val Val Ser Val Leu Thr Val Leu His Gln Asp Trp
    530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Glu Glu Met Thr Lys Asn
            580                 585                 590

Gln Val Ser Leu Trp Cys Leu Val Lys Gly Phe Tyr Pro Ser Asp Ile
        595                 600                 605

Ala Val Glu Trp Glu Ser Asn Gly Gln Pro Glu Asn Asn Tyr Lys Thr
    610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro Gly Lys
        675

<210> SEQ ID NO 62
<211> LENGTH: 685
<212> TYPE: PRT
<213> ORGANISM: Artificial Sequence
<220> FEATURE:
<223> OTHER INFORMATION: Synthetic Construct

<400> SEQUENCE: 62

-continued

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Ala Gly Ala Tyr Ala Met Asp Val Trp Gly Gln
        100                 105                 110

Gly Thr Leu Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
            245                 250                 255

Cys Ala Ala Ser Gly Phe Asn Ile Lys Asp Thr Tyr Ile His Trp Val
        260                 265                 270

Arg Gln Ala Pro Gly Lys Gly Leu Glu Trp Val Ala Arg Ile Tyr Pro
    275                 280                 285

Thr Asn Gly Tyr Thr Arg Tyr Ala Asp Ser Val Lys Gly Arg Phe Thr
290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
            325                 330                 335

Asp Gly Phe Tyr Ala Met Asp Tyr Trp Gly Gln Gly Thr Leu Val Thr
        340                 345                 350

Val Ser Ser Ala Ser Thr Lys Gly Pro Ser Val Phe Pro Leu Ala Pro
    355                 360                 365

Ser Ser Lys Ser Thr Ser Gly Gly Thr Ala Ala Leu Gly Cys Leu Val
370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
            405                 410                 415
```

```
Leu Tyr Ser Leu Ser Ser Val Val Thr Val Pro Ser Ser Leu Gly
                420                 425                 430

Thr Gln Thr Tyr Ile Cys Asn Val Asn His Lys Pro Ser Asn Thr Lys
            435                 440                 445

Val Asp Lys Lys Val Glu Pro Lys Ser Cys Asp Lys Thr His Thr Cys
    450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
            500                 505                 510

Phe Asn Trp Tyr Val Asp Gly Val Glu Val His Asn Ala Lys Thr Lys
        515                 520                 525

Pro Arg Glu Glu Gln Tyr Gly Ser Thr Tyr Arg Val Val Ser Val Leu
    530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590

Arg Glu Glu Met Thr Lys Asn Gln Val Ser Leu Trp Cys Leu Val Lys
        595                 600                 605

Gly Phe Tyr Pro Ser Asp Ile Ala Val Glu Trp Glu Ser Asn Gly Gln
    610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
        675                 680                 685

<210> SEQ ID NO 63
<211> LENGTH: 678
<212> TYPE: PRT
<213> ORGANISM: Artificial Sequence
<220> FEATURE:
<223> OTHER INFORMATION: Synthetic Construct

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

-continued

Ser Arg Trp Gly Gly Thr Gly Ala Tyr Ala Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
                245                 250                 255

Ile Lys Asp Thr Tyr Ile His Trp Val Arg Gln Ala Pro Gly Lys Gly
            260                 265                 270

Leu Glu Trp Val Ala Arg Ile Tyr Pro Thr Asn Gly Tyr Thr Arg Tyr
        275                 280                 285

Ala Asp Ser Val Lys Gly Arg Phe Thr Ile Ser Ala Asp Thr Ser Lys
290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
                325                 330                 335

Tyr Trp Gly Gln Gly Thr Leu Val Thr Val Ser Ser Ala Ser Thr Lys
            340                 345                 350

Gly Pro Ser Val Phe Pro Leu Ala Pro Ser Ser Lys Ser Thr Ser Gly
        355                 360                 365

Gly Thr Ala Ala Leu Gly Cys Leu Val Lys Asp Tyr Phe Pro Glu Pro
    370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Lys Val Glu Pro
        435                 440                 445

Lys Ser Cys Asp Lys Thr His Thr Cys Pro Pro Cys Pro Ala Pro Glu
    450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Gly

```
                515                 520                 525
Ser Thr Tyr Arg Val Val Ser Val Leu Thr Val Leu His Gln Asp Trp
530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Glu Glu Met Thr Lys Asn
                580                 585                 590

Gln Val Ser Leu Trp Cys Leu Val Lys Gly Phe Tyr Pro Ser Asp Ile
                595                 600                 605

Ala Val Glu Trp Glu Ser Asn Gly Gln Pro Glu Asn Asn Tyr Lys Thr
610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
                660                 665                 670

Ser Leu Ser Pro Gly Lys
                675

<210> SEQ ID NO 64
<211> LENGTH: 685
<212> TYPE: PRT
<213> ORGANISM: Artificial Sequence
<220> FEATURE:
<223> OTHER INFORMATION: Synthetic Construct

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Ala Tyr Ala Met Asp Val Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

```
              195                 200                 205
Pro Ser Asn Thr Lys Val Asp Lys Lys Val Glu Pro Lys Ser Cys Asp
210                 215                 220

Lys Thr His Thr Gly Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                    245                 250                 255

Cys Ala Ala Ser Gly Phe Asn Ile Lys Asp Thr Tyr Ile His Trp Val
                260                 265                 270

Arg Gln Ala Pro Gly Lys Gly Leu Glu Trp Val Ala Arg Ile Tyr Pro
            275                 280                 285

Thr Asn Gly Tyr Thr Arg Tyr Ala Asp Ser Val Lys Gly Arg Phe Thr
290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
                325                 330                 335

Asp Gly Phe Tyr Ala Met Asp Tyr Trp Gly Gln Gly Thr Leu Val Thr
                340                 345                 350

Val Ser Ser Ala Ser Thr Lys Gly Pro Ser Val Phe Pro Leu Ala Pro
            355                 360                 365

Ser Ser Lys Ser Thr Ser Gly Gly Thr Ala Ala Leu Gly Cys Leu Val
370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
                420                 425                 430

Thr Gln Thr Tyr Ile Cys Asn Val Asn His Lys Pro Ser Asn Thr Lys
            435                 440                 445

Val Asp Lys Lys Val Glu Pro Lys Ser Cys Asp Lys Thr His Thr Cys
450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
                500                 505                 510

Phe Asn Trp Tyr Val Asp Gly Val Glu Val His Asn Ala Lys Thr Lys
            515                 520                 525

Pro Arg Glu Glu Gln Tyr Gly Ser Thr Tyr Arg Val Val Ser Val Leu
530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
                580                 585                 590

Arg Glu Glu Met Thr Lys Asn Gln Val Ser Leu Trp Cys Leu Val Lys
            595                 600                 605

Gly Phe Tyr Pro Ser Asp Ile Ala Val Glu Trp Glu Ser Asn Gly Gln
610                 615                 620
```

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
            645                 650                 655

Gln Gly Asn Val Phe Ser Cys Ser Val Met His Glu Ala Leu His Asn
        660                 665                 670

His Tyr Thr Gln Lys Ser Leu Ser Leu Ser Pro Gly Lys
        675                 680                 685

<210> SEQ ID NO 65
<211> LENGTH: 678
<212> TYPE: PRT
<213> ORGANISM: Artificial Sequence
<220> FEATURE:
<223> OTHER INFORMATION: Synthetic Construct

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
                245                 250                 255

Ile Lys Asp Thr Tyr Ile His Trp Val Arg Gln Ala Pro Gly Lys Gly
            260                 265                 270

Leu Glu Trp Val Ala Arg Ile Tyr Pro Thr Asn Gly Tyr Thr Arg Tyr
        275                 280                 285

Ala Asp Ser Val Lys Gly Arg Phe Thr Ile Ser Ala Asp Thr Ser Lys
    290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
            325                 330                 335

Tyr Trp Gly Gln Gly Thr Leu Val Thr Val Ser Ser Ala Ser Thr Lys
        340                 345                 350

Gly Pro Ser Val Phe Pro Leu Ala Pro Ser Ser Lys Ser Thr Ser Gly
    355                 360                 365

Gly Thr Ala Ala Leu Gly Cys Leu Val Lys Asp Tyr Phe Pro Glu Pro
370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Lys Val Glu Pro
        435                 440                 445

Lys Ser Cys Asp Lys Thr His Thr Cys Pro Pro Cys Pro Ala Pro Glu
    450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Gly
        515                 520                 525

Ser Thr Tyr Arg Val Val Ser Val Leu Thr Val Leu His Gln Asp Trp
    530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Glu Glu Met Thr Lys Asn
            580                 585                 590

Gln Val Ser Leu Trp Cys Leu Val Lys Gly Phe Tyr Pro Ser Asp Ile
        595                 600                 605

Ala Val Glu Trp Glu Ser Asn Gly Gln Pro Glu Asn Asn Tyr Lys Thr
    610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro Gly Lys
        675

<210> SEQ ID NO 66
<211> LENGTH: 685
<212> TYPE: PRT
<213> ORGANISM: Artificial Sequence
<220> FEATURE:

<223> OTHER INFORMATION: Synthetic Construct

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
            260                 265                 270

Arg Gln Ala Pro Gly Lys Gly Leu Glu Trp Val Ala Arg Ile Tyr Pro
        275                 280                 285

Thr Asn Gly Tyr Thr Arg Tyr Ala Asp Ser Val Lys Gly Arg Phe Thr
    290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
                325                 330                 335

Asp Gly Phe Tyr Ala Met Asp Tyr Trp Gly Gln Gly Thr Leu Val Thr
            340                 345                 350

Val Ser Ser Ala Ser Thr Lys Gly Pro Ser Val Phe Pro Leu Ala Pro
        355                 360                 365

Ser Ser Lys Ser Thr Ser Gly Gly Thr Ala Ala Leu Gly Cys Leu Val
    370                 375                 380

Lys Asp Tyr Phe Pro Glu Pro Val Thr Val Ser Trp Asn Ser Gly Ala
385                 390                 395                 400

-continued

Leu Thr Ser Gly Val His Thr Phe Pro Ala Val Leu Gln Ser Ser Gly
            405                 410                 415

Leu Tyr Ser Leu Ser Ser Val Val Thr Val Pro Ser Ser Ser Leu Gly
        420                 425                 430

Thr Gln Thr Tyr Ile Cys Asn Val Asn His Lys Pro Ser Asn Thr Lys
    435                 440                 445

Val Asp Lys Lys Val Glu Pro Lys Ser Cys Asp Lys Thr His Thr Cys
450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
            485                 490                 495

Val Thr Cys Val Val Val Asp Val Ser His Glu Asp Pro Glu Val Lys
        500                 505                 510

Phe Asn Trp Tyr Val Asp Gly Val Glu Val His Asn Ala Lys Thr Lys
    515                 520                 525

Pro Arg Glu Glu Gln Tyr Gly Ser Thr Tyr Arg Val Val Ser Val Leu
530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
            565                 570                 575

Ala Lys Gly Gln Pro Arg Glu Pro Gln Val Tyr Thr Leu Pro Pro Ser
        580                 585                 590

Arg Glu Glu Met Thr Lys Asn Gln Val Ser Leu Trp Cys Leu Val Lys
    595                 600                 605

Gly Phe Tyr Pro Ser Asp Ile Ala Val Glu Trp Glu Ser Asn Gly Gln
610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
            645                 650                 655

Gln Gly Asn Val Phe Ser Cys Ser Val Met His Glu Ala Leu His Asn
        660                 665                 670

His Tyr Thr Gln Lys Ser Leu Ser Leu Ser Pro Gly Lys
    675                 680                 685

<210> SEQ ID NO 67
<211> LENGTH: 678
<212> TYPE: PRT
<213> ORGANISM: Artificial Sequence
<220> FEATURE:
<223> OTHER INFORMATION: Synthetic Construct

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

```
Leu Gln Met Asn Ser Leu Arg Ala Glu Asp Thr Ala Val Tyr Tyr Cys
                    85                  90                  95

Ser Arg Trp Gly Gly Thr Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
                245                 250                 255

Ile Lys Asp Thr Tyr Ile His Trp Val Arg Gln Ala Pro Gly Lys Gly
            260                 265                 270

Leu Glu Trp Val Ala Arg Ile Tyr Pro Thr Asn Gly Tyr Thr Arg Tyr
        275                 280                 285

Ala Asp Ser Val Lys Gly Arg Phe Thr Ile Ser Ala Asp Thr Ser Lys
    290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
                325                 330                 335

Tyr Trp Gly Gln Gly Thr Leu Val Thr Val Ser Ser Ala Ser Thr Lys
            340                 345                 350

Gly Pro Ser Val Phe Pro Leu Ala Pro Ser Ser Lys Ser Thr Ser Gly
        355                 360                 365

Gly Thr Ala Ala Leu Gly Cys Leu Val Lys Asp Tyr Phe Pro Glu Pro
    370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Lys Val Glu Pro
        435                 440                 445

Lys Ser Cys Asp Lys Thr His Thr Cys Pro Pro Cys Pro Ala Pro Glu
    450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
```

```
            500                 505                 510
Val Glu Val His Asn Ala Lys Thr Lys Pro Arg Glu Glu Gln Tyr Gly
        515                 520                 525

Ser Thr Tyr Arg Val Val Ser Val Leu Thr Val Leu His Gln Asp Trp
    530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Glu Glu Met Thr Lys Asn
            580                 585                 590

Gln Val Ser Leu Trp Cys Leu Val Lys Gly Phe Tyr Pro Ser Asp Ile
        595                 600                 605

Ala Val Glu Trp Glu Ser Asn Gly Gln Pro Glu Asn Asn Tyr Lys Thr
    610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro Gly Lys
            675

<210> SEQ ID NO 68
<211> LENGTH: 685
<212> TYPE: PRT
<213> ORGANISM: Artificial Sequence
<220> FEATURE:
<223> OTHER INFORMATION: Synthetic Construct

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
            180                 185                 190
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Gly Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
            260                 265                 270

Arg Gln Ala Pro Gly Lys Gly Leu Glu Trp Val Ala Arg Ile Tyr Pro
        275                 280                 285

Thr Asn Gly Tyr Thr Arg Tyr Ala Asp Ser Val Lys Gly Arg Phe Thr
    290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
                325                 330                 335

Asp Gly Phe Tyr Ala Met Asp Tyr Trp Gly Gln Gly Thr Leu Val Thr
            340                 345                 350

Val Ser Ser Ala Ser Thr Lys Gly Pro Ser Val Phe Pro Leu Ala Pro
        355                 360                 365

Ser Ser Lys Ser Thr Ser Gly Gly Thr Ala Ala Leu Gly Cys Leu Val
    370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
            420                 425                 430

Thr Gln Thr Tyr Ile Cys Asn Val Asn His Lys Pro Ser Asn Thr Lys
        435                 440                 445

Val Asp Lys Lys Val Glu Pro Lys Ser Cys Asp Lys Thr His Thr Cys
    450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
            500                 505                 510

Phe Asn Trp Tyr Val Asp Gly Val Glu Val His Asn Ala Lys Thr Lys
        515                 520                 525

Pro Arg Glu Glu Gln Tyr Gly Ser Thr Tyr Arg Val Val Ser Val Leu
    530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590

Arg Glu Glu Met Thr Lys Asn Gln Val Ser Leu Trp Cys Leu Val Lys
        595                 600                 605
```

```
Gly Phe Tyr Pro Ser Asp Ile Ala Val Glu Trp Glu Ser Asn Gly Gln
        610                 615                 620
Pro Glu Asn Asn Tyr Lys Thr Thr Pro Pro Val Leu Asp Ser Asp Gly
625                 630                 635                 640
Ser Phe Phe Leu Tyr Ser Lys Leu Thr Val Asp Lys Ser Arg Trp Gln
                645                 650                 655
Gln Gly Asn Val Phe Ser Cys Ser Val Met His Glu Ala Leu His Asn
            660                 665                 670
His Tyr Thr Gln Lys Ser Leu Ser Leu Ser Pro Gly Lys
        675                 680                 685

<210> SEQ ID NO 69
<211> LENGTH: 678
<212> TYPE: PRT
<213> ORGANISM: Artificial Sequence
<220> FEATURE:
<223> OTHER INFORMATION: Synthetic Construct

<400> SEQUENCE: 69

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Glu Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Thr Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Glu Val Gln Leu Val Glu Ser Gly Gly Gly Leu Val
225                 230                 235                 240
Gln Pro Gly Gly Ser Leu Arg Leu Ser Cys Ala Ala Ser Gly Phe Asn
                245                 250                 255
Ile Lys Asp Thr Tyr Ile His Trp Val Arg Gln Ala Pro Gly Lys Gly
            260                 265                 270
Leu Glu Trp Val Ala Arg Ile Tyr Pro Thr Asn Gly Tyr Thr Arg Tyr
        275                 280                 285
```

Ala Asp Ser Val Lys Gly Arg Phe Thr Ile Ser Ala Asp Thr Ser Lys
290                 295                 300
Asn Thr Ala Tyr Leu Gln Met Asn Ser Leu Arg Ala Glu Asp Thr Ala
305                 310                 315                 320
Val Tyr Tyr Cys Ser Arg Trp Gly Gly Asp Gly Phe Tyr Ala Met Asp
            325                 330                 335
Tyr Trp Gly Gln Gly Thr Leu Val Thr Val Ser Ser Ala Ser Thr Lys
        340                 345                 350
Gly Pro Ser Val Phe Pro Leu Ala Pro Ser Ser Lys Ser Thr Ser Gly
    355                 360                 365
Gly Thr Ala Ala Leu Gly Cys Leu Val Lys Asp Tyr Phe Pro Glu Pro
370                 375                 380
Val Thr Val Ser Trp Asn Ser Gly Ala Leu Thr Ser Gly Val His Thr
385                 390                 395                 400
Phe Pro Ala Val Leu Gln Ser Ser Gly Leu Tyr Ser Leu Ser Ser Val
            405                 410                 415
Val Thr Val Pro Ser Ser Ser Leu Gly Thr Gln Thr Tyr Ile Cys Asn
        420                 425                 430
Val Asn His Lys Pro Ser Asn Thr Lys Val Asp Lys Val Glu Pro
    435                 440                 445
Lys Ser Cys Asp Lys Thr His Thr Cys Pro Pro Cys Pro Ala Pro Glu
450                 455                 460
Leu Leu Gly Gly Pro Ser Val Phe Leu Phe Pro Pro Lys Pro Lys Asp
465                 470                 475                 480
Thr Leu Met Ile Ser Arg Thr Pro Glu Val Thr Cys Val Val Val Asp
            485                 490                 495
Val Ser His Glu Asp Pro Glu Val Lys Phe Asn Trp Tyr Val Asp Gly
        500                 505                 510
Val Glu Val His Asn Ala Lys Thr Lys Pro Arg Glu Glu Gln Tyr Gly
    515                 520                 525
Ser Thr Tyr Arg Val Val Ser Val Leu Thr Val Leu His Gln Asp Trp
530                 535                 540
Leu Asn Gly Lys Glu Tyr Lys Cys Lys Val Ser Asn Lys Ala Leu Pro
545                 550                 555                 560
Ala Pro Ile Glu Lys Thr Ile Ser Lys Ala Lys Gly Gln Pro Arg Glu
            565                 570                 575
Pro Gln Val Tyr Thr Leu Pro Pro Ser Arg Glu Glu Met Thr Lys Asn
        580                 585                 590
Gln Val Ser Leu Trp Cys Leu Val Lys Gly Phe Tyr Pro Ser Asp Ile
    595                 600                 605
Ala Val Glu Trp Glu Ser Asn Gly Gln Pro Glu Asn Asn Tyr Lys Thr
610                 615                 620
Thr Pro Pro Val Leu Asp Ser Asp Gly Ser Phe Phe Leu Tyr Ser Lys
625                 630                 635                 640
Leu Thr Val Asp Lys Ser Arg Trp Gln Gln Gly Asn Val Phe Ser Cys
            645                 650                 655
Ser Val Met His Glu Ala Leu His Asn His Tyr Thr Gln Lys Ser Leu
        660                 665                 670
Ser Leu Ser Pro Gly Lys
        675

<210> SEQ ID NO 70
<211> LENGTH: 685

```
<212> TYPE: PRT
<213> ORGANISM: Artificial Sequence
<220> FEATURE:
<223> OTHER INFORMATION: Synthetic Construct

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
            260                 265                 270

Arg Gln Ala Pro Gly Lys Gly Leu Glu Trp Val Ala Arg Ile Tyr Pro
        275                 280                 285

Thr Asn Gly Tyr Thr Arg Tyr Ala Asp Ser Val Lys Gly Arg Phe Thr
    290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
                325                 330                 335

Asp Gly Phe Tyr Ala Met Asp Tyr Trp Gly Gln Gly Thr Leu Val Thr
            340                 345                 350

Val Ser Ser Ala Ser Thr Lys Gly Pro Ser Val Phe Pro Leu Ala Pro
        355                 360                 365

Ser Ser Lys Ser Thr Ser Gly Gly Thr Ala Ala Leu Gly Cys Leu Val
    370                 375                 380
```

```
Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
            405                 410                 415

Leu Tyr Ser Leu Ser Ser Val Val Thr Val Pro Ser Ser Ser Leu Gly
            420                 425                 430

Thr Gln Thr Tyr Ile Cys Asn Val Asn His Lys Pro Ser Asn Thr Lys
        435                 440                 445

Val Asp Lys Lys Val Glu Pro Lys Ser Cys Asp Lys Thr His Thr Cys
    450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
            500                 505                 510

Phe Asn Trp Tyr Val Asp Gly Val Glu Val His Asn Ala Lys Thr Lys
        515                 520                 525

Pro Arg Glu Glu Gln Tyr Gly Ser Thr Tyr Arg Val Val Ser Val Leu
    530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590

Arg Glu Glu Met Thr Lys Asn Gln Val Ser Leu Trp Cys Leu Val Lys
        595                 600                 605

Gly Phe Tyr Pro Ser Asp Ile Ala Val Glu Trp Glu Ser Asn Gly Gln
    610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
        675                 680                 685

<210> SEQ ID NO 71
<211> LENGTH: 678
<212> TYPE: PRT
<213> ORGANISM: Artificial Sequence
<220> FEATURE:
<223> OTHER INFORMATION: Synthetic Construct

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60
```

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                   90                  95

Ser Arg Trp Gly Gly Thr Gly Phe Tyr Ala Met Asp Val Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
            245                 250                 255

Ile Lys Asp Thr Tyr Ile His Trp Val Arg Gln Ala Pro Gly Lys Gly
            260                 265                 270

Leu Glu Trp Val Ala Arg Ile Tyr Pro Thr Asn Gly Tyr Thr Arg Tyr
            275                 280                 285

Ala Asp Ser Val Lys Gly Arg Phe Thr Ile Ser Ala Asp Thr Ser Lys
            290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
                325                 330                 335

Tyr Trp Gly Gln Gly Thr Leu Val Thr Val Ser Ser Ala Ser Thr Lys
            340                 345                 350

Gly Pro Ser Val Phe Pro Leu Ala Pro Ser Ser Lys Ser Thr Ser Gly
            355                 360                 365

Gly Thr Ala Ala Leu Gly Cys Leu Val Lys Asp Tyr Phe Pro Glu Pro
            370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
            405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Lys Val Glu Pro
            435                 440                 445

Lys Ser Cys Asp Lys Thr His Thr Cys Pro Pro Cys Pro Ala Pro Glu
            450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
```

```
                485                 490                 495
Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Gly
            515                 520                 525

Ser Thr Tyr Arg Val Val Ser Val Leu Thr Val Leu His Gln Asp Trp
            530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Glu Glu Met Thr Lys Asn
            580                 585                 590

Gln Val Ser Leu Trp Cys Leu Val Lys Gly Phe Tyr Pro Ser Asp Ile
            595                 600                 605

Ala Val Glu Trp Glu Ser Asn Gly Gln Pro Glu Asn Asn Tyr Lys Thr
            610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro Gly Lys
            675

<210> SEQ ID NO 72
<211> LENGTH: 685
<212> TYPE: PRT
<213> ORGANISM: Artificial Sequence
<220> FEATURE:
<223> OTHER INFORMATION: Synthetic Construct

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

```
                    165                 170                 175
Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Val Glu Pro Lys Ser Cys Asp
        210                 215                 220

Lys Thr His Thr Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
                260                 265                 270

Arg Gln Ala Pro Gly Lys Gly Leu Glu Trp Val Ala Arg Ile Tyr Pro
            275                 280                 285

Thr Asn Gly Tyr Thr Arg Tyr Ala Asp Ser Val Lys Gly Arg Phe Thr
        290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
                325                 330                 335

Asp Gly Phe Tyr Ala Met Asp Tyr Trp Gly Gln Gly Thr Leu Val Thr
            340                 345                 350

Val Ser Ser Ala Ser Thr Lys Gly Pro Ser Val Phe Pro Leu Ala Pro
            355                 360                 365

Ser Ser Lys Ser Thr Ser Gly Gly Thr Ala Ala Leu Gly Cys Leu Val
        370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
            420                 425                 430

Thr Gln Thr Tyr Ile Cys Asn Val Asn His Lys Pro Ser Asn Thr Lys
        435                 440                 445

Val Asp Lys Lys Val Glu Pro Lys Ser Cys Asp Lys Thr His Thr Cys
450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
            500                 505                 510

Phe Asn Trp Tyr Val Asp Gly Val Glu Val His Asn Ala Lys Thr Lys
        515                 520                 525

Pro Arg Glu Glu Gln Tyr Gly Ser Thr Tyr Arg Val Val Ser Val Leu
        530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590
```

```
Arg Glu Glu Met Thr Lys Asn Gln Val Ser Leu Trp Cys Leu Val Lys
            595                 600                 605

Gly Phe Tyr Pro Ser Asp Ile Ala Val Glu Trp Glu Ser Asn Gly Gln
        610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
            675                 680                 685

<210> SEQ ID NO 73
<211> LENGTH: 678
<212> TYPE: PRT
<213> ORGANISM: Artificial Sequence
<220> FEATURE:
<223> OTHER INFORMATION: Synthetic Construct

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
                245                 250                 255

Ile Lys Asp Thr Tyr Ile His Trp Val Arg Gln Ala Pro Gly Lys Gly
            260                 265                 270
```

```
Leu Glu Trp Val Ala Arg Ile Tyr Pro Thr Asn Gly Tyr Thr Arg Tyr
            275                 280                 285

Ala Asp Ser Val Lys Gly Arg Phe Thr Ile Ser Ala Asp Thr Ser Lys
290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
                325                 330                 335

Tyr Trp Gly Gln Gly Thr Leu Val Thr Val Ser Ser Ala Ser Thr Lys
                340                 345                 350

Gly Pro Ser Val Phe Pro Leu Ala Pro Ser Ser Lys Ser Thr Ser Gly
            355                 360                 365

Gly Thr Ala Ala Leu Gly Cys Leu Val Lys Asp Tyr Phe Pro Glu Pro
            370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Lys Val Glu Pro
            435                 440                 445

Lys Ser Cys Asp Lys Thr His Thr Cys Pro Pro Cys Pro Ala Pro Glu
450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Gly
            515                 520                 525

Ser Thr Tyr Arg Val Val Ser Val Leu Thr Val Leu His Gln Asp Trp
            530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Glu Glu Met Thr Lys Asn
                580                 585                 590

Gln Val Ser Leu Trp Cys Leu Val Lys Gly Phe Tyr Pro Ser Asp Ile
            595                 600                 605

Ala Val Glu Trp Glu Ser Asn Gly Gln Pro Glu Asn Asn Tyr Lys Thr
            610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
                660                 665                 670

Ser Leu Ser Pro Gly Lys
            675
```

<210> SEQ ID NO 74
<211> LENGTH: 685
<212> TYPE: PRT
<213> ORGANISM: Artificial Sequence
<220> FEATURE:
<223> OTHER INFORMATION: Synthetic Construct

<400> SEQUENCE: 74

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
            260                 265                 270

Arg Gln Ala Pro Gly Lys Gly Leu Glu Trp Val Ala Arg Ile Tyr Pro
        275                 280                 285

Thr Asn Gly Tyr Thr Arg Tyr Ala Asp Ser Val Lys Gly Arg Phe Thr
    290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
                325                 330                 335

Asp Gly Phe Tyr Ala Met Asp Tyr Trp Gly Gln Gly Thr Leu Val Thr
            340                 345                 350

Val Ser Ser Ala Ser Thr Lys Gly Pro Ser Val Phe Pro Leu Ala Pro
        355                 360                 365
```

-continued

Ser Ser Lys Ser Thr Ser Gly Gly Thr Ala Ala Leu Gly Cys Leu Val
    370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
            405                 410                 415

Leu Tyr Ser Leu Ser Ser Val Val Thr Val Pro Ser Ser Ser Leu Gly
        420                 425                 430

Thr Gln Thr Tyr Ile Cys Asn Val Asn His Lys Pro Ser Asn Thr Lys
    435                 440                 445

Val Asp Lys Lys Val Glu Pro Lys Ser Cys Asp Lys Thr His Thr Cys
450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
            485                 490                 495

Val Thr Cys Val Val Val Asp Val Ser His Glu Asp Pro Glu Val Lys
        500                 505                 510

Phe Asn Trp Tyr Val Asp Gly Val Glu Val His Asn Ala Lys Thr Lys
    515                 520                 525

Pro Arg Glu Glu Gln Tyr Gly Ser Thr Tyr Arg Val Val Ser Val Leu
530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
            565                 570                 575

Ala Lys Gly Gln Pro Arg Glu Pro Gln Val Tyr Thr Leu Pro Pro Ser
        580                 585                 590

Arg Glu Glu Met Thr Lys Asn Gln Val Ser Leu Trp Cys Leu Val Lys
    595                 600                 605

Gly Phe Tyr Pro Ser Asp Ile Ala Val Glu Trp Glu Ser Asn Gly Gln
610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
            645                 650                 655

Gln Gly Asn Val Phe Ser Cys Ser Val Met His Glu Ala Leu His Asn
        660                 665                 670

His Tyr Thr Gln Lys Ser Leu Ser Leu Ser Pro Gly Lys
    675                 680                 685

<210> SEQ ID NO 75
<211> LENGTH: 678
<212> TYPE: PRT
<213> ORGANISM: Artificial Sequence
<220> FEATURE:
<223> OTHER INFORMATION: Synthetic Construct

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Thr Gly Phe Tyr Ala Met Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
                245                 250                 255

Ile Lys Asp Thr Tyr Ile His Trp Val Arg Gln Ala Pro Gly Lys Gly
            260                 265                 270

Leu Glu Trp Val Ala Arg Ile Tyr Pro Thr Asn Gly Tyr Thr Arg Tyr
        275                 280                 285

Ala Asp Ser Val Lys Gly Arg Phe Thr Ile Ser Ala Asp Thr Ser Lys
290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
                325                 330                 335

Tyr Trp Gly Gln Gly Thr Leu Val Thr Val Ser Ser Ala Ser Thr Lys
            340                 345                 350

Gly Pro Ser Val Phe Pro Leu Ala Pro Ser Ser Lys Ser Thr Ser Gly
        355                 360                 365

Gly Thr Ala Ala Leu Gly Cys Leu Val Lys Asp Tyr Phe Pro Glu Pro
370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Lys Val Glu Pro
        435                 440                 445

Lys Ser Cys Asp Lys Thr His Thr Cys Pro Pro Cys Pro Ala Pro Glu
450                 455                 460

Leu Leu Gly Gly Pro Ser Val Phe Leu Phe Pro Pro Lys Pro Lys Asp

```
              465                 470                 475                 480
         Thr Leu Met Ile Ser Arg Thr Pro Glu Val Thr Cys Val Val Asp
                         485                 490                 495

Val Ser His Glu Asp Pro Glu Val Lys Phe Asn Trp Tyr Val Asp Gly
                     500                 505                 510

Val Glu Val His Asn Ala Lys Thr Lys Pro Arg Glu Glu Gln Tyr Gly
                     515                 520                 525

Ser Thr Tyr Arg Val Val Ser Val Leu Thr Val Leu His Gln Asp Trp
                 530                 535                 540

Leu Asn Gly Lys Glu Tyr Lys Cys Lys Val Ser Asn Lys Ala Leu Pro
         545                 550                 555                 560

Ala Pro Ile Glu Lys Thr Ile Ser Lys Ala Lys Gly Gln Pro Arg Glu
                         565                 570                 575

Pro Gln Val Tyr Thr Leu Pro Pro Ser Arg Glu Glu Met Thr Lys Asn
                     580                 585                 590

Gln Val Ser Leu Trp Cys Leu Val Lys Gly Phe Tyr Pro Ser Asp Ile
                     595                 600                 605

Ala Val Glu Trp Glu Ser Asn Gly Gln Pro Glu Asn Asn Tyr Lys Thr
                     610                 615                 620

Thr Pro Pro Val Leu Asp Ser Asp Gly Ser Phe Phe Leu Tyr Ser Lys
         625                 630                 635                 640

Leu Thr Val Asp Lys Ser Arg Trp Gln Gln Gly Asn Val Phe Ser Cys
                         645                 650                 655

Ser Val Met His Glu Ala Leu His Asn His Tyr Thr Gln Lys Ser Leu
                     660                 665                 670

Ser Leu Ser Pro Gly Lys
                     675

<210> SEQ ID NO 76
<211> LENGTH: 685
<212> TYPE: PRT
<213> ORGANISM: Artificial Sequence
<220> FEATURE:
<223> OTHER INFORMATION: Synthetic Construct

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

-continued

```
            145                 150                 155                 160
Trp Asn Ser Gly Ala Leu Thr Ser Gly Val His Thr Phe Pro Ala Val
                    165                 170                 175
Leu Gln Ser Ser Gly Leu Tyr Ser Leu Ser Val Val Thr Val Pro
                    180                 185                 190
Ser Ser Ser Leu Gly Thr Gln Thr Tyr Ile Cys Asn Val Asn His Lys
                    195                 200                 205
Pro Ser Asn Thr Lys Val Asp Lys Lys Val Glu Pro Lys Ser Cys Asp
        210                 215                 220
Lys Thr His Thr Gly Gly Gly Ser Gly Gly Glu Val Gln Leu Val
225                 230                 235                 240
Glu Ser Gly Gly Gly Leu Val Gln Pro Gly Gly Ser Leu Arg Leu Ser
                    245                 250                 255
Cys Ala Ala Ser Gly Phe Asn Ile Lys Asp Thr Tyr Ile His Trp Val
                    260                 265                 270
Arg Gln Ala Pro Gly Lys Gly Leu Glu Trp Val Ala Arg Ile Tyr Pro
                    275                 280                 285
Thr Asn Gly Tyr Thr Arg Tyr Ala Asp Ser Val Lys Gly Arg Phe Thr
        290                 295                 300
Ile Ser Ala Asp Thr Ser Lys Asn Thr Ala Tyr Leu Gln Met Asn Ser
305                 310                 315                 320
Leu Arg Ala Glu Asp Thr Ala Val Tyr Tyr Cys Ser Arg Trp Gly Gly
                    325                 330                 335
Asp Gly Phe Tyr Ala Met Asp Tyr Trp Gly Gln Gly Thr Leu Val Thr
                    340                 345                 350
Val Ser Ser Ala Ser Thr Lys Gly Pro Ser Val Phe Pro Leu Ala Pro
                    355                 360                 365
Ser Ser Lys Ser Thr Ser Gly Gly Thr Ala Ala Leu Gly Cys Leu Val
        370                 375                 380
Lys Asp Tyr Phe Pro Glu Pro Val Thr Val Ser Trp Asn Ser Gly Ala
385                 390                 395                 400
Leu Thr Ser Gly Val His Thr Phe Pro Ala Val Leu Gln Ser Ser Gly
                    405                 410                 415
Leu Tyr Ser Leu Ser Ser Val Val Thr Val Pro Ser Ser Ser Leu Gly
                    420                 425                 430
Thr Gln Thr Tyr Ile Cys Asn Val Asn His Lys Pro Ser Asn Thr Lys
                    435                 440                 445
Val Asp Lys Lys Val Glu Pro Lys Ser Cys Asp Lys Thr His Thr Cys
        450                 455                 460
Pro Pro Cys Pro Ala Pro Glu Leu Leu Gly Gly Pro Ser Val Phe Leu
465                 470                 475                 480
Phe Pro Pro Lys Pro Lys Asp Thr Leu Met Ile Ser Arg Thr Pro Glu
                    485                 490                 495
Val Thr Cys Val Val Val Asp Val Ser His Glu Asp Pro Glu Val Lys
                    500                 505                 510
Phe Asn Trp Tyr Val Asp Gly Val Glu Val His Asn Ala Lys Thr Lys
                    515                 520                 525
Pro Arg Glu Glu Gln Tyr Gly Ser Thr Tyr Arg Val Val Ser Val Leu
        530                 535                 540
Thr Val Leu His Gln Asp Trp Leu Asn Gly Lys Glu Tyr Lys Cys Lys
545                 550                 555                 560
Val Ser Asn Lys Ala Leu Pro Ala Pro Ile Glu Lys Thr Ile Ser Lys
                    565                 570                 575
```

Ala Lys Gly Gln Pro Arg Glu Pro Gln Val Tyr Thr Leu Pro Pro Ser
            580                 585                 590

Arg Glu Glu Met Thr Lys Asn Gln Val Ser Leu Trp Cys Leu Val Lys
            595                 600                 605

Gly Phe Tyr Pro Ser Asp Ile Ala Val Glu Trp Glu Ser Asn Gly Gln
            610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
            675                 680                 685

<210> SEQ ID NO 77
<211> LENGTH: 678
<212> TYPE: PRT
<213> ORGANISM: Artificial Sequence
<220> FEATURE:
<223> OTHER INFORMATION: Synthetic Construct

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Ala Tyr Ala Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
                245                 250                 255

```
Ile Lys Asp Thr Tyr Ile His Trp Val Arg Gln Ala Pro Gly Lys Gly
            260                 265                 270

Leu Glu Trp Val Ala Arg Ile Tyr Pro Thr Asn Gly Tyr Thr Arg Tyr
        275                 280                 285

Ala Asp Ser Val Lys Gly Arg Phe Thr Ile Ser Ala Asp Thr Ser Lys
    290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Asp Gly Phe Tyr Ala Met Asp
                325                 330                 335

Tyr Trp Gly Gln Gly Thr Leu Val Thr Val Ser Ser Ala Ser Thr Lys
        340                 345                 350

Gly Pro Ser Val Phe Pro Leu Ala Pro Ser Ser Lys Ser Thr Ser Gly
    355                 360                 365

Gly Thr Ala Ala Leu Gly Cys Leu Val Lys Asp Tyr Phe Pro Glu Pro
370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
            405                 410                 415

Val Thr Val Pro Ser Ser Ser Leu Gly Thr Gln Thr Tyr Ile Cys Asn
        420                 425                 430

Val Asn His Lys Pro Ser Asn Thr Lys Val Asp Lys Lys Val Glu Pro
    435                 440                 445

Lys Ser Cys Asp Lys Thr His Thr Cys Pro Pro Cys Pro Ala Pro Glu
    450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
            485                 490                 495

Val Ser His Glu Asp Pro Glu Val Lys Phe Asn Trp Tyr Val Asp Gly
        500                 505                 510

Val Glu Val His Asn Ala Lys Thr Lys Pro Arg Glu Glu Gln Tyr Gly
    515                 520                 525

Ser Thr Tyr Arg Val Val Ser Val Leu Thr Val Leu His Gln Asp Trp
530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
            565                 570                 575

Pro Gln Val Tyr Thr Leu Pro Pro Ser Arg Glu Glu Met Thr Lys Asn
        580                 585                 590

Gln Val Ser Leu Trp Cys Leu Val Lys Gly Phe Tyr Pro Ser Asp Ile
    595                 600                 605

Ala Val Glu Trp Glu Ser Asn Gly Gln Pro Glu Asn Asn Tyr Lys Thr
    610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
            645                 650                 655

Ser Val Met His Glu Ala Leu His Asn His Tyr Thr Gln Lys Ser Leu
        660                 665                 670
```

Ser Leu Ser Pro Gly Lys
        675

<210> SEQ ID NO 78
<211> LENGTH: 685
<212> TYPE: PRT
<213> ORGANISM: Artificial Sequence
<220> FEATURE:
<223> OTHER INFORMATION: Synthetic Construct

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Ala Tyr Ala Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
            260                 265                 270

Arg Gln Ala Pro Gly Lys Gly Leu Glu Trp Val Ala Arg Ile Tyr Pro
        275                 280                 285

Thr Asn Gly Tyr Thr Arg Tyr Ala Asp Ser Val Lys Gly Arg Phe Thr
    290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
                325                 330                 335

Asp Gly Phe Tyr Ala Met Asp Tyr Trp Gly Gln Gly Thr Leu Val Thr
            340                 345                 350

```
Val Ser Ser Ala Ser Thr Lys Gly Pro Ser Val Phe Pro Leu Ala Pro
            355                 360                 365

Ser Ser Lys Ser Thr Ser Gly Gly Thr Ala Ala Leu Gly Cys Leu Val
    370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
                420                 425                 430

Thr Gln Thr Tyr Ile Cys Asn Val Asn His Lys Pro Ser Asn Thr Lys
                435                 440                 445

Val Asp Lys Lys Val Glu Pro Lys Ser Cys Asp Lys Thr His Thr Cys
450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
                500                 505                 510

Phe Asn Trp Tyr Val Asp Gly Val Glu Val His Asn Ala Lys Thr Lys
            515                 520                 525

Pro Arg Glu Glu Gln Tyr Gly Ser Thr Tyr Arg Val Val Ser Val Leu
            530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
                580                 585                 590

Arg Glu Glu Met Thr Lys Asn Gln Val Ser Leu Trp Cys Leu Val Lys
            595                 600                 605

Gly Phe Tyr Pro Ser Asp Ile Ala Val Glu Trp Glu Ser Asn Gly Gln
610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
            675                 680                 685

<210> SEQ ID NO 79
<211> LENGTH: 678
<212> TYPE: PRT
<213> ORGANISM: Artificial Sequence
<220> FEATURE:
<223> OTHER INFORMATION: Synthetic Construct

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

-continued

Tyr Ile His Trp Val Arg Gln Ala Pro Gly Lys Gly Leu Glu Trp Val
         35                  40                  45
Ala Arg Ile Tyr Pro Thr Glu Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Ala Gly Ala Tyr Ala Met Asp Val Trp Gly Gln
             100                 105                 110
Gly Thr Leu Val Thr Val Ser Ser Ala Ser Thr Lys Gly Pro Ser Val
             115                 120                 125
Phe Pro Leu Ala Pro Ser Ser Lys Ser Thr Ser Gly Gly Thr Ala Ala
         130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                 165                 170                 175
Leu Gln Ser Ser Gly Leu Tyr Ser Leu Ser Ser Val Val Thr Val Pro
             180                 185                 190
Ser Ser Ser Leu Gly Thr Gln Thr Tyr Ile Cys Asn Val Asn His Lys
         195                 200                 205
Pro Ser Asn Thr Lys Val Asp Lys Lys Val Glu Pro Lys Ser Cys Asp
         210                 215                 220
Lys Thr His Thr Glu Val Gln Leu Val Glu Ser Gly Gly Gly Leu Val
225                 230                 235                 240
Gln Pro Gly Gly Ser Leu Arg Leu Ser Cys Ala Ala Ser Gly Phe Asn
                 245                 250                 255
Ile Lys Asp Thr Tyr Ile His Trp Val Arg Gln Ala Pro Gly Lys Gly
             260                 265                 270
Leu Glu Trp Val Ala Arg Ile Tyr Pro Thr Asn Gly Tyr Thr Arg Tyr
         275                 280                 285
Ala Asp Ser Val Lys Gly Arg Phe Thr Ile Ser Ala Asp Thr Ser Lys
290                 295                 300
Asn Thr Ala Tyr Leu Gln Met Asn Ser Leu Arg Ala Glu Asp Thr Ala
305                 310                 315                 320
Val Tyr Tyr Cys Ser Arg Trp Gly Gly Asp Gly Phe Tyr Ala Met Asp
                 325                 330                 335
Tyr Trp Gly Gln Gly Thr Leu Val Thr Val Ser Ser Ala Ser Thr Lys
             340                 345                 350
Gly Pro Ser Val Phe Pro Leu Ala Pro Ser Ser Lys Ser Thr Ser Gly
         355                 360                 365
Gly Thr Ala Ala Leu Gly Cys Leu Val Lys Asp Tyr Phe Pro Glu Pro
     370                 375                 380
Val Thr Val Ser Trp Asn Ser Gly Ala Leu Thr Ser Gly Val His Thr
385                 390                 395                 400
Phe Pro Ala Val Leu Gln Ser Ser Gly Leu Tyr Ser Leu Ser Ser Val
                 405                 410                 415
Val Thr Val Pro Ser Ser Ser Leu Gly Thr Gln Thr Tyr Ile Cys Asn
             420                 425                 430
Val Asn His Lys Pro Ser Asn Thr Lys Val Asp Lys Lys Val Glu Pro
         435                 440                 445
Lys Ser Cys Asp Lys Thr His Thr Cys Pro Pro Cys Pro Ala Pro Glu

```
                    450                 455                 460
Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Gly
            515                 520                 525

Ser Thr Tyr Arg Val Val Ser Val Leu Thr Val Leu His Gln Asp Trp
        530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Glu Glu Met Thr Lys Asn
            580                 585                 590

Gln Val Ser Leu Trp Cys Leu Val Lys Gly Phe Tyr Pro Ser Asp Ile
        595                 600                 605

Ala Val Glu Trp Glu Ser Asn Gly Gln Pro Glu Asn Asn Tyr Lys Thr
        610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro Gly Lys
        675

<210> SEQ ID NO 80
<211> LENGTH: 685
<212> TYPE: PRT
<213> ORGANISM: Artificial Sequence
<220> FEATURE:
<223> OTHER INFORMATION: Synthetic Construct

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Ala Gly Ala Tyr Ala Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
```

```
            130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
            260                 265                 270

Arg Gln Ala Pro Gly Lys Gly Leu Glu Trp Val Ala Arg Ile Tyr Pro
        275                 280                 285

Thr Asn Gly Tyr Thr Arg Tyr Ala Asp Ser Val Lys Gly Arg Phe Thr
    290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
                325                 330                 335

Asp Gly Phe Tyr Ala Met Asp Tyr Trp Gly Gln Gly Thr Leu Val Thr
            340                 345                 350

Val Ser Ser Ala Ser Thr Lys Gly Pro Ser Val Phe Pro Leu Ala Pro
        355                 360                 365

Ser Ser Lys Ser Thr Ser Gly Gly Thr Ala Ala Leu Gly Cys Leu Val
    370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
            420                 425                 430

Thr Gln Thr Tyr Ile Cys Asn Val Asn His Lys Pro Ser Asn Thr Lys
        435                 440                 445

Val Asp Lys Lys Val Glu Pro Lys Ser Cys Asp Lys Thr His Thr Cys
    450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
            500                 505                 510

Phe Asn Trp Tyr Val Asp Gly Val Glu Val His Asn Ala Lys Thr Lys
        515                 520                 525

Pro Arg Glu Glu Gln Tyr Gly Ser Thr Tyr Arg Val Val Ser Val Leu
    530                 535                 540

Thr Val Leu His Gln Asp Trp Leu Asn Gly Lys Glu Tyr Lys Cys Lys
545                 550                 555                 560
```

```
Val Ser Asn Lys Ala Leu Pro Ala Pro Ile Glu Lys Thr Ile Ser Lys
            565                 570                 575

Ala Lys Gly Gln Pro Arg Glu Pro Gln Val Tyr Thr Leu Pro Pro Ser
        580                 585                 590

Arg Glu Glu Met Thr Lys Asn Gln Val Ser Leu Trp Cys Leu Val Lys
    595                 600                 605

Gly Phe Tyr Pro Ser Asp Ile Ala Val Glu Trp Glu Ser Asn Gly Gln
610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
            645                 650                 655

Gln Gly Asn Val Phe Ser Cys Ser Val Met His Glu Ala Leu His Asn
        660                 665                 670

His Tyr Thr Gln Lys Ser Leu Ser Leu Ser Pro Gly Lys
    675                 680                 685

<210> SEQ ID NO 81
<211> LENGTH: 678
<212> TYPE: PRT
<213> ORGANISM: Artificial Sequence
<220> FEATURE:
<223> OTHER INFORMATION: Synthetic Construct

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Thr Gly Phe Tyr Ala Met Asp Tyr Trp Gly Gln
        100                 105                 110

Gly Thr Leu Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
    210                 215                 220

Lys Thr His Thr Glu Val Gln Leu Val Glu Ser Gly Gly Gly Leu Val
225                 230                 235                 240
```

```
Gln Pro Gly Gly Ser Leu Arg Leu Ser Cys Ala Ala Ser Gly Phe Asn
                245                 250                 255

Ile Lys Asp Thr Tyr Ile His Trp Val Arg Gln Ala Pro Gly Lys Gly
            260                 265                 270

Leu Glu Trp Val Ala Arg Ile Tyr Pro Thr Asn Gly Tyr Thr Arg Tyr
        275                 280                 285

Ala Asp Ser Val Lys Gly Arg Phe Thr Ile Ser Ala Asp Thr Ser Lys
    290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
                325                 330                 335

Tyr Trp Gly Gln Gly Thr Leu Val Thr Val Ser Ser Ala Ser Thr Lys
            340                 345                 350

Gly Pro Ser Val Phe Pro Leu Ala Pro Ser Ser Lys Ser Thr Ser Gly
        355                 360                 365

Gly Thr Ala Ala Leu Gly Cys Leu Val Lys Asp Tyr Phe Pro Glu Pro
    370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Lys Val Glu Pro
        435                 440                 445

Lys Ser Cys Asp Lys Thr His Thr Cys Pro Pro Cys Pro Ala Pro Glu
    450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Gly
        515                 520                 525

Ser Thr Tyr Arg Val Val Ser Val Leu Thr Val Leu His Gln Asp Trp
    530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Glu Glu Met Thr Lys Asn
            580                 585                 590

Gln Val Ser Leu Trp Cys Leu Val Lys Gly Phe Tyr Pro Ser Asp Ile
        595                 600                 605

Ala Val Glu Trp Glu Ser Asn Gly Gln Pro Glu Asn Asn Tyr Lys Thr
    610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655
```

```
Ser Val Met His Glu Ala Leu His Asn His Tyr Thr Gln Lys Ser Leu
            660                 665                 670
Ser Leu Ser Pro Gly Lys
            675

<210> SEQ ID NO 82
<211> LENGTH: 685
<212> TYPE: PRT
<213> ORGANISM: Artificial Sequence
<220> FEATURE:
<223> OTHER INFORMATION: Synthetic Construct

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
            260                 265                 270

Arg Gln Ala Pro Gly Lys Gly Leu Glu Trp Val Ala Arg Ile Tyr Pro
        275                 280                 285

Thr Asn Gly Tyr Thr Arg Tyr Ala Asp Ser Val Lys Gly Arg Phe Thr
    290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
                325                 330                 335
```

```
Asp Gly Phe Tyr Ala Met Asp Tyr Trp Gly Gln Gly Thr Leu Val Thr
            340                 345                 350

Val Ser Ser Ala Ser Thr Lys Gly Pro Ser Val Phe Pro Leu Ala Pro
        355                 360                 365

Ser Ser Lys Ser Thr Ser Gly Gly Thr Ala Ala Leu Gly Cys Leu Val
    370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
            420                 425                 430

Thr Gln Thr Tyr Ile Cys Asn Val Asn His Lys Pro Ser Asn Thr Lys
        435                 440                 445

Val Asp Lys Lys Val Glu Pro Lys Ser Cys Asp Lys Thr His Thr Cys
    450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
            500                 505                 510

Phe Asn Trp Tyr Val Asp Gly Val Glu Val His Asn Ala Lys Thr Lys
        515                 520                 525

Pro Arg Glu Glu Gln Tyr Gly Ser Thr Tyr Arg Val Val Ser Val Leu
    530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590

Arg Glu Glu Met Thr Lys Asn Gln Val Ser Leu Trp Cys Leu Val Lys
        595                 600                 605

Gly Phe Tyr Pro Ser Asp Ile Ala Val Glu Trp Glu Ser Asn Gly Gln
    610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
        675                 680                 685

<210> SEQ ID NO 83
<211> LENGTH: 678
<212> TYPE: PRT
<213> ORGANISM: Artificial Sequence
<220> FEATURE:
<223> OTHER INFORMATION: Synthetic Construct

<400> SEQUENCE: 83

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Glu Gly Tyr Thr Arg Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ser Arg Trp Gly Gly Thr Gly Phe Tyr Ala Met Asp Val Trp Gly Gln
             100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
     130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
             165                 170                 175

Leu Gln Ser Ser Gly Leu Tyr Ser Leu Ser Ser Val Val Thr Val Pro
         180                 185                 190

Ser Ser Ser Leu Gly Thr Gln Thr Tyr Ile Cys Asn Val Asn His Lys
             195                 200                 205

Pro Ser Asn Thr Lys Val Asp Lys Lys Val Glu Pro Lys Ser Cys Asp
210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
             245                 250                 255

Ile Lys Asp Thr Tyr Ile His Trp Val Arg Gln Ala Pro Gly Lys Gly
         260                 265                 270

Leu Glu Trp Val Ala Arg Ile Tyr Pro Thr Asn Gly Tyr Thr Arg Tyr
     275                 280                 285

Ala Asp Ser Val Lys Gly Arg Phe Thr Ile Ser Ala Asp Thr Ser Lys
     290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
             325                 330                 335

Tyr Trp Gly Gln Gly Thr Leu Val Thr Val Ser Ser Ala Ser Thr Lys
         340                 345                 350

Gly Pro Ser Val Phe Pro Leu Ala Pro Ser Ser Lys Ser Thr Ser Gly
     355                 360                 365

Gly Thr Ala Ala Leu Gly Cys Leu Val Lys Asp Tyr Phe Pro Glu Pro
     370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
             405                 410                 415

Val Thr Val Pro Ser Ser Ser Leu Gly Thr Gln Thr Tyr Ile Cys Asn
             420                 425                 430

Val Asn His Lys Pro Ser Asn Thr Lys Val Asp Lys Lys Val Glu Pro

```
                435                 440                 445
Lys Ser Cys Asp Lys Thr His Thr Cys Pro Pro Cys Pro Ala Pro Glu
450                 455                 460
Leu Leu Gly Gly Pro Ser Val Phe Leu Phe Pro Pro Lys Pro Lys Asp
465                 470                 475                 480
Thr Leu Met Ile Ser Arg Thr Pro Glu Val Thr Cys Val Val Val Asp
                485                 490                 495
Val Ser His Glu Asp Pro Glu Val Lys Phe Asn Trp Tyr Val Asp Gly
                500                 505                 510
Val Glu Val His Asn Ala Lys Thr Lys Pro Arg Glu Glu Gln Tyr Gly
                515                 520                 525
Ser Thr Tyr Arg Val Val Ser Val Leu Thr Val Leu His Gln Asp Trp
                530                 535                 540
Leu Asn Gly Lys Glu Tyr Lys Cys Lys Val Ser Asn Lys Ala Leu Pro
545                 550                 555                 560
Ala Pro Ile Glu Lys Thr Ile Ser Lys Ala Lys Gly Gln Pro Arg Glu
                565                 570                 575
Pro Gln Val Tyr Thr Leu Pro Pro Ser Arg Glu Glu Met Thr Lys Asn
                580                 585                 590
Gln Val Ser Leu Trp Cys Leu Val Lys Gly Phe Tyr Pro Ser Asp Ile
                595                 600                 605
Ala Val Glu Trp Glu Ser Asn Gly Gln Pro Glu Asn Asn Tyr Lys Thr
                610                 615                 620
Thr Pro Pro Val Leu Asp Ser Asp Gly Ser Phe Phe Leu Tyr Ser Lys
625                 630                 635                 640
Leu Thr Val Asp Lys Ser Arg Trp Gln Gln Gly Asn Val Phe Ser Cys
                645                 650                 655
Ser Val Met His Glu Ala Leu His Asn His Tyr Thr Gln Lys Ser Leu
                660                 665                 670
Ser Leu Ser Pro Gly Lys
                675

<210> SEQ ID NO 84
<211> LENGTH: 685
<212> TYPE: PRT
<213> ORGANISM: Artificial Sequence
<220> FEATURE:
<223> OTHER INFORMATION: Synthetic Construct

<400> SEQUENCE: 84

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
                20                  25                  30
Tyr Ile His Trp Val Arg Gln Ala Pro Gly Lys Gly Leu Glu Trp Val
                35                  40                  45
Ala Arg Ile Tyr Pro Thr Glu Gly Tyr Thr Arg Tyr Ala Asp Ser Val
                50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Thr Gly Phe Tyr Ala Met Asp Val Trp Gly Gln
                100                 105                 110
Gly Thr Leu Val Thr Val Ser Ser Ala Ser Thr Lys Gly Pro Ser Val
```

```
            115                 120                 125
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
            260                 265                 270

Arg Gln Ala Pro Gly Lys Gly Leu Glu Trp Val Ala Arg Ile Tyr Pro
        275                 280                 285

Thr Asn Gly Tyr Thr Arg Tyr Ala Asp Ser Val Lys Gly Arg Phe Thr
    290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
                325                 330                 335

Asp Gly Phe Tyr Ala Met Asp Tyr Trp Gly Gln Gly Thr Leu Val Thr
            340                 345                 350

Val Ser Ser Ala Ser Thr Lys Gly Pro Ser Val Phe Pro Leu Ala Pro
        355                 360                 365

Ser Ser Lys Ser Thr Ser Gly Gly Thr Ala Ala Leu Gly Cys Leu Val
    370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
            420                 425                 430

Thr Gln Thr Tyr Ile Cys Asn Val Asn His Lys Pro Ser Asn Thr Lys
        435                 440                 445

Val Asp Lys Lys Val Glu Pro Lys Ser Cys Asp Lys Thr His Thr Cys
    450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
            500                 505                 510

Phe Asn Trp Tyr Val Asp Gly Val Glu Val His Asn Ala Lys Thr Lys
        515                 520                 525

Pro Arg Glu Glu Gln Tyr Gly Ser Thr Tyr Arg Val Val Ser Val Leu
    530                 535                 540
```

```
Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
            565                 570                 575

Ala Lys Gly Gln Pro Arg Glu Pro Gln Val Tyr Thr Leu Pro Pro Ser
        580                 585                 590

Arg Glu Glu Met Thr Lys Asn Gln Val Ser Leu Trp Cys Leu Val Lys
        595                 600                 605

Gly Phe Tyr Pro Ser Asp Ile Ala Val Glu Trp Glu Ser Asn Gly Gln
        610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
            645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
            675                 680                 685

<210> SEQ ID NO 85
<211> LENGTH: 678
<212> TYPE: PRT
<213> ORGANISM: Artificial Sequence
<220> FEATURE:
<223> OTHER INFORMATION: Synthetic Construct

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220
```

-continued

```
Lys Thr His Thr Glu Val Gln Leu Val Glu Ser Gly Gly Leu Val
225                 230                 235                 240

Gln Pro Gly Gly Ser Leu Arg Leu Ser Cys Ala Ala Ser Gly Phe Asn
            245                 250                 255

Ile Lys Asp Thr Tyr Ile His Trp Val Arg Gln Ala Pro Gly Lys Gly
        260                 265                 270

Leu Glu Trp Val Ala Arg Ile Tyr Pro Thr Asn Gly Tyr Thr Arg Tyr
    275                 280                 285

Ala Asp Ser Val Lys Gly Arg Phe Thr Ile Ser Ala Asp Thr Ser Lys
290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
            325                 330                 335

Tyr Trp Gly Gln Gly Thr Leu Val Thr Val Ser Ser Ala Ser Thr Lys
        340                 345                 350

Gly Pro Ser Val Phe Pro Leu Ala Pro Ser Ser Lys Ser Thr Ser Gly
    355                 360                 365

Gly Thr Ala Ala Leu Gly Cys Leu Val Lys Asp Tyr Phe Pro Glu Pro
370                 375                 380

Val Thr Val Ser Trp Asn Ser Gly Ala Leu Thr Ser Gly Val His Thr
            385                 390                 395                 400

Phe Pro Ala Val Leu Gln Ser Ser Gly Leu Tyr Ser Leu Ser Ser Val
        405                 410                 415

Val Thr Val Pro Ser Ser Ser Leu Gly Thr Gln Thr Tyr Ile Cys Asn
    420                 425                 430

Val Asn His Lys Pro Ser Asn Thr Lys Val Asp Lys Lys Val Glu Pro
435                 440                 445

Lys Ser Cys Asp Lys Thr His Thr Cys Pro Pro Cys Pro Ala Pro Glu
450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
            485                 490                 495

Val Ser His Glu Asp Pro Glu Val Lys Phe Asn Trp Tyr Val Asp Gly
        500                 505                 510

Val Glu Val His Asn Ala Lys Thr Lys Pro Arg Glu Glu Gln Tyr Gly
    515                 520                 525

Ser Thr Tyr Arg Val Val Ser Val Leu Thr Val Leu His Gln Asp Trp
530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
            565                 570                 575

Pro Gln Val Tyr Thr Leu Pro Pro Ser Arg Glu Glu Met Thr Lys Asn
        580                 585                 590

Gln Val Ser Leu Trp Cys Leu Val Lys Gly Phe Tyr Pro Ser Asp Ile
    595                 600                 605

Ala Val Glu Trp Glu Ser Asn Gly Gln Pro Glu Asn Asn Tyr Lys Thr
610                 615                 620

Thr Pro Pro Val Leu Asp Ser Asp Gly Ser Phe Phe Leu Tyr Ser Lys
625                 630                 635                 640
```

```
Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro Gly Lys
        675

<210> SEQ ID NO 86
<211> LENGTH: 685
<212> TYPE: PRT
<213> ORGANISM: Artificial Sequence
<220> FEATURE:
<223> OTHER INFORMATION: Synthetic Construct

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Gly Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
            260                 265                 270

Arg Gln Ala Pro Gly Lys Gly Leu Glu Trp Val Ala Arg Ile Tyr Pro
        275                 280                 285

Thr Asn Gly Tyr Thr Arg Tyr Ala Asp Ser Val Lys Gly Arg Phe Thr
290                 295                 300

Ile Ser Ala Asp Thr Ser Lys Asn Thr Ala Tyr Leu Gln Met Asn Ser
305                 310                 315                 320
```

```
Leu Arg Ala Glu Asp Thr Ala Val Tyr Tyr Cys Ser Arg Trp Gly Gly
            325                 330                 335

Asp Gly Phe Tyr Ala Met Asp Tyr Trp Gly Gln Gly Thr Leu Val Thr
        340                 345                 350

Val Ser Ser Ala Ser Thr Lys Gly Pro Ser Val Phe Pro Leu Ala Pro
    355                 360                 365

Ser Ser Lys Ser Thr Ser Gly Gly Thr Ala Ala Leu Gly Cys Leu Val
370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
            405                 410                 415

Leu Tyr Ser Leu Ser Ser Val Val Thr Val Pro Ser Ser Ser Leu Gly
        420                 425                 430

Thr Gln Thr Tyr Ile Cys Asn Val Asn His Lys Pro Ser Asn Thr Lys
    435                 440                 445

Val Asp Lys Lys Val Glu Pro Lys Ser Cys Asp Lys Thr His Thr Cys
450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
            485                 490                 495

Val Thr Cys Val Val Val Asp Val Ser His Glu Asp Pro Glu Val Lys
        500                 505                 510

Phe Asn Trp Tyr Val Asp Gly Val Glu Val His Asn Ala Lys Thr Lys
    515                 520                 525

Pro Arg Glu Glu Gln Tyr Gly Ser Thr Tyr Arg Val Val Ser Val Leu
530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
            565                 570                 575

Ala Lys Gly Gln Pro Arg Glu Pro Gln Val Tyr Thr Leu Pro Pro Ser
        580                 585                 590

Arg Glu Glu Met Thr Lys Asn Gln Val Ser Leu Trp Cys Leu Val Lys
    595                 600                 605

Gly Phe Tyr Pro Ser Asp Ile Ala Val Glu Trp Glu Ser Asn Gly Gln
610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
            645                 650                 655

Gln Gly Asn Val Phe Ser Cys Ser Val Met His Glu Ala Leu His Asn
        660                 665                 670

His Tyr Thr Gln Lys Ser Leu Ser Leu Ser Pro Gly Lys
    675                 680                 685

<210> SEQ ID NO 87
<211> LENGTH: 678
<212> TYPE: PRT
<213> ORGANISM: Artificial Sequence
<220> FEATURE:
<223> OTHER INFORMATION: Synthetic Construct

<400> SEQUENCE: 87
```

-continued

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Glu Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Thr Gly Phe Tyr Ala Met Asp Val Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
        180                 185                 190
Ser Ser Ser Leu Gly Thr Gln Thr Tyr Ile Cys Asn Val Asn His Lys
    195                 200                 205
Pro Ser Asn Thr Lys Val Asp Lys Lys Val Glu Pro Lys Ser Cys Asp
210                 215                 220
Lys Thr His Thr Glu Val Gln Leu Val Glu Ser Gly Gly Gly Leu Val
225                 230                 235                 240
Gln Pro Gly Gly Ser Leu Arg Leu Ser Cys Ala Ala Ser Gly Phe Asn
            245                 250                 255
Ile Lys Asp Thr Tyr Ile His Trp Val Arg Gln Ala Pro Gly Lys Gly
        260                 265                 270
Leu Glu Trp Val Ala Arg Ile Tyr Pro Thr Asn Gly Tyr Thr Arg Tyr
    275                 280                 285
Ala Asp Ser Val Lys Gly Arg Phe Thr Ile Ser Ala Asp Thr Ser Lys
290                 295                 300
Asn Thr Ala Tyr Leu Gln Met Asn Ser Leu Arg Ala Glu Asp Thr Ala
305                 310                 315                 320
Val Tyr Tyr Cys Ser Arg Trp Gly Gly Asp Gly Phe Tyr Ala Met Asp
            325                 330                 335
Tyr Trp Gly Gln Gly Thr Leu Val Thr Val Ser Ser Ala Ser Thr Lys
        340                 345                 350
Gly Pro Ser Val Phe Pro Leu Ala Pro Ser Ser Lys Ser Thr Ser Gly
    355                 360                 365
Gly Thr Ala Ala Leu Gly Cys Leu Val Lys Asp Tyr Phe Pro Glu Pro
370                 375                 380
Val Thr Val Ser Trp Asn Ser Gly Ala Leu Thr Ser Gly Val His Thr
385                 390                 395                 400
Phe Pro Ala Val Leu Gln Ser Ser Gly Leu Tyr Ser Leu Ser Ser Val
            405                 410                 415
Val Thr Val Pro Ser Ser Ser Leu Gly Thr Gln Thr Tyr Ile Cys Asn
```

```
            420             425             430
Val Asn His Lys Pro Ser Asn Thr Lys Val Asp Lys Lys Val Glu Pro
            435             440             445

Lys Ser Cys Asp Lys Thr His Thr Cys Pro Pro Cys Pro Ala Pro Glu
450             455             460

Leu Leu Gly Gly Pro Ser Val Phe Leu Phe Pro Pro Lys Pro Lys Asp
465             470             475             480

Thr Leu Met Ile Ser Arg Thr Pro Glu Val Thr Cys Val Val Val Asp
            485             490             495

Val Ser His Glu Asp Pro Glu Val Lys Phe Asn Trp Tyr Val Asp Gly
            500             505             510

Val Glu Val His Asn Ala Lys Thr Lys Pro Arg Glu Glu Gln Tyr Gly
            515             520             525

Ser Thr Tyr Arg Val Val Ser Val Leu Thr Val Leu His Gln Asp Trp
            530             535             540

Leu Asn Gly Lys Glu Tyr Lys Cys Lys Val Ser Asn Lys Ala Leu Pro
545             550             555             560

Ala Pro Ile Glu Lys Thr Ile Ser Lys Ala Lys Gly Gln Pro Arg Glu
            565             570             575

Pro Gln Val Tyr Thr Leu Pro Pro Ser Arg Glu Glu Met Thr Lys Asn
            580             585             590

Gln Val Ser Leu Trp Cys Leu Val Lys Gly Phe Tyr Pro Ser Asp Ile
            595             600             605

Ala Val Glu Trp Glu Ser Asn Gly Gln Pro Glu Asn Asn Tyr Lys Thr
            610             615             620

Thr Pro Pro Val Leu Asp Ser Asp Gly Ser Phe Phe Leu Tyr Ser Lys
625             630             635             640

Leu Thr Val Asp Lys Ser Arg Trp Gln Gln Gly Asn Val Phe Ser Cys
            645             650             655

Ser Val Met His Glu Ala Leu His Asn His Tyr Thr Gln Lys Ser Leu
            660             665             670

Ser Leu Ser Pro Gly Lys
            675

<210> SEQ ID NO 88
<211> LENGTH: 685
<212> TYPE: PRT
<213> ORGANISM: Artificial Sequence
<220> FEATURE:
<223> OTHER INFORMATION: Synthetic Construct

<400> SEQUENCE: 88

Glu Val Gln Leu Val Glu Ser Gly Gly Gly Leu Val Gln Pro Gly Gly
1               5               10              15

Ser Leu Arg Leu Ser Cys Ala Ala Ser Gly Phe Asn Ile Lys Asp Thr
            20              25              30

Tyr Ile His Trp Val Arg Gln Ala Pro Gly Lys Gly Leu Glu Trp Val
            35              40              45

Ala Arg Ile Tyr Pro Thr Glu Gly Tyr Thr Arg Tyr Ala Asp Ser Val
            50              55              60

Lys Gly Arg Phe Thr Ile Ser Ala Asp Thr Ser Lys Asn Thr Ala Tyr
65              70              75              80

Leu Gln Met Asn Ser Leu Arg Ala Glu Asp Thr Ala Val Tyr Tyr Cys
            85              90              95

Ser Arg Trp Gly Gly Thr Gly Phe Tyr Ala Met Asp Val Trp Gly Gln
```

```
                  100                 105                 110
Gly Thr Leu Val Thr Val Ser Ser Ala Ser Thr Lys Gly Pro Ser Val
              115                 120                 125
Phe Pro Leu Ala Pro Ser Ser Lys Ser Thr Ser Gly Gly Thr Ala Ala
              130                 135                 140
Leu Gly Cys Leu Val Lys Asp Tyr Phe Pro Glu Pro Val Thr Val Ser
145               150                 155                 160
Trp Asn Ser Gly Ala Leu Thr Ser Gly Val His Thr Phe Pro Ala Val
                  165                 170                 175
Leu Gln Ser Ser Gly Leu Tyr Ser Leu Ser Ser Val Val Thr Val Pro
              180                 185                 190
Ser Ser Ser Leu Gly Thr Gln Thr Tyr Ile Cys Asn Val Asn His Lys
              195                 200                 205
Pro Ser Asn Thr Lys Val Asp Lys Lys Val Glu Pro Lys Ser Cys Asp
              210                 215                 220
Lys Thr His Thr Gly Gly Gly Ser Gly Gly Glu Val Gln Leu Val
225               230                 235                 240
Glu Ser Gly Gly Gly Leu Val Gln Pro Gly Gly Ser Leu Arg Leu Ser
                  245                 250                 255
Cys Ala Ala Ser Gly Phe Asn Ile Lys Asp Thr Tyr Ile His Trp Val
                  260                 265                 270
Arg Gln Ala Pro Gly Lys Gly Leu Glu Trp Val Ala Arg Ile Tyr Pro
              275                 280                 285
Thr Asn Gly Tyr Thr Arg Tyr Ala Asp Ser Val Lys Gly Arg Phe Thr
              290                 295                 300
Ile Ser Ala Asp Thr Ser Lys Asn Thr Ala Tyr Leu Gln Met Asn Ser
305               310                 315                 320
Leu Arg Ala Glu Asp Thr Ala Val Tyr Tyr Cys Ser Arg Trp Gly Gly
                  325                 330                 335
Asp Gly Phe Tyr Ala Met Asp Tyr Trp Gly Gln Gly Thr Leu Val Thr
                  340                 345                 350
Val Ser Ser Ala Ser Thr Lys Gly Pro Ser Val Phe Pro Leu Ala Pro
                  355                 360                 365
Ser Ser Lys Ser Thr Ser Gly Gly Thr Ala Ala Leu Gly Cys Leu Val
              370                 375                 380
Lys Asp Tyr Phe Pro Glu Pro Val Thr Val Ser Trp Asn Ser Gly Ala
385               390                 395                 400
Leu Thr Ser Gly Val His Thr Phe Pro Ala Val Leu Gln Ser Ser Gly
                  405                 410                 415
Leu Tyr Ser Leu Ser Ser Val Val Thr Val Pro Ser Ser Ser Leu Gly
                  420                 425                 430
Thr Gln Thr Tyr Ile Cys Asn Val Asn His Lys Pro Ser Asn Thr Lys
              435                 440                 445
Val Asp Lys Lys Val Glu Pro Lys Ser Cys Asp Lys Thr His Thr Cys
              450                 455                 460
Pro Pro Cys Pro Ala Pro Glu Leu Leu Gly Gly Pro Ser Val Phe Leu
465               470                 475                 480
Phe Pro Pro Lys Pro Lys Asp Thr Leu Met Ile Ser Arg Thr Pro Glu
                  485                 490                 495
Val Thr Cys Val Val Val Asp Val Ser His Glu Asp Pro Glu Val Lys
                  500                 505                 510
Phe Asn Trp Tyr Val Asp Gly Val Glu Val His Asn Ala Lys Thr Lys
              515                 520                 525
```

```
Pro Arg Glu Glu Gln Tyr Gly Ser Thr Tyr Arg Val Val Ser Val Leu
        530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590

Arg Glu Glu Met Thr Lys Asn Gln Val Ser Leu Trp Cys Leu Val Lys
        595                 600                 605

Gly Phe Tyr Pro Ser Asp Ile Ala Val Glu Trp Glu Ser Asn Gly Gln
    610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
        675                 680                 685

<210> SEQ ID NO 89
<211> LENGTH: 678
<212> TYPE: PRT
<213> ORGANISM: Artificial Sequence
<220> FEATURE:
<223> OTHER INFORMATION: Synthetic Construct

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

-continued

Pro Ser Asn Thr Lys Val Asp Lys Val Glu Pro Lys Ser Cys Asp
    210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
                245                 250                 255

Ile Lys Asp Thr Tyr Ile His Trp Val Arg Gln Ala Pro Gly Lys Gly
            260                 265                 270

Leu Glu Trp Val Ala Arg Ile Tyr Pro Thr Asn Gly Tyr Thr Arg Tyr
        275                 280                 285

Ala Asp Ser Val Lys Gly Arg Phe Thr Ile Ser Ala Asp Thr Ser Lys
    290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Asp Gly Phe Tyr Ala Met Asp
                325                 330                 335

Tyr Trp Gly Gln Gly Thr Leu Val Thr Val Ser Ser Ala Ser Thr Lys
            340                 345                 350

Gly Pro Ser Val Phe Pro Leu Ala Pro Ser Ser Lys Ser Thr Ser Gly
        355                 360                 365

Gly Thr Ala Ala Leu Gly Cys Leu Val Lys Asp Tyr Phe Pro Glu Pro
    370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Lys Val Glu Pro
        435                 440                 445

Lys Ser Cys Asp Lys Thr His Thr Cys Pro Pro Cys Pro Ala Pro Glu
    450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Gly
        515                 520                 525

Ser Thr Tyr Arg Val Val Ser Val Leu Thr Val Leu His Gln Asp Trp
    530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Glu Glu Met Thr Lys Asn
            580                 585                 590

Gln Val Ser Leu Trp Cys Leu Val Lys Gly Phe Tyr Pro Ser Asp Ile
        595                 600                 605

Ala Val Glu Trp Glu Ser Asn Gly Gln Pro Glu Asn Asn Tyr Lys Thr
    610                 615                 620

```
Thr Pro Pro Val Leu Asp Ser Asp Gly Ser Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro Gly Lys
        675

<210> SEQ ID NO 90
<211> LENGTH: 685
<212> TYPE: PRT
<213> ORGANISM: Artificial Sequence
<220> FEATURE:
<223> OTHER INFORMATION: Synthetic Construct

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Gly Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
            260                 265                 270

Arg Gln Ala Pro Gly Lys Gly Leu Glu Trp Val Ala Arg Ile Tyr Pro
        275                 280                 285

Thr Asn Gly Tyr Thr Arg Tyr Ala Asp Ser Val Lys Gly Arg Phe Thr
    290                 295                 300
```

```
Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
            325                 330                 335

Asp Gly Phe Tyr Ala Met Asp Tyr Trp Gly Gln Gly Thr Leu Val Thr
            340                 345                 350

Val Ser Ser Ala Ser Thr Lys Gly Pro Ser Val Phe Pro Leu Ala Pro
        355                 360                 365

Ser Ser Lys Ser Thr Ser Gly Gly Thr Ala Ala Leu Gly Cys Leu Val
        370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
            420                 425                 430

Thr Gln Thr Tyr Ile Cys Asn Val Asn His Lys Pro Ser Asn Thr Lys
        435                 440                 445

Val Asp Lys Lys Val Glu Pro Lys Ser Cys Asp Lys Thr His Thr Cys
450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
            500                 505                 510

Phe Asn Trp Tyr Val Asp Gly Val Glu Val His Asn Ala Lys Thr Lys
        515                 520                 525

Pro Arg Glu Glu Gln Tyr Gly Ser Thr Tyr Arg Val Val Ser Val Leu
        530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590

Arg Glu Glu Met Thr Lys Asn Gln Val Ser Leu Trp Cys Leu Val Lys
        595                 600                 605

Gly Phe Tyr Pro Ser Asp Ile Ala Val Glu Trp Glu Ser Asn Gly Gln
610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
        675                 680                 685

<210> SEQ ID NO 91
<211> LENGTH: 678
<212> TYPE: PRT
<213> ORGANISM: Artificial Sequence
<220> FEATURE:
<223> OTHER INFORMATION: Synthetic Construct
```

<400> SEQUENCE: 91

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
        100                 105                 110

Gly Thr Leu Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
            245                 250                 255

Ile Lys Asp Thr Tyr Ile His Trp Val Arg Gln Ala Pro Gly Lys Gly
        260                 265                 270

Leu Glu Trp Val Ala Arg Ile Tyr Pro Thr Asn Gly Tyr Thr Arg Tyr
    275                 280                 285

Ala Asp Ser Val Lys Gly Arg Phe Thr Ile Ser Ala Asp Thr Ser Lys
290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
            325                 330                 335

Tyr Trp Gly Gln Gly Thr Leu Val Thr Val Ser Ser Ala Ser Thr Lys
        340                 345                 350

Gly Pro Ser Val Phe Pro Leu Ala Pro Ser Ser Lys Ser Thr Ser Gly
    355                 360                 365

Gly Thr Ala Ala Leu Gly Cys Leu Val Lys Asp Tyr Phe Pro Glu Pro
370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
```

```
                    405                 410                 415
Val Thr Val Pro Ser Ser Leu Gly Thr Gln Thr Tyr Ile Cys Asn
            420                 425                 430

Val Asn His Lys Pro Ser Asn Thr Lys Val Asp Lys Lys Val Glu Pro
        435                 440                 445

Lys Ser Cys Asp Lys Thr His Thr Cys Pro Pro Cys Pro Ala Pro Glu
    450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Gly
        515                 520                 525

Ser Thr Tyr Arg Val Val Ser Val Leu Thr Val Leu His Gln Asp Trp
    530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Glu Glu Met Thr Lys Asn
            580                 585                 590

Gln Val Ser Leu Trp Cys Leu Val Lys Gly Phe Tyr Pro Ser Asp Ile
        595                 600                 605

Ala Val Glu Trp Glu Ser Asn Gly Gln Pro Glu Asn Asn Tyr Lys Thr
    610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro Gly Lys
            675

<210> SEQ ID NO 92
<211> LENGTH: 685
<212> TYPE: PRT
<213> ORGANISM: Artificial Sequence
<220> FEATURE:
<223> OTHER INFORMATION: Synthetic Construct

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
```

```
                    85                  90                  95
Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
                210                 215                 220

Lys Thr His Thr Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
                260                 265                 270

Arg Gln Ala Pro Gly Lys Gly Leu Glu Trp Val Ala Arg Ile Tyr Pro
                275                 280                 285

Thr Asn Gly Tyr Thr Arg Tyr Ala Asp Ser Val Lys Gly Arg Phe Thr
                290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
                325                 330                 335

Asp Gly Phe Tyr Ala Met Asp Tyr Trp Gly Gln Gly Thr Leu Val Thr
                340                 345                 350

Val Ser Ser Ala Ser Thr Lys Gly Pro Ser Val Phe Pro Leu Ala Pro
                355                 360                 365

Ser Ser Lys Ser Thr Ser Gly Gly Thr Ala Ala Leu Gly Cys Leu Val
                370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
                420                 425                 430

Thr Gln Thr Tyr Ile Cys Asn Val Asn His Lys Pro Ser Asn Thr Lys
                435                 440                 445

Val Asp Lys Lys Val Glu Pro Lys Ser Cys Asp Lys Thr His Thr Cys
450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
                500                 505                 510
```

Phe Asn Trp Tyr Val Asp Gly Val Glu Val His Asn Ala Lys Thr Lys
            515                 520                 525

Pro Arg Glu Glu Gln Tyr Gly Ser Thr Tyr Arg Val Val Ser Val Leu
        530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590

Arg Glu Glu Met Thr Lys Asn Gln Val Ser Leu Trp Cys Leu Val Lys
        595                 600                 605

Gly Phe Tyr Pro Ser Asp Ile Ala Val Glu Trp Glu Ser Asn Gly Gln
610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
        675                 680                 685

<210> SEQ ID NO 93
<211> LENGTH: 678
<212> TYPE: PRT
<213> ORGANISM: Artificial Sequence
<220> FEATURE:
<223> OTHER INFORMATION: Synthetic Construct

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

```
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
                245                 250                 255

Ile Lys Asp Thr Tyr Ile His Trp Val Arg Gln Ala Pro Gly Lys Gly
                260                 265                 270

Leu Glu Trp Val Ala Arg Ile Tyr Pro Thr Asn Gly Tyr Thr Arg Tyr
            275                 280                 285

Ala Asp Ser Val Lys Gly Arg Phe Thr Ile Ser Ala Asp Thr Ser Lys
    290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
                325                 330                 335

Tyr Trp Gly Gln Gly Thr Leu Val Thr Val Ser Ser Ala Ser Thr Lys
            340                 345                 350

Gly Pro Ser Val Phe Pro Leu Ala Pro Ser Ser Lys Ser Thr Ser Gly
            355                 360                 365

Gly Thr Ala Ala Leu Gly Cys Leu Val Lys Asp Tyr Phe Pro Glu Pro
    370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Gln Thr Tyr Ile Cys Asn
            420                 425                 430

Val Asn His Lys Pro Ser Asn Thr Lys Val Asp Lys Lys Val Glu Pro
            435                 440                 445

Lys Ser Cys Asp Lys Thr His Thr Cys Pro Pro Cys Pro Ala Pro Glu
    450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Gly
            515                 520                 525

Ser Thr Tyr Arg Val Val Ser Val Leu Thr Val Leu His Gln Asp Trp
    530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Glu Glu Met Thr Lys Asn
            580                 585                 590

Gln Val Ser Leu Trp Cys Leu Val Lys Gly Phe Tyr Pro Ser Asp Ile
            595                 600                 605
```

```
Ala Val Glu Trp Glu Ser Asn Gly Gln Pro Glu Asn Asn Tyr Lys Thr
610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro Gly Lys
            675

<210> SEQ ID NO 94
<211> LENGTH: 685
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
            260                 265                 270

Arg Gln Ala Pro Gly Lys Gly Leu Glu Trp Val Ala Arg Ile Tyr Pro
        275                 280                 285
```

Thr Asn Gly Tyr Thr Arg Tyr Ala Asp Ser Val Lys Gly Arg Phe Thr
290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ser Arg Trp Gly Gly
            325                 330                 335

Asp Gly Phe Tyr Ala Met Asp Tyr Trp Gly Gln Gly Thr Leu Val Thr
            340                 345                 350

Val Ser Ser Ala Ser Thr Lys Gly Pro Ser Val Phe Pro Leu Ala Pro
        355                 360                 365

Ser Ser Lys Ser Thr Ser Gly Gly Thr Ala Ala Leu Gly Cys Leu Val
370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
            420                 425                 430

Thr Gln Thr Tyr Ile Cys Asn Val Asn His Lys Pro Ser Asn Thr Lys
            435                 440                 445

Val Asp Lys Lys Val Glu Pro Lys Ser Cys Asp Lys Thr His Thr Cys
450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
            500                 505                 510

Phe Asn Trp Tyr Val Asp Gly Val Glu Val His Asn Ala Lys Thr Lys
            515                 520                 525

Pro Arg Glu Glu Gln Tyr Gly Ser Thr Tyr Arg Val Val Ser Val Leu
530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590

Arg Glu Glu Met Thr Lys Asn Gln Val Ser Leu Trp Cys Leu Val Lys
            595                 600                 605

Gly Phe Tyr Pro Ser Asp Ile Ala Val Glu Trp Glu Ser Asn Gly Gln
610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
            675                 680                 685

<210> SEQ ID NO 95
<211> LENGTH: 678
<212> TYPE: PRT

<213> ORGANISM: Artificial Sequence
<220> FEATURE:
<223> OTHER INFORMATION: Synthetic Construct

<400> SEQUENCE: 95

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Ala Gly Ala Tyr Ala Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Glu Val Gln Leu Val Glu Ser Gly Gly Gly Leu Val
225                 230                 235                 240

Gln Pro Gly Gly Ser Leu Arg Leu Ser Cys Ala Ala Ser Gly Phe Asn
                245                 250                 255

Ile Lys Asp Thr Tyr Ile His Trp Val Arg Gln Ala Pro Gly Lys Gly
            260                 265                 270

Leu Glu Trp Val Ala Arg Ile Tyr Pro Thr Asn Gly Tyr Thr Arg Tyr
        275                 280                 285

Ala Asp Ser Val Lys Gly Arg Phe Thr Ile Ser Ala Asp Thr Ser Lys
    290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
                325                 330                 335

Tyr Trp Gly Gln Gly Thr Leu Val Thr Val Ser Ser Ala Ser Thr Lys
            340                 345                 350

Gly Pro Ser Val Phe Pro Leu Ala Pro Ser Ser Lys Ser Thr Ser Gly
        355                 360                 365

Gly Thr Ala Ala Leu Gly Cys Leu Val Lys Asp Tyr Phe Pro Glu Pro
    370                 375                 380

Val Thr Val Ser Trp Asn Ser Gly Ala Leu Thr Ser Gly Val His Thr
```

```
            385                 390                 395                 400
        Phe Pro Ala Val Leu Gln Ser Ser Gly Leu Tyr Ser Leu Ser Ser Val
                        405                 410                 415

Val Thr Val Pro Ser Ser Leu Gly Thr Gln Thr Tyr Ile Cys Asn
                        420                 425                 430

Val Asn His Lys Pro Ser Asn Thr Lys Val Asp Lys Lys Val Glu Pro
                        435                 440                 445

Lys Ser Cys Asp Lys Thr His Thr Cys Pro Pro Cys Pro Ala Pro Glu
                450                 455                 460

Leu Leu Gly Gly Pro Ser Val Phe Leu Phe Pro Pro Lys Pro Lys Asp
        465                 470                 475                 480

Thr Leu Met Ile Ser Arg Thr Pro Glu Val Thr Cys Val Val Val Asp
                        485                 490                 495

Val Ser His Glu Asp Pro Glu Val Lys Phe Asn Trp Tyr Val Asp Gly
                        500                 505                 510

Val Glu Val His Asn Ala Lys Thr Lys Pro Arg Glu Glu Gln Tyr Gly
                        515                 520                 525

Ser Thr Tyr Arg Val Val Ser Val Leu Thr Val Leu His Gln Asp Trp
                530                 535                 540

Leu Asn Gly Lys Glu Tyr Lys Cys Lys Val Ser Asn Lys Ala Leu Pro
        545                 550                 555                 560

Ala Pro Ile Glu Lys Thr Ile Ser Lys Ala Lys Gly Gln Pro Arg Glu
                        565                 570                 575

Pro Gln Val Tyr Thr Leu Pro Pro Ser Arg Glu Glu Met Thr Lys Asn
                        580                 585                 590

Gln Val Ser Leu Trp Cys Leu Val Lys Gly Phe Tyr Pro Ser Asp Ile
                        595                 600                 605

Ala Val Glu Trp Glu Ser Asn Gly Gln Pro Glu Asn Asn Tyr Lys Thr
                        610                 615                 620

Thr Pro Pro Val Leu Asp Ser Asp Gly Ser Phe Phe Leu Tyr Ser Lys
        625                 630                 635                 640

Leu Thr Val Asp Lys Ser Arg Trp Gln Gln Gly Asn Val Phe Ser Cys
                        645                 650                 655

Ser Val Met His Glu Ala Leu His Asn His Tyr Thr Gln Lys Ser Leu
                        660                 665                 670

Ser Leu Ser Pro Gly Lys
                        675

<210> SEQ ID NO 96
<211> LENGTH: 685
<212> TYPE: PRT
<213> ORGANISM: Artificial Sequence
<220> FEATURE:
<223> OTHER INFORMATION: Synthetic Construct

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
                35                  40                  45

Ala Arg Ile Tyr Pro Thr Asn Gly Tyr Thr Arg Tyr Ala Asp Ser Val
                50                  55                  60

Lys Gly Arg Phe Thr Ile Ser Ala Asp Thr Ser Lys Asn Thr Ala Tyr
```

```
                65                    70                    75                   80
Leu Gln Met Asn Ser Leu Arg Ala Glu Asp Thr Ala Val Tyr Tyr Cys
                        85                    90                    95
Ser Arg Trp Gly Gly Ala Gly Ala Tyr Ala Met Asp Val Trp Gly Gln
                    100                   105                   110
Gly Thr Leu Val Thr Val Ser Ala Ser Thr Lys Gly Pro Ser Val
                115                   120                   125
Phe Pro Leu Ala Pro Ser Ser Lys Ser Thr Ser Gly Gly Thr Ala Ala
130                   135                   140
Leu Gly Cys Leu Val Lys Asp Tyr Phe Pro Glu Pro Val Thr Val Ser
145                   150                   155                   160
Trp Asn Ser Gly Ala Leu Thr Ser Gly Val His Thr Phe Pro Ala Val
                    165                   170                   175
Leu Gln Ser Ser Gly Leu Tyr Ser Leu Ser Ser Val Val Thr Val Pro
                180                   185                   190
Ser Ser Ser Leu Gly Thr Gln Thr Tyr Ile Cys Asn Val Asn His Lys
                195                   200                   205
Pro Ser Asn Thr Lys Val Asp Lys Lys Val Glu Pro Lys Ser Cys Asp
210                   215                   220
Lys Thr His Thr Gly Gly Gly Gly Ser Gly Gly Glu Val Gln Leu Val
225                   230                   235                   240
Glu Ser Gly Gly Gly Leu Val Gln Pro Gly Gly Ser Leu Arg Leu Ser
                    245                   250                   255
Cys Ala Ala Ser Gly Phe Asn Ile Lys Asp Thr Tyr Ile His Trp Val
                260                   265                   270
Arg Gln Ala Pro Gly Lys Gly Leu Glu Trp Val Ala Arg Ile Tyr Pro
                275                   280                   285
Thr Asn Gly Tyr Thr Arg Tyr Ala Asp Ser Val Lys Gly Arg Phe Thr
                290                   295                   300
Ile Ser Ala Asp Thr Ser Lys Asn Thr Ala Tyr Leu Gln Met Asn Ser
305                   310                   315                   320
Leu Arg Ala Glu Asp Thr Ala Val Tyr Tyr Cys Ser Arg Trp Gly Gly
                    325                   330                   335
Asp Gly Phe Tyr Ala Met Asp Tyr Trp Gly Gln Gly Thr Leu Val Thr
                340                   345                   350
Val Ser Ser Ala Ser Thr Lys Gly Pro Ser Val Phe Pro Leu Ala Pro
                355                   360                   365
Ser Ser Lys Ser Thr Ser Gly Gly Thr Ala Ala Leu Gly Cys Leu Val
                370                   375                   380
Lys Asp Tyr Phe Pro Glu Pro Val Thr Val Ser Trp Asn Ser Gly Ala
385                   390                   395                   400
Leu Thr Ser Gly Val His Thr Phe Pro Ala Val Leu Gln Ser Ser Gly
                    405                   410                   415
Leu Tyr Ser Leu Ser Ser Val Val Thr Val Pro Ser Ser Ser Leu Gly
                420                   425                   430
Thr Gln Thr Tyr Ile Cys Asn Val Asn His Lys Pro Ser Asn Thr Lys
                435                   440                   445
Val Asp Lys Lys Val Glu Pro Lys Ser Cys Asp Lys Thr His Thr Cys
450                   455                   460
Pro Pro Cys Pro Ala Pro Glu Leu Leu Gly Gly Pro Ser Val Phe Leu
465                   470                   475                   480
Phe Pro Pro Lys Pro Lys Asp Thr Leu Met Ile Ser Arg Thr Pro Glu
                485                   490                   495
```

```
Val Thr Cys Val Val Asp Val Ser His Glu Asp Pro Glu Val Lys
            500                 505                 510

Phe Asn Trp Tyr Val Asp Gly Val Glu Val His Asn Ala Lys Thr Lys
        515                 520                 525

Pro Arg Glu Glu Gln Tyr Gly Ser Thr Tyr Arg Val Val Ser Val Leu
    530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590

Arg Glu Glu Met Thr Lys Asn Gln Val Ser Leu Trp Cys Leu Val Lys
        595                 600                 605

Gly Phe Tyr Pro Ser Asp Ile Ala Val Glu Trp Glu Ser Asn Gly Gln
    610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
        675                 680                 685

<210> SEQ ID NO 97
<211> LENGTH: 678
<212> TYPE: PRT
<213> ORGANISM: Artificial Sequence
<220> FEATURE:
<223> OTHER INFORMATION: Synthetic Construct

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Ala Gly Ala Tyr Ala Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Thr Val Pro
            180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Glu Val Gln Leu Val Glu Ser Gly Gly Leu Val
225             230                 235                 240

Gln Pro Gly Gly Ser Leu Arg Leu Ser Cys Ala Ala Ser Gly Phe Asn
                245                 250                 255

Ile Lys Asp Thr Tyr Ile His Trp Val Arg Gln Ala Pro Gly Lys Gly
                260                 265                 270

Leu Glu Trp Val Ala Arg Ile Tyr Pro Thr Asn Gly Tyr Thr Arg Tyr
                275                 280                 285

Ala Asp Ser Val Lys Gly Arg Phe Thr Ile Ser Ala Asp Thr Ser Lys
                290                 295                 300

Asn Thr Ala Tyr Leu Gln Met Asn Ser Leu Arg Ala Glu Asp Thr Ala
305                 310                 315                 320

Val Tyr Tyr Cys Ser Arg Trp Gly Gly Asp Gly Phe Tyr Ala Met Asp
                325                 330                 335

Tyr Trp Gly Gln Gly Thr Leu Val Thr Val Ser Ser Ala Ser Thr Lys
                340                 345                 350

Gly Pro Ser Val Phe Pro Leu Ala Pro Ser Ser Lys Ser Thr Ser Gly
                355                 360                 365

Gly Thr Ala Ala Leu Gly Cys Leu Val Lys Asp Tyr Phe Pro Glu Pro
                370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Ser Ser Leu Gly Thr Gln Thr Tyr Ile Cys Asn
                420                 425                 430

Val Asn His Lys Pro Ser Asn Thr Lys Val Asp Lys Lys Val Glu Pro
                435                 440                 445

Lys Ser Cys Asp Lys Thr His Thr Cys Pro Pro Cys Pro Ala Pro Glu
                450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
                500                 505                 510

Val Glu Val His Asn Ala Lys Thr Lys Pro Arg Glu Glu Gln Tyr Gly
                515                 520                 525

Ser Thr Tyr Arg Val Val Ser Val Leu Thr Val Leu His Gln Asp Trp
                530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Glu Glu Met Thr Lys Asn
                580                 585                 590
```

```
Gln Val Ser Leu Trp Cys Leu Val Lys Gly Phe Tyr Pro Ser Asp Ile
            595                 600                 605

Ala Val Glu Trp Glu Ser Asn Gly Gln Pro Glu Asn Asn Tyr Lys Thr
610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro Gly Lys
            675

<210> SEQ ID NO 98
<211> LENGTH: 685
<212> TYPE: PRT
<213> ORGANISM: Artificial Sequence
<220> FEATURE:
<223> OTHER INFORMATION: Synthetic Construct

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Ala Gly Ala Tyr Ala Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asn Ile Lys Asp Thr Tyr Ile His Trp Val
            260                 265                 270
```

-continued

```
Arg Gln Ala Pro Gly Lys Gly Leu Glu Trp Val Ala Arg Ile Tyr Pro
            275                 280                 285
Thr Asn Gly Tyr Thr Arg Tyr Ala Asp Ser Val Lys Gly Arg Phe Thr
        290                 295                 300
Ile Ser Ala Asp Thr Ser Lys Asn Thr Ala Tyr Leu Gln Met Asn Ser
305                 310                 315                 320
Leu Arg Ala Glu Asp Thr Ala Val Tyr Tyr Cys Ser Arg Trp Gly Gly
                325                 330                 335
Asp Gly Phe Tyr Ala Met Asp Tyr Trp Gly Gln Gly Thr Leu Val Thr
            340                 345                 350
Val Ser Ser Ala Ser Thr Lys Gly Pro Ser Val Phe Pro Leu Ala Pro
        355                 360                 365
Ser Ser Lys Ser Thr Ser Gly Gly Thr Ala Ala Leu Gly Cys Leu Val
370                 375                 380
Lys Asp Tyr Phe Pro Glu Pro Val Thr Val Ser Trp Asn Ser Gly Ala
385                 390                 395                 400
Leu Thr Ser Gly Val His Thr Phe Pro Ala Val Leu Gln Ser Ser Gly
                405                 410                 415
Leu Tyr Ser Leu Ser Ser Val Val Thr Val Pro Ser Ser Ser Leu Gly
            420                 425                 430
Thr Gln Thr Tyr Ile Cys Asn Val Asn His Lys Pro Ser Asn Thr Lys
        435                 440                 445
Val Asp Lys Lys Val Glu Pro Lys Ser Cys Asp Lys Thr His Thr Cys
    450                 455                 460
Pro Pro Cys Pro Ala Pro Glu Leu Leu Gly Gly Pro Ser Val Phe Leu
465                 470                 475                 480
Phe Pro Pro Lys Pro Lys Asp Thr Leu Met Ile Ser Arg Thr Pro Glu
                485                 490                 495
Val Thr Cys Val Val Val Asp Val Ser His Glu Asp Pro Glu Val Lys
            500                 505                 510
Phe Asn Trp Tyr Val Asp Gly Val Glu Val His Asn Ala Lys Thr Lys
        515                 520                 525
Pro Arg Glu Glu Gln Tyr Gly Ser Thr Tyr Arg Val Val Ser Val Leu
    530                 535                 540
Thr Val Leu His Gln Asp Trp Leu Asn Gly Lys Glu Tyr Lys Cys Lys
545                 550                 555                 560
Val Ser Asn Lys Ala Leu Pro Ala Pro Ile Glu Lys Thr Ile Ser Lys
                565                 570                 575
Ala Lys Gly Gln Pro Arg Glu Pro Gln Val Tyr Thr Leu Pro Pro Ser
            580                 585                 590
Arg Glu Glu Met Thr Lys Asn Gln Val Ser Leu Trp Cys Leu Val Lys
        595                 600                 605
Gly Phe Tyr Pro Ser Asp Ile Ala Val Glu Trp Glu Ser Asn Gly Gln
    610                 615                 620
Pro Glu Asn Asn Tyr Lys Thr Thr Pro Pro Val Leu Asp Ser Asp Gly
625                 630                 635                 640
Ser Phe Phe Leu Tyr Ser Lys Leu Thr Val Asp Lys Ser Arg Trp Gln
                645                 650                 655
Gln Gly Asn Val Phe Ser Cys Ser Val Met His Glu Ala Leu His Asn
            660                 665                 670
His Tyr Thr Gln Lys Ser Leu Ser Leu Ser Pro Gly Lys
        675                 680                 685
```

BISPECIFIC ANTIGEN-BINDING MOLECULES AND METHODS OF USE

SEQUENCE LISTING

The instant application contains a Sequence Listing which has been submitted electronically in ASCII format and is hereby incorporated by reference in its entirety. Said ASCII copy, created on Feb. 6, 2019, is named 50474-162002_Sequence_Listing_02.06.19_ST25 and is 293,645 bytes in size.

FIELD OF THE INVENTION

The present invention relates generally to bispecific antigen-binding molecules, compositions thereof, and methods for treating diseases, such as cancer.

BACKGROUND

Manipulating cell-to-cell contact between particular cell types in a patient represents a promising approach for treating various disease conditions. For example, bispecific antigen-binding molecules (e.g., bispecific antibodies) having two arms, each specific to a different target antigen, are under development for their ability to bring immune cells into contact with target cells. Such bispecific antibodies have shown promise in various disorders, such as cancer, in which potent immune-mediated killing of tumor target cells has been observed in clinical trials. To confer tumor-specificity, tumor-targeting arms of bispecific antibodies have been designed to target antigens that are overexpressed on tumor cells.

Existing bispecific antibodies can have several limitations, including short half-lives and toxicity to healthy tissues. Bispecific antibodies that rely on tumor cell overexpression of a target antigen often kill healthy, non-tumor cells that express normal levels of the antigen. Such on-target, off-tumor effects limit the therapeutic index of the bispecific antibody therapy by restraining the maximum dose tolerated by the subject. Thus, there is an unmet need in the field for the development of bispecific antigen-binding molecules (e.g., bispecific antibodies) with enhanced selectivity to a target cell or tissue.

SUMMARY OF THE INVENTION

The present invention relates to bispecific antigen-binding molecules having a monovalent arm and a bivalent arm (e.g., T cell-dependent bispecific (TDB) antibodies having a monovalent arm and a bivalent arm).

In one aspect, the invention features a bispecific antigen-binding molecule comprising a monovalent arm and a bivalent arm, wherein: (a) the monovalent arm comprises a first antigen-binding moiety, wherein the C-terminus of the first antigen-binding moiety is fused to the N-terminus of a first Fc subunit; (b) the bivalent arm comprises a second antigen-binding moiety and a third antigen-binding moiety, wherein the C-terminus of the third antigen-binding moiety is fused to the N-terminus of the second antigen-binding moiety, and the C-terminus of the second antigen-binding moiety is fused to an N-terminus of a second Fc subunit; and (c) the first Fc subunit is associated with the second Fc subunit to form an Fc domain, wherein the first antigen-binding moiety is capable of specific binding to a first target antigen, and the second antigen-binding moiety and the third antigen-binding moiety are each capable of specific binding to a second target cell antigen. In some embodiments, the first target antigen is an activating T cell antigen, such as CD3, and/or the second target cell antigen is a tumor antigen (e.g., HER2). In some embodiments, the tumor antigen is expressed on (a) a tumor cell in a subject and (b) at least one type of non-tumor cell in the subject.

In some embodiments, the ratio of tumor antigen copy number on the non-tumor cells to the tumor cells is from 1:10 to 1:1,000 (e.g., from 1:100 to 1:200). In some embodiments, the tumor antigen copy number is from $10^2$ to $10^5$ on a non-tumor cell and from $10^3$ to $10^7$ on a tumor cell.

In some embodiments, the tumor antigen copy number (e.g., average tumor antigen copy number, e.g., HER2 copy number, e.g., average HER2 copy number) on the tumor cells (e.g., HER2-positive tumor cells) is greater than $10^5$ per cell (e.g., from $10^5$ to $10^7$ per cell, or from $10^5$ to $10^6$ per cell).

In some embodiments, the tumor antigen copy number (e.g., average tumor antigen copy number, e.g., HER2 copy number, e.g., average HER2 copy number) is ≥200,000 per tumor cell (e.g., HER2-positive tumor cell). In some embodiments, the tumor antigen copy number (e.g., average tumor antigen copy number, e.g., HER2 copy number, e.g., average HER2 copy number) is ≤200,000 per non-tumor cell (e.g., non-cancerous cell, e.g., healthy cell).

In some embodiments, the monovalent binding affinity ($K_D$) of the second antigen-binding moiety and/or the third antigen-binding moiety is from 10 nM to 100 nM (e.g., from 20 nM to 90 nM, from 30 nM to 80 nM, from 40 nM to 60 nM, e.g., from 25 nM to 55 nM). In one embodiment, the monovalent binding affinity ($K_D$) of the second antigen-binding moiety and/or the third antigen-binding moiety is from 20 nM to 50 nM. In one embodiment, the monovalent binding affinity ($K_D$) of the second antigen-binding moiety and the third antigen-binding moiety is from 20 nM to 50 nM.

In some embodiments, the monovalent $K_D$ of the second antigen-binding moiety is the $K_D$ of the second antigen-binding moiety in Fab format measured using surface plasmon resonance (e.g., BIACORE® surface plasmon resonance) and wherein the monovalent $K_D$ of the third antigen-binding moiety is the $K_D$ of the third antigen-binding moiety in Fab format measured using surface plasmon resonance (e.g., BIACORE® surface plasmon resonance).

In some embodiments, the monovalent dissociation rate of the second antigen-binding moiety and/or the third antigen-binding moiety is from $10^{-3}$/second to $10^{-1}$/second (e.g., from $10^{-2}$/second to $30^{-2}$/second). In some embodiments, the monovalent $K_D$ of the first antigen-binding moiety is from 10 nM to 100 nM (e.g., from 20 nM to 90 nM, from 20 nM to 80 nM, from 30 nM to 70 nM, or from 40 nM to 60 nM).

In any of the preceding embodiments, the first antigen-binding moiety may be a Fab molecule ($Fab_A$) comprising a variable heavy chain ($VH_A$) region and a variable light chain ($VL_A$) region; the second antigen-binding moiety is a Fab molecule ($Fab_{B1}$) comprising a variable heavy chain ($VH_{B1}$) region and a variable light chain ($VL_{B1}$) region; and/or the third antigen-binding moiety is a Fab molecule ($Fab_{B2}$) comprising a variable heavy chain ($VH_{B2}$) region and a variable light chain ($VL_{B2}$) region. Thus, in some embodiments, the first antigen-binding moiety is a $Fab_A$ comprising a $VH_A$ region and a $VL_A$ region, the second antigen-binding moiety is a $Fab_{B1}$ comprising a $VH_{B1}$ region and a $VL_{B1}$ region, and third antigen-binding moiety is a $Fab_{B2}$ comprising a $VH_{B2}$ region and a $VL_{B2}$ region.

In some embodiments, the $VH_{B1}$ and the $VH_{B2}$ share at least 95% sequence identity. Additionally or alternatively, the $VL_{B1}$ and the $VL_{B2}$ share at least 95% sequence identity. Additionally or alternatively, the $VH_{B1}$ and the $VH_{B2}$ share at least 95% sequence identity and/or the $VL_{B1}$ and the $VL_{B2}$ share at least 95% sequence identity.

In some embodiments, the $VH_{B1}$ region and/or the $VH_{B2}$ region comprises an amino acid substitution at one, two, three, or all four residues of N54, D98, F100, and/or Y102, according to the Kabat numbering system. For example, the $VH_{B1}$ region and/or the $VH_{B2}$ region may feature an amino acid substitution at one, two, three, four, or all five of the following residues: N54E, D98A, D98T, F100A, and/or Y102V, according to the Kabat numbering system.

In some embodiments, the $VL_{B1}$ region and/or the $VL_{B2}$ region comprises an amino acid substitution at one, two, or all three residues of N30, Y55, and/or H91, according to the Kabat numbering system. For example, the $VL_{B1}$ region and/or the $VL_{B2}$ region may feature an amino acid substitution at one, two, or all three of the following residues: N30S, Y55E, and/or H91A.

In some embodiments, the bispecific antigen-binding molecule features a $VH_{B1}$ region which comprises one, two, or all three of the following HVRs: (a) an HVR-H1 comprising the amino acid sequence of SEQ ID NO: 11, (b) an HVR-H2 comprising the amino acid sequence of SEQ ID NO: 12, or (c) an HVR-H3 comprising the amino acid sequence of SEQ ID NO: 13. In some embodiments, the $VH_{B1}$ region comprises an amino acid sequence having at least 95% sequence identity to SEQ ID NO: 17 (e.g., at least 96% sequence identity to SEQ ID NO: 17, at least 97% sequence identity to SEQ ID NO: 17, at least 98% sequence identity to SEQ ID NO: 17, at least 99% sequence identity to SEQ ID NO: 17, or 100% sequence identity to SEQ ID NO: 17). For example, in some embodiments, the $VH_{B1}$ region comprises the amino acid sequence of SEQ ID NO: 17. In some embodiments, the $VL_{B1}$ region comprises one, two, or all three of the following HVRs: (a) an HVR-L1 comprising the amino acid sequence of SEQ ID NO: 14, (b) an HVR-L2 comprising the amino acid sequence of SEQ ID NO: 15, or (c) an HVR-L3 comprising the amino acid sequence of SEQ ID NO: 16. In some embodiments, the $VL_{B1}$ region comprises an amino acid sequence having at least 95% sequence identity to SEQ ID NO: 18 (e.g., at least 96% sequence identity to SEQ ID NO: 18, at least 97% sequence identity to SEQ ID NO: 18, at least 98% sequence identity to SEQ ID NO: 18, at least 99% sequence identity to SEQ ID NO: 18, or 100% sequence identity to SEQ ID NO: 18). For example, in some embodiments, the $VL_{B1}$ region comprises the amino acid sequence of SEQ ID NO: 18.

In some embodiments, the $VH_{B1}$ comprises the following HVRs: (a) an HVR-H1 comprising the amino acid sequence of SEQ ID NO: 11, (b) an HVR-H2 comprising the amino acid sequence of SEQ ID NO: 12, and (c) an HVR-H3 comprising the amino acid sequence of SEQ ID NO: 13; and the $VL_{B1}$ comprises the following HVRs: (d) an HVR-L1 comprising the amino acid sequence of SEQ ID NO: 14, (e) an HVR-L2 comprising the amino acid sequence of SEQ ID NO: 15, and (f) an HVR-L3 comprising the amino acid sequence of SEQ ID NO: 16. In some embodiments, the $VH_{B1}$ region comprises an amino acid sequence having at least 95% sequence identity to SEQ ID NO: 17 (e.g., at least 96% sequence identity to SEQ ID NO: 17, at least 97% sequence identity to SEQ ID NO: 17, at least 98% sequence identity to SEQ ID NO: 17, at least 99% sequence identity to SEQ ID NO: 17, or 100% sequence identity to SEQ ID NO: 17); and the $VL_{B1}$ region comprises an amino acid sequence having at least 95% sequence identity to SEQ ID NO: 18 (e.g., at least 96% sequence identity to SEQ ID NO: 18, at least 97% sequence identity to SEQ ID NO: 18, at least 98% sequence identity to SEQ ID NO: 18, at least 99% sequence identity to SEQ ID NO: 18, or 100% sequence identity to SEQ ID NO: 18). For example, in some embodiments, the $VH_{B1}$ region comprises the amino acid of SEQ ID NO: 17; and the $VL_{B1}$ region comprises the amino acid sequence of SEQ ID NO: 18.

In some embodiments, the $VH_{B2}$ region comprises one, two, or all three of the following HVRs: (a) an HVR-H1 comprising the amino acid sequence of SEQ ID NO: 11, (b) an HVR-H2 comprising the amino acid sequence of SEQ ID NO: 12, or (c) an HVR-H3 comprising the amino acid sequence of SEQ ID NO: 13. In some embodiments, the $VH_{B2}$ region comprises an amino acid sequence having at least 95% sequence identity to SEQ ID NO: 17 (e.g., at least 96% sequence identity to SEQ ID NO: 17, at least 97% sequence identity to SEQ ID NO: 17, at least 98% sequence identity to SEQ ID NO: 17, at least 99% sequence identity to SEQ ID NO: 17, or 100% sequence identity to SEQ ID NO: 17). In some embodiments, the $VH_{B2}$ region comprises the amino acid sequence of SEQ ID NO: 17. In some embodiments, the $VL_{B2}$ region comprises one, two, or all three of the following HVRs: (a) an HVR-L1 comprising the amino acid sequence of SEQ ID NO: 14, (b) an HVR-L2 comprising the amino acid sequence of SEQ ID NO: 15, or (c) an HVR-L3 comprising the amino acid sequence of SEQ ID NO: 16.

In some embodiments, the $VL_{B2}$ region comprises an amino acid sequence having at least 95% sequence identity to SEQ ID NO: 18 (e.g., at least 96% sequence identity to SEQ ID NO: 18, at least 97% sequence identity to SEQ ID NO: 18, at least 98% sequence identity to SEQ ID NO: 18, at least 99% sequence identity to SEQ ID NO: 18, or 100% sequence identity to SEQ ID NO: 18). In some embodiments, the $VL_{B2}$ region comprises the amino acid sequence of SEQ ID NO: 18.

In some embodiments, the $VH_{B2}$ comprises the following HVRs: (a) an HVR-H1 comprising the amino acid sequence of SEQ ID NO: 11, (b) an HVR-H2 comprising the amino acid sequence of SEQ ID NO: 12, and (c) an HVR-H3 comprising the amino acid sequence of SEQ ID NO: 13; and the $VL_{B2}$ comprises the following HVRs: (d) an HVR-L1 comprising the amino acid sequence of SEQ ID NO: 14, (e) an HVR-L2 comprising the amino acid sequence of SEQ ID NO: 15, and (f) an HVR-L3 comprising the amino acid sequence of SEQ ID NO: 16. In some embodiments, the $VH_{B2}$ region comprises an amino acid sequence having at least 95% sequence identity to SEQ ID NO: 17 (e.g., at least 96% sequence identity to SEQ ID NO: 17, at least 97% sequence identity to SEQ ID NO: 17, at least 98% sequence identity to SEQ ID NO: 17, at least 99% sequence identity to SEQ ID NO: 17, or 100% sequence identity to SEQ ID NO: 17); and the $VL_{B2}$ region comprises an amino acid sequence having at least 95% sequence identity to SEQ ID NO: 18 (e.g., at least 96% sequence identity to SEQ ID NO: 18, at least 97% sequence identity to SEQ ID NO: 18, at least 98% sequence identity to SEQ ID NO: 18, at least 99% sequence identity to SEQ ID NO: 18, or 100% sequence identity to SEQ ID NO: 18). In some embodiments, the $VH_{B2}$ region comprises the amino acid of SEQ ID NO: 17; and the $VL_{B2}$ region comprises the amino acid sequence of SEQ ID NO: 18.

In some embodiments, the $VL_{B1}$ region and/or the $VL_{B2}$ region comprises an amino acid substitution at H91. For example, in some embodiments, the H91 residue is substituted with an amino acid having a nonpolar side chain. In some embodiments, the $VL_{B1}$ region and/or the $VL_{B2}$ region comprises the amino acid substitution of H91A. In some embodiments, the $VL_{B1}$ region and/or the $VL_{B2}$ region comprises an amino acid substitution at Y55. For example, in some embodiments, the Y55 residue is substituted with an amino acid having an acidic side chain. In some embodiments, the $VL_{B1}$ region and/or the $VL_{B2}$ region comprises the amino acid substitution of Y55E. In some embodiments, the $VH_{B1}$ region and/or the $VH_{B2}$ region comprises an amino acid substitution at F100 and/or Y102. For example, in some embodiments, the F100 residue and/or the Y102 residue is substituted with an amino acid having a nonpolar side chain. In some embodiments, the $VH_{B1}$ region and/or the $VH_{B2}$ region comprises the amino acid substitution of F100A and/or Y102V.

In some embodiments, the $VL_{B1}$ region and/or the $VL_{B2}$ region comprises one or more liability fixed residues, e.g., one or more liability fixed residues comprising the amino acid substitution of N30S. Additionally or alternatively, the $VH_{B1}$ region and/or the $VH_{B2}$ region may feature one or more liability fixed residues, e.g., one or more liability fixed residues comprising one or more an amino acid substitutions selected from the group consisting of N54E, D98A, and D98T.

In some embodiments, the bispecific antigen-binding molecule features a $VH_{B1}$ region which comprises one, two, or all three of the following HVRs: (a) an HVR-H1 comprising the amino acid sequence of SEQ ID NO: 11, (b) an HVR-H2 comprising the amino acid sequence of SEQ ID NO: 19, or (c) an HVR-H3 comprising the amino acid sequence of SEQ ID NO: 20. In some embodiments, the $VH_{B1}$ region comprises an amino acid sequence having at least 95% sequence identity to SEQ ID NO: 24 (e.g., at least 96% sequence identity to SEQ ID NO: 24, at least 97% sequence identity to SEQ ID NO: 24, at least 98% sequence identity to SEQ ID NO: 24, at least 99% sequence identity to SEQ ID NO: 24, or 100% sequence identity to SEQ ID NO: 24). For example, in some embodiments, the $VH_{B1}$ region comprises the amino acid sequence of SEQ ID NO: 24. In some embodiments, the $VL_{B1}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 22, or (c) an HVR-L3 comprising the amino acid sequence of SEQ ID NO: 26. In some embodiments, the $VL_{B1}$ region comprises an amino acid sequence having at least 95% sequence identity to SEQ ID NO: 27 (e.g., at least 96% sequence identity to SEQ ID NO: 27, at least 97% sequence identity to SEQ ID NO: 27, at least 98% sequence identity to SEQ ID NO: 27, at least 99% sequence identity to SEQ ID NO: 27, or 100% sequence identity to SEQ ID NO: 27). For example, in some embodiments, the $VL_{B1}$ region comprises the amino acid sequence of SEQ ID NO: 27. For example, in some embodiments, the bispecific antigen-binding molecule is an anti-HER2 bispecific antigen-binding molecule (e.g., 4D5 H91A-1Fab-IgG TDB).

In some embodiments, the $VH_{B1}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 20; and the $VL_{B1}$ comprises the following HVRs: (d) an HVR-L1 comprising the amino acid sequence of SEQ ID NO: 21, (e) an HVR-L2 comprising the amino acid sequence of SEQ ID NO: 22, and (f) an HVR-L3 comprising the amino acid sequence of SEQ ID NO: 26. In some embodiments, the $VH_{B1}$ region comprises an amino acid sequence having at least 95% sequence identity to SEQ ID NO: 24 (e.g., at least 96% sequence identity to SEQ ID NO: 24, at least 97% sequence identity to SEQ ID NO: 24, at least 98% sequence identity to SEQ ID NO: 24, at least 99% sequence identity to SEQ ID NO: 24, or 100% sequence identity to SEQ ID NO: 24); and the $VL_{B1}$ region comprises an amino acid sequence having at least 95% sequence identity to SEQ ID NO: 27 (e.g., at least 96% sequence identity to SEQ ID NO: 27, at least 97% sequence identity to SEQ ID NO: 27, at least 98% sequence identity to SEQ ID NO: 27, at least 99% sequence identity to SEQ ID NO: 27, or 100% sequence identity to SEQ ID NO: 27). For example, in some embodiments, the $VH_{B1}$ region comprises the amino acid of SEQ ID NO: 24; and the $VL_{B1}$ region comprises the amino acid sequence of SEQ ID NO: 27. For example, in some embodiments, the bispecific antigen-binding molecule is an anti-HER2 bispecific antigen-binding molecule (e.g., 4D5 H91A-1Fab-IgG TDB).

In some embodiments, the $VH_{B2}$ region comprises one, two, or all three of the following HVRs: (a) an HVR-H1 comprising the amino acid sequence of SEQ ID NO: 11, (b) an HVR-H2 comprising the amino acid sequence of SEQ ID NO: 19, or (c) an HVR-H3 comprising the amino acid sequence of SEQ ID NO: 20. In some embodiments, the $VH_{B2}$ region comprises an amino acid sequence having at least 95% sequence identity to SEQ ID NO: 24 (e.g., at least 96% sequence identity to SEQ ID NO: 24, at least 97% sequence identity to SEQ ID NO: 24, at least 98% sequence identity to SEQ ID NO: 24, at least 99% sequence identity to SEQ ID NO: 24, or 100% sequence identity to SEQ ID NO: 24). In some embodiments, the $VH_{B2}$ region comprises the amino acid sequence of SEQ ID NO: 24. In some embodiments, the $VL_{B2}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 22, or (c) an HVR-L3 comprising the amino acid sequence of SEQ ID NO: 26. In some embodiments, the $VL_{B2}$ region comprises an amino acid sequence having at least 95% sequence identity to SEQ ID NO: 27 (e.g., at least 96% sequence identity to SEQ ID NO: 18, at least 97% sequence identity to SEQ ID NO: 27, at least 98% sequence identity to SEQ ID NO: 27, at least 99% sequence identity to SEQ ID NO: 27, or 100% sequence identity to SEQ ID NO: 27). In some embodiments, the $VL_{B2}$ region comprises the amino acid sequence of SEQ ID NO: 27. For example, in some embodiments, the bispecific antigen-binding molecule is an anti-HER2 bispecific antigen-binding molecule (e.g., 4D5 H91A-1Fab-IgG TDB).

In some embodiments, the $VH_{B2}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 20; and the $VL_{B2}$ comprises the following HVRs: (d) an HVR-L1 comprising the amino acid sequence of SEQ ID NO: 21, (e) an HVR-L2 comprising the amino acid sequence of SEQ ID NO: 22, and (f) an HVR-L3 comprising the amino acid sequence of SEQ ID NO: 26. In some embodiments, the $VH_{B2}$ region comprises an amino acid sequence having at least 95% sequence identity to SEQ ID NO: 24 (e.g., at least 96% sequence identity to SEQ ID NO: 24, at least 97% sequence identity to SEQ ID NO: 24, at least 98% sequence identity to SEQ ID NO: 24, at least 99% sequence identity to SEQ ID NO: 24, or 100% sequence identity to SEQ ID NO: 24); and the VL$_{B2}$ region comprises an amino acid sequence having at least 95% sequence identity to SEQ ID NO: 27 (e.g., at least 96% sequence identity to SEQ ID NO: 27, at least 97% sequence identity to SEQ ID NO: 27, at least 98% sequence identity to SEQ ID NO: 27, at least 99% sequence identity to SEQ ID NO: 27, or 100% sequence identity to SEQ ID NO: 27). In some embodiments, the VH$_{B2}$ region comprises the amino acid of SEQ ID NO: 24; and the VL$_{B2}$ region comprises the amino acid sequence of SEQ ID NO: 27. For example, in some embodiments, the bispecific antigen-binding molecule is an anti-HER2 bispecific antigen-binding molecule (e.g., 4D5 H91A-1Fab-IgG TDB).

In some embodiments, the bispecific antigen-binding molecule features a VH$_{B1}$ region which comprises one, two, or all three of the following HVRs: (a) an HVR-H1 comprising the amino acid sequence of SEQ ID NO: 11, (b) an HVR-H2 comprising the amino acid sequence of SEQ ID NO: 19, or (c) an HVR-H3 comprising the amino acid sequence of SEQ ID NO: 32. In some embodiments, the VH$_{B1}$ region comprises an amino acid sequence having at least 95% sequence identity to SEQ ID NO: 33 (e.g., at least 96% sequence identity to SEQ ID NO: 33, at least 97% sequence identity to SEQ ID NO: 33, at least 98% sequence identity to SEQ ID NO: 33, at least 99% sequence identity to SEQ ID NO: 33, or 100% sequence identity to SEQ ID NO: 33). For example, in some embodiments, the VH$_{B1}$ region comprises the amino acid sequence of SEQ ID NO: 33. In some embodiments, the VL$_{B1}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 22, or (c) an HVR-L3 comprising the amino acid sequence of SEQ ID NO: 23. In some embodiments, the VL$_{B1}$ region comprises an amino acid sequence having at least 95% sequence identity to SEQ ID NO: 25 (e.g., at least 96% sequence identity to SEQ ID NO: 25, at least 97% sequence identity to SEQ ID NO: 25, at least 98% sequence identity to SEQ ID NO: 25, at least 99% sequence identity to SEQ ID NO: 25, or 100% sequence identity to SEQ ID NO: 25). For example, in some embodiments, the VL$_{B1}$ region comprises the amino acid sequence of SEQ ID NO: 25. For example, in some embodiments, the bispecific antigen-binding molecule is an anti-HER2 bispecific antigen-binding molecule (e.g., 4D5 D98A.F100A.Y102V-1Fab-IgG TDB).

In some embodiments, the VH$_{B1}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 32; and the VL$_{B1}$ comprises the following HVRs: (d) an HVR-L1 comprising the amino acid sequence of SEQ ID NO: 21, (e) an HVR-L2 comprising the amino acid sequence of SEQ ID NO: 22, and (f) an HVR-L3 comprising the amino acid sequence of SEQ ID NO: 23. In some embodiments, the VH$_{B1}$ region comprises an amino acid sequence having at least 95% sequence identity to SEQ ID NO: 33 (e.g., at least 96% sequence identity to SEQ ID NO: 33, at least 97% sequence identity to SEQ ID NO: 33, at least 98% sequence identity to SEQ ID NO: 33, at least 99% sequence identity to SEQ ID NO: 33, or 100% sequence identity to SEQ ID NO: 33); and the VL$_{B1}$ region comprises an amino acid sequence having at least 95% sequence identity to SEQ ID NO: 25 (e.g., at least 96% sequence identity to SEQ ID NO: 25, at least 97% sequence identity to SEQ ID NO: 25, at least 98% sequence identity to SEQ ID NO: 25, at least 99% sequence identity to SEQ ID NO: 25, or 100% sequence identity to SEQ ID NO: 25). For example, in some embodiments, the VH$_{B1}$ region comprises the amino acid of SEQ ID NO: 33; and the VL$_{B1}$ region comprises the amino acid sequence of SEQ ID NO: 25. For example, in some embodiments, the bispecific antigen-binding molecule is an anti-HER2 bispecific antigen-binding molecule (e.g., 4D5 D98A.F100A.Y102V-1Fab-IgG TDB).

In some embodiments, the VH$_{B2}$ region comprises one, two, or all three of the following HVRs: (a) an HVR-H1 comprising the amino acid sequence of SEQ ID NO: 11, (b) an HVR-H2 comprising the amino acid sequence of SEQ ID NO: 19, or (c) an HVR-H3 comprising the amino acid sequence of SEQ ID NO: 32. In some embodiments, the VH$_{B2}$ region comprises an amino acid sequence having at least 95% sequence identity to SEQ ID NO: 33 (e.g., at least 96% sequence identity to SEQ ID NO: 33, at least 97% sequence identity to SEQ ID NO: 33, at least 98% sequence identity to SEQ ID NO: 33, at least 99% sequence identity to SEQ ID NO: 33, or 100% sequence identity to SEQ ID NO: 33). In some embodiments, the VH$_{B2}$ region comprises the amino acid sequence of SEQ ID NO: 33. In some embodiments, the VL$_{B2}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 22, or (c) an HVR-L3 comprising the amino acid sequence of SEQ ID NO: 23. In some embodiments, the VL$_{B2}$ region comprises an amino acid sequence having at least 95% sequence identity to SEQ ID NO: 25 (e.g., at least 96% sequence identity to SEQ ID NO: 25, at least 97% sequence identity to SEQ ID NO: 25, at least 98% sequence identity to SEQ ID NO: 25, at least 99% sequence identity to SEQ ID NO: 25, or 100% sequence identity to SEQ ID NO: 25). In some embodiments, the VL$_{B2}$ region comprises the amino acid sequence of SEQ ID NO: 25. For example, in some embodiments, the bispecific antigen-binding molecule is an anti-HER2 bispecific antigen-binding molecule (e.g., 4D5 D98A.F100A.Y102V-1Fab-IgG TDB).

In some embodiments, the VH$_{B2}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 32; and the VL$_{B2}$ comprises the following HVRs: (d) an HVR-L1 comprising the amino acid sequence of SEQ ID NO: 21, (e) an HVR-L2 comprising the amino acid sequence of SEQ ID NO: 22, and (f) an HVR-L3 comprising the amino acid sequence of SEQ ID NO: 23. In some embodiments, the VH$_{B2}$ region comprises an amino acid sequence having at least 95% sequence identity to SEQ ID NO: 33 (e.g., at least 96% sequence identity to SEQ ID NO: 33, at least 97% sequence identity to SEQ ID NO: 33, at least 98% sequence identity to SEQ ID NO: 33, at least 99% sequence identity to SEQ ID NO: 33, or 100% sequence identity to SEQ ID NO: 33); and the VL$_{B2}$ region comprises an amino acid sequence having at least 95% sequence identity to SEQ ID NO: 25 (e.g., at least 96% sequence identity to SEQ ID NO: 25, at least 97% sequence identity to SEQ ID NO: 25, at least 98% sequence identity to SEQ ID NO: 25, at least 99% sequence identity to SEQ ID NO: 25, or 100% sequence identity to SEQ ID NO: 25). In some embodiments, the VH$_{B2}$ region comprises the amino acid of SEQ ID NO: 33; and the VL$_{B2}$ region comprises the amino acid sequence of SEQ ID NO: 25. For example, in some embodiments, the bispecific antigen-binding molecule is an anti-HER2 bispecific antigen-binding molecule (e.g., 4D5 D98A.F100A.Y102V-1Fab-IgG TDB).

In some embodiments, the bispecific antigen-binding molecule features a $VH_{B1}$ region which comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 37. In some embodiments, the $VH_{B1}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41). For example, in some embodiments, the $VH_{B1}$ region comprises the amino acid sequence of SEQ ID NO: 41. In some embodiments, the $VL_{B1}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 29, or (c) an HVR-L3 comprising the amino acid sequence of SEQ ID NO: 26. In some embodiments, the $VL_{B1}$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). For example, in some embodiments, the $VL_{B1}$ region comprises the amino acid sequence of SEQ ID NO: 48. For example, in some embodiments, the bispecific antigen-binding molecule is an anti-HER2 bispecific antigen-binding molecule (e.g., 4D5 Y55E.H91A.N54E.D98T-1Fab-IgG TDB).

In some embodiments, the $VH_{B1}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 37; and the $VL_{B1}$ comprises the following HVRs: (d) an HVR-L1 comprising the amino acid sequence of SEQ ID NO: 21, (e) an HVR-L2 comprising the amino acid sequence of SEQ ID NO: 29, and (f) an HVR-L3 comprising the amino acid sequence of SEQ ID NO: 26. In some embodiments, the $VH_{B1}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41); and the $VL_{B1}$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). For example, in some embodiments, the $VH_{B1}$ region comprises the amino acid of SEQ ID NO: 41; and the $VL_{B1}$ region comprises the amino acid sequence of SEQ ID NO: 48. For example, in some embodiments, the bispecific antigen-binding molecule is an anti-HER2 bispecific antigen-binding molecule (e.g., 4D5 Y55E.H91A.N54E.D98T-1Fab-IgG TDB).

In some embodiments, the $VH_{B2}$ region comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 37. In some embodiments, the $VH_{B2}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41). In some embodiments, the $VH_{B2}$ region comprises the amino acid sequence of SEQ ID NO: 41. In some embodiments, the $VL_{B2}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 29, or (c) an HVR-L3 comprising the amino acid sequence of SEQ ID NO: 26. In some embodiments, the $VL_{B2}$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). In some embodiments, the $VL_{B2}$ region comprises the amino acid sequence of SEQ ID NO: 48. For example, in some embodiments, the bispecific antigen-binding molecule is an anti-HER2 bispecific antigen-binding molecule (e.g., 4D5 Y55E.H91A.N54E.D98T-1Fab-IgG TDB).

In some embodiments, the $VH_{B2}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 37; and the $VL_{B2}$ comprises the following HVRs: (d) an HVR-L1 comprising the amino acid sequence of SEQ ID NO: 21, (e) an HVR-L2 comprising the amino acid sequence of SEQ ID NO: 29, and (f) an HVR-L3 comprising the amino acid sequence of SEQ ID NO: 26. In some embodiments, the $VH_{B2}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41); and the $VL_{B2}$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). In some embodiments, the $VH_{B2}$ region comprises the amino acid of SEQ ID NO: 41; and the $VL_{B2}$ region comprises the amino acid sequence of SEQ ID NO: 48. For example, in some embodiments, the bispecific antigen-binding molecule is an anti-HER2 bispecific antigen-binding molecule (e.g., 4D5 Y55E.H91A.N54E.D98T-1Fab-IgG TDB).

In some embodiments, the bispecific antigen-binding molecule features a $VH_{B1}$ region which comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 43. In some embodiments, the $VH_{B1}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44). For example, in some embodiments, the $VH_{B1}$ region comprises the amino acid sequence of SEQ ID NO: 44. In some embodiments, the $VL_{B1}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 29, or (c) an HVR-L3 comprising the amino acid sequence of SEQ ID NO: 26. In some embodiments, the $VL_{B1}$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). For example, in some embodiments, the $VL_{B1}$ region comprises the amino acid sequence of SEQ ID NO: 48. For example, in some embodiments, the bispecific antigen-binding molecule is an anti-HER2 bispecific antigen-binding molecule (e.g., 4D5 Y55E.H91A.N54E.D98T.Y102V-1Fab-IgG TDB).

In some embodiments, the $VH_{B1}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 43; and the $VL_{B1}$ comprises the following HVRs: (d) an HVR-L1 comprising the amino acid sequence of SEQ ID NO: 21, (e) an HVR-L2 comprising the amino acid sequence of SEQ ID NO: 29, and (f) an HVR-L3 comprising the amino acid sequence of SEQ ID NO: 26. In some embodiments, the $VH_{B1}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44); and the $VL_{B1}$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). For example, in some embodiments, the $VH_{B1}$ region comprises the amino acid of SEQ ID NO: 41; and the $VL_{B1}$ region comprises the amino acid sequence of SEQ ID NO: 48. For example, in some embodiments, the bispecific antigen-binding molecule is an anti-HER2 bispecific antigen-binding molecule (e.g., 4D5 Y55E.H91A.N54E.D98T.Y102V-1Fab-IgG TDB).

In some embodiments, the $VH_{B2}$ region comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 43. In some embodiments, the $VH_{B2}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44). In some embodiments, the $VH_{B2}$ region comprises the amino acid sequence of SEQ ID NO: 44. In some embodiments, the $VL_{B2}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 29, or (c) an HVR-L3 comprising the amino acid sequence of SEQ ID NO: 26. In some embodiments, the $VL_{B2}$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). In some embodiments, the $VL_{B2}$ region comprises the amino acid sequence of SEQ ID NO: 48. For example, in some embodiments, the bispecific antigen-binding molecule is an anti-HER2 bispecific antigen-binding molecule (e.g., 4D5 Y55E.H91A.N54E.D98T.Y102V-1Fab-IgG TDB).

In some embodiments, the $VH_{B2}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 43; and the $VL_{B2}$ comprises the following HVRs: (d) an HVR-L1 comprising the amino acid sequence of SEQ ID NO: 21, (e) an HVR-L2 comprising the amino acid sequence of SEQ ID NO: 29, and (f) an HVR-L3 comprising the amino acid sequence of SEQ ID NO: 26. In some embodiments, the $VH_{B2}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44); and the $VL_{B2}$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). In some embodiments, the $VH_{B2}$ region comprises the amino acid of SEQ ID NO: 44; and the $VL_{B2}$ region comprises the amino acid sequence of SEQ ID NO: 48. For example, in some embodiments, the bispecific antigen-binding molecule is an anti-HER2 bispecific antigen-binding molecule (e.g., 4D5 Y55E.H91A.N54E.D98T.Y102V-1Fab-IgG TDB).

In some embodiments, the bispecific antigen-binding molecule features a $VH_{B1}$ region which comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 37. In some embodiments, the $VH_{B1}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41). For example, in some embodiments, the $VH_{B1}$ region comprises the amino acid sequence of SEQ ID NO: 41. In some embodiments, the $VL_{B1}$ region comprises one, two, or all three of the following HVRs: (a) an HVR-L1 comprising the amino acid sequence of SEQ ID NO: 38, (b) an HVR-L2 comprising the amino acid sequence of SEQ ID NO: 29, or (c) an HVR-L3 comprising the amino acid sequence of SEQ ID NO: 26. In some embodiments, the $VL_{B1}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). For example, in some embodiments, the $VL_{B1}$ region comprises the amino acid sequence of SEQ ID NO: 49. For example, in some embodiments, the bispecific antigen-binding molecule is an anti-HER2 bispecific antigen-binding molecule (e.g., 4D5 N30S.Y55E.H91A.N54E.D98T-1Fab-IgG TDB).

In some embodiments, the $VH_{B1}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 37; and the $VL_{B1}$ comprises the following HVRs: (d) an HVR-L1 comprising the amino acid sequence of SEQ ID NO: 38, (e) an HVR-L2 comprising the amino acid sequence of SEQ ID NO: 29, and (f) an HVR-L3 comprising the amino acid sequence of SEQ ID NO: 26. In some embodiments, the $VH_{B1}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41); and the $VL_{B1}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). For example, in some embodiments, the $VH_{B1}$ region comprises the amino acid of SEQ ID NO: 41; and the $VL_{B1}$ region comprises the amino acid sequence of SEQ ID NO: 49. For example, in some embodiments, the bispecific antigen-binding molecule is an anti-HER2 bispecific antigen-binding molecule (e.g., 4D5 N30S.Y55E.H91A.N54E.D98T-1Fab-IgG TDB).

In some embodiments, the $VH_{B2}$ region comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 37. In some embodiments, the $VH_{B2}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41). In some embodiments, the $VH_{B2}$ region comprises the amino acid sequence of SEQ ID NO: 41. In some embodiments, the $VL_{B2}$ region comprises one, two, or all three of the following HVRs: (a) an HVR-L1 comprising the amino acid sequence of SEQ ID NO: 38, (b) an HVR-L2 comprising the amino acid sequence of SEQ ID NO: 29, or (c) an HVR-L3 comprising the amino acid sequence of SEQ ID NO: 26. In some embodiments, the $VL_{B2}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). In some embodiments, the $VL_{B2}$ region comprises the amino acid sequence of SEQ ID NO: 49. For example, in some embodiments, the bispecific antigen-binding molecule is an anti-HER2 bispecific antigen-binding molecule (e.g., 4D5 N30S.Y55E.H91A.N54E.D98T-1Fab-IgG TDB).

In some embodiments, the $VH_{B2}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 37; and the $VL_{B2}$ comprises the following HVRs: (d) an HVR-L1 comprising the amino acid sequence of SEQ ID NO: 38, (e) an HVR-L2 comprising the amino acid sequence of SEQ ID NO: 29, and (f) an HVR-L3 comprising the amino acid sequence of SEQ ID NO: 26. In some embodiments, the $VH_{B2}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41); and the $VL_{B2}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). In some embodiments, the $VH_{B2}$ region comprises the amino acid of SEQ ID NO: 41; and the $VL_{B2}$ region comprises the amino acid sequence of SEQ ID NO: 49. For example, in some embodiments, the bispecific antigen-binding molecule is an anti-HER2 bispecific antigen-binding molecule (e.g., 4D5 N30S.Y55E.H91A.N54E.D98T-1Fab-IgG TDB).

In some embodiments, the bispecific antigen-binding molecule features a $VH_{B1}$ region which comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 43. In some embodiments, the $VH_{B1}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44). For example, in some embodiments, the $VH_{B1}$ region comprises the amino acid sequence of SEQ ID NO: 44. In some embodiments, the $VL_{B1}$ region comprises one, two, or all three of the following HVRs: (a) an HVR-L1 comprising the amino acid sequence of SEQ ID NO: 38, (b) an HVR-L2 comprising the amino acid sequence of SEQ ID NO: 29, or (c) an HVR-L3 comprising the amino acid sequence of SEQ ID NO: 26. In some embodiments, the $VL_{B1}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). For example, in some embodiments, the $VL_{B1}$ region comprises the amino acid sequence of SEQ ID NO: 49. For example, in some embodiments, the bispecific antigen-binding molecule is an anti-HER2 bispecific antigen-binding molecule (e.g., 4D5 N30S.Y55E.H91A.N54E.D98T.Y102V-1Fab-IgG TDB).

In some embodiments, the VH$_{B1}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 43; and the VL$_{B1}$ comprises the following HVRs: (d) an HVR-L1 comprising the amino acid sequence of SEQ ID NO: 38, (e) an HVR-L2 comprising the amino acid sequence of SEQ ID NO: 29, and (f) an HVR-L3 comprising the amino acid sequence of SEQ ID NO: 26. In some embodiments, the VH$_{B1}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44); and the VL$_{B1}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). For example, in some embodiments, the VH$_{B1}$ region comprises the amino acid of SEQ ID NO: 44; and the VL$_{B1}$ region comprises the amino acid sequence of SEQ ID NO: 49. For example, in some embodiments, the bispecific antigen-binding molecule is an anti-HER2 bispecific antigen-binding molecule (e.g., 4D5 N30S.Y55E.H91A.N54E.D98T.Y102V-1Fab-IgG TDB).

In some embodiments, the VH$_{B2}$ region comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 43. In some embodiments, the VH$_{B2}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44). In some embodiments, the VH$_{B2}$ region comprises the amino acid sequence of SEQ ID NO: 44. In some embodiments, the VL$_{B2}$ region comprises one, two, or all three of the following HVRs: (a) an HVR-L1 comprising the amino acid sequence of SEQ ID NO: 38, (b) an HVR-L2 comprising the amino acid sequence of SEQ ID NO: 29, or (c) an HVR-L3 comprising the amino acid sequence of SEQ ID NO: 26.

In some embodiments, the VL$_{B2}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). In some embodiments, the VL$_{B2}$ region comprises the amino acid sequence of SEQ ID NO: 49. For example, in some embodiments, the bispecific antigen-binding molecule is an anti-HER2 bispecific antigen-binding molecule (e.g., 4D5 N30S.Y55E.H91A.N54E.D98T.Y102V-1Fab-IgG TDB).

In some embodiments, the VH$_{B2}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 43; and the VL$_{B2}$ comprises the following HVRs: (d) an HVR-L1 comprising the amino acid sequence of SEQ ID NO: 38, (e) an HVR-L2 comprising the amino acid sequence of SEQ ID NO: 29, and (f) an HVR-L3 comprising the amino acid sequence of SEQ ID NO: 26. In some embodiments, the VH$_{B2}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44); and the VL$_{B2}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). In some embodiments, the VH$_{B2}$ region comprises the amino acid of SEQ ID NO: 44; and the VL$_{B2}$ region comprises the amino acid sequence of SEQ ID NO: 49. For example, in some embodiments, the bispecific antigen-binding molecule is an anti-HER2 bispecific antigen-binding molecule (e.g., 4D5 N30S.Y55E.H91A.N54E.D98T.Y102V-1Fab-IgG TDB).

In some embodiments, the bispecific antigen-binding molecule of any of the preceding embodiments features a VH$_A$ region comprising one, two, or all three of the following HVRs: (a) an HVR-H1 comprising the amino acid sequence of SEQ ID NO: 1, (b) an HVR-H2 comprising the amino acid sequence of SEQ ID NO: 2, or (c) an HVR-H3 comprising the amino acid sequence of SEQ ID NO: 3. In some embodiments, the VH$_A$ region comprises an amino acid sequence having at least 95% sequence identity to SEQ ID NO: 7 (e.g., at least 96% sequence identity to SEQ ID NO: 7, at least 97% sequence identity to SEQ ID NO: 7, at least 98% sequence identity to SEQ ID NO: 7, at least 99% sequence identity to SEQ ID NO: 7, or 100% sequence identity to SEQ ID NO: 7). For example, in some embodiments, the VH$_A$ region comprises the amino acid sequence of SEQ ID NO: 7. In some embodiments, the VL$_A$ region comprises one, two, or all three of the following HVRs: (a) an HVR-L1 comprising the amino acid sequence of SEQ ID NO: 4, (b) an HVR-L2 comprising the amino acid sequence of SEQ ID NO: 5, or (c) an HVR-L3 comprising the amino acid sequence of SEQ ID NO: 6. In some embodiments, the VL$_A$ region comprises an amino acid sequence having at least 95% sequence identity to SEQ ID NO: 8 (e.g., at least 96% sequence identity to SEQ ID NO: 8, at least 97% sequence identity to SEQ ID NO: 8, at least 98% sequence identity to SEQ ID NO: 8, at least 99% sequence identity to SEQ ID NO: 8, or 100% sequence identity to SEQ ID NO: 8). For example, in some embodiments, the VL$_A$ region comprises the amino acid sequence of SEQ ID NO: 8. For example, in some embodiments, the bispecific antigen-binding molecule is an anti-CD3 bispecific antigen-binding molecule (e.g., an anti-CD3/HER2 1 Fab-IgG TDB, e.g., an anti-CD3/HER2 1 Fab-IgG TDB having a 40G5c CD3 binding domain).

In some embodiments, the VH$_A$ comprises the following HVRs: (a) an HVR-H1 comprising the amino acid sequence of SEQ ID NO: 1, (b) an HVR-H2 comprising the amino acid sequence of SEQ ID NO: 2, and (c) an HVR-H3 comprising the amino acid sequence of SEQ ID NO: 3; and the VL$_A$ comprises the following HVRs: (d) an HVR-L1 comprising the amino acid sequence of SEQ ID NO: 4, (e) an HVR-L2 comprising the amino acid sequence of SEQ ID NO: 5, and (f) an HVR-L3 comprising the amino acid sequence of SEQ ID NO: 6. In some embodiments, the VH$_A$ region comprises an amino acid sequence having at least 95% sequence identity to SEQ ID NO: 7 (e.g., at least 96% sequence identity to SEQ ID NO: 7, at least 97% sequence identity to SEQ ID NO: 7, at least 98% sequence identity to SEQ ID NO: 7, at least 99% sequence identity to SEQ ID NO: 7, or 100% sequence identity to SEQ ID NO: 7); and the $VL_A$ region comprises an amino acid sequence having at least 95% sequence identity to SEQ ID NO: 8 (e.g., at least 96% sequence identity to SEQ ID NO: 8, at least 97% sequence identity to SEQ ID NO: 8, at least 98% sequence identity to SEQ ID NO: 8, at least 99% sequence identity to SEQ ID NO: 8, or 100% sequence identity to SEQ ID NO: 8). In some embodiments, the $VH_A$ region comprises the amino acid of SEQ ID NO: 7; and the $VL_A$ region comprises the amino acid sequence of SEQ ID NO: 8. For example, in some embodiments, the bispecific antigen-binding molecule is an anti-CD3 bispecific antigen-binding molecule (e.g., an anti-CD3/HER2 1 Fab-IgG TDB, e.g., an anti-CD3/HER2 1 Fab-IgG TDB having a 40G5c CD3 binding domain).

In another aspect, the invention features a bispecific antigen-binding molecule comprising a monovalent arm and a bivalent arm, wherein: (a) the monovalent arm comprises a $Fab_A$, wherein the C-terminus of the $Fab_A$ is fused to an N-terminus of a first Fc subunit, and wherein the $Fab_A$ comprises the following HVRs: (i) an HVR-H1 comprising the amino acid sequence of SEQ ID NO: 1, (ii) an HVR-H2 comprising the amino acid sequence of SEQ ID NO: 2, (iii) an HVR-H3 comprising the amino acid sequence of SEQ ID NO: 3, (iv) an HVR-L1 comprising the amino acid sequence of SEQ ID NO: 4, (v) an HVR-L2 comprising the amino acid sequence of SEQ ID NO: 5, and (vi) an HVR-L3 comprising the amino acid sequence of SEQ ID NO: 6; (b) the bivalent arm comprises a $Fab_{B1}$ and a $Fab_{B2}$, wherein the C-terminus of the $Fab_{B2}$ is fused to the N-terminus of the $Fab_{B1}$, and the C-terminus of the $Fab_{B1}$ is fused to an N-terminus of a second Fc subunit, wherein the $Fab_{B1}$ and the $Fab_{B2}$ each comprise the following HVRs: (i) an HVR-H1 comprising the amino acid sequence of SEQ ID NO: 11, (ii) an HVR-H2 comprising the amino acid sequence of SEQ ID NO: 12, (iii) an HVR-H3 comprising the amino acid sequence of SEQ ID NO: 13, (iv) an HVR-L1 comprising the amino acid sequence of SEQ ID NO: 14, (v) an HVR-L2 comprising the amino acid sequence of SEQ ID NO: 15, and (vi) an HVR-L3 comprising the amino acid sequence of SEQ ID NO: 16; and (c) the first Fc subunit is associated with the second Fc subunit to form an Fc domain. In some embodiments, (a) the $Fab_A$ comprises a $VH_A$ region and a $VL_A$ region, wherein the $VH_A$ region comprises an amino acid sequence having at least 95% sequence identity to SEQ ID NO: 7, and the $VL_A$ region comprises an amino acid sequence having at least 95% sequence identity to SEQ ID NO: 8; (b) the $Fab_{B1}$ comprises a $VH_{B1}$ region and a $VL_{B1}$ region, wherein the $VH_{B1}$ region comprises an amino acid sequence having at least 95% sequence identity to SEQ ID NO: 17, and the $VL_{B1}$ region comprises an amino acid sequence having at least 95% sequence identity to SEQ ID NO: 18; and (c) the $Fab_{B2}$ comprises a $VH_{B2}$ region and a $VL_{B2}$ region, wherein the $VH_{B2}$ region comprises an amino acid sequence having at least 95% sequence identity to SEQ ID NO: 17, and the $VL_{B2}$ region comprises an amino acid sequence having at least 95% sequence identity to SEQ ID NO: 18. For example, in some embodiments, (a) the $VH_A$ region comprises the amino acid sequence of SEQ ID NO: 7, and the $VL_A$ region comprises the amino acid sequence of SEQ ID NO: 8; (b) the $VH_{B1}$ region comprises the amino acid sequence of SEQ ID NO: 17, and the $VL_{B1}$ region comprises the amino acid sequence of SEQ ID NO: 18; and (c) the $VH_{B2}$ region comprises the amino acid sequence of SEQ ID NO: 17, and the $VL_{B2}$ region comprises the amino acid sequence of SEQ ID NO: 18.

In another aspect, the invention provides a bispecific antigen-binding molecule comprising a monovalent arm and a bivalent arm, wherein: (a) the monovalent arm comprises a $Fab_A$, wherein the C-terminus of the $Fab_A$ is fused to an N-terminus of a first Fc subunit, and wherein the $Fab_A$ comprises the following HVRs: (i) an HVR-H1 comprising the amino acid sequence of SEQ ID NO: 1, (ii) an HVR-H2 comprising the amino acid sequence of SEQ ID NO: 2, (iii) an HVR-H3 comprising the amino acid sequence of SEQ ID NO: 3, (iv) an HVR-L1 comprising the amino acid sequence of SEQ ID NO: 4, (v) an HVR-L2 comprising the amino acid sequence of SEQ ID NO: 5, and (vi) an HVR-L3 comprising the amino acid sequence of SEQ ID NO: 6; (b) the bivalent arm comprises a $Fab_{B1}$ and a $Fab_{B2}$, wherein the C-terminus of the $Fab_{B2}$ is fused to the N-terminus of the $Fab_{B1}$, and the C-terminus of the $Fab_{B1}$ is fused to an N-terminus of a second Fc subunit, wherein the $Fab_{B1}$ and the $Fab_{B2}$ each comprise the following HVRs: (i) an HVR-H1 comprising the amino acid sequence of SEQ ID NO: 11, (ii) an HVR-H2 comprising the amino acid sequence of SEQ ID NO: 19, (iii) an HVR-H3 comprising the amino acid sequence of SEQ ID NO: 20, (iv) an HVR-L1 comprising the amino acid sequence of SEQ ID NO: 22, (v) an HVR-L2 comprising the amino acid sequence of SEQ ID NO: 22, and (vi) an HVR-L3 comprising the amino acid sequence of SEQ ID NO: 26; and (c) the first Fc subunit is associated with the second Fc subunit to form an Fc domain. In some embodiments, (a) the $Fab_A$ comprises a $VH_A$ region and a $VL_A$ region, wherein the $VH_A$ region comprises an amino acid sequence having at least 95% sequence identity to SEQ ID NO: 7, and the $VL_A$ region comprises an amino acid sequence having at least 95% sequence identity to SEQ ID NO: 8; (b) the $Fab_{B1}$ comprises a $VH_{B1}$ region and a $VL_{B1}$ region, wherein the $VH_{B1}$ region comprises an amino acid sequence having at least 95% sequence identity to SEQ ID NO: 24, and the $VL_{B1}$ region comprises an amino acid sequence having at least 95% sequence identity to SEQ ID NO: 27; and (c) the $Fab_{B2}$ comprises a $VH_{B2}$ region and a $VL_{B2}$ region, wherein the $VH_{B2}$ region comprises an amino acid sequence having at least 95% sequence identity to SEQ ID NO: 24, and the $VL_{B2}$ region comprises an amino acid sequence having at least 95% sequence identity to SEQ ID NO: 27. For example, in some embodiments, (a) the $VH_A$ region comprises the amino acid sequence of SEQ ID NO: 7, and the $VL_A$ region comprises the amino acid sequence of SEQ ID NO: 8; (b) the $VH_{B1}$ region comprises the amino acid sequence of SEQ ID NO: 24, and the $VL_{B1}$ region comprises the amino acid sequence of SEQ ID NO: 27; and (c) the $VH_{B2}$ region comprises the amino acid sequence of SEQ ID NO: 24, and the $VL_{B2}$ region comprises the amino acid sequence of SEQ ID NO: 27.

In yet another aspect, the invention features a bispecific antigen-binding molecule comprising a monovalent arm and a bivalent arm, wherein: (a) the monovalent arm comprises a $Fab_A$, wherein the C-terminus of the $Fab_A$ is fused to an N-terminus of a first Fc subunit, and wherein the $Fab_A$ comprises the following HVRs: (i) an HVR-H1 comprising the amino acid sequence of SEQ ID NO: 1, (ii) an HVR-H2 comprising the amino acid sequence of SEQ ID NO: 2, (iii) an HVR-H3 comprising the amino acid sequence of SEQ ID NO: 3, (iv) an HVR-L1 comprising the amino acid sequence of SEQ ID NO: 4, (v) an HVR-L2 comprising the amino acid sequence of SEQ ID NO: 5, and (vi) an HVR-L3 comprising the amino acid sequence of SEQ ID NO: 6; (b) the bivalent arm comprises a Fab$_{B1}$ and a Fab$_{B2}$, wherein the C-terminus of the Fab$_{B2}$ is fused to the N-terminus of the Fab$_{B1}$, and the C-terminus of the Fab$_{B1}$ is fused to an N-terminus of a second Fc subunit, wherein the Fab$_{B1}$ and the Fab$_{B2}$ each comprise the following HVRs: (i) an HVR-H1 comprising the amino acid sequence of SEQ ID NO: 11, (ii) an HVR-H2 comprising the amino acid sequence of SEQ ID NO: 19, (iii) an HVR-H3 comprising the amino acid sequence of SEQ ID NO: 32, (iv) an HVR-L1 comprising the amino acid sequence of SEQ ID NO: 21, (v) an HVR-L2 comprising the amino acid sequence of SEQ ID NO: 22, and (vi) an HVR-L3 comprising the amino acid sequence of SEQ ID NO: 23; and (c) the first Fc subunit is associated with the second Fc subunit to form an Fc domain. In some embodiments, (a) the Fab$_A$ comprises a VH$_A$ region and a VL$_A$ region, wherein the VH$_A$ region comprises an amino acid sequence having at least 95% sequence identity to SEQ ID NO: 7, and the VL$_A$ region comprises an amino acid sequence having at least 95% sequence identity to SEQ ID NO: 8; (b) the Fab$_{B1}$ comprises a VH$_{B1}$ region and a VL$_{B1}$ region, wherein the VH$_{B1}$ region comprises an amino acid sequence having at least 95% sequence identity to SEQ ID NO: 33, and the VL$_{B1}$ region comprises an amino acid sequence having at least 95% sequence identity to SEQ ID NO: 25; and (c) the Fab$_{B2}$ comprises a VH$_{B2}$ region and a VL$_{B2}$ region, wherein the VH$_{B2}$ region comprises an amino acid sequence having at least 95% sequence identity to SEQ ID NO: 33, and the VL$_{B2}$ region comprises an amino acid sequence having at least 95% sequence identity to SEQ ID NO: 25. For example, in some embodiments, (a) the VH$_A$ region comprises the amino acid sequence of SEQ ID NO: 7, and the VL$_A$ region comprises the amino acid sequence of SEQ ID NO: 8; (b) the VH$_{B1}$ region comprises the amino acid sequence of SEQ ID NO: 33, and the VL$_{B1}$ region comprises the amino acid sequence of SEQ ID NO: 25; and (c) the VH$_{B2}$ region comprises the amino acid sequence of SEQ ID NO: 33, and the VL$_{B2}$ region comprises the amino acid sequence of SEQ ID NO: 25.

In another aspect, the invention features a bispecific antigen-binding molecule comprising a monovalent arm and a bivalent arm, wherein: (a) the monovalent arm comprises a Fab$_A$, wherein the C-terminus of the Fab$_A$ is fused to an N-terminus of a first Fc subunit, and wherein the Fab$_A$ comprises the following HVRs: (i) an HVR-H1 comprising the amino acid sequence of SEQ ID NO: 1, (ii) an HVR-H2 comprising the amino acid sequence of SEQ ID NO: 2, (iii) an HVR-H3 comprising the amino acid sequence of SEQ ID NO: 3, (iv) an HVR-L1 comprising the amino acid sequence of SEQ ID NO: 4, (v) an HVR-L2 comprising the amino acid sequence of SEQ ID NO: 5, and (vi) an HVR-L3 comprising the amino acid sequence of SEQ ID NO: 6; (b) the bivalent arm comprises a Fab$_{B1}$ and a Fab$_{B2}$, wherein the C-terminus of the Fab$_{B2}$ is fused to the N-terminus of the Fab$_{B1}$, and the C-terminus of the Fab$_{B1}$ is fused to an N-terminus of a second Fc subunit, wherein the Fab$_{B1}$ and the Fab$_{B2}$ each comprise the following HVRs: (i) an HVR-H1 comprising the amino acid sequence of SEQ ID NO: 11, (ii) an HVR-H2 comprising the amino acid sequence of SEQ ID NO: 36, (iii) an HVR-H3 comprising the amino acid sequence of SEQ ID NO: 37, (iv) an HVR-L1 comprising the amino acid sequence of SEQ ID NO: 21, (v) an HVR-L2 comprising the amino acid sequence of SEQ ID NO: 29, and (vi) an HVR-L3 comprising the amino acid sequence of SEQ ID NO: 26; and (c) the first Fc subunit is associated with the second Fc subunit to form an Fc domain. In some embodiments, (a) the Fab$_A$ comprises a VH$_A$ region and a VL$_A$ region, wherein the VH$_A$ region comprises an amino acid sequence having at least 95% sequence identity to SEQ ID NO: 7, and the VL$_A$ region comprises an amino acid sequence having at least 95% sequence identity to SEQ ID NO: 8; (b) the Fab$_{B1}$ comprises a VH$_{B1}$ region and a VL$_{B1}$ region, wherein the VH$_{B1}$ region comprises an amino acid sequence having at least 95% sequence identity to SEQ ID NO: 41, and the VL$_{B1}$ region comprises an amino acid sequence having at least 95% sequence identity to SEQ ID NO: 48; and (c) the Fab$_{B2}$ comprises a VH$_{B2}$ region and a VL$_{B2}$ region, wherein the VH$_{B2}$ region comprises an amino acid sequence having at least 95% sequence identity to SEQ ID NO: 41, and the VL$_{B2}$ region comprises an amino acid sequence having at least 95% sequence identity to SEQ ID NO: 48. For example, in some embodiments, (a) the VH$_A$ region comprises the amino acid sequence of SEQ ID NO: 7, and the VL$_A$ region comprises the amino acid sequence of SEQ ID NO: 8; (b) the VH$_{B1}$ region comprises the amino acid sequence of SEQ ID NO: 41, and the VL$_{B1}$ region comprises the amino acid sequence of SEQ ID NO: 48; and (c) the VH$_{B2}$ region comprises the amino acid sequence of SEQ ID NO: 41, and the VL$_{B2}$ region comprises the amino acid sequence of SEQ ID NO: 48.

In another aspect, the invention features a bispecific antigen-binding molecule comprising a monovalent arm and a bivalent arm, wherein: (a) the monovalent arm comprises a Fab$_A$, wherein the C-terminus of the Fab$_A$ is fused to an N-terminus of a first Fc subunit, and wherein the Fab$_A$ comprises the following HVRs: (i) an HVR-H1 comprising the amino acid sequence of SEQ ID NO: 1, (ii) an HVR-H2 comprising the amino acid sequence of SEQ ID NO: 2, (iii) an HVR-H3 comprising the amino acid sequence of SEQ ID NO: 3, (iv) an HVR-L1 comprising the amino acid sequence of SEQ ID NO: 4, (v) an HVR-L2 comprising the amino acid sequence of SEQ ID NO: 5, and (vi) an HVR-L3 comprising the amino acid sequence of SEQ ID NO: 6; (b) the bivalent arm comprises a Fab$_{B1}$ and a Fab$_{B2}$, wherein the C-terminus of the Fab$_{B2}$ is fused to the N-terminus of the Fab$_{B1}$, and the C-terminus of the Fab$_{B1}$ is fused to an N-terminus of a second Fc subunit, wherein the Fab$_{B1}$ and the Fab$_{B2}$ each comprise the following HVRs: (i) an HVR-H1 comprising the amino acid sequence of SEQ ID NO: 11, (ii) an HVR-H2 comprising the amino acid sequence of SEQ ID NO: 36, (iii) an HVR-H3 comprising the amino acid sequence of SEQ ID NO: 43, (iv) an HVR-L1 comprising the amino acid sequence of SEQ ID NO: 21, (v) an HVR-L2 comprising the amino acid sequence of SEQ ID NO: 29, and (vi) an HVR-L3 comprising the amino acid sequence of SEQ ID NO: 26; and (c) the first Fc subunit is associated with the second Fc subunit to form an Fc domain. In some embodiments, (a) the Fab$_A$ comprises a VH$_A$ region and a VL$_A$ region, wherein the VH$_A$ region comprises an amino acid sequence having at least 95% sequence identity to SEQ ID NO: 7, and the VL$_A$ region comprises an amino acid sequence having at least 95% sequence identity to SEQ ID NO: 8; (b) the Fab$_{B1}$ comprises a VH$_{B1}$ region and a VL$_{B1}$ region, wherein the VH$_{B1}$ region comprises an amino acid sequence having at least 95% sequence identity to SEQ ID NO: 44, and the VL$_{B1}$ region comprises an amino acid sequence having at least 95% sequence identity to SEQ ID NO: 48; and (c) the Fab$_{B2}$ comprises a VH$_{B2}$ region and a VL$_{B2}$ region, wherein the VH$_{B2}$ region comprises an amino acid sequence having at least 95% sequence identity to SEQ ID NO: 44, and the VL$_{B2}$ region comprises an amino acid sequence having at least 95% sequence identity to SEQ ID NO: 48. For example, in some embodiments, (a) the VH$_A$ region comprises the amino acid sequence of SEQ ID NO: 7, and the VL$_A$ region comprises the amino acid sequence of SEQ ID NO: 8; (b) the VH$_{B1}$ region comprises the amino acid sequence of SEQ ID NO: 44, and the VL$_{B1}$ region comprises the amino acid sequence of SEQ ID NO: 48; and (c) the VH$_{B2}$ region comprises the amino acid sequence of SEQ ID NO: 44, and the VL$_{B2}$ region comprises the amino acid sequence of SEQ ID NO: 48. For example, in some embodiments, the bispecific antigen-binding molecule is an anti-CD3/HER2 bispecific antigen-binding molecule (e.g., an anti-CD3/HER2 1 Fab-IgG TDB, e.g., an anti-CD3/HER2 1 Fab-IgG TDB having a 40G5c CD3 binding domain and two 4D5 Y55E.H91A.N54E.D98T.Y102V HER2 binding domains).

In yet another aspect, the invention provides a bispecific antigen-binding molecule comprising a monovalent arm and a bivalent arm, wherein: (a) the monovalent arm comprises a Fab$_A$, wherein the C-terminus of the Fab$_A$ is fused to an N-terminus of a first Fc subunit, and wherein the Fab$_A$ comprises the following HVRs: (i) an HVR-H1 comprising the amino acid sequence of SEQ ID NO: 1, (ii) an HVR-H2 comprising the amino acid sequence of SEQ ID NO: 2, (iii) an HVR-H3 comprising the amino acid sequence of SEQ ID NO: 3, (iv) an HVR-L1 comprising the amino acid sequence of SEQ ID NO: 4, (v) an HVR-L2 comprising the amino acid sequence of SEQ ID NO: 5, and (vi) an HVR-L3 comprising the amino acid sequence of SEQ ID NO: 6; (b) the bivalent arm comprises a Fab$_{B1}$ and a Fab$_{B2}$, wherein the C-terminus of the Fab$_{B2}$ is fused to the N-terminus of the Fab$_{B1}$, and the C-terminus of the Fab$_{B1}$ is fused to an N-terminus of a second Fc subunit, wherein the Fab$_{B1}$ and the Fab$_{B2}$ each comprise the following HVRs: (i) an HVR-H1 comprising the amino acid sequence of SEQ ID NO: 11, (ii) an HVR-H2 comprising the amino acid sequence of SEQ ID NO: 36, (iii) an HVR-H3 comprising the amino acid sequence of SEQ ID NO: 37, (iv) an HVR-L1 comprising the amino acid sequence of SEQ ID NO: 38, (v) an HVR-L2 comprising the amino acid sequence of SEQ ID NO: 29, and (vi) an HVR-L3 comprising the amino acid sequence of SEQ ID NO: 26; and (c) the first Fc subunit is associated with the second Fc subunit to form an Fc domain. In some embodiments, (a) the Fab$_A$ comprises a VH$_A$ region and a VL$_A$ region, wherein the VH$_A$ region comprises an amino acid sequence having at least 95% sequence identity to SEQ ID NO: 7, and the VL$_A$ region comprises an amino acid sequence having at least 95% sequence identity to SEQ ID NO: 8; (b) the Fab$_{B1}$ comprises a VH$_{B1}$ region and a VL$_{B1}$ region, wherein the VH$_{B1}$ region comprises an amino acid sequence having at least 95% sequence identity to SEQ ID NO: 41, and the VL$_{B1}$ region comprises an amino acid sequence having at least 95% sequence identity to SEQ ID NO: 49; and (c) the Fab$_{B2}$ comprises a VH$_{B2}$ region and a VL$_{B2}$ region, wherein the VH$_{B2}$ region comprises an amino acid sequence having at least 95% sequence identity to SEQ ID NO: 41, and the VL$_{B2}$ region comprises an amino acid sequence having at least 95% sequence identity to SEQ ID NO: 49. For example, in some embodiments, (a) the VH$_A$ region comprises the amino acid sequence of SEQ ID NO: 7, and the VL$_A$ region comprises the amino acid sequence of SEQ ID NO: 8; (b) the VH$_{B1}$ region comprises the amino acid sequence of SEQ ID NO: 41, and the VL$_{B1}$ region comprises the amino acid sequence of SEQ ID NO: 49; and (c) the VH$_{B2}$ region comprises the amino acid sequence of SEQ ID NO: 41, and the VL$_{B2}$ region comprises the amino acid sequence of SEQ ID NO: 49. For example, in some embodiments, the bispecific antigen-binding molecule is an anti-CD3/HER2 bispecific antigen-binding molecule (e.g., an anti-CD3/HER2 1 Fab-IgG TDB, e.g., an anti-CD3/HER2 1 Fab-IgG TDB having a 40G5c CD3 binding domain and two 4D5 N30S.Y55E.H91A.N54E.D98T HER2 binding domains).

In another aspect, the invention features a bispecific antigen-binding molecule comprising a monovalent arm and a bivalent arm, wherein: (a) the monovalent arm comprises a Fab$_A$, wherein the C-terminus of the Fab$_A$ is fused to an N-terminus of a first Fc subunit, and wherein the Fab$_A$ comprises the following HVRs: (i) an HVR-H1 comprising the amino acid sequence of SEQ ID NO: 1, (ii) an HVR-H2 comprising the amino acid sequence of SEQ ID NO: 2, (iii) an HVR-H3 comprising the amino acid sequence of SEQ ID NO: 3, (iv) an HVR-L1 comprising the amino acid sequence of SEQ ID NO: 4, (v) an HVR-L2 comprising the amino acid sequence of SEQ ID NO: 5, and (vi) an HVR-L3 comprising the amino acid sequence of SEQ ID NO: 6; (b) the bivalent arm comprises a Fab$_{B1}$ and a Fab$_{B2}$, wherein the C-terminus of the Fab$_{B2}$ is fused to the N-terminus of the Fab$_{B1}$, and the C-terminus of the Fab$_{B1}$ is fused to an N-terminus of a second Fc subunit, wherein the Fab$_{B1}$ and the Fab$_{B2}$ each comprise the following HVRs: (i) an HVR-H1 comprising the amino acid sequence of SEQ ID NO: 11, (ii) an HVR-H2 comprising the amino acid sequence of SEQ ID NO: 36, (iii) an HVR-H3 comprising the amino acid sequence of SEQ ID NO: 43, (iv) an HVR-L1 comprising the amino acid sequence of SEQ ID NO: 38, (v) an HVR-L2 comprising the amino acid sequence of SEQ ID NO: 29, and (vi) an HVR-L3 comprising the amino acid sequence of SEQ ID NO: 26; and (c) the first Fc subunit is associated with the second Fc subunit to form an Fc domain. In some embodiments, (a) the Fab$_A$ comprises a VH$_A$ region and a VL$_A$ region, wherein the VH$_A$ region comprises an amino acid sequence having at least 95% sequence identity to SEQ ID NO: 7, and the VL$_A$ region comprises an amino acid sequence having at least 95% sequence identity to SEQ ID NO: 8; (b) the Fab$_{B1}$ comprises a VH$_{B1}$ region and a VL$_{B1}$ region, wherein the VH$_{B1}$ region comprises an amino acid sequence having at least 95% sequence identity to SEQ ID NO: 44, and the VL$_{B1}$ region comprises an amino acid sequence having at least 95% sequence identity to SEQ ID NO: 49; and (c) the Fab$_{B2}$ comprises a VH$_{B2}$ region and a VL$_{B2}$ region, wherein the VH$_{B2}$ region comprises an amino acid sequence having at least 95% sequence identity to SEQ ID NO: 44, and the VL$_{B2}$ region comprises an amino acid sequence having at least 95% sequence identity to SEQ ID NO: 49. For example, in some embodiments, (a) the VH$_A$ region comprises the amino acid sequence of SEQ ID NO: 7, and the VL$_A$ region comprises the amino acid sequence of SEQ ID NO: 8; (b) the VH$_{B1}$ region comprises the amino acid sequence of SEQ ID NO: 44, and the VL$_{B1}$ region comprises the amino acid sequence of SEQ ID NO: 49; and (c) the VH$_{B2}$ region comprises the amino acid sequence of SEQ ID NO: 44, and the VL$_{B2}$ region comprises the amino acid sequence of SEQ ID NO: 49. For example, in some embodiments, the bispecific antigen-binding molecule is an anti-CD3/HER2 bispecific antigen-binding molecule (e.g., an anti-CD3/HER2 1 Fab-IgG TDB, e.g., an anti-CD3/HER2 1 Fab-IgG TDB having a 40G5c CD3 binding domain and two 4D5 N30S.Y55E.H91A.N54E.D98T.Y102V HER2 binding domains).

In some embodiments of any of the preceding aspects, the Fc domain is an IgG Fc domain (e.g., an IgG$_1$ or IgG$_4$ Fc domain). The Fc domain can be a human Fc domain. In some embodiments, the Fc domain comprises one or more amino acid substitution that reduces binding to an Fc receptor and/or effector function. For example, in some embodiments, the one or more amino acid substitutions that reduces binding to an Fc receptor and/or effector function is at one or more position selected from the group of L234, L235, and P329 (e.g., wherein the first Fc subunit and the second Fc subunit each comprises the amino acid substitutions of L234A, L235A and P329G). In some embodiments, the one or more amino acid substitutions that reduces binding to an Fc receptor and/or effector function is at N297 (e.g., N297G). In some embodiments, the Fc receptor is an Fcγ receptor. In some embodiments, the effector function is antibody-dependent cell-mediated cytotoxicity (ADCC).

In some embodiments of any of the preceding aspects, the Fc domain comprises a modification configured to promote the association of the first Fc subunit with the second Fc subunit. In some embodiments, an amino acid residue in the CH3 domain of the second Fc subunit is replaced with an amino acid residue having a larger side chain volume, thereby generating a protuberance within the CH3 domain of the second Fc subunit which is positionable in a cavity within the CH3 domain of the first Fc subunit, and an amino acid residue in the CH3 domain of the first Fc subunit is replaced with an amino acid residue having a smaller side chain volume, thereby generating a cavity within the CH3 domain of the first Fc subunit within which the protuberance within the CH3 domain of the second Fc subunit is positionable. In some embodiments, the CH3 domain of the second Fc subunit comprises the amino acid substitution of T366, and the CH3 domain of the first Fc subunit comprises amino acid substitutions at one, two, or all three of T366, L368, and/or Y407. In some embodiments, the CH3 domain of the second Fc subunit comprises the amino acid substitution of T366W, and the CH3 domain of the first Fc subunit comprises one, two, or all three amino acid substitutions of T366S, L368A, and/or Y407V.

In some embodiments of any of the preceding aspects, the C-terminus of the third antigen-binding moiety is fused to the N-terminus of the second antigen-binding moiety via a peptide linker. The peptide linker can be 5-20 amino acids in length (e.g., 5-10, 10-15, or 15-20, e.g., 5, 6, 7, 8, 9, 10, 11, 12, 13, 14, 15, 16, 17, 18, 19, or 20 amino acids in length).

In some embodiments, the peptide linker comprises the amino acid sequence of SEQ ID NO: 50. In some embodiments, the antigen-binding molecule comprises an amino acid sequence having at least 95% sequence identity to SEQ ID NO: 55 (e.g., at least 96% sequence identity to SEQ ID NO: 55, at least 97% sequence identity to SEQ ID NO: 55, at least 98% sequence identity to SEQ ID NO: 55, at least 99% sequence identity to SEQ ID NO: 55, or 100% sequence identity to SEQ ID NO: 55). In some embodiments, the antigen-binding molecule comprises an amino acid sequence having at least 95% sequence identity SEQ ID NO: 59 (e.g., at least 96% sequence identity to SEQ ID NO: 59, at least 97% sequence identity to SEQ ID NO: 59, at least 98% sequence identity to SEQ ID NO: 59, at least 99% sequence identity to SEQ ID NO: 59, or 100% sequence identity to SEQ ID NO: 59). In some embodiments, the antigen-binding molecule comprises an amino acid sequence having at least 95% sequence identity SEQ ID NO: 63 (e.g., at least 96% sequence identity to SEQ ID NO: 63, at least 97% sequence identity to SEQ ID NO: 63, at least 98% sequence identity to SEQ ID NO: 63, at least 99% sequence identity to SEQ ID NO: 63, or 100% sequence identity to SEQ ID NO: 63). In some embodiments, the antigen-binding molecule comprises an amino acid sequence having at least 95% sequence identity SEQ ID NO: 83 (e.g., at least 96% sequence identity to SEQ ID NO: 83, at least 97% sequence identity to SEQ ID NO: 83, at least 98% sequence identity to SEQ ID NO: 83, at least 99% sequence identity to SEQ ID NO: 83, or 100% sequence identity to SEQ ID NO: 83). In some embodiments, the antigen-binding molecule comprises an amino acid sequence having at least 95% sequence identity SEQ ID NO: 85 (e.g., at least 96% sequence identity to SEQ ID NO: 85, at least 97% sequence identity to SEQ ID NO: 85, at least 98% sequence identity to SEQ ID NO: 85, at least 99% sequence identity to SEQ ID NO: 85, or 100% sequence identity to SEQ ID NO: 85). In some embodiments, the antigen-binding molecule comprises an amino acid sequence having at least 95% sequence identity SEQ ID NO: 87 (e.g., at least 96% sequence identity to SEQ ID NO: 87, at least 97% sequence identity to SEQ ID NO: 87, at least 98% sequence identity to SEQ ID NO: 87, at least 99% sequence identity to SEQ ID NO: 87, or 100% sequence identity to SEQ ID NO: 87). In some embodiments, the antigen-binding molecule comprises an amino acid sequence having at least 95% sequence identity SEQ ID NO: 89 (e.g., at least 96% sequence identity to SEQ ID NO: 89, at least 97% sequence identity to SEQ ID NO: 89, at least 98% sequence identity to SEQ ID NO: 89, at least 99% sequence identity to SEQ ID NO: 89, or 100% sequence identity to SEQ ID NO: 89).

In some embodiments, the peptide linker comprises the amino acid sequence of SEQ ID NO: 51. In some embodiments, the antigen-binding molecule comprises an amino acid sequence having at least 95% sequence identity to SEQ ID NO: 56 (e.g., at least 96% sequence identity to SEQ ID NO: 56, at least 97% sequence identity to SEQ ID NO: 56, at least 98% sequence identity to SEQ ID NO: 56, at least 99% sequence identity to SEQ ID NO: 56, or 100% sequence identity to SEQ ID NO: 56). In some embodiments, the antigen-binding molecule comprises an amino acid sequence having at least 95% sequence identity SEQ ID NO: 60 (e.g., at least 96% sequence identity to SEQ ID NO: 60, at least 97% sequence identity to SEQ ID NO: 60, at least 98% sequence identity to SEQ ID NO: 60, at least 99% sequence identity to SEQ ID NO: 60, or 100% sequence identity to SEQ ID NO: 60). In some embodiments, the antigen-binding molecule comprises an amino acid sequence having at least 95% sequence identity SEQ ID NO: 64 (e.g., at least 96% sequence identity to SEQ ID NO: 64, at least 97% sequence identity to SEQ ID NO: 64, at least 98% sequence identity to SEQ ID NO: 64, at least 99% sequence identity to SEQ ID NO: 64, or 100% sequence identity to SEQ ID NO: 64). In some embodiments, the antigen-binding molecule comprises an amino acid sequence having at least 95% sequence identity SEQ ID NO: 84 (e.g., at least 96% sequence identity to SEQ ID NO: 84, at least 97% sequence identity to SEQ ID NO: 84, at least 98% sequence identity to SEQ ID NO: 84, at least 99% sequence identity to SEQ ID NO: 84, or 100% sequence identity to SEQ ID NO: 84). In some embodiments, the antigen-binding molecule comprises an amino acid sequence having at least 95% sequence identity SEQ ID NO: 86 (e.g., at least 96% sequence identity to SEQ ID NO: 86, at least 97% sequence identity to SEQ ID NO: 86, at least 98% sequence identity to SEQ ID NO: 86, at least 99% sequence identity to SEQ ID NO: 86, or 100% sequence identity to SEQ ID NO: 86). In some embodiments, the antigen-binding molecule comprises an amino acid sequence having at least 95% sequence identity SEQ ID NO: 88 (e.g., at least 96% sequence identity to SEQ ID NO: 88, at least 97% sequence identity to SEQ ID NO: 88, at least 98% sequence identity to SEQ ID NO: 88, at least 99% sequence identity to SEQ ID NO: 88, or 100% sequence identity to SEQ ID NO: 88). In some embodiments, the antigen-binding molecule comprises an amino acid sequence having at least 95% sequence identity SEQ ID NO: 90 (e.g., at least 96% sequence identity to SEQ ID NO: 90, at least 97% sequence identity to SEQ ID NO: 90, at least 98% sequence identity to SEQ ID NO: 90, at least 99% sequence identity to SEQ ID NO: 90, or 100% sequence identity to SEQ ID NO: 90).

In another aspect, the invention features an isolated nucleic acid encoding the bispecific antigen-binding molecule of any of the preceding aspects.

In another aspect, the invention provides a vector comprising an isolated nucleic acid encoding the bispecific antigen-binding molecule of any of the preceding aspects.

In another aspect, the invention provides a host cell (e.g., an isolated host cell) comprising a vector comprising an isolated nucleic acid encoding the bispecific antigen-binding molecule of any of the preceding aspects. In some embodiments, the host cell is a mammalian cell (e.g., a Chinese hamster ovary (CHO) cell). In other embodiments, the host cell is a prokaryotic cell (e.g., an E. coli cell).

In another aspect, the invention features a method of producing the bispecific antigen-binding molecule of any of the preceding aspects. In some embodiments, the method comprises culturing any of the host cells described above (e.g., a host cell comprising a vector comprising an isolated nucleic acid encoding the bispecific antigen-binding molecule of any of the preceding aspects) in a culture medium. In some embodiments, the method further comprises recovering the bispecific antigen-binding molecule from the host cell or the culture medium.

In another aspect, the invention features a set of isolated nucleic acids encoding the bispecific antigen-binding molecule of any of the preceding aspects (e.g., a set comprising two, three, four, or more isolated nucleic acids encoding the bispecific antigen-binding molecule of any of the preceding aspects).

In some embodiments, a set of isolated nucleic acids includes a first isolated nucleic acid and a second isolated nucleic acid, wherein the first isolated nucleic acid encodes one or more amino acid sequences of a first arm of the bispecific antigen-binding molecule and the second isolated nucleic acid encodes one or more amino acid sequences of a second arm of the bispecific antigen-binding molecule.

In another aspect, the invention provides a set of vectors, wherein each vector of the set comprises an isolated nucleic acid of a set of isolated nucleic acids, wherein the set of isolated nucleic acids encoding the bispecific antigen-binding molecule of any of the preceding aspects (e.g., a set comprising two, three, four, or more isolated nucleic acids encoding the bispecific antigen-binding molecule of any of the preceding aspects).

In another aspect, the invention provides a set of host cells (e.g., a set of isolated host cells). In some embodiments, each host cell of the set comprises an isolated nucleic acid of a set of isolated nucleic acids, wherein the set of isolated nucleic acids encoding the bispecific antigen-binding molecule of any of the preceding aspects (e.g., a set comprising two, three, four, or more isolated nucleic acids encoding the bispecific antigen-binding molecule of any of the preceding aspects). In some embodiments, each host cell of the set comprises a vector comprising an isolated nucleic acid of a set of isolated nucleic acids, wherein the set of isolated nucleic acids encoding the bispecific antigen-binding molecule of any of the preceding aspects (e.g., a set comprising two, three, four, or more isolated nucleic acids encoding the bispecific antigen-binding molecule of any of the preceding aspects). In some embodiments, the set of host cells comprises mammalian cells (e.g., CHO cells). In some embodiments, the set of host cells comprises prokaryotic cells (e.g., E. coli cells).

In another aspect, the invention provides a method of producing the bispecific antigen-binding molecule of any of the preceding aspects, wherein the method comprises culturing the set of host cells of the preceding aspect in a culture medium. In some embodiments, the method further comprises recovering the bispecific antigen-binding molecule from the set of host cells or the culture medium.

In another aspect, the invention features an immunoconjugate comprising the bispecific antigen-binding molecule of any of the preceding aspects and a cytotoxic agent.

In yet another aspect, the invention provides a composition comprising the bispecific antigen-binding molecule of any of the preceding aspects. In some embodiments, the composition further comprises a pharmaceutically acceptable carrier, excipient, or diluent. For example, in some embodiments, the composition is a pharmaceutical composition. In some embodiments, the composition further comprises a PD-1 axis binding antagonist or an additional therapeutic agent.

In another aspect, the invention features a bispecific antigen-binding molecule of any one of the preceding aspects for use as a medicament. For example, in some embodiments, the bispecific antigen-binding molecules described herein are for use in treating or delaying progression of a cell proliferative disorder (e.g., cancer) or an autoimmune disorder in a subject in need thereof. In some embodiments, the bispecific antigen-binding molecule of any of the preceding aspects are for use in enhancing immune function in a subject having a cell proliferative disorder (e.g., cancer, e.g., a HER2-positive cancer) or an autoimmune disorder.

In another aspect, the invention features a use of the bispecific antigen-binding molecule of any of the preceding aspects in the manufacture of a medicament for treating or delaying progression of a disorder. In another aspect, the invention features a use of the bispecific antigen-binding molecule of any of the preceding aspects in the manufacture of a medicament for enhancing immune function in a subject having a disorder. In some embodiments, the disorder is a cell proliferative disorder (e.g., cancer, e.g., a HER2-positive cancer) or an autoimmune disorder.

In yet another aspect, the invention features a method of treating or delaying the progression of a disorder in a subject in need thereof, the method comprising administering to the subject the bispecific antigen-binding molecule of any of the preceding aspects. In another aspect, the invention provides a method of enhancing immune function in a subject having a disorder, the method comprising administering to the subject the bispecific antigen-binding molecule of any of the preceding aspects. In some embodiments, the disorder is a cell proliferative disorder (e.g., cancer, e.g., a HER2-positive cancer) or an autoimmune disorder.

In another aspect, the invention features a method of treating or delaying the progression of a disorder in a subject in need thereof, wherein the method comprises: (a) determining an expression of HER2 on a tumor cell, wherein the tumor cell expresses HER2 at an average copy number of 200,000 or more copies per cell; and (b) administering to the subject the bispecific antigen-binding molecule of any of the preceding aspects. In some embodiments, the disorder is a cell proliferative disorder (e.g., cancer, e.g., a HER2-positive cancer) or an autoimmune disorder.

In another aspect, the invention provides a method of enhancing immune function in a subject having a disorder, wherein the method comprises: (a) determining an expression of HER2 on a tumor cell, wherein the tumor cell expresses HER2 at an average copy number of 200,000 or more copies per cell; and (b) administering to the subject the bispecific antigen-binding molecule of any of the preceding aspects. In some embodiments, the disorder is a cell proliferative disorder (e.g., cancer, e.g., a HER2-positive cancer) or an autoimmune disorder.

In some embodiments of any of the preceding aspects, the cancer is selected from the group consisting of breast cancer, gastric cancer, colorectal cancer, non-small cell lung cancer, renal cancer, bladder cancer, pancreatic cancer, prostate cancer, liver cancer, head and neck cancer, melanoma, ovarian cancer, mesothelioma, glioblastoma, endometrial cancer, and osteosarcoma. In some embodiments, the cancer is a HER2-positive cancer (e.g., a HER2-positive breast cancer, a HER2-positive gastric cancer, a HER2-positive colorectal cancer, a HER2-positive non-small cell lung cancer, a HER2-positive renal cancer, a HER2-positive bladder cancer, a HER2-positive pancreatic cancer, a HER2-positive prostate cancer, a HER2-positive liver cancer, a HER2-positive head and neck cancer, a HER2-positive melanoma, a HER2-positive ovarian cancer, a HER2-positive mesothelioma, a HER2-positive glioblastoma, a HER2-positive endometrial cancer, or a HER2-positive osteosarcoma).

In some embodiments, the HER2-positive cancer (e.g., the HER2-positive breast cancer, the HER2-positive gastric cancer, the HER2-positive colorectal cancer, the HER2-positive non-small cell lung cancer, the HER2-positive renal cancer, the HER2-positive bladder cancer, the HER2-positive pancreatic cancer, the HER2-positive prostate cancer, the HER2-positive liver cancer, the HER2-positive head and neck cancer, the HER2-positive melanoma, the HER2-positive ovarian cancer, the HER2-positive mesothelioma, the HER2-positive glioblastoma, the HER2-positive endometrial cancer, or the HER2-positive osteosarcoma) is characterized by tumor cells that express HER2 at a copy number (e.g., an average copy number) of at least 200,000 per cell (e.g., at least 250,000 HER2 copies per cell, at least 300,000 HER2 copies per cell, at least 400,000 HER2 copies per cell, at least 500,000 HER2 copies per cell, at least 600,000 HER2 copies per cell, at least 700,000 HER2 copies per cell, at least 750,000 HER2 copies per cell, at least 800,000 HER2 copies per cell, at least 900,000 HER2 copies per cell, at least 1,000,000 HER2 copies per cell, at least 1,200,000 HER2 copies per cell, at least 1,500,000 HER2 copies per cell, at least 2,000,000 HER2 copies per cell, at least 2,500,000 HER2 copies per cell, at least 3,000,000 HER2 copies per cell, or more, e.g., from 200,000 to 3,000,000 HER2 copies per cell, from 250,000 to 2,500,000 HER2 copies per cell, from 300,000 to 2,000,000 HER2 copies per cell, from 400,000 to 1,500,000 HER2 copies per cell, or from 500,000 to 1,000,000 HER2 copies per cell, e.g., from 200,000 to 1,000,000 HER2 copies per cell (e.g., from 200,000 to 250,000 HER2 copies per cell, from 250,000 to 300,000 HER2 copies per cell, from 300,000 to 400,000 HER2 copies per cell, from 400,000 to 500,000 HER2 copies per cell, from 500,000 to 750,000 HER2 copies per cell, or from 750,000 to 1,000,000 HER2 copies per cell) or from 1,000,000 to 3,000,000 HER2 copies per cell (e.g., from 1,000,000 to 1,500,000 HER2 copies per cell, from 1,500,000 to 2,000,000 HER2 copies per cell, from 2,000,000 to 2,500,000 HER2 copies per cell, or from 2,500,000 to 3,000,000 HER2 copies per cell).

In some embodiments of any of the preceding aspects, the bispecific antigen-binding molecule is administered to the subject in a dosage of about 0.01 mg/kg to about 10 mg/kg (e.g., about 0.1 mg/kg to about 10 mg/kg, e.g., about 1 mg/kg).

In some embodiments, a PD-1 axis binding antagonist and/or an additional therapeutic agent is administered to the subject. In some embodiments, the PD-1 axis binding antagonist or additional therapeutic agent is administered prior to or subsequent to the administration of the bispecific antigen-binding molecule. In some embodiments, the PD-1 axis binding antagonist or additional therapeutic agent is administered concurrently with the bispecific antigen-binding molecule. In some embodiments, the PD-1 axis binding antagonist is selected from the group consisting of a PD-L1 binding antagonist (e.g., atezolizumab (MPDL3280A), YW243.55.S70, MDX-1105, MEDI4736 (durvalumab), and MSB0010718C (avelumab)), a PD-1 binding antagonist (e.g., MDX-1106 (nivolumab), MK-3475 (pembrolizumab), CT-011 (pidilizumab), MEDI-0680 (AMP-514), PDR001 (spartalizumab), REGN2810 (cemiplimab), and BGB-108), and a PD-L2 binding antagonist (e.g., an antibody or an immunoadhesin).

In some embodiments, the bispecific antigen-binding molecule is administered subcutaneously, intravenously, intramuscularly, topically, orally, transdermally, intraperitoneally, intraorbitally, by implantation, by inhalation, intrathecally, intraventricularly, or intranasally. For example, in some embodiments, the bispecific antigen-binding molecule is administered subcutaneously. In other embodiments, the bispecific antigen-binding molecule is administered intravenously.

In some embodiments of any of the preceding aspects, the subject is a human.

In another aspect, the invention features a kit comprising: (a) a composition comprising the bispecific antigen-binding molecule of any of the preceding aspects; and (b) a package insert comprising instructions for administering the composition to a subject to treat or delay progression of a disorder (e.g., a cell proliferative disorder (e.g., cancer) or an autoimmune disorder). In some embodiments, the composition further comprises a pharmaceutically acceptable carrier, excipient, or diluent.

BRIEF DESCRIPTION OF THE DRAWINGS

FIGS. 2A-2F are graphs showing dose response curves of relative killing of SKBR3 cells (open squares) and MCF7 cells (solid dots) by various monovalent HER2 TDB (IgG TDB) molecules. Data are represented as mean±standard deviation. FIG. 2A is a graph showing dose response curves of target cell killing by the wild-type 4D5 IgG TDB antibody (trastuzumab). FIG. 2B is a graph showing dose response curves of target cell killing by the 4D5 antibody variant, Y55E.Y102V-TDB. FIG. 2C is a graph showing dose response curves of target cell killing by the 4D5 antibody variant, Y55E.D98A.F100A.Y102V-IgG TDB. FIG. 2D is a graph showing dose response curves of target cell killing by the 4D5 antibody variant, D98A.F100A.Y102V-IgG TDB. FIG. 2E is a graph showing dose response curves of target cell killing by the 4D5 antibody variant, H91A-IgG TDB. FIG. 2F is a graph showing dose response curves of target cell killing by the 4D5 antibody variant, Y100A-IgG TDB.

FIGS. 32A-32K is a series of sensorgrams showing binding kinetics of 4D5 IgG TDB antibodies to human HER2, as measured using BIACORE® surface plasmon resonance. FIG. 32A is a sensorgram showing binding kinetics of the wildtype 4D5 IgG TDB; FIG. 32B is a sensorgram showing binding kinetics of the 4D5 H91A-IgG TDB; FIG. 32C is a sensorgram showing binding kinetics of the 4D5 Y55E.H91A-IgG TDB; FIG. 32D is a sensorgram showing binding kinetics of the 4D5 Y55E.D98A.F100A.Y102V-IgG TDB; FIG. 32E is a sensorgram showing binding kinetics of the 4D5 D98A.F100A.Y102V-IgG TDB; FIG. 32F is a sensorgram showing binding kinetics of the 4D5 H91A.D98A.F100A.Y102V-IgG TDB; FIG. 32G is a sensorgram showing binding kinetics of the 4D5 Y55E.H91A.D98A.F100A.Y102V-IgG TDB; FIG. 32H is a sensorgram showing binding kinetics of the 4D5 Y55E.Y102V-IgG TDB; FIG. 32I is a sensorgram showing binding kinetics of the 4D5 Y102V-IgG TDB; FIG. 32J is a sensorgram showing binding kinetics of the 4D5 H91A.Y102V-IgG TDB; and FIG. 32K is a sensorgram showing binding kinetics of the 4D5 Y55E.H91A.Y102V-IgG TDB.

DETAILED DESCRIPTION OF EMBODIMENTS OF THE INVENTION

I. Definitions

Figure 1:
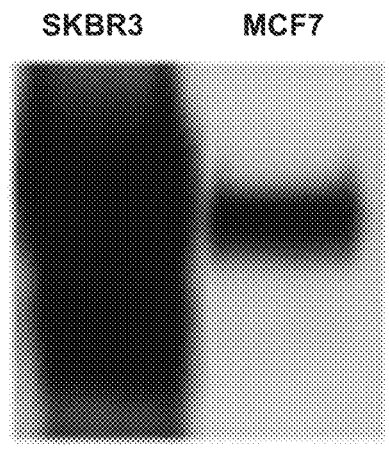
FIG. 1 is an immunoblot showing the relative expression of HER2 protein by SKBR3 cells and MCF7 cells.

The term "about" as used herein refers to the usual error range for the respective value readily known to the skilled person in this technical field. Reference to "about" a value or parameter herein includes (and describes) embodiments that are directed to that value or parameter per se.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the equilibrium dissociation constant ($K_D$). Affinity can be measured by common methods known in the art, including those described herein. Specific illustrative and exemplary embodiments for measuring binding affinity are described in the following.

As used herein, the term "specifically binds to" or is "specific for," as used herein, refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has an equilibrium dissociation constant ($K_D$) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

By "antigen-binding moiety" is meant a part of a compound or a molecule that specifically binds to a target epitope, antigen, ligand, or receptor. Molecules featuring antigen-binding moieties include, but are not limited to, antibodies (e.g., monoclonal, polyclonal, recombinant, humanized, and chimeric antibodies), antibody fragments or portions thereof (e.g., Fab fragments, Fab'2, scFv antibodies, SMIP, domain antibodies, diabodies, minibodies, scFv-Fc, affibodies, nanobodies, and VH and/or VL domains of antibodies), receptors, ligands, aptamers, and other molecules having an identified binding partner. An "affinity matured" antibody refers to an antibody with one or more alterations in one or more hypervariable regions (HVRs), compared to a parent antibody which does not possess such alterations, such alterations resulting in an improvement in the affinity of the antibody for antigen.

As used herein, the term "monovalent," for example, in the context of a monovalent arm of a bispecific antigen-binding molecule, refers to a molecule or a portion thereof (e.g., a portion of an antigen-binding molecule, e.g., one of two arms of a bispecific antigen-binding molecule) that has a single antigen-binding moiety. Thus, a monovalent molecule or portion thereof is capable of specific binding to exactly one antigen. The "monovalent binding affinity" or "monovalent $K_D$" of one of the two antigen-binding moieties of a bivalent arm of a bispecific antibody (e.g., one of the HER2 antigen-binding moieties of a 1Fab-IgG TDB) refers to the binding affinity of the antigen-binding moiety in monovalent form, i.e., as a monovalent arm of a bispecific antibody capable of specific binding to two different antigens or as a Fab molecule.

As used herein, the term "bivalent," for example, in the context of a bivalent arm of a bispecific antigen-binding molecule, refers to a molecule or a portion thereof (e.g., a portion of an antigen-binding molecule, e.g., one of two arms of a bispecific antigen-binding molecule) that has exactly two antigen-binding moieties, each of which is capable of specific binding to an antigen. Thus, a bivalent molecule or portion thereof is capable of specific binding to two antigens or two different epitopes on the same antigen (e.g., two HER2 antigens expressed on the surface of a single tumor cell).

The term "cluster of differentiation 3" or "CD3," as used herein, refers to any native CD3 from any vertebrate source, including mammals such as primates (e.g. humans) and rodents (e.g., mice and rats), unless otherwise indicated, including, for example, CD3ε, CD3γ, CD3α, and CD3β chains. The term encompasses "full-length," unprocessed CD3 (e.g., unprocessed or unmodified CD3ε or CD3γ), as well as any form of CD3 that results from processing in the cell. The term also encompasses naturally occurring variants of CD3, including, for example, splice variants or allelic variants. CD3 includes, for example, human CD3ε protein (NCBI RefSeq No. NP_000724), which is 207 amino acids in length, and human CD3γ protein (NCBI RefSeq No. NP_000064), which is 182 amino acids in length.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one embodiment, the extent of binding of an anti-CD3 antibody to an unrelated, non-CD3 protein is less than about 10% of the binding of the antibody to CD3 as measured, e.g., by a radioimmunoassay (RIA). In certain embodiments, an antibody that binds to CD3 has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-CD3 antibody binds to an epitope of CD3 that is conserved among CD3 from different species.

The terms "Fc region" or "Fc domain" are herein used interchangeably to refer to a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. The term encompasses truncated Fc regions, such as those having a C-terminal truncation (e.g., a AGK truncation, e.g., as described in Hu, et al., Biotechnol. Prog. 2017, 33: 786-794 and Jiang, et al., J. Pharm. Sci. 2016, 105: 2066-2072. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, M D, 1991. A "subunit" of an Fc domain as used herein refers to one of the two polypeptides forming the dimeric Fc domain, i.e. a polypeptide comprising C-terminal constant regions of an immunoglobulin heavy chain, capable of stable self-association. In one embodiment, a subunit of an IgG Fc domain comprises an IgG CH2 and an IgG CH3 constant domain.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full-length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Nat. Acad. Sci. USA, 103:3557-3562 (2006) regarding human antibodies generated via a human B-cell hybridoma technology.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 Daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-10$^1$ (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-10$^1$ (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., Nature 352:624-628 (1991).

An "immunoconjugate" is an antibody conjugated to one or more heterologous molecule(s), including but not limited to a cytotoxic agent.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.OD. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

As used herein, the term "liability fix" (and any grammatical derivation thereof) refers to an amino acid substitution configured to enhance the chemical stability of the antibody (e.g., reduced rate of deamidation and/or isomerization), for example, by replacing an amino acid residue prone to deamidation or isomerization with a comparably inert amino acid residue or by replacing an amino acid flanking the residue prone to deamination or isomerization with a comparably inert amino acid residue. Examples of liability fixes to reduce deamidation include substitution of asparagine with serine or glutamic acid (e.g., N30S or N54E). Examples of liability fixes to reduce isomerization include substitution of aspartic acid with alanine or threonine (e.g., D98A or D98T).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-CD3 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "package insert" is used to refer to instructions customarily included in commercial packages of therapeutic products, that contain information about the indications, usage, dosage, administration, combination therapy, contraindications and/or warnings concerning the use of such therapeutic products.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "administering" is meant a method of giving a dosage of a compound (e.g., an anti-CD3 antibody of the invention or a nucleic acid encoding an anti-CD3 antibody of the invention) or a composition (e.g., a pharmaceutical composition, e.g., a pharmaceutical composition including an anti-CD3 antibody of the invention) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The method of administration can vary depending on various factors (e.g., the compound or composition being administered and the severity of the condition, disease, or disorder being treated).

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

As used herein, "delaying progression" of a disorder or disease means to defer, hinder, slow, retard, stabilize, and/or postpone development of the disease or disorder (e.g., a cell proliferative disorder, e.g., cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

By "reduce" or "inhibit" is meant the ability to cause an overall decrease, for example, of 20% or greater, of 50% or greater, or of 75%, 85%, 90%, 95%, or greater. In certain embodiments, reduce or inhibit can refer to the effector function of an antibody that is mediated by the antibody Fc region, such effector functions specifically including complement-dependent cytotoxicity (CDC), antibody-dependent cellular cytotoxicity (ADCG), and antibody-dependent cellular phagocytosis (ADCP).

A "subject" or an "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the subject or individual is a human.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is a tumor.

The terms "cancer" and "cancerous" refer to or describe the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, 1, or 2 cancer. Examples of a cancer include, but are not limited to, breast cancer, gastric cancer, colorectal cancer, non-small cell lung cancer, non-Hodgkin's lymphoma (NHL), B cell lymphoma, B cell leukemia, multiple myeloma, renal cancer, prostate cancer, liver cancer, head and neck cancer, melanoma, ovarian cancer, mesothelioma, glioblastoma, germinal-center B-cell-like (GCB) diffuse large B cell lymphoma (DLBCL), activated B cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenström macroglobulinemia (WM), central nervous system lymphoma (CNSL), Burkitt's lymphoma (BL), B cell prolymphocytic leukemia, splenic marginal zone lymphoma, hairy cell leukemia, splenic lymphoma/leukemia, splenic diffuse red pulp small B cell lymphoma, hairy cell leukemia variant, a heavy chain disease, γ heavy chain disease, μ heavy chain disease, plasma cell myeloma, solitary plasmacytoma of bone, extraosseous plasmacytoma, extranodal marginal zone lymphoma of mucosa-associated lymphoid tissue (MALT lymphoma), nodal marginal zone lymphoma, pediatric nodal marginal zone lymphoma, pediatric follicular lymphoma, primary cutaneous follicle centre lymphoma, T cell/histiocyte rich large B cell lymphoma, primary DLBCL of the central nervous system, primary cutaneous DLBCL (leg type), Epstein-Barr virus (EBV)-positive DLBCL of the elderly, DLBCL associated with chronic inflammation, lymphomatoid granulomatosis, primary mediastinal (thymic) large B cell lymphoma, intravascular large B cell lymphoma, anaplastic lymphoma kinase (ALK)-positive large B cell lymphoma, plasmablastic lymphoma, large B cell lymphoma arising in HHV8-associated multicentric Castleman disease, primary effusion lymphoma, large B cell lymphoma, unclassifiable, with features intermediate between diffuse large B-cell lymphoma and Burkitt lymphoma, or large B cell lymphoma, unclassifiable, with features intermediate between diffuse large B-cell lymphoma and classical Hodgkin lymphoma)). In some embodiments, the cancer is a HER2-positive cancer (e.g., a HER2-positive breast cancer or a HER2-positive gastric cancer).

The term "HER2-positive" cancer comprises cancer cells which have higher than normal levels of HER2. Examples of HER2-positive cancer include HER2-positive breast cancer and HER2-positive gastric cancer. Optionally, HER2-positive cancer has an immunohistochemistry (IHC) score of 2+ or 3+ and/or an in situ hybridization (ISH) amplification ratio ≥2.0.

The term "tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The term "tumor antigen," as used herein, may be understood as those antigens that are presented on tumor cells. These antigens can be presented on the cell surface with an extracellular part, which is often combined with a transmembrane and cytoplasmic part of the molecule. These antigens can sometimes be presented only by tumor cells and never by the normal ones. Tumor antigens can be exclusively expressed on tumor cells or might represent a tumor specific mutation compared to normal cells. In this case, they are called tumor-specific antigens. More common are tumor antigens that are presented by tumor cells and normal cells, and they are called tumor-associated antigens. These tumor-associated antigens can be overexpressed compared to normal cells or are accessible for antibody binding in tumor cells due to the less compact structure of the tumor tissue compared to normal tissue.

An "effective amount" of a compound, for example, a bispecific antigen-binding molecule of the invention or a composition (e.g., pharmaceutical composition) thereof, is at least the minimum amount required to achieve the desired therapeutic or prophylactic result, such as a measurable improvement or prevention of a particular disorder (e.g., a cell proliferative disorder, e.g., cancer). An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

The term "PD-1 axis binding antagonist" refers to a molecule that inhibits the interaction of a PD-1 axis binding partner with one or more of its binding partners, so as to remove T cell dysfunction resulting from signaling on the PD-1 signaling axis, with a result being restored or enhanced T cell function. As used herein, a PD-1 axis binding antagonist includes a PD-1 binding antagonist and a PD-L1 binding antagonist, as well as molecules that interfere with the interaction between PD-L1 and PD-1 (e.g., a PD-L2-Fc fusion).

As used herein, a "PD-1 binding antagonist" is a molecule that decreases, blocks, inhibits, abrogates or interferes with signal transduction resulting from the interaction of PD-1 with one or more of its binding partners, such as PD-L1 and/or PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies and antigen-binding fragments thereof, immunoadhesins, fusion proteins, oligopeptides, small molecule antagonists, polynucleotide antagonists, and other molecules that decrease, block, inhibit, abrogate or interfere with signal transduction resulting from the interaction of PD-1 with PD-L1 and/or PD-L2. In one embodiment, a PD-1 binding antagonist reduces the negative signal mediated by or through cell surface proteins expressed on T lymphocytes and other cells through PD-1 or PD-L1 so as to render a dysfunctional T-cell less dysfunctional. In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (pembrolizumab) described herein. In another specific aspect, a PD-1 binding antagonist is CT-011 (pidilizumab) described herein. In another specific aspect, a PD-1 binding antagonist is MEDI-0680 (AMP-514). In another specific aspect, a PD-1 binding antagonist is PDR001 (spartalizumab). In another specific aspect, a PD-1 binding antagonist is REGN2810 (cemiplimab). In another specific aspect, a PD-1 binding antagonist is BGB-108. In another specific aspect, a PD-1 binding antagonist is AMP-224 described herein.

As used herein, a "PD-L1 binding antagonist" is a molecule that decreases, blocks, inhibits, abrogates or interferes with signal transduction resulting from the interaction of PD-L1 with either one or more of its binding partners, such as PD-1 and/or B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, PD-L1 binding antagonists include anti-PD-L1 antibodies and antigen-binding fragments thereof, immunoadhesins, fusion proteins, oligopeptides, small molecule antagonists, polynucleotide antagonists, and other molecules that decrease, block, inhibit, abrogate or interfere with signal transduction resulting from the interaction of PD-L1 with one or more of its binding partners, such as PD-1 and/or B7-1. In one embodiment, a PD-L1 binding antagonist reduces the negative signal mediated by or through cell surface proteins expressed on T lymphocytes and other cells through PD-L1 or PD-1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is atezolizumab (CAS Registry Number: 1422185-06-5), also known as MPDL3280A, described herein. In still another specific aspect, an anti-PD-L1 antibody is MEDI4736 (druvalumab) described herein. In still another specific aspect, an anti-PD-L1 antibody is MSB0010718C (avelumab) described herein.

The terms "Programmed Death Ligand 1" and "PD-L1" refer herein to a native sequence PD-L1 polypeptide, polypeptide variants (i.e., PD-L1 polypeptide variants), and fragments of a native sequence polypeptide and polypeptide variants (which are further defined herein). The PD-L1 polypeptide described herein may be that which is isolated from a variety of sources, such as from human tissue types or from another source, or prepared by recombinant or synthetic methods.

A "native sequence PD-L1 polypeptide" comprises a polypeptide having the same amino acid sequence as the corresponding PD-L1 polypeptide derived from nature.

A "PD-L1 polypeptide variant," or variations thereof, means a PD-L1 polypeptide, generally an active PD-L1 polypeptide, as defined herein having at least about 80% amino acid sequence identity with any of the native sequence PD-L1 polypeptide sequences as disclosed herein. Such PD-L1 polypeptide variants include, for instance, PD-L1 polypeptides wherein one or more amino acid residues are added, or deleted, at the N- or C-terminus of a native amino acid sequence. Ordinarily, a PD-L1 polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a native sequence PD-L1 polypeptide sequence as disclosed herein. Ordinarily, PD-L1 polypeptide variants are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 281, 282, 283, 284, 285, 286, 287, 288, or 289 amino acids in length, or more. Optionally, PD-L1 polypeptide variants will have no more than one conservative amino acid substitution as compared to a native PD-L1 polypeptide sequence, alternatively no more than 2, 3, 4, 5, 6, 7, 8, 9, or 10 conservative amino acid substitutions as compared to a native PD-L1 polypeptide sequence.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen-binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

II. Compositions

In one aspect, the invention is based, in part, on bispecific antigen-binding molecules (e.g., bispecific antibodies). In certain embodiments, the bispecific antigen-binding molecules have a monovalent arm capable of specific binding to a first antigen (e.g., a T cell antigen, e.g., CD3) and a bivalent arm capable of specific binding to two additional antigens (e.g., tumor antigens, e.g., two HER2 antigens). For example, the bivalent arm may comprise two antigen-binding moieties, each capable of specific binding to a target antigen (e.g., HER2) to increase the avidity of the bispecific antigen-binding molecule to a cell expressing high levels of the target antigen. Bispecific antigen-binding molecules of the invention are useful, for example, for treating or delaying the progression of a cell proliferative disorder (e.g., cancer) or an autoimmune disorder, or for enhancing immune function in a subject having such a disorder.

Figure 35A:
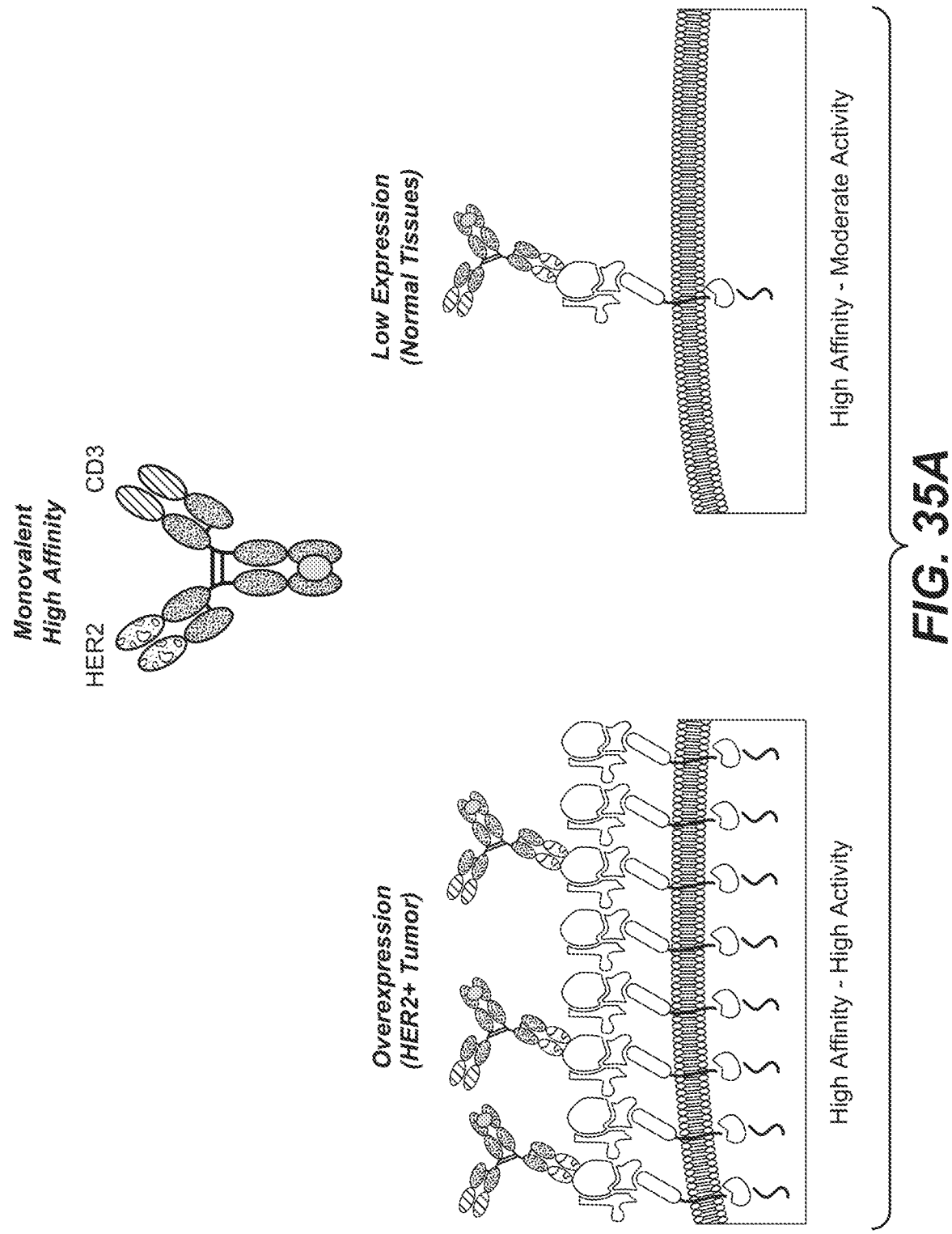
FIG. 35A is a schematic representation showing binding and activity of anti-HER2-CD3 IgG-TDBs with monovalent high affinity binding.
Figure 35B:
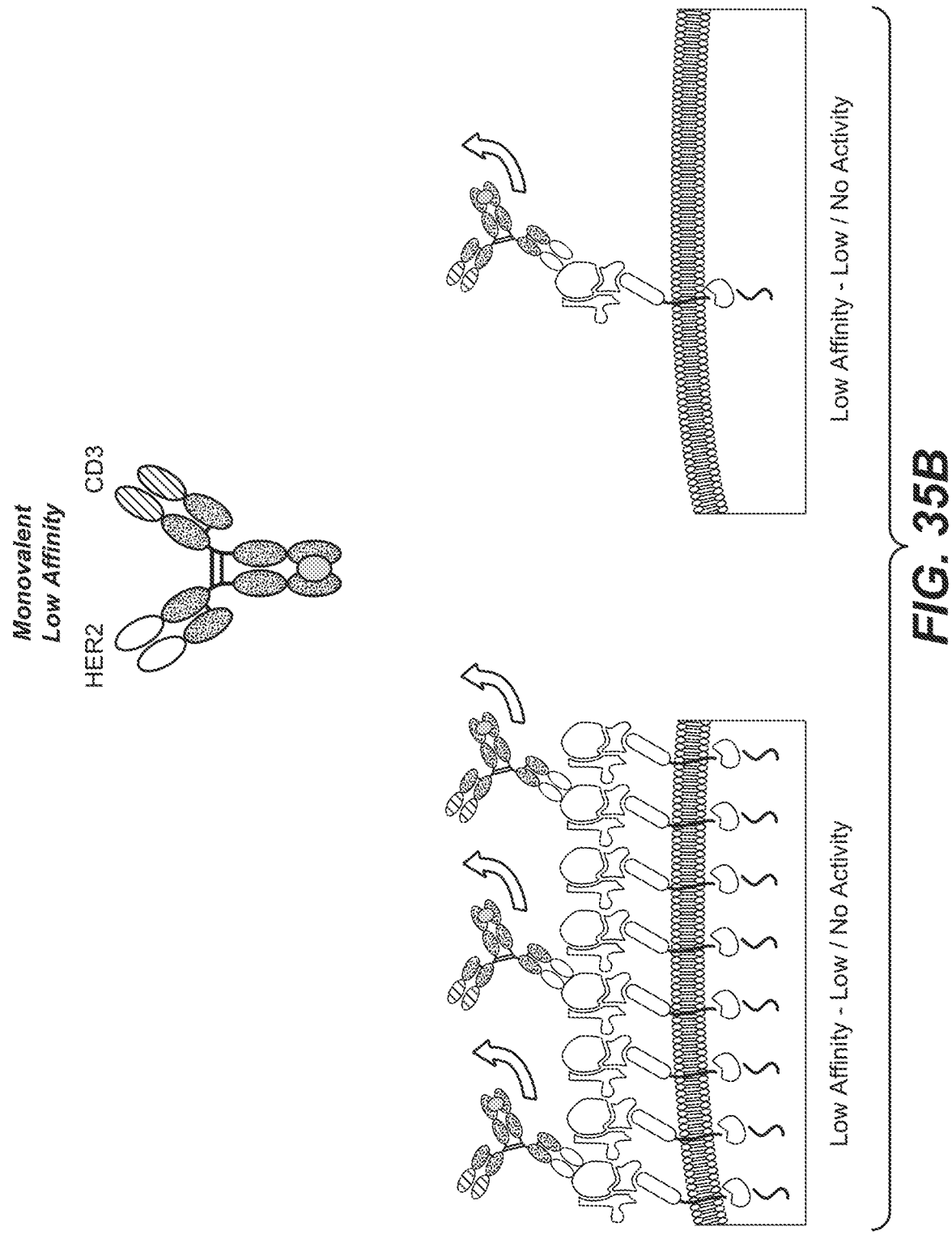
FIG. 35B is a schematic representation showing binding and activity of anti-HER2-CD3 IgG-TDBs with monovalent low affinity binding.
Figure 35C:
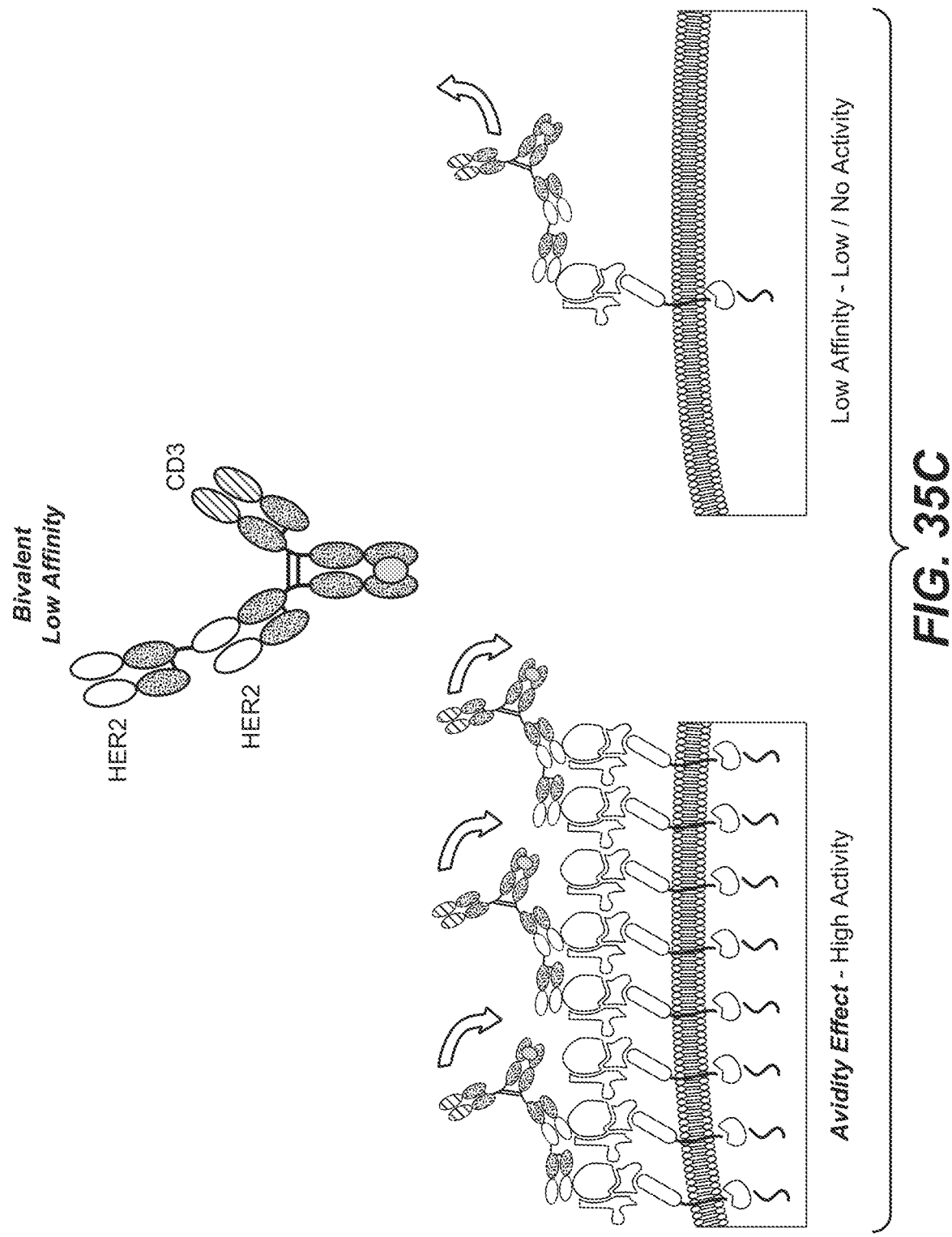
FIG. 35C is a schematic representation showing that bivalent HER2 binding at appropriate affinity (monovalent KD 20-50 nM) results in high binding to HER2-overexpressing cells due to avidity of the anti-HER2-CD3 1Fab-IgG TDB.

The 1Fab-IgG TDBs of the present invention selectively kill tumor cells which overexpress the targeted tumor antigen with high potency, while sparing cells that express low amounts of the targeted tumor antigen, e.g., cells of normal or healthy human tissues. Selectivity is based on the avidity of two low affinity anti-tumor antigen Fab arms to high target density on cells that overexpress the tumor antigen. The increased selectivity to the tumor antigen overexpressing cells mitigates the on-target adverse effects of TDB. For example, using HER2 as the targeted tumor antigen, anti-HER2-IgG TDB with monovalent high affinity binding to HER2 bind to both HER2 over-expressing cells and cells that express low level of HER2. Therapeutic index of this TDB is based on higher activity on HER2 over-expressing cells due to high HER2 density. At high TDB doses, high affinity IgG1 HER2-TDB can affect cells that express low level of HER2 and has therefore risk of on-target off-tumor autoimmunity on normal tissues (FIG. 35A). Engineering the HER2 binding arm to have lower affinity results in lower binding and TDB activity in both HER2 over-expressing cells and cells that express low level of HER2, but does not improve selectivity (FIG. 35B). Bivalent HER2 binding at appropriate affinity (monovalent $K_D$ ~20-50 nM) results in high binding to HER2-over-expressing cells due to avidity of the anti-HER2 1 Fab-IgG TDB. The avidity effect is dependent on high HER2 density, and 1Fab-IgG TDB therefore does not bind to cells expressing low levels of HER2, e.g., cells of normal or healthy human tissues. As cell-binding correlates with the ability of TDBs to recruit T cell activity, the anti-HER2 1 Fab-IgG TDB selectively kills only cells that over express HER2 and has reduced risk of inducing on-target off-tumor autoimmunity on normal tissues (FIG. 35C).

Exemplary Bispecific Antigen-Binding Molecules

In one aspect, the invention provides isolated bispecific antigen-binding molecules (e.g., bispecific antibodies) having a monovalent arm and a bivalent arm. For example, in one aspect, the invention provides a bispecific antigen-binding molecule having a monovalent arm and a bivalent arm, wherein (a) the monovalent arm comprises a first antigen-binding moiety, and (b) the bivalent arm comprises a second antigen-binding moiety and a third antigen-binding moiety. In some embodiments, the C-terminus of the first antigen-binding moiety is fused to the N-terminus of a first Fc subunit, the C-terminus of the third antigen-binding moiety is fused to the N-terminus of the second antigen-binding moiety, and the C-terminus of the second antigen-binding moiety is fused to an N-terminus of a second Fc subunit. In some embodiments, the first Fc subunit is associated with the second Fc subunit to form an Fc domain. In some embodiments, the first antigen-binding moiety is capable of specific binding to a first target cell antigen, and the second antigen-binding moiety and the third antigen-binding moiety are each capable of specific binding to a second target cell antigen (e.g., at the same epitope or at different epitopes on the second target cell antigen).

The first antigen-binding moiety may be a Fab molecule (Fab$_A$) comprising a variable heavy chain (VH$_A$) region and a variable light chain (VL$_A$) region; the second antigen-binding moiety may be a Fab molecule (Fab$_{B1}$) comprising a variable heavy chain (VH$_{B1}$) region and a variable light chain (VL$_{B1}$) region; and/or the third antigen-binding moiety may be a Fab molecule (Fab$_{B2}$) comprising a variable heavy chain (VH$_{B2}$) region and a variable light chain (VL$_{B2}$) region. Thus, in some instances, the first antigen-binding moiety may be a Fab$_A$ comprising a VH$_A$ region and a VL$_A$ region, the second antigen-binding moiety may be a Fab$_{B1}$ comprising a VH$_{B1}$ region and a VL$_{B1}$ region, and third antigen-binding moiety may be a Fab$_{B2}$ comprising a VH$_{B2}$ region and a VL$_{B2}$ region. The VH$_{B1}$ and the VH$_{B2}$ may share at least 95% sequence identity (e.g., 95%, 96%, 97%, 98%, 99%, or 100% sequence identity). Additionally or alternatively, the VL$_{B1}$ and the VL$_{B2}$ may share at least 95% sequence identity (e.g., 95%, 96%, 97%, 98%, 99%, or 100% sequence identity).

A 1Fab-IgG molecule refers to a bispecific antigen-binding molecule having a first antigen binding moiety, a second antigen-binding moiety, and a third antigen-binding moiety, wherein the first antigen-binding moiety is a Fab$_A$ comprising a VH$_A$ region and a VL$_A$ region, the second antigen-binding moiety is a Fab$_{B1}$ comprising a VH$_{B1}$ region and a VL$_{B1}$ region, and the third antigen-binding moiety is a Fab$_{B2}$ comprising a VH$_{B2}$ region and a VL$_{B2}$ region, wherein the VH$_{B1}$ and the VH$_{B2}$ share at least 95% sequence identity (e.g., 95%, 96%, 97%, 98%, 99%, or 100% sequence identity), and the VL$_{B1}$ and the VL$_{B2}$ share at least 95% sequence identity (e.g., 95%, 96%, 97%, 98%, 99%, or 100% sequence identity). 1Fab-IgG molecules have a monovalent arm comprising the first antigen-binding moiety that binds a first target antigen and a bivalent arm comprising the second and third antigen-binding moieties, wherein each of the second and third antigen-binding molecules specifically bind a second target cell antigen. In some embodiments, a 1Fab-IgG molecule is a 1Fab-IgG T-cell dependent bispecific molecule (1Fab-IgG TDB) where the monovalent arm specifically binds an antigen on the surface of a T cell, and each antigen-binding moiety of the bivalent arm specifically binds an antigen on the surface of a second target cell (e.g., a tumor cell). As with a TDB with a standard bivalent IgG format (IgG TDB), 1Fab-IgG TDBs recruit cytolytic T cells to kill the cells expressing the targeted antigen.

For example, an anti-CD3/HER2 1 Fab-IgG TDB has a monovalent arm that specifically binds CD3 (e.g., a CD3 molecule on the surface of a T cell) and a bivalent arm that has two antigen-binding moieties that each specifically bind HER2 (e.g., a HER2 molecule on the surface of a tumor cell). The two antigen-binding moieties on the bivalent arm may bind the same epitope, or each antigen-binding moiety on the bivalent arm may bind a different epitope on the same antigen. In one embodiment, the bivalent arm binds to the same epitope as 4D5. In one embodiment, the bivalent arm binds to domain IV of HER2. In one embodiment, the antigen-binding moiety on the monovalent arm, specific for CD3, is a 40G5c Fab, and each of the two antigen-binding moieties on the bivalent arm, specific for HER2, is a variant of a 4D5 Fab. Particular embodiments are exemplified herein.

The bispecific antigen-binding molecules of the invention can provide increased sensitivity to cells that preferentially express a high density of antigen (e.g., tumor antigen), which, in many cases, reduces damage to healthy tissues (e.g., by activating T cells to engage tumor cells rather than healthy cells expressing low levels of tumor antigen). Accordingly, in some embodiments, a tumor antigen is expressed on (a) a tumor cell in a subject and (b) at least one type of non-tumor cell in the subject (e.g., at a lower density than its expression on tumor cells). In some embodiments, the ratio of tumor antigen copy number on the non-tumor cells to the tumor cells is from 1:2 to 1:1,000,000 (e.g., from 1:3 to 1:500,000, from 1:4 to 1:100,000, from 1:5 to 1:50,000, from 1:6 to 1:40,000, from 1:7 to 1: 20,000, from 1:8 to 1:10,000, from 1:9 to 1:5,000, from 1:10 to 1:1,000, from 1:20 to 1:500, from 1:50 to 1:400, or from 1:100 to 1:200, e.g., from 1:2 to 1:10, from 1:10 to 1:20, from 1:20 to 1:50, from 1:50 to 1:100, from 1:100 to 1:200, from 1:200 to 1:300, from 1:300 to 1:400, from 1:400 to 1:500, from 1:500 to 1:600, from 1:600 to 1:700, from 1:700 to 1:800, from 1:800 to 1:900, from 1:900 to 1:1,000, from 1:1,000 to 1:5,000, from 1:5,000 to 1:10,000, from 1:10,000 to 1:50,000, from 1:50,000 to 1:100,000, from 1:100,000 to 1:500,000, or from 1:500,000 to 1:1,000,000, e.g., about 1:2, about 1:3, about 1:4, about 1:5, about 1:6, about 1:7, about 1:8, about 1:9, about 1:10, about 1:15, about 1:20, about 1:25, about 1:30, about 1:35, about 1:40, about 1:50, about 1:60, about 1:70, about 1:80, about 1:90, about 1:100, about 1:125, about 1:150, about 1:175, about 1:200, about 1:300, about 1:400, about 1:500, about 1:1,000, about 1:10,000, about 1:100,000, or about 1:1,000,000).

In some embodiments, the tumor antigen copy number on a non-tumor cell is from $10^1$ to $10^6$ (e.g., from $10^1$ to $10^6$, from $10^1$ to $10^5$, from $10^1$ to $10^4$, from $10^1$ to $10^3$, from $10^1$ to $10^2$, from $10^2$ to $10^6$, from $10^2$ to $10^5$, from $10^2$ to $10^4$, from $10^2$ to $10^3$, from $10^3$ to $10^6$, from $10^3$ to $10^5$, from $10^3$ to $10^4$, from $10^4$ to $10^6$, from $10^4$ to $10^5$, or from $10^5$ to $10^6$, e.g., about $10^1$, $10^2$, $10^3$, $10^4$, $10^5$, or $10^6$). In some embodiments, the tumor antigen copy number on a tumor cell is from $10^2$ to $10^7$ (e.g., from $10^2$ to $10^7$, from $10^2$ to $10^6$, from $10^2$ to $10^5$, from $10^2$ to $10^4$, from $10^2$ to $10^3$, from $10^3$ to $10^7$, from $10^3$ to $10^6$, from $10^3$ to $10^5$, from $10^3$ to $10^4$, from $10^4$ to $10^7$, from $10^4$ to $10^6$, from $10^4$ to $10^5$, from $10^5$ to $10^7$, from $10^5$ to $10^6$, or from $10^6$ to $10^7$, e.g., about $10^2$, $10^3$, $10^4$, $10^5$, $10^6$, or 107).

In some embodiments, the tumor antigen copy number is from $10^1$ to $10^6$ on a non-tumor cell and from $10^2$ to $10^8$ on a tumor cell (e.g., from $10^2$ to $10^5$ on a non-tumor cell and from $10^3$ to $10^7$ on a tumor cell, from $10^2$ to $10^5$ on a non-tumor cell and from $10^4$ to $10^7$ on a tumor cell, from $10^3$ to $10^5$ on a non-tumor cell and from $10^5$ to $10^7$ on a tumor cell, from $10^3$ to $10^4$ on a non-tumor cell and from $10^5$ to $10^6$ on a tumor cell, or from $10^4$ to $10^5$ on a non-tumor cell and from $10^6$ to $10^7$ on a tumor cell).

In some embodiments, the tumor antigen copy number (e.g., average tumor antigen copy number, e.g., HER2 copy number, e.g., average HER2 copy number) is from $10^1$ to $2.0 \times 10^5$ on a non-tumor cell and at least $2.0 \times 10^5$ on a tumor cell.

Tumor cells bound by an antigen-binding molecule of the present invention may express HER2 at a copy number (e.g., an average copy number) of at least 200,000 per cell (e.g., at least 250,000 HER2 copies per cell, at least 300,000 HER2 copies per cell, at least 400,000 HER2 copies per cell, at least 500,000 HER2 copies per cell, at least 600,000 HER2 copies per cell, at least 700,000 HER2 copies per cell, at least 750,000 HER2 copies per cell, at least 800,000 HER2 copies per cell, at least 900,000 HER2 copies per cell, at least 1,000,000 HER2 copies per cell, at least 1,200,000 HER2 copies per cell, at least 1,500,000 HER2 copies per cell, at least 2,000,000 HER2 copies per cell, at least 2,500,000 HER2 copies per cell, at least 3,000,000 HER2 copies per cell, or more, e.g., from 200,000 to 3,000,000 HER2 copies per cell, from 250,000 to 2,500,000 HER2 copies per cell, from 300,000 to 2,000,000 HER2 copies per cell, from 400,000 to 1,500,000 HER2 copies per cell, or from 500,000 to 1,000,000 HER2 copies per cell, e.g., from 200,000 to 1,000,000 HER2 copies per cell (e.g., from 200,000 to 250,000 HER2 copies per cell, from 250,000 to 300,000 HER2 copies per cell, from 300,000 to 400,000 HER2 copies per cell, from 400,000 to 500,000 HER2 copies per cell, from 500,000 to 750,000 HER2 copies per cell, or from 750,000 to 1,000,000 HER2 copies per cell) or from 1,000,000 to 3,000,000 HER2 copies per cell (e.g., from 1,000,000 to 1,500,000 HER2 copies per cell, from 1,500,000 to 2,000,000 HER2 copies per cell, from 2,000,000 to 2,500,000 HER2 copies per cell, or from 2,500,000 to 3,000,000 HER2 copies per cell). Thus, HER2-positive tumor cells having any of the aforementioned HER2 expression characteristics may be preferentially killed (e.g., selectively killed) by T cells upon binding of an antigen-binding molecule of the present invention, relative to non-tumor cells that have little or no HER2 expression (e.g., less than 200,000 HER2 copies per cell, e.g., from 0 to 200,000 HER2 copies per cell, from 0 to 150,000 HER2 copies per cell, from 0 to 100,000 HER2 copies per cell, from 0 to 50,000 HER2 copies per cell, from 0 to 20,000 HER2 copies per cell, from 0 to 10,000 HER2 copies per cell, from 0 to 5,000 HER2 copies per cell, or from 0 to 1,000 HER2 copies per cell).

Tumor antigen copy number (e.g., average tumor antigen copy number, e.g., HER2 copy number, e.g., average HER2 copy number) can be quantified using any suitable means known in the art or described herein. For example, HER2 copy number can be quantified using fluorescence quantitation by flow cytometry (e.g., using beads of known Molecules of Equivalent Soluble Fluorochrome (MESF)).

In some embodiments, the monovalent binding affinity ($K_D$) of the second antigen-binding moiety and/or the third antigen-binding moiety is from 10 nM to 100 nM (e.g., from 20 nM to 90 nM, from 30 nM to 80 nM, from 40 nM to 60 nM, e.g., from 25 nM to 55 nM). In one embodiment, the monovalent binding affinity ($K_D$) of the second antigen-binding moiety and/or the third antigen-binding moiety is from 20 nM to 50 nM. In one embodiment, the monovalent binding affinity ($K_D$) of the second antigen-binding moiety and the third antigen-binding moiety is from 20 nM to 50 nM.

In some embodiments, the monovalent dissociation rate of the second antigen-binding moiety and/or the third antigen-binding moiety is from $10^{-3}$/second to $10^{-1}$/second (e.g., from $10^{-2}$/second to $30^{-2}$/second).

In some embodiments, a first target antigen is an activating T cell antigen, such as CD3. Various T cell antigen-binding moieties are known in the art and suitable for use as part of the present invention. For example, in certain embodiments of the present invention, a suitable first antigen-binding moiety is the antibody clone 40G5c, or a fragment and/or variant thereof, e.g., as described in U.S. Publication No. 2015/0166661, which is incorporated herein by reference in its entirety. In particular embodiments, the first antigen-binding moiety is an anti-CD3 Fab (e.g., 40G5c) comprising an HVR-H1 of SEQ ID NO: 1, an HVR-H2 of SEQ ID NO: 2, an HVR-H3 of SEQ ID NO: 3, an HVR-L1 of SEQ ID NO: 4, an HVR-L2 of SEQ ID NO: 5, and an HVR-L3 of SEQ ID NO: 6. In some embodiments, the first antigen-binding moiety is an anti-CD3 Fab (e.g., 40G5c) comprising a VH of SEQ ID NO: 7 and a VL of SEQ ID NO: 8. Amino acid sequences of 40G5c are also provided in Table 1.

TABLE 1

SEQ ID NOs corresponding to hypervariable region (HVR) and variable region heavy (VH) and light (VL) chain amino acid sequences for exemplary antibody clones.

|  | HVR | | | | | | V | |
| --- | --- | --- | --- | --- | --- | --- | --- | --- |
|  | H1 | H2 | H3 | L1 | L2 | L3 | VH | VL |
| 40G5c | 1 | 2 | 3 | 4 | 5 | 6 | 7 | 8 |
| 4D5 Consensus | 11 | 12 | 13 | 14 | 15 | 16 | 17 | 18 |
| 4D5 Wildtype (trastuzumab) | 11 | 19 | 20 | 21 | 22 | 23 | 24 | 25 |
| 4D5-H91A | 11 | 19 | 20 | 21 | 22 | 26 | 24 | 27 |
| 4D5-Y55E.Y102V | 11 | 19 | 28 | 21 | 29 | 23 | 30 | 31 |
| 4D5-D98A.F100A.Y102V | 11 | 19 | 32 | 21 | 22 | 23 | 33 | 25 |
| 4D5-D98T.F100A.Y102V | 11 | 19 | 34 | 21 | 22 | 23 | 35 | 25 |
| 4D5-N30S.N54E.D98T | 11 | 36 | 37 | 38 | 22 | 23 | 39 | 40 |
| 4D5-N30S.H91A.N54E.D98T | 11 | 36 | 37 | 38 | 22 | 26 | 41 | 42 |
| 4D5-H91A.N54E.D98T | 11 | 36 | 37 | 21 | 22 | 26 | 41 | 27 |
| 4D5-N30S.Y55E.N54E.D98T.Y102V | 11 | 36 | 43 | 38 | 29 | 23 | 44 | 45 |
| 4D5-N30S | 11 | 19 | 20 | 38 | 22 | 23 | 24 | 40 |
| 4D5-N54E.D98T | 11 | 36 | 37 | 21 | 22 | 23 | 41 | 25 |
| 4D5-N30S.N54E.D98T.F100A.Y102V | 11 | 36 | 34 | 38 | 22 | 23 | 46 | 40 |
| 4D5-N30S.N54E.D98A.F100A.Y102V | 11 | 36 | 32 | 38 | 22 | 23 | 47 | 40 |
| 4D5-Y55E.H91A.N54E.D98T | 11 | 36 | 37 | 21 | 29 | 26 | 41 | 48 |
| 4D5-Y55E.H91A.N54E.D98T.Y102V | 11 | 36 | 43 | 21 | 29 | 26 | 44 | 48 |
| 4D5-N30S.Y55E.H91A.N54E.D98T | 11 | 36 | 37 | 38 | 29 | 26 | 41 | 49 |
| 4D5-N30S.Y55E.H91A.N54E.D98T.Y102V | 11 | 36 | 43 | 38 | 29 | 26 | 44 | 49 |
| 4D5-Y102V | 11 | 19 | 28 | 21 | 22 | 23 | 30 | 25 |
| 4D5-N30A.H91A | 11 | 19 | 20 | 53 | 22 | 26 | 24 | 54 |
| 4D5-Y55E.H91A | 11 | 19 | 20 | 21 | 29 | 26 | 24 | 48 |
| 4D5-D98A.F100A.Y102V | 11 | 19 | 32 | 21 | 22 | 23 | 33 | 25 |
| 4D5-Y55E.D98A.F100A.Y102V | 11 | 19 | 32 | 21 | 29 | 23 | 33 | 31 |

In some embodiments, the first antigen-binding moiety binds to a human CD3 polypeptide or a cynomolgus monkey (cyno) CD3 polypeptide. In some embodiments, the human CD3 polypeptide or the cyno CD3 polypeptide is a human CD3ε polypeptide or a cyno CD3ε polypeptide, respectively. In some embodiments, the human CD3 polypeptide or the cyno CD3 polypeptide is a human CD3γ polypeptide or a cyno CD3γ polypeptide, respectively. Additional antigen-binding moieties (e.g., Fab molecules) that bind to CD3 are known in the art and described, for example, in U.S. Publication No. 2015/0166661, and can be adapted for use as part of the present invention.

In some embodiments, the monovalent $K_D$ of the first antigen-binding moiety binds the human CD3ε polypeptide with a $K_D$ of 250 nM or lower. In some embodiments, the anti-CD3 antibody binds the human CD3ε polypeptide with a $K_D$ of 100 nM or lower. In some embodiments, the anti-CD3 antibody binds the human CD3ε polypeptide with a $K_D$ of 15 nM or lower. In some embodiments, the anti-CD3 antibody binds the human CD3ε polypeptide with a $K_D$ of 10 nM or lower. In some embodiments, the anti-CD3 antibody binds the human CD3ε polypeptide with a $K_D$ of 5 nM or lower. In some embodiments, the monovalent $K_D$ of the first antigen-binding moiety is from 10 nM to 100 nM (e.g., from 20 nM to 90 nM, from 20 nM to 80 nM, from 30 nM to 70 nM, or from 40 nM to 60 nM).

In some embodiments, the second target cell antigen is a tumor antigen.

The tumor antigen may be HER2. A suitable second and/or third antigen-binding moiety that binds HER2 is the antibody 4D5, or a fragment and/or variant thereof. Amino acid sequences of 4D5, and substitution variants thereof, are shown in Table 1 and described, for example, in U.S. Publication No. 2015/0166661, which is incorporated herein by reference in its entirety. In one embodiment, the second and/or third antigen-binding moiety binds to the same epitope as the antibody 4D5 (humanized version thereof known as trastuzumab (HERCEPTIN®; Genentech, Inc., South San Francisco, CA), Molina, et al., Cancer Research 2001, 61 (12): 4744-4749). In one embodiment, the second and the third antigen-binding moiety binds to the same epitope as the antibody 4D5.

In one embodiment, the second and/or third antigen-binding moiety binds to the same epitope as the antibody 2C4 (humanized version thereof known as pertuzumab (PERJETA®; Genentech, Inc., South San Francisco, CA), Franklin et al. *Cancer Cell* 2004, 5: 317-328). In one embodiment, the second and the third antigen-binding moiety binds to the same epitope as the antibody 2C4.

In one embodiment, the second and/or third antigen-binding moiety binds to the same epitope as the antibody 7C2 (U.S. Pat. No. 9,518,118). In one embodiment, the second and the third antigen-binding moiety binds to the same epitope as the antibody 7C2.

Figure 36:
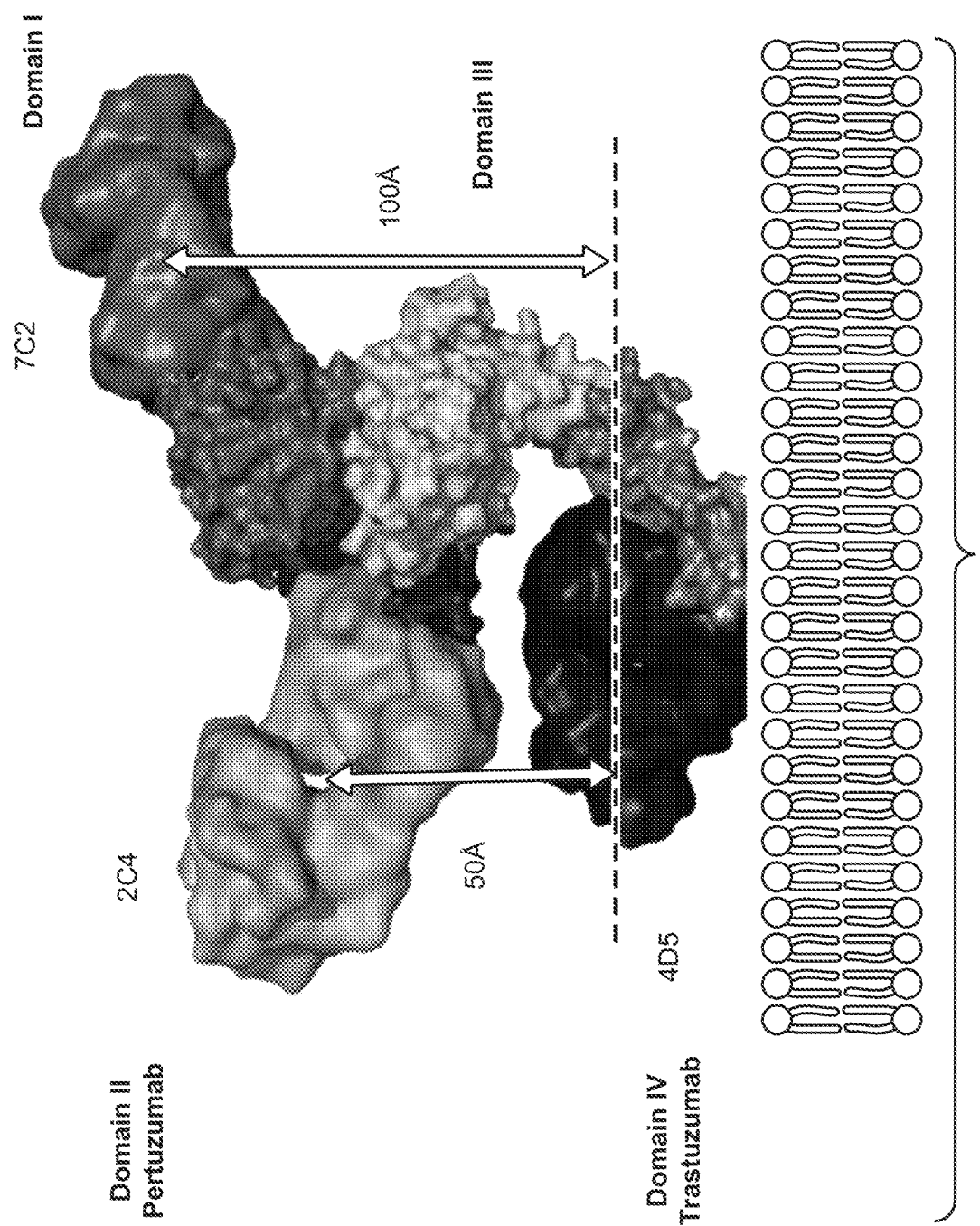
FIG. 36 provides the crystal structure of the HER2 extracellular domain (ECD) and highlights the regions to which the different HER2 antibodies bind.

FIG. 36 provides the crystal structure of the HER2 ECD and highlights the regions to which the different HER2 antibodies bind. 4D5 binds to an epitope in domain IV of HER2 that is the protein region closest to the cellular membrane. 2C4 binds to an epitope in domain II of HER2 that is 50 Angstroms from the region to which hu4D5 binds. 7C2 binds to an epitope in domain I of HER2 that is 100 Angstroms from the HER2 region bound by hu4D5.

In one embodiment, the second and/or third antigen-binding moiety binds to domain IV of HER2.

In one embodiment, the second and the third antigen-binding moiety binds to domain IV of HER2. In one embodiment, the second and/or third antigen-binding moiety binds to domain II of HER2. In one embodiment, the second and the third antigen-binding moiety binds to domain II of HER2.

In one embodiment, the second and/or third antigen-binding moiety binds to domain I of HER2.

In one embodiment, the second and the third antigen-binding moiety binds to domain I of HER2.

In one embodiment, the second-binding moiety binds to domain IV of HER2 and the third antigen-binding moiety binds to domain I of HER2.

In one embodiment, the second-binding moiety binds to domain IV of HER2 and the third antigen-binding moiety binds to domain II of HER2.

In one embodiment, the second-binding moiety binds to domain II of HER2 and the third antigen-binding moiety binds to domain I of HER2.

In some embodiments, the bispecific antigen-binding molecule of any of the preceding embodiments features a $VH_A$ region comprising one, two, or all three of the following HVRs: (a) an HVR-H1 comprising the amino acid sequence of SEQ ID NO: 1, (b) an HVR-H2 comprising the amino acid sequence of SEQ ID NO: 2, or (c) an HVR-H3 comprising the amino acid sequence of SEQ ID NO: 3. In some embodiments, the $VH_A$ region comprises an amino acid sequence having at least 95% sequence identity to SEQ ID NO: 7 (e.g., at least 96% sequence identity to SEQ ID NO: 7, at least 97% sequence identity to SEQ ID NO: 7, at least 98% sequence identity to SEQ ID NO: 7, at least 99% sequence identity to SEQ ID NO: 7, or 100% sequence identity to SEQ ID NO: 7). For example, in some embodiments, the $VH_A$ region comprises the amino acid sequence of SEQ ID NO: 7. In some embodiments, the $VL_A$ region comprises one, two, or all three of the following HVRs: (a) an HVR-L1 comprising the amino acid sequence of SEQ ID NO: 4, (b) an HVR-L2 comprising the amino acid sequence of SEQ ID NO: 5, or (c) an HVR-L3 comprising the amino acid sequence of SEQ ID NO: 6. In some embodiments, the $VL_A$ region comprises an amino acid sequence having at least 95% sequence identity to SEQ ID NO: 8 (e.g., at least 96% sequence identity to SEQ ID NO: 8, at least 97% sequence identity to SEQ ID NO: 8, at least 98% sequence identity to SEQ ID NO: 8, at least 99% sequence identity to SEQ ID NO: 8, or 100% sequence identity to SEQ ID NO: 8). For example, in some embodiments, the $VL_A$ region comprises the amino acid sequence of SEQ ID NO: 8. For example, in some embodiments, the bispecific antigen-binding molecule is an anti-CD3 bispecific antigen-binding molecule (e.g., an anti-CD3/HER2 1 Fab-IgG TDB, e.g., an anti-CD3/HER2 1 Fab-IgG TDB having a 40G5c CD3 binding domain).

In some embodiments, the $VH_A$ comprises the following HVRs: (a) an HVR-H1 comprising the amino acid sequence of SEQ ID NO: 1, (b) an HVR-H2 comprising the amino acid sequence of SEQ ID NO: 2, and (c) an HVR-H3 comprising the amino acid sequence of SEQ ID NO: 3; and the $VL_A$ comprises the following HVRs: (d) an HVR-L1 comprising the amino acid sequence of SEQ ID NO: 4, (e) an HVR-L2 comprising the amino acid sequence of SEQ ID NO: 5, and (f) an HVR-L3 comprising the amino acid sequence of SEQ ID NO: 6. In some embodiments, the $VH_A$ region comprises an amino acid sequence having at least 95% sequence identity to SEQ ID NO: 7 (e.g., at least 96% sequence identity to SEQ ID NO: 7, at least 97% sequence identity to SEQ ID NO: 7, at least 98% sequence identity to SEQ ID NO: 7, at least 99% sequence identity to SEQ ID NO: 7, or 100% sequence identity to SEQ ID NO: 7); and the $VL_A$ region comprises an amino acid sequence having at least 95% sequence identity to SEQ ID NO: 8 (e.g., at least 96% sequence identity to SEQ ID NO: 8, at least 97% sequence identity to SEQ ID NO: 8, at least 98% sequence identity to SEQ ID NO: 8, at least 99% sequence identity to SEQ ID NO: 8, or 100% sequence identity to SEQ ID NO: 8). In some embodiments, the $VH_A$ region comprises the amino acid of SEQ ID NO: 7; and the $VL_A$ region comprises the amino acid sequence of SEQ ID NO: 8. For example, in some embodiments, the bispecific antigen-binding molecule is an anti-CD3 bispecific antigen-binding molecule (e.g., an anti-CD3/HER2 1 Fab-IgG TDB, e.g., an anti-CD3/HER2 1 Fab-IgG TDB having a 40G5c CD3 binding domain).

In some embodiments, the $VH_{B1}$ region and/or the $VH_{B2}$ region comprises an amino acid substitution at one, two, three, or all four residues of N54, D98, F100, and/or Y102, according to the Kabat numbering system. For example, the $VH_{B1}$ region and/or the $VH_{B2}$ region may feature an amino acid substitution at one, two, three, four, or all five of the following residues: N54E, D98A, D98T, F100A, and/or Y102V, according to the Kabat numbering system.

In some embodiments, the $VL_{B1}$ region and/or the $VL_{B2}$ region comprises an amino acid substitution at one, two, or all three residues of N30, Y55, and/or H91, according to the Kabat numbering system. For example, the $VL_{B1}$ region and/or the $VL_{B2}$ region may feature an amino acid substitution at one, two, or all three of the following residues: N30S, Y55E, and/or H91A.

In some embodiments, the bispecific antigen-binding molecule features a $VH_{B1}$ region which comprises one, two, or all three of the following HVRs: (a) an HVR-H1 comprising the amino acid sequence of SEQ ID NO: 11, (b) an HVR-H2 comprising the amino acid sequence of SEQ ID NO: 12, or (c) an HVR-H3 comprising the amino acid sequence of SEQ ID NO: 13. In some embodiments, the $VH_{B1}$ region comprises an amino acid sequence having at least 95% sequence identity to SEQ ID NO: 17 (e.g., at least 96% sequence identity to SEQ ID NO: 17, at least 97% sequence identity to SEQ ID NO: 17, at least 98% sequence identity to SEQ ID NO: 17, at least 99% sequence identity to SEQ ID NO: 17, or 100% sequence identity to SEQ ID NO: 17). For example, in some embodiments, the $VH_{B1}$ region comprises the amino acid sequence of SEQ ID NO: 17. In some embodiments, the $VL_{B1}$ region comprises one, two, or all three of the following HVRs: (a) an HVR-L1 comprising the amino acid sequence of SEQ ID NO: 14, (b) an HVR-L2 comprising the amino acid sequence of SEQ ID NO: 15, or (c) an HVR-L3 comprising the amino acid sequence of SEQ ID NO: 16. In some embodiments, the $VL_{B1}$ region comprises an amino acid sequence having at least 95% sequence identity to SEQ ID NO: 18 (e.g., at least 96% sequence identity to SEQ ID NO: 18, at least 97% sequence identity to SEQ ID NO: 18, at least 98% sequence identity to SEQ ID NO: 18, at least 99% sequence identity to SEQ ID NO: 18, or 100% sequence identity to SEQ ID NO: 18). For example, in some embodiments, the $VL_{B1}$ region comprises the amino acid sequence of SEQ ID NO: 18.

In some embodiments, the $VH_{B1}$ comprises the following HVRs: (a) an HVR-H1 comprising the amino acid sequence of SEQ ID NO: 11, (b) an HVR-H2 comprising the amino acid sequence of SEQ ID NO: 12, and (c) an HVR-H3 comprising the amino acid sequence of SEQ ID NO: 13; and the $VL_{B1}$ comprises the following HVRs: (d) an HVR-L1 comprising the amino acid sequence of SEQ ID NO: 14, (e) an HVR-L2 comprising the amino acid sequence of SEQ ID NO: 15, and (f) an HVR-L3 comprising the amino acid sequence of SEQ ID NO: 16. In some embodiments, the $VH_{B1}$ region comprises an amino acid sequence having at least 95% sequence identity to SEQ ID NO: 17 (e.g., at least 96% sequence identity to SEQ ID NO: 17, at least 97% sequence identity to SEQ ID NO: 17, at least 98% sequence identity to SEQ ID NO: 17, at least 99% sequence identity to SEQ ID NO: 17, or 100% sequence identity to SEQ ID NO: 17); and the $VL_{B1}$ region comprises an amino acid sequence having at least 95% sequence identity to SEQ ID NO: 18 (e.g., at least 96% sequence identity to SEQ ID NO: 18, at least 97% sequence identity to SEQ ID NO: 18, at least 98% sequence identity to SEQ ID NO: 18, at least 99% sequence identity to SEQ ID NO: 18, or 100% sequence identity to SEQ ID NO: 18). For example, in some embodiments, the $VH_{B1}$ region comprises the amino acid of SEQ ID NO: 17; and the $VL_{B1}$ region comprises the amino acid sequence of SEQ ID NO: 18.

In some embodiments, the $VH_{B2}$ region comprises one, two, or all three of the following HVRs: (a) an HVR-H1 comprising the amino acid sequence of SEQ ID NO: 11, (b) an HVR-H2 comprising the amino acid sequence of SEQ ID NO: 12, or (c) an HVR-H3 comprising the amino acid sequence of SEQ ID NO: 13. In some embodiments, the $VH_{B2}$ region comprises an amino acid sequence having at least 95% sequence identity to SEQ ID NO: 17 (e.g., at least 96% sequence identity to SEQ ID NO: 17, at least 97% sequence identity to SEQ ID NO: 17, at least 98% sequence identity to SEQ ID NO: 17, at least 99% sequence identity to SEQ ID NO: 17, or 100% sequence identity to SEQ ID NO: 17). In some embodiments, the $VH_{B2}$ region comprises the amino acid sequence of SEQ ID NO: 17. In some embodiments, the $VL_{B2}$ region comprises one, two, or all three of the following HVRs: (a) an HVR-L1 comprising the amino acid sequence of SEQ ID NO: 14, (b) an HVR-L2 comprising the amino acid sequence of SEQ ID NO: 15, or (c) an HVR-L3 comprising the amino acid sequence of SEQ ID NO: 16. In some embodiments, the $VL_{B2}$ region comprises an amino acid sequence having at least 95% sequence identity to SEQ ID NO: 18 (e.g., at least 96% sequence identity to SEQ ID NO: 18, at least 97% sequence identity to SEQ ID NO: 18, at least 98% sequence identity to SEQ ID NO: 18, at least 99% sequence identity to SEQ ID NO: 18, or 100% sequence identity to SEQ ID NO: 18). In some embodiments, the $VL_{B2}$ region comprises the amino acid sequence of SEQ ID NO: 18.

In some embodiments, the $VH_{B2}$ comprises the following HVRs: (a) an HVR-H1 comprising the amino acid sequence of SEQ ID NO: 11, (b) an HVR-H2 comprising the amino acid sequence of SEQ ID NO: 12, and (c) an HVR-H3 comprising the amino acid sequence of SEQ ID NO: 13; and the $VL_{B2}$ comprises the following HVRs: (d) an HVR-L1 comprising the amino acid sequence of SEQ ID NO: 14, (e) an HVR-L2 comprising the amino acid sequence of SEQ ID NO: 15, and (f) an HVR-L3 comprising the amino acid sequence of SEQ ID NO: 16. In some embodiments, the $VH_{B2}$ region comprises an amino acid sequence having at least 95% sequence identity to SEQ ID NO: 17 (e.g., at least 96% sequence identity to SEQ ID NO: 17, at least 97% sequence identity to SEQ ID NO: 17, at least 98% sequence identity to SEQ ID NO: 17, at least 99% sequence identity to SEQ ID NO: 17, or 100% sequence identity to SEQ ID NO: 17); and the $VL_{B2}$ region comprises an amino acid sequence having at least 95% sequence identity to SEQ ID NO: 18 (e.g., at least 96% sequence identity to SEQ ID NO: 18, at least 97% sequence identity to SEQ ID NO: 18, at least 98% sequence identity to SEQ ID NO: 18, at least 99% sequence identity to SEQ ID NO: 18, or 100% sequence identity to SEQ ID NO: 18). In some embodiments, the $VH_{B2}$ region comprises the amino acid of SEQ ID NO: 17; and the $VL_{B2}$ region comprises the amino acid sequence of SEQ ID NO: 18.

In some embodiments, the VL$_{B1}$ region and/or the VL$_{B2}$ region comprises an amino acid substitution at H91. For example, in some embodiments, the H91 residue is substituted with an amino acid having a nonpolar side chain. In some embodiments, the VL$_{B1}$ region and/or the VL$_{B2}$ region comprises the amino acid substitution of H91A. In some embodiments, the VL$_{B1}$ region and/or the VL$_{B2}$ region comprises an amino acid substitution at Y55. For example, in some embodiments, the Y55 residue is substituted with an amino acid having an acidic side chain. In some embodiments, the VL$_{B1}$ region and/or the VL$_{B2}$ region comprises the amino acid substitution of Y55E. In some embodiments, the VH$_{B1}$ region and/or the VH$_{B2}$ region comprises an amino acid substitution at F100 and/or Y102. For example, in some embodiments, the F100 residue and/or the Y102 residue is substituted with an amino acid having a nonpolar side chain. In some embodiments, the VH$_{B1}$ region and/or the VH$_{B2}$ region comprises the amino acid substitution of F100A and/or Y102V.

In some embodiments of the bispecific antigen-binding moieties, the VL$_{B1}$ region and/or the VLB$_2$ region comprises one or more liability fixed residues, e.g., one or more liability fixed residues comprising the amino acid substitution of N30S. Additionally or alternatively, the VH$_{B1}$ region and/or the VH$_{B2}$ region may feature one or more liability fixed residues, e.g., one or more liability fixed residues comprising one or more an amino acid substitutions selected from the group consisting of N54E, D98A, and D98T.

The bispecific antigen-binding molecule may feature a mutation at residue H91 of the light chain of the second and/or third antigen-binding moiety (e.g., H91A). For example, in some embodiments, the bispecific antigen-binding molecule features a VH$_{B1}$ region which comprises one, two, or all three of the following HVRs: (a) an HVR-H1 comprising the amino acid sequence of SEQ ID NO: 11, (b) an HVR-H2 comprising the amino acid sequence of SEQ ID NO: 19, or (c) an HVR-H3 comprising the amino acid sequence of SEQ ID NO: 20. In some embodiments, the VH$_{B1}$ region comprises an amino acid sequence having at least 95% sequence identity to SEQ ID NO: 24 (e.g., at least 96% sequence identity to SEQ ID NO: 24, at least 97% sequence identity to SEQ ID NO: 24, at least 98% sequence identity to SEQ ID NO: 24, at least 99% sequence identity to SEQ ID NO: 24, or 100% sequence identity to SEQ ID NO: 24). For example, in some embodiments, the VH$_{B1}$ region comprises the amino acid sequence of SEQ ID NO: 24. In some embodiments, the VL$_{B1}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 22, or (c) an HVR-L3 comprising the amino acid sequence of SEQ ID NO: 26. In some embodiments, the VL$_{B1}$ region comprises an amino acid sequence having at least 95% sequence identity to SEQ ID NO: 27 (e.g., at least 96% sequence identity to SEQ ID NO: 27, at least 97% sequence identity to SEQ ID NO: 27, at least 98% sequence identity to SEQ ID NO: 27, at least 99% sequence identity to SEQ ID NO: 27, or 100% sequence identity to SEQ ID NO: 27). For example, in some embodiments, the VL$_{B1}$ region comprises the amino acid sequence of SEQ ID NO: 27.

In some embodiments, the VH$_{B1}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 20; and the VL$_{B1}$ comprises the following HVRs: (d) an HVR-L1 comprising the amino acid sequence of SEQ ID NO: 21, (e) an HVR-L2 comprising the amino acid sequence of SEQ ID NO: 22, and (f) an HVR-L3 comprising the amino acid sequence of SEQ ID NO: 26. In some embodiments, the VH$_{B1}$ region comprises an amino acid sequence having at least 95% sequence identity to SEQ ID NO: 24 (e.g., at least 96% sequence identity to SEQ ID NO: 24, at least 97% sequence identity to SEQ ID NO: 24, at least 98% sequence identity to SEQ ID NO: 24, at least 99% sequence identity to SEQ ID NO: 24, or 100% sequence identity to SEQ ID NO: 24); and the VL$_{B1}$ region comprises an amino acid sequence having at least 95% sequence identity to SEQ ID NO: 27 (e.g., at least 96% sequence identity to SEQ ID NO: 27, at least 97% sequence identity to SEQ ID NO: 27, at least 98% sequence identity to SEQ ID NO: 27, at least 99% sequence identity to SEQ ID NO: 27, or 100% sequence identity to SEQ ID NO: 27). For example, in some embodiments, the VH$_{B1}$ region comprises the amino acid of SEQ ID NO: 24; and the VL$_{B1}$ region comprises the amino acid sequence of SEQ ID NO: 27.

In some embodiments, the VH$_{B2}$ region comprises one, two, or all three of the following HVRs: (a) an HVR-H1 comprising the amino acid sequence of SEQ ID NO: 11, (b) an HVR-H2 comprising the amino acid sequence of SEQ ID NO: 19, or (c) an HVR-H3 comprising the amino acid sequence of SEQ ID NO: 20. In some embodiments, the VH$_{B2}$ region comprises an amino acid sequence having at least 95% sequence identity to SEQ ID NO: 24 (e.g., at least 96% sequence identity to SEQ ID NO: 24, at least 97% sequence identity to SEQ ID NO: 24, at least 98% sequence identity to SEQ ID NO: 24, at least 99% sequence identity to SEQ ID NO: 24, or 100% sequence identity to SEQ ID NO: 24). In some embodiments, the VH$_{B2}$ region comprises the amino acid sequence of SEQ ID NO: 24. In some embodiments, the VL$_{B2}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 22, or (c) an HVR-L3 comprising the amino acid sequence of SEQ ID NO: 26. In some embodiments, the VL$_{B2}$ region comprises an amino acid sequence having at least 95% sequence identity to SEQ ID NO: 27 (e.g., at least 96% sequence identity to SEQ ID NO: 18, at least 97% sequence identity to SEQ ID NO: 27, at least 98% sequence identity to SEQ ID NO: 27, at least 99% sequence identity to SEQ ID NO: 27, or 100% sequence identity to SEQ ID NO: 27). In some embodiments, the VL$_{B2}$ region comprises the amino acid sequence of SEQ ID NO: 27.

In some instances, the VH$_{B2}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 20; and the VL$_{B2}$ comprises the following HVRs: (d) an HVR-L1 comprising the amino acid sequence of SEQ ID NO: 21, (e) an HVR-L2 comprising the amino acid sequence of SEQ ID NO: 22, and (f) an HVR-L3 comprising the amino acid sequence of SEQ ID NO: 26. In some embodiments, the VH$_{B2}$ region comprises an amino acid sequence having at least 95% sequence identity to SEQ ID NO: 24 (e.g., at least 96% sequence identity to SEQ ID NO: 24, at least 97% sequence identity to SEQ ID NO: 24, at least 98% sequence identity to SEQ ID NO: 24, at least 99% sequence identity to SEQ ID NO: 24, or 100% sequence identity to SEQ ID NO: 24); and the VL$_{B2}$ region comprises an amino acid sequence having at least 95% sequence identity to SEQ ID NO: 27 (e.g., at least 96% sequence identity to SEQ ID NO:

27, at least 97% sequence identity to SEQ ID NO: 27, at least 98% sequence identity to SEQ ID NO: 27, at least 99% sequence identity to SEQ ID NO: 27, or 100% sequence identity to SEQ ID NO: 27). In some embodiments, the VH$_{B2}$ region comprises the amino acid of SEQ ID NO: 24; and the VL$_{B2}$ region comprises the amino acid sequence of SEQ ID NO: 27. For example, in some embodiments, the bispecific antigen-binding molecule is an anti-HER2 bispecific antigen-binding molecule (e.g., 4D5 H91A-1Fab-IgG TDB).

In other instances, the bispecific antigen-binding molecule may feature mutations at residues D98, F100, and Y102 of the heavy chain of the second and/or third antigen-binding moiety (e.g., D98A, F100A, and Y102V). In some embodiments, the bispecific antigen-binding molecule features a VH$_{B1}$ region which comprises one, two, or all three of the following HVRs: (a) an HVR-H1 comprising the amino acid sequence of SEQ ID NO: 11, (b) an HVR-H2 comprising the amino acid sequence of SEQ ID NO: 19, or (c) an HVR-H3 comprising the amino acid sequence of SEQ ID NO: 32. In some embodiments, the VH$_{B1}$ region comprises an amino acid sequence having at least 95% sequence identity to SEQ ID NO: 33 (e.g., at least 96% sequence identity to SEQ ID NO: 33, at least 97% sequence identity to SEQ ID NO: 33, at least 98% sequence identity to SEQ ID NO: 33, at least 99% sequence identity to SEQ ID NO: 33, or 100% sequence identity to SEQ ID NO: 33). For example, in some embodiments, the VH$_{B1}$ region comprises the amino acid sequence of SEQ ID NO: 33. In some embodiments, the VL$_{B1}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 22, or (c) an HVR-L3 comprising the amino acid sequence of SEQ ID NO: 23. In some embodiments, the VL$_{B1}$ region comprises an amino acid sequence having at least 95% sequence identity to SEQ ID NO: 25 (e.g., at least 96% sequence identity to SEQ ID NO: 25, at least 97% sequence identity to SEQ ID NO: 25, at least 98% sequence identity to SEQ ID NO: 25, at least 99% sequence identity to SEQ ID NO: 25, or 100% sequence identity to SEQ ID NO: 25). For example, in some embodiments, the VL$_{B1}$ region comprises the amino acid sequence of SEQ ID NO: 25.

In some embodiments, the VH$_{B1}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 32; and the VL$_{B1}$ comprises the following HVRs: (d) an HVR-L1 comprising the amino acid sequence of SEQ ID NO: 21, (e) an HVR-L2 comprising the amino acid sequence of SEQ ID NO: 22, and (f) an HVR-L3 comprising the amino acid sequence of SEQ ID NO: 23. In some embodiments, the VH$_{B1}$ region comprises an amino acid sequence having at least 95% sequence identity to SEQ ID NO: 33 (e.g., at least 96% sequence identity to SEQ ID NO: 33, at least 97% sequence identity to SEQ ID NO: 33, at least 98% sequence identity to SEQ ID NO: 33, at least 99% sequence identity to SEQ ID NO: 33, or 100% sequence identity to SEQ ID NO: 33); and the VL$_{B1}$ region comprises an amino acid sequence having at least 95% sequence identity to SEQ ID NO: 25 (e.g., at least 96% sequence identity to SEQ ID NO: 25, at least 97% sequence identity to SEQ ID NO: 25, at least 98% sequence identity to SEQ ID NO: 25, at least 99% sequence identity to SEQ ID NO: 25, or 100% sequence identity to SEQ ID NO: 25). In some embodiments, the VH$_{B1}$ region comprises the amino acid of SEQ ID NO: 33; and the VL$_{B1}$ region comprises the amino acid sequence of SEQ ID NO: 25.

In some embodiments, the VH$_{B2}$ region comprises one, two, or all three of the following HVRs: (a) an HVR-H1 comprising the amino acid sequence of SEQ ID NO: 11, (b) an HVR-H2 comprising the amino acid sequence of SEQ ID NO: 19, or (c) an HVR-H3 comprising the amino acid sequence of SEQ ID NO: 32. In some embodiments, the VH$_{B2}$ region comprises an amino acid sequence having at least 95% sequence identity to SEQ ID NO: 33 (e.g., at least 96% sequence identity to SEQ ID NO: 33, at least 97% sequence identity to SEQ ID NO: 33, at least 98% sequence identity to SEQ ID NO: 33, at least 99% sequence identity to SEQ ID NO: 33, or 100% sequence identity to SEQ ID NO: 33). In some embodiments, the VH$_{B2}$ region comprises the amino acid sequence of SEQ ID NO: 33. In some embodiments, the VL$_{B2}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 22, or (c) an HVR-L3 comprising the amino acid sequence of SEQ ID NO: 23. In some embodiments, the VL$_{B2}$ region comprises an amino acid sequence having at least 95% sequence identity to SEQ ID NO: 25 (e.g., at least 96% sequence identity to SEQ ID NO: 25, at least 97% sequence identity to SEQ ID NO: 25, at least 98% sequence identity to SEQ ID NO: 25, at least 99% sequence identity to SEQ ID NO: 25, or 100% sequence identity to SEQ ID NO: 25). In some embodiments, the VL$_{B2}$ region comprises the amino acid sequence of SEQ ID NO: 25.

In some embodiments, the VH$_{B2}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 32; and the VL$_{B2}$ comprises the following HVRs: (d) an HVR-L1 comprising the amino acid sequence of SEQ ID NO: 21, (e) an HVR-L2 comprising the amino acid sequence of SEQ ID NO: 22, and (f) an HVR-L3 comprising the amino acid sequence of SEQ ID NO: 23. In some embodiments, the VH$_{B2}$ region comprises an amino acid sequence having at least 95% sequence identity to SEQ ID NO: 33 (e.g., at least 96% sequence identity to SEQ ID NO: 33, at least 97% sequence identity to SEQ ID NO: 33, at least 98% sequence identity to SEQ ID NO: 33, at least 99% sequence identity to SEQ ID NO: 33, or 100% sequence identity to SEQ ID NO: 33); and the VL$_{B2}$ region comprises an amino acid sequence having at least 95% sequence identity to SEQ ID NO: 25 (e.g., at least 96% sequence identity to SEQ ID NO: 25, at least 97% sequence identity to SEQ ID NO: 25, at least 98% sequence identity to SEQ ID NO: 25, at least 99% sequence identity to SEQ ID NO: 25, or 100% sequence identity to SEQ ID NO: 25). In some embodiments, the VH$_{B2}$ region comprises the amino acid of SEQ ID NO: 33; and the VL$_{B2}$ region comprises the amino acid sequence of SEQ ID NO: 25. For example, in some embodiments, the bispecific antigen-binding molecule is an anti-HER2 bispecific antigen-binding molecule (e.g., 4D5 D98A.F100A.Y102V-1Fab-IgG TDB).

In other embodiments, the bispecific antigen-binding molecule may feature mutations at residues Y55 and H91 of the light chain and at residues N54 and D98 of the heavy chain of the second and/or third antigen-binding moiety (e.g., Y55E, H91A, N54E, and D98T). In some embodiments, the bispecific antigen-binding molecule features a VH$_{B1}$ region which comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 37. In some embodiments, the VH$_{B1}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41). For example, in some embodiments, the VH$_{B1}$ region comprises the amino acid sequence of SEQ ID NO: 41. In some embodiments, the VL$_{B1}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 29, or (c) an HVR-L3 comprising the amino acid sequence of SEQ ID NO: 26. In some embodiments, the VL$_{B1}$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). For example, in some embodiments, the VL$_{B1}$ region comprises the amino acid sequence of SEQ ID NO: 48.

In some embodiments, the VH$_{B1}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 37; and the VL$_{B1}$ comprises the following HVRs: (d) an HVR-L1 comprising the amino acid sequence of SEQ ID NO: 21, (e) an HVR-L2 comprising the amino acid sequence of SEQ ID NO: 29, and (f) an HVR-L3 comprising the amino acid sequence of SEQ ID NO: 26. In some embodiments, the VH$_{B1}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41); and the VL$_{B1}$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). For example, in some embodiments, the VH$_{B1}$ region comprises the amino acid of SEQ ID NO: 41; and the VL$_{B1}$ region comprises the amino acid sequence of SEQ ID NO: 48.

In some embodiments, the VH$_{B2}$ region comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 37. In some embodiments, the VH$_{B2}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41). In some embodiments, the VH$_{B2}$ region comprises the amino acid sequence of SEQ ID NO: 41. In some embodiments, the VL$_{B2}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 29, or (c) an HVR-L3 comprising the amino acid sequence of SEQ ID NO: 26. In some embodiments, the VLB$_2$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). In some embodiments, the VL$_{B2}$ region comprises the amino acid sequence of SEQ ID NO: 48.

In some embodiments, the VH$_{B2}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 37; and the VL$_{B2}$ comprises the following HVRs: (d) an HVR-L1 comprising the amino acid sequence of SEQ ID NO: 21, (e) an HVR-L2 comprising the amino acid sequence of SEQ ID NO: 29, and (f) an HVR-L3 comprising the amino acid sequence of SEQ ID NO: 26. In some embodiments, the VH$_{B2}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41); and the VL$_{B2}$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). In some embodiments, the VH$_{B2}$ region comprises the amino acid of SEQ ID NO: 41; and the VL$_{B2}$ region comprises the amino acid sequence of SEQ ID NO: 48. For example, in some embodiments, the bispecific antigen-binding molecule is an anti-HER2 bispecific antigen-binding molecule (e.g., 4D5 Y55E.H91A.N54E.D98T-1Fab-IgG TDB).

In other embodiments, the bispecific antigen-binding molecule may feature mutations at residues Y55 and H91 of the light chain and at residues N54, D98, and Y102 of the heavy chain of the second and/or third antigen-binding moiety (e.g., Y55E, H91A, N54E, D98T, and Y102). In some embodiments, the bispecific antigen-binding molecule features a VH$_{B1}$ region which comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 43. In some embodiments, the VH$_{B1}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44). For example, in some embodiments, the VH$_{B1}$ region comprises the amino acid sequence of SEQ ID NO: 44. In some embodiments, the VL$_{B1}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 29, or (c) an HVR-L3 comprising the amino acid sequence of SEQ ID NO: 26. In some embodiments, the $VL_{B1}$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). For example, in some embodiments, the $VL_{B1}$ region comprises the amino acid sequence of SEQ ID NO: 48.

In some embodiments, the $VH_{B1}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 43; and the $VL_{B1}$ comprises the following HVRs: (d) an HVR-L1 comprising the amino acid sequence of SEQ ID NO: 21, (e) an HVR-L2 comprising the amino acid sequence of SEQ ID NO: 29, and (f) an HVR-L3 comprising the amino acid sequence of SEQ ID NO: 26. In some embodiments, the $VH_{B1}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44); and the $VL_{B1}$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). For example, in some embodiments, the $VH_{B1}$ region comprises the amino acid of SEQ ID NO: 41; and the $VL_{B1}$ region comprises the amino acid sequence of SEQ ID NO: 48.

In some embodiments, the $VH_{B2}$ region comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 43. In some embodiments, the $VH_{B2}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44). In some embodiments, the $VH_{B2}$ region comprises the amino acid sequence of SEQ ID NO: 44. In some embodiments, the $VL_{B2}$ region comprises one, two, or all three of the following HVRs: (a) an HVR-L1 comprising the amino acid sequence of SEQ ID NO: 21, (b) an HVR-L2 comprising the amino acid sequence of SEQ ID NO: 29, or (c) an HVR-L3 comprising the amino acid sequence of SEQ ID NO: 26. In some embodiments, the $VL_{B2}$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). In some embodiments, the $VL_{B2}$ region comprises the amino acid sequence of SEQ ID NO: 48.

In some embodiments, the $VH_{B2}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 43; and the $VL_{B2}$ comprises the following HVRs: (d) an HVR-L1 comprising the amino acid sequence of SEQ ID NO: 21, (e) an HVR-L2 comprising the amino acid sequence of SEQ ID NO: 29, and (f) an HVR-L3 comprising the amino acid sequence of SEQ ID NO: 26. In some embodiments, the $VH_{B2}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44); and the $VL_{B2}$ region comprises an amino acid sequence having at least 95% sequence identity to SEQ ID NO: 48 (e.g., at least 96% sequence identity to SEQ ID NO: 48, at least 97% sequence identity to SEQ ID NO: 48, at least 98% sequence identity to SEQ ID NO: 48, at least 99% sequence identity to SEQ ID NO: 48, or 100% sequence identity to SEQ ID NO: 48). In some embodiments, the $VH_{B2}$ region comprises the amino acid of SEQ ID NO: 44; and the $VL_{B2}$ region comprises the amino acid sequence of SEQ ID NO: 48. For example, in some embodiments, the bispecific antigen-binding molecule is an anti-HER2 bispecific antigen-binding molecule (e.g., 4D5 Y55E.H91A.N54E.D98T.Y102V-1Fab-IgG TDB).

In other embodiments, the bispecific antigen-binding molecule may feature mutations at residues N30, Y55, and H91 of the light chain and at residues N54 and D98 of the heavy chain of the second and/or third antigen-binding moiety (e.g., N30S, Y55E, H91A, N54E, and D98T). In some embodiments, the bispecific antigen-binding molecule features a $VH_{B1}$ region which comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 37. In some embodiments, the $VH_{B1}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41). For example, in some embodiments, the $VH_{B1}$ region comprises the amino acid sequence of SEQ ID NO: 41. In some embodiments, the $VL_{B1}$ region comprises one, two, or all three of the following HVRs: (a) an HVR-L1 comprising the amino acid sequence of SEQ ID NO: 38, (b) an HVR-L2 comprising the amino acid sequence of SEQ ID NO: 29, or (c) an HVR-L3 comprising the amino acid sequence of SEQ ID NO: 26. In some embodiments, the $VL_{B1}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). For example, in some embodiments, the $VL_{B1}$ region comprises the amino acid sequence of SEQ ID NO: 49.

In some embodiments, the $VH_{B1}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 37; and the $VL_{B1}$ comprises the following HVRs: (d) an HVR-L1 comprising the amino acid sequence of SEQ ID NO: 38, (e) an HVR-L2 comprising the amino acid sequence of SEQ ID NO: 29, and (f) an HVR-L3 comprising the amino acid sequence of SEQ ID NO: 26. In some embodiments, the $VH_{B1}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41); and the $VL_{B1}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). For example, in some embodiments, the $VH_{B1}$ region comprises the amino acid of SEQ ID NO: 41; and the $VL_{B1}$ region comprises the amino acid sequence of SEQ ID NO: 49.

In some embodiments, the $VH_{B2}$ region comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 37. In some embodiments, the $VH_{B2}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41). In some embodiments, the $VH_{B2}$ region comprises the amino acid sequence of SEQ ID NO: 41. In some embodiments, the $VL_{B2}$ region comprises one, two, or all three of the following HVRs: (a) an HVR-L1 comprising the amino acid sequence of SEQ ID NO: 38, (b) an HVR-L2 comprising the amino acid sequence of SEQ ID NO: 29, or (c) an HVR-L3 comprising the amino acid sequence of SEQ ID NO: 26. In some embodiments, the $VL_{B2}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). In some embodiments, the $VL_{B2}$ region comprises the amino acid sequence of SEQ ID NO: 49.

In some embodiments, the $VH_{B2}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 37; and the $VL_{B2}$ comprises the following HVRs: (d) an HVR-L1 comprising the amino acid sequence of SEQ ID NO: 38, (e) an HVR-L2 comprising the amino acid sequence of SEQ ID NO: 29, and (f) an HVR-L3 comprising the amino acid sequence of SEQ ID NO: 26. In some embodiments, the $VH_{B2}$ region comprises an amino acid sequence having at least 95% sequence identity to SEQ ID NO: 41 (e.g., at least 96% sequence identity to SEQ ID NO: 41, at least 97% sequence identity to SEQ ID NO: 41, at least 98% sequence identity to SEQ ID NO: 41, at least 99% sequence identity to SEQ ID NO: 41, or 100% sequence identity to SEQ ID NO: 41); and the $VL_{B2}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). In some embodiments, the $VH_{B2}$ region comprises the amino acid of SEQ ID NO: 41; and the $VL_{B2}$ region comprises the amino acid sequence of SEQ ID NO: 49. For example, in some embodiments, the bispecific antigen-binding molecule is an anti-HER2 bispecific antigen-binding molecule (e.g., 4D5 N30S.Y55E.H91A.N54E.D98T-1Fab-IgG TDB).

In other embodiments, the bispecific antigen-binding molecule may feature mutations at residues N30, Y55, and H91 of the light chain and at residues N54, D98, and Y102 of the heavy chain of the second and/or third antigen-binding moiety (e.g., N30S, Y55E, H91A, N54E, D98T, and Y102V). In some embodiments, the bispecific antigen-binding molecule features a $VH_{B1}$ region which comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 43. In some embodiments, the $VH_{B1}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44). For example, in some embodiments, the $VH_{B1}$ region comprises the amino acid sequence of SEQ ID NO: 44. In some embodiments, the $VL_{B1}$ region comprises one, two, or all three of the following HVRs: (a) an HVR-L1 comprising the amino acid sequence of SEQ ID NO: 38, (b) an HVR-L2 comprising the amino acid sequence of SEQ ID NO: 29, or (c) an HVR-L3 comprising the amino acid sequence of SEQ ID NO: 26. In some embodiments, the $VL_{B1}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). For example, in some embodiments, the $VL_{B1}$ region comprises the amino acid sequence of SEQ ID NO: 49.

In some embodiments, the $VH_{B1}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 43; and the $VL_{B1}$ comprises the following HVRs: (d) an HVR-L1 comprising the amino acid sequence of SEQ ID NO: 38, (e) an HVR-L2 comprising the amino acid sequence of SEQ ID NO: 29, and (f) an HVR-L3 comprising the amino acid sequence of SEQ ID NO: 26. In some embodiments, the $VH_{B1}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44); and the $VL_{B1}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). For example, in some embodiments, the $VH_{B1}$ region comprises the amino acid of SEQ ID NO: 44; and the VL$_{B1}$ region comprises the amino acid sequence of SEQ ID NO: 49.

In some embodiments, the VH$_{B2}$ region comprises one, two, or all three of the following HVRs: (a) an HVR-H1 comprising the amino acid sequence of SEQ ID NO: 11, (b) an HVR-H2 comprising the amino acid sequence of SEQ ID NO: 36, or (c) an HVR-H3 comprising the amino acid sequence of SEQ ID NO: 43. In some embodiments, the VH$_{B2}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44). In some embodiments, the VH$_{B2}$ region comprises the amino acid sequence of SEQ ID NO: 44. In some embodiments, the VL$_{B2}$ region comprises one, two, or all three of the following HVRs: (a) an HVR-L1 comprising the amino acid sequence of SEQ ID NO: 38, (b) an HVR-L2 comprising the amino acid sequence of SEQ ID NO: 29, or (c) an HVR-L3 comprising the amino acid sequence of SEQ ID NO: 26. In some embodiments, the VL$_{B2}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). In some embodiments, the VL$_{B2}$ region comprises the amino acid sequence of SEQ ID NO: 49.

In some embodiments, the VH$_{B2}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 43; and the VL$_{B2}$ comprises the following HVRs: (d) an HVR-L1 comprising the amino acid sequence of SEQ ID NO: 38, (e) an HVR-L2 comprising the amino acid sequence of SEQ ID NO: 29, and (f) an HVR-L3 comprising the amino acid sequence of SEQ ID NO: 26. In some embodiments, the VH$_{B2}$ region comprises an amino acid sequence having at least 95% sequence identity to SEQ ID NO: 44 (e.g., at least 96% sequence identity to SEQ ID NO: 44, at least 97% sequence identity to SEQ ID NO: 44, at least 98% sequence identity to SEQ ID NO: 44, at least 99% sequence identity to SEQ ID NO: 44, or 100% sequence identity to SEQ ID NO: 44); and the VL$_{B2}$ region comprises an amino acid sequence having at least 95% sequence identity to SEQ ID NO: 49 (e.g., at least 96% sequence identity to SEQ ID NO: 49, at least 97% sequence identity to SEQ ID NO: 49, at least 98% sequence identity to SEQ ID NO: 49, at least 99% sequence identity to SEQ ID NO: 49, or 100% sequence identity to SEQ ID NO: 49). In some embodiments, the VH$_{B2}$ region comprises the amino acid of SEQ ID NO: 44; and the VL$_{B2}$ region comprises the amino acid sequence of SEQ ID NO: 49. For example, in some embodiments, the bispecific antigen-binding molecule is an anti-HER2 bispecific antigen-binding molecule (e.g., 4D5 N30S.Y55E.H91A.N54E.D98T.Y102V-1Fab-IgG TDB).

In some embodiments, the VH$_{B1}$ and/or the VH$_{B2}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 28; and the VL$_{B1}$ and/or the VL$_{B2}$ comprises the following HVRs: (d) an HVR-L1 comprising the amino acid sequence of SEQ ID NO: 21, (e) an HVR-L2 comprising the amino acid sequence of SEQ ID NO: 29, and (f) an HVR-L3 comprising the amino acid sequence of SEQ ID NO: 30. In some embodiments, the VH$_{B1}$ and/or the VH$_{B2}$ comprises an amino acid sequence having at least 95% sequence identity (e.g., at least 96%, at least 97%, at least 98%, at least 99% sequence identity) to, or the sequence of, SEQ ID NO: 30 and the VL$_{B1}$ and/or the VL$_{B2}$ comprises an amino acid sequence having at least 95% sequence identity (e.g., at least 96%, at least 97%, at least 98%, at least 99% sequence identity) to, or the sequence of, SEQ ID NO: 31.

In some embodiments, the VH$_{B1}$ and/or the VH$_{B2}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 34; and the VL$_{B1}$ and/or the VL$_{B2}$ comprises the following HVRs: (d) an HVR-L1 comprising the amino acid sequence of SEQ ID NO: 21, (e) an HVR-L2 comprising the amino acid sequence of SEQ ID NO: 22, and (f) an HVR-L3 comprising the amino acid sequence of SEQ ID NO: 23. In some embodiments, the VH$_{B1}$ and/or the VH$_{B2}$ comprises an amino acid sequence having at least 95% sequence identity (e.g., at least 96%, at least 97%, at least 98%, at least 99% sequence identity) to, or the sequence of, SEQ ID NO: 35 and the VL$_{B1}$ and/or the VL$_{B2}$ comprises an amino acid sequence having at least 95% sequence identity (e.g., at least 96%, at least 97%, at least 98%, at least 99% sequence identity) to, or the sequence of, SEQ ID NO: 25.

In some embodiments, the VH$_{B1}$ and/or the VH$_{B2}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 37; and the VL$_{B1}$ and/or the VL$_{B2}$ comprises the following HVRs: (d) an HVR-L1 comprising the amino acid sequence of SEQ ID NO: 38, (e) an HVR-L2 comprising the amino acid sequence of SEQ ID NO: 22, and (f) an HVR-L3 comprising the amino acid sequence of SEQ ID NO: 23. In some embodiments, the VH$_{B1}$ and/or the VH$_{B2}$ comprises an amino acid sequence having at least 95% sequence identity (e.g., at least 96%, at least 97%, at least 98%, at least 99% sequence identity) to, or the sequence of, SEQ ID NO: 39 and the VL$_{B1}$ and/or the VL$_{B2}$ comprises an amino acid sequence having at least 95% sequence identity (e.g., at least 96%, at least 97%, at least 98%, at least 99% sequence identity) to, or the sequence of, SEQ ID NO: 40.

In some embodiments, the VH$_{B1}$ and/or the VH$_{B2}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 37; and the VL$_{B1}$ and/or the VL$_{B2}$ comprises the following HVRs: (d) an HVR-L1 comprising the amino acid sequence of SEQ ID NO: 38, (e) an HVR-L2 comprising the amino acid sequence of SEQ ID NO: 22, and (f) an HVR-L3 comprising the amino acid sequence of SEQ ID NO: 26. In some embodiments, the VH$_{B1}$ and/or the VH$_{B2}$ comprises an amino acid sequence having at least 95% sequence identity (e.g., at least 96%, at least 97%, at least 98%, at least 99% sequence identity) to, or the sequence of, SEQ ID NO: 41 and the VL$_{B1}$ and/or the VL$_{B2}$ comprises an amino acid sequence having at least 95% sequence identity (e.g., at least 96%, at least 97%, at least 98%, at least 99% sequence identity) to, or the sequence of, SEQ ID NO: 42.

In some embodiments, the VH$_{B1}$ and/or the VH$_{B2}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 37; and the $VL_{B1}$ and/or the $VL_{B2}$ comprises the following HVRs: (d) an HVR-L1 comprising the amino acid sequence of SEQ ID NO: 21, (e) an HVR-L2 comprising the amino acid sequence of SEQ ID NO: 22, and (f) an HVR-L3 comprising the amino acid sequence of SEQ ID NO: 26. In some embodiments, the $VH_{B1}$ and/or the $VH_{B2}$ comprises an amino acid sequence having at least 95% sequence identity (e.g., at least 96%, at least 97%, at least 98%, at least 99% sequence identity) to, or the sequence of, SEQ ID NO: 41 and the $VL_{B1}$ and/or the $VL_{B2}$ comprises an amino acid sequence having at least 95% sequence identity (e.g., at least 96%, at least 97%, at least 98%, at least 99% sequence identity) to, or the sequence of, SEQ ID NO: 27.

In some embodiments, the $VH_{B1}$ and/or the $VH_{B2}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 43; and the $VL_{B1}$ and/or the $VL_{B2}$ comprises the following HVRs: (d) an HVR-L1 comprising the amino acid sequence of SEQ ID NO: 38, (e) an HVR-L2 comprising the amino acid sequence of SEQ ID NO: 29, and (f) an HVR-L3 comprising the amino acid sequence of SEQ ID NO: 23. In some embodiments, the $VH_{B1}$ and/or the $VH_{B2}$ comprises an amino acid sequence having at least 95% sequence identity (e.g., at least 96%, at least 97%, at least 98%, at least 99% sequence identity) to, or the sequence of, SEQ ID NO: 44 and the $VL_{B1}$ and/or the $VL_{B2}$ comprises an amino acid sequence having at least 95% sequence identity (e.g., at least 96%, at least 97%, at least 98%, at least 99% sequence identity) to, or the sequence of, SEQ ID NO: 45.

In some embodiments, the $VH_{B1}$ and/or the $VH_{B2}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 20; and the $VL_{B1}$ and/or the $VL_{B2}$ comprises the following HVRs: (d) an HVR-L1 comprising the amino acid sequence of SEQ ID NO: 38, (e) an HVR-L2 comprising the amino acid sequence of SEQ ID NO: 22, and (f) an HVR-L3 comprising the amino acid sequence of SEQ ID NO: 23. In some embodiments, the $VH_{B1}$ and/or the $VH_{B2}$ comprises an amino acid sequence having at least 95% sequence identity (e.g., at least 96%, at least 97%, at least 98%, at least 99% sequence identity) to, or the sequence of, SEQ ID NO: 24 and the $VL_{B1}$ and/or the $VL_{B2}$ comprises an amino acid sequence having at least 95% sequence identity (e.g., at least 96%, at least 97%, at least 98%, at least 99% sequence identity) to, or the sequence of, SEQ ID NO: 40.

In some embodiments, the $VH_{B1}$ and/or the $VH_{B2}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 37; and the $VL_{B1}$ and/or the $VL_{B2}$ comprises the following HVRs: (d) an HVR-L1 comprising the amino acid sequence of SEQ ID NO: 21, (e) an HVR-L2 comprising the amino acid sequence of SEQ ID NO: 22, and (f) an HVR-L3 comprising the amino acid sequence of SEQ ID NO: 23. In some embodiments, the $VH_{B1}$ and/or the $VH_{B2}$ comprises an amino acid sequence having at least 95% sequence identity (e.g., at least 96%, at least 97%, at least 98%, at least 99% sequence identity) to, or the sequence of, SEQ ID NO: 41 and the $VL_{B1}$ and/or the $VL_{B2}$ comprises an amino acid sequence having at least 95% sequence identity (e.g., at least 96%, at least 97%, at least 98%, at least 99% sequence identity) to, or the sequence of, SEQ ID NO: 25.

In some embodiments, the $VH_{B1}$ and/or the $VH_{B2}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 34; and the $VL_{B1}$ and/or the $VL_{B2}$ comprises the following HVRs: (d) an HVR-L1 comprising the amino acid sequence of SEQ ID NO: 38, (e) an HVR-L2 comprising the amino acid sequence of SEQ ID NO: 22, and (f) an HVR-L3 comprising the amino acid sequence of SEQ ID NO: 23. In some embodiments, the $VH_{B1}$ and/or the $VH_{B2}$ comprises an amino acid sequence having at least 95% sequence identity (e.g., at least 96%, at least 97%, at least 98%, at least 99% sequence identity) to, or the sequence of, SEQ ID NO: 46 and the $VL_{B1}$ and/or the $VL_{B2}$ comprises an amino acid sequence having at least 95% sequence identity (e.g., at least 96%, at least 97%, at least 98%, at least 99% sequence identity) to, or the sequence of, SEQ ID NO: 40.

In some embodiments, the $VH_{B1}$ and/or the $VH_{B2}$ comprises the following HVRs: (a) an HVR-H1 comprising the amino acid sequence of SEQ ID NO: 11, (b) an HVR-H2 comprising the amino acid sequence of SEQ ID NO: 36, and (c) an HVR-H3 comprising the amino acid sequence of SEQ ID NO: 32; and the $VL_{B1}$ and/or the $VL_{B2}$ comprises the following HVRs: (d) an HVR-L1 comprising the amino acid sequence of SEQ ID NO: 38, (e) an HVR-L2 comprising the amino acid sequence of SEQ ID NO: 22, and (f) an HVR-L3 comprising the amino acid sequence of SEQ ID NO: 23. In some embodiments, the $VH_{B1}$ and/or the $VH_{B2}$ comprises an amino acid sequence having at least 95% sequence identity (e.g., at least 96%, at least 97%, at least 98%, at least 99% sequence identity) to, or the sequence of, SEQ ID NO: 47 and the $VL_{B1}$ and/or the $VL_{B2}$ comprises an amino acid sequence having at least 95% sequence identity (e.g., at least 96%, at least 97%, at least 98%, at least 99% sequence identity) to, or the sequence of, SEQ ID NO: 40.

In some embodiments, the $VH_{B1}$ and/or the $VH_{B2}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 28; and the $VL_{B1}$ and/or the $VL_{B2}$ comprises the following HVRs: (d) an HVR-L1 comprising the amino acid sequence of SEQ ID NO: 21, (e) an HVR-L2 comprising the amino acid sequence of SEQ ID NO: 22, and (f) an HVR-L3 comprising the amino acid sequence of SEQ ID NO: 23. In some embodiments, the $VH_{B1}$ and/or the $VH_{B2}$ comprises an amino acid sequence having at least 95% sequence identity (e.g., at least 96%, at least 97%, at least 98%, at least 99% sequence identity) to, or the sequence of, SEQ ID NO: 30 and the $VL_{B1}$ and/or the $VL_{B2}$ comprises an amino acid sequence having at least 95% sequence identity (e.g., at least 96%, at least 97%, at least 98%, at least 99% sequence identity) to, or the sequence of, SEQ ID NO: 25.

In some embodiments, the $VH_{B1}$ and/or the $VH_{B2}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 20; and the $VL_{B1}$ and/or the $VL_{B2}$ comprises the following HVRs: (d) an HVR-L1 comprising the amino acid sequence of SEQ ID NO: 53, (e) an HVR-L2 comprising the amino acid sequence of SEQ ID NO: 22, and (f) an HVR-L3 comprising the amino acid sequence of SEQ ID NO: 26. In some embodiments, the $VH_{B1}$ and/or the $VH_{B2}$ comprises an amino acid sequence having at least 95% sequence identity (e.g., at least 96%, at least 97%, at least 98%, at least 99% sequence identity) to, or the sequence of, SEQ ID NO: 24 and the VL$_{B1}$ and/or the VL$_{B2}$ comprises an amino acid sequence having at least 95% sequence identity (e.g., at least 96%, at least 97%, at least 98%, at least 99% sequence identity) to, or the sequence of, SEQ ID NO: 54.

In some embodiments, the VH$_{B1}$ and/or the VH$_{B2}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 20; and the VL$_{B1}$ and/or the VL$_{B2}$ comprises the following HVRs: (d) an HVR-L1 comprising the amino acid sequence of SEQ ID NO: 21, (e) an HVR-L2 comprising the amino acid sequence of SEQ ID NO: 29, and (f) an HVR-L3 comprising the amino acid sequence of SEQ ID NO: 26. In some embodiments, the VH$_{B1}$ and/or the VH$_{B2}$ comprises an amino acid sequence having at least 95% sequence identity (e.g., at least 96%, at least 97%, at least 98%, at least 99% sequence identity) to, or the sequence of, SEQ ID NO: 24 and the VL$_{B1}$ and/or the VL$_{B2}$ comprises an amino acid sequence having at least 95% sequence identity (e.g., at least 96%, at least 97%, at least 98%, at least 99% sequence identity) to, or the sequence of, SEQ ID NO: 48.

In some embodiments, the VH$_{B1}$ and/or the VH$_{B2}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 32; and the VL$_{B1}$ and/or the VL$_{B2}$ comprises the following HVRs: (d) an HVR-L1 comprising the amino acid sequence of SEQ ID NO: 21, (e) an HVR-L2 comprising the amino acid sequence of SEQ ID NO: 22, and (f) an HVR-L3 comprising the amino acid sequence of SEQ ID NO: 23. In some embodiments, the VH$_{B1}$ and/or the VH$_{B2}$ comprises an amino acid sequence having at least 95% sequence identity (e.g., at least 96%, at least 97%, at least 98%, at least 99% sequence identity) to, or the sequence of, SEQ ID NO: 33 and the VL$_{B1}$ and/or the VL$_{B2}$ comprises an amino acid sequence having at least 95% sequence identity (e.g., at least 96%, at least 97%, at least 98%, at least 99% sequence identity) to, or the sequence of, SEQ ID NO: 25.

In some embodiments, the VH$_{B1}$ and/or the VH$_{B2}$ comprises the following HVRs: (a) an HVR-H1 comprising the amino acid sequence of SEQ ID NO: 11, (b) an HVR-H2 comprising the amino acid sequence of SEQ ID NO: 19, and (c) an HVR-H3 comprising the amino acid sequence of SEQ ID NO: 32; and the VL$_{B1}$ and/or the VL$_{B2}$ comprises the following HVRs: (d) an HVR-L1 comprising the amino acid sequence of SEQ ID NO: 21, (e) an HVR-L2 comprising the amino acid sequence of SEQ ID NO: 29, and (f) an HVR-L3 comprising the amino acid sequence of SEQ ID NO: 23. In some embodiments, the VH$_{B1}$ and/or the VH$_{B2}$ comprises an amino acid sequence having at least 95% sequence identity (e.g., at least 96%, at least 97%, at least 98%, at least 99% sequence identity) to, or the sequence of, SEQ ID NO: 33 and the VL$_{B1}$ and/or the VL$_{B2}$ comprises an amino acid sequence having at least 95% sequence identity (e.g., at least 96%, at least 97%, at least 98%, at least 99% sequence identity) to, or the sequence of, SEQ ID NO: 31.

In another aspect, the invention features a bispecific antigen-binding molecule comprising a monovalent arm and a bivalent arm, wherein: (a) the monovalent arm comprises a Fab$_A$, wherein the C-terminus of the Fab$_A$ is fused to an N-terminus of a first Fc subunit, and wherein the Fab$_A$ comprises the following HVRs: (i) an HVR-H1 comprising the amino acid sequence of SEQ ID NO: 1, (ii) an HVR-H2 comprising the amino acid sequence of SEQ ID NO: 2, (iii) an HVR-H3 comprising the amino acid sequence of SEQ ID NO: 3, (iv) an HVR-L1 comprising the amino acid sequence of SEQ ID NO: 4, (v) an HVR-L2 comprising the amino acid sequence of SEQ ID NO: 5, and (vi) an HVR-L3 comprising the amino acid sequence of SEQ ID NO: 6; (b) the bivalent arm comprises a Fab$_{B1}$ and a Fab$_{B2}$, wherein the C-terminus of the Fab$_{B2}$ is fused to the N-terminus of the Fab$_{B1}$, and the C-terminus of the Fab$_{B1}$ is fused to an N-terminus of a second Fc subunit, wherein the Fab$_{B1}$ and the Fab$_{B2}$ each comprise the following HVRs: (i) an HVR-H1 comprising the amino acid sequence of SEQ ID NO: 11, (ii) an HVR-H2 comprising the amino acid sequence of SEQ ID NO: 12, (iii) an HVR-H3 comprising the amino acid sequence of SEQ ID NO: 13, (iv) an HVR-L1 comprising the amino acid sequence of SEQ ID NO: 14, (v) an HVR-L2 comprising the amino acid sequence of SEQ ID NO: 15, and (vi) an HVR-L3 comprising the amino acid sequence of SEQ ID NO: 16; and (c) the first Fc subunit is associated with the second Fc subunit to form an Fc domain. In some embodiments, (a) the Fab$_A$ comprises a VH$_A$ region and a VL$_A$ region, wherein the VH$_A$ region comprises an amino acid sequence having at least 95% sequence identity to SEQ ID NO: 7, and the VL$_A$ region comprises an amino acid sequence having at least 95% sequence identity to SEQ ID NO: 8; (b) the Fab$_{B1}$ comprises a VH$_{B1}$ region and a VL$_{B1}$ region, wherein the VH$_{B1}$ region comprises an amino acid sequence having at least 95% sequence identity to SEQ ID NO: 17, and the VL$_{B1}$ region comprises an amino acid sequence having at least 95% sequence identity to SEQ ID NO: 18; and (c) the Fab$_{B2}$ comprises a VH$_{B2}$ region and a VL$_{B2}$ region, wherein the VH$_{B2}$ region comprises an amino acid sequence having at least 95% sequence identity to SEQ ID NO: 17, and the VL$_{B2}$ region comprises an amino acid sequence having at least 95% sequence identity to SEQ ID NO: 18. For example, in some embodiments, (a) the VH$_A$ region comprises the amino acid sequence of SEQ ID NO: 7, and the VL$_A$ region comprises the amino acid sequence of SEQ ID NO: 8; (b) the VH$_{B1}$ region comprises the amino acid sequence of SEQ ID NO: 17, and the VL$_{B1}$ region comprises the amino acid sequence of SEQ ID NO: 18; and (c) the VH$_{B2}$ region comprises the amino acid sequence of SEQ ID NO: 17, and the VL$_{B2}$ region comprises the amino acid sequence of SEQ ID NO: 18.

In another aspect, the invention provides a bispecific antigen-binding molecule comprising a monovalent arm and a bivalent arm, wherein: (a) the monovalent arm comprises a Fab$_A$, wherein the C-terminus of the Fab$_A$ is fused to an N-terminus of a first Fc subunit, and wherein the Fab$_A$ comprises the following HVRs: (i) an HVR-H1 comprising the amino acid sequence of SEQ ID NO: 1, (ii) an HVR-H2 comprising the amino acid sequence of SEQ ID NO: 2, (iii) an HVR-H3 comprising the amino acid sequence of SEQ ID NO: 3, (iv) an HVR-L1 comprising the amino acid sequence of SEQ ID NO: 4, (v) an HVR-L2 comprising the amino acid sequence of SEQ ID NO: 5, and (vi) an HVR-L3 comprising the amino acid sequence of SEQ ID NO: 6; (b) the bivalent arm comprises a Fab$_{B1}$ and a Fab$_{B2}$, wherein the C-terminus of the Fab$_{B2}$ is fused to the N-terminus of the Fab$_{B1}$, and the C-terminus of the Fab$_{B1}$ is fused to an N-terminus of a second Fc subunit, wherein the Fab$_{B1}$ and the Fab$_{B2}$ each comprise the following HVRs: (i) an HVR-H1 comprising the amino acid sequence of SEQ ID NO: 11, (ii) an HVR-H2 comprising the amino acid sequence of SEQ ID NO: 19, (iii) an HVR-H3 comprising the amino acid sequence of SEQ ID NO: 20, (iv) an HVR-L1 comprising the amino acid sequence of SEQ ID NO: 22, (v) an HVR-L2 comprising the amino acid sequence of SEQ ID NO: 22, and (vi) an HVR-L3 comprising the amino acid sequence of SEQ ID NO: 26; and (c) the first Fc subunit is associated with the second Fc subunit to form an Fc domain. In some embodiments, (a) the $Fab_A$ comprises a $VH_A$ region and a $VL_A$ region, wherein the $VH_A$ region comprises an amino acid sequence having at least 95% sequence identity to SEQ ID NO: 7, and the $VL_A$ region comprises an amino acid sequence having at least 95% sequence identity to SEQ ID NO: 8; (b) the $Fab_{B1}$ comprises a $VH_{B1}$ region and a $VL_{B1}$ region, wherein the $VH_{B1}$ region comprises an amino acid sequence having at least 95% sequence identity to SEQ ID NO: 24, and the $VL_{B1}$ region comprises an amino acid sequence having at least 95% sequence identity to SEQ ID NO: 27; and (c) the $Fab_{B2}$ comprises a $VH_{B2}$ region and a $VL_{B2}$ region, wherein the $VH_{B2}$ region comprises an amino acid sequence having at least 95% sequence identity to SEQ ID NO: 24, and the $VL_{B2}$ region comprises an amino acid sequence having at least 95% sequence identity to SEQ ID NO: 27. For example, in some embodiments, (a) the $VH_A$ region comprises the amino acid sequence of SEQ ID NO: 7, and the $VL_A$ region comprises the amino acid sequence of SEQ ID NO: 8; (b) the $VH_{B1}$ region comprises the amino acid sequence of SEQ ID NO: 24, and the $VL_{B1}$ region comprises the amino acid sequence of SEQ ID NO: 27; and (c) the $VH_{B2}$ region comprises the amino acid sequence of SEQ ID NO: 24, and the $VL_{B2}$ region comprises the amino acid sequence of SEQ ID NO: 27.

In yet another aspect, the invention features a bispecific antigen-binding molecule comprising a monovalent arm and a bivalent arm, wherein: (a) the monovalent arm comprises a $Fab_A$, wherein the C-terminus of the $Fab_A$ is fused to an N-terminus of a first Fc subunit, and wherein the $Fab_A$ comprises the following HVRs: (i) an HVR-H1 comprising the amino acid sequence of SEQ ID NO: 1, (ii) an HVR-H2 comprising the amino acid sequence of SEQ ID NO: 2, (iii) an HVR-H3 comprising the amino acid sequence of SEQ ID NO: 3, (iv) an HVR-L1 comprising the amino acid sequence of SEQ ID NO: 4, (v) an HVR-L2 comprising the amino acid sequence of SEQ ID NO: 5, and (vi) an HVR-L3 comprising the amino acid sequence of SEQ ID NO: 6; (b) the bivalent arm comprises a $Fab_{B1}$ and a $Fab_{B2}$, wherein the C-terminus of the $Fab_{B2}$ is fused to the N-terminus of the $Fab_{B1}$, and the C-terminus of the $Fab_{B1}$ is fused to an N-terminus of a second Fc subunit, wherein the $Fab_{B1}$ and the $Fab_{B2}$ each comprise the following HVRs: (i) an HVR-H1 comprising the amino acid sequence of SEQ ID NO: 11, (ii) an HVR-H2 comprising the amino acid sequence of SEQ ID NO: 19, (iii) an HVR-H3 comprising the amino acid sequence of SEQ ID NO: 32, (iv) an HVR-L1 comprising the amino acid sequence of SEQ ID NO: 21, (v) an HVR-L2 comprising the amino acid sequence of SEQ ID NO: 22, and (vi) an HVR-L3 comprising the amino acid sequence of SEQ ID NO: 23; and (c) the first Fc subunit is associated with the second Fc subunit to form an Fc domain. In some embodiments, (a) the $Fab_A$ comprises a $VH_A$ region and a $VL_A$ region, wherein the $VH_A$ region comprises an amino acid sequence having at least 95% sequence identity to SEQ ID NO: 7, and the $VL_A$ region comprises an amino acid sequence having at least 95% sequence identity to SEQ ID NO: 8; (b) the $Fab_{B1}$ comprises a $VH_{B1}$ region and a $VL_{B1}$ region, wherein the $VH_{B1}$ region comprises an amino acid sequence having at least 95% sequence identity to SEQ ID NO: 33, and the $VL_{B1}$ region comprises an amino acid sequence having at least 95% sequence identity to SEQ ID NO: 25; and (c) the $Fab_{B2}$ comprises a $VH_{B2}$ region and a $VL_{B2}$ region, wherein the $VH_{B2}$ region comprises an amino acid sequence having at least 95% sequence identity to SEQ ID NO: 33, and the $VL_{B2}$ region comprises an amino acid sequence having at least 95% sequence identity to SEQ ID NO: 25. For example, in some embodiments, (a) the $VH_A$ region comprises the amino acid sequence of SEQ ID NO: 7, and the $VL_A$ region comprises the amino acid sequence of SEQ ID NO: 8; (b) the $VH_{B1}$ region comprises the amino acid sequence of SEQ ID NO: 33, and the $VL_{B1}$ region comprises the amino acid sequence of SEQ ID NO: 25; and (c) the $VH_{B2}$ region comprises the amino acid sequence of SEQ ID NO: 33, and the $VL_{B2}$ region comprises the amino acid sequence of SEQ ID NO: 25.

In another aspect, the invention features a bispecific antigen-binding molecule comprising a monovalent arm and a bivalent arm, wherein: (a) the monovalent arm comprises a $Fab_A$, wherein the C-terminus of the $Fab_A$ is fused to an N-terminus of a first Fc subunit, and wherein the $Fab_A$ comprises the following HVRs: (i) an HVR-H1 comprising the amino acid sequence of SEQ ID NO: 1, (ii) an HVR-H2 comprising the amino acid sequence of SEQ ID NO: 2, (iii) an HVR-H3 comprising the amino acid sequence of SEQ ID NO: 3, (iv) an HVR-L1 comprising the amino acid sequence of SEQ ID NO: 4, (v) an HVR-L2 comprising the amino acid sequence of SEQ ID NO: 5, and (vi) an HVR-L3 comprising the amino acid sequence of SEQ ID NO: 6; (b) the bivalent arm comprises a $Fab_{B1}$ and a $Fab_{B2}$, wherein the C-terminus of the $Fab_{B2}$ is fused to the N-terminus of the $Fab_{B1}$, and the C-terminus of the $Fab_{B1}$ is fused to an N-terminus of a second Fc subunit, wherein the $Fab_{B1}$ and the $Fab_{B2}$ each comprise the following HVRs: (i) an HVR-H1 comprising the amino acid sequence of SEQ ID NO: 11, (ii) an HVR-H2 comprising the amino acid sequence of SEQ ID NO: 36, (iii) an HVR-H3 comprising the amino acid sequence of SEQ ID NO: 37, (iv) an HVR-L1 comprising the amino acid sequence of SEQ ID NO: 21, (v) an HVR-L2 comprising the amino acid sequence of SEQ ID NO: 29, and (vi) an HVR-L3 comprising the amino acid sequence of SEQ ID NO: 26; and (c) the first Fc subunit is associated with the second Fc subunit to form an Fc domain. In some embodiments, (a) the $Fab_A$ comprises a $VH_A$ region and a $VL_A$ region, wherein the $VH_A$ region comprises an amino acid sequence having at least 95% sequence identity to SEQ ID NO: 7, and the $VL_A$ region comprises an amino acid sequence having at least 95% sequence identity to SEQ ID NO: 8; (b) the $Fab_{B1}$ comprises a $VH_{B1}$ region and a $VL_{B1}$ region, wherein the $VH_{B1}$ region comprises an amino acid sequence having at least 95% sequence identity to SEQ ID NO: 41, and the $VL_{B1}$ region comprises an amino acid sequence having at least 95% sequence identity to SEQ ID NO: 48; and (c) the $Fab_{B2}$ comprises a $VH_{B2}$ region and a $VL_{B2}$ region, wherein the $VH_{B2}$ region comprises an amino acid sequence having at least 95% sequence identity to SEQ ID NO: 41, and the $VL_{B2}$ region comprises an amino acid sequence having at least 95% sequence identity to SEQ ID NO: 48. For example, in some embodiments, (a) the $VH_A$ region comprises the amino acid sequence of SEQ ID NO: 7, and the $VL_A$ region comprises the amino acid sequence of SEQ ID NO: 8; (b) the $VH_{B1}$ region comprises the amino acid sequence of SEQ ID NO: 41, and the $VL_{B1}$ region comprises the amino acid sequence of SEQ ID NO: 48; and (c) the $VH_{B2}$ region comprises the amino acid sequence of SEQ ID NO: 41, and the $VL_{B2}$ region comprises the amino acid sequence of SEQ ID NO: 48.

In another aspect, the invention features a bispecific antigen-binding molecule comprising a monovalent arm and a bivalent arm, wherein: (a) the monovalent arm comprises a Fab$_A$, wherein the C-terminus of the Fab$_A$ is fused to an N-terminus of a first Fc subunit, and wherein the Fab$_A$ comprises the following HVRs: (i) an HVR-H1 comprising the amino acid sequence of SEQ ID NO: 1, (ii) an HVR-H2 comprising the amino acid sequence of SEQ ID NO: 2, (iii) an HVR-H3 comprising the amino acid sequence of SEQ ID NO: 3, (iv) an HVR-L1 comprising the amino acid sequence of SEQ ID NO: 4, (v) an HVR-L2 comprising the amino acid sequence of SEQ ID NO: 5, and (vi) an HVR-L3 comprising the amino acid sequence of SEQ ID NO: 6; (b) the bivalent arm comprises a Fab$_{B1}$ and a Fab$_{B2}$, wherein the C-terminus of the Fab$_{B2}$ is fused to the N-terminus of the Fab$_{B1}$, and the C-terminus of the Fab$_{B1}$ is fused to an N-terminus of a second Fc subunit, wherein the Fab$_{B1}$ and the Fab$_{B2}$ each comprise the following HVRs: (i) an HVR-H1 comprising the amino acid sequence of SEQ ID NO: 11, (ii) an HVR-H2 comprising the amino acid sequence of SEQ ID NO: 36, (iii) an HVR-H3 comprising the amino acid sequence of SEQ ID NO: 43, (iv) an HVR-L1 comprising the amino acid sequence of SEQ ID NO: 21, (v) an HVR-L2 comprising the amino acid sequence of SEQ ID NO: 29, and (vi) an HVR-L3 comprising the amino acid sequence of SEQ ID NO: 26; and (c) the first Fc subunit is associated with the second Fc subunit to form an Fc domain. In some embodiments, (a) the Fab$_A$ comprises a VH$_A$ region and a VL$_A$ region, wherein the VH$_A$ region comprises an amino acid sequence having at least 95% sequence identity to SEQ ID NO: 7, and the VL$_A$ region comprises an amino acid sequence having at least 95% sequence identity to SEQ ID NO: 8; (b) the Fab$_{B1}$ comprises a VH$_{B1}$ region and a VL$_{B1}$ region, wherein the VH$_{B1}$ region comprises an amino acid sequence having at least 95% sequence identity to SEQ ID NO: 44, and the VL$_{B1}$ region comprises an amino acid sequence having at least 95% sequence identity to SEQ ID NO: 48; and (c) the Fab$_{B2}$ comprises a VH$_{B2}$ region and a VL$_{B2}$ region, wherein the VH$_{B2}$ region comprises an amino acid sequence having at least 95% sequence identity to SEQ ID NO: 44, and the VL$_{B2}$ region comprises an amino acid sequence having at least 95% sequence identity to SEQ ID NO: 48. For example, in some embodiments, (a) the VH$_A$ region comprises the amino acid sequence of SEQ ID NO: 7, and the VL$_A$ region comprises the amino acid sequence of SEQ ID NO: 8; (b) the VH$_{B1}$ region comprises the amino acid sequence of SEQ ID NO: 44, and the VL$_{B1}$ region comprises the amino acid sequence of SEQ ID NO: 48; and (c) the VH$_{B2}$ region comprises the amino acid sequence of SEQ ID NO: 44, and the VL$_{B2}$ region comprises the amino acid sequence of SEQ ID NO: 48. For example, in some embodiments, the bispecific antigen-binding molecule is an anti-CD3/HER2 bispecific antigen-binding molecule (e.g., an anti-CD3/HER2 1 Fab-IgG TDB, e.g., an anti-CD3/HER2 1 Fab-IgG TDB having a 40G5c CD3 binding domain and two 4D5 Y55E.H91A.N54E.D98T.Y102V HER2 binding domains).

In yet another aspect, the invention provides a bispecific antigen-binding molecule comprising a monovalent arm and a bivalent arm, wherein: (a) the monovalent arm comprises a Fab$_A$, wherein the C-terminus of the Fab$_A$ is fused to an N-terminus of a first Fc subunit, and wherein the Fab$_A$ comprises the following HVRs: (i) an HVR-H1 comprising the amino acid sequence of SEQ ID NO: 1, (ii) an HVR-H2 comprising the amino acid sequence of SEQ ID NO: 2, (iii) an HVR-H3 comprising the amino acid sequence of SEQ ID NO: 3, (iv) an HVR-L1 comprising the amino acid sequence of SEQ ID NO: 4, (v) an HVR-L2 comprising the amino acid sequence of SEQ ID NO: 5, and (vi) an HVR-L3 comprising the amino acid sequence of SEQ ID NO: 6; (b) the bivalent arm comprises a Fab$_{B1}$ and a Fab$_{B2}$, wherein the C-terminus of the Fab$_{B2}$ is fused to the N-terminus of the Fab$_{B1}$, and the C-terminus of the Fab$_{B1}$ is fused to an N-terminus of a second Fc subunit, wherein the Fab$_{B1}$ and the Fab$_{B2}$ each comprise the following HVRs: (i) an HVR-H1 comprising the amino acid sequence of SEQ ID NO: 11, (ii) an HVR-H2 comprising the amino acid sequence of SEQ ID NO: 36, (iii) an HVR-H3 comprising the amino acid sequence of SEQ ID NO: 37, (iv) an HVR-L1 comprising the amino acid sequence of SEQ ID NO: 38, (v) an HVR-L2 comprising the amino acid sequence of SEQ ID NO: 29, and (vi) an HVR-L3 comprising the amino acid sequence of SEQ ID NO: 26; and (c) the first Fc subunit is associated with the second Fc subunit to form an Fc domain. In some embodiments, (a) the Fab$_A$ comprises a VH$_A$ region and a VL$_A$ region, wherein the VH$_A$ region comprises an amino acid sequence having at least 95% sequence identity to SEQ ID NO: 7, and the VL$_A$ region comprises an amino acid sequence having at least 95% sequence identity to SEQ ID NO: 8; (b) the Fab$_{B1}$ comprises a VH$_{B1}$ region and a VL$_{B1}$ region, wherein the VH$_{B1}$ region comprises an amino acid sequence having at least 95% sequence identity to SEQ ID NO: 41, and the VL$_{B1}$ region comprises an amino acid sequence having at least 95% sequence identity to SEQ ID NO: 49; and (c) the Fab$_{B2}$ comprises a VH$_{B2}$ region and a VL$_{B2}$ region, wherein the VH$_{B2}$ region comprises an amino acid sequence having at least 95% sequence identity to SEQ ID NO: 41, and the VL$_{B2}$ region comprises an amino acid sequence having at least 95% sequence identity to SEQ ID NO: 49. For example, in some embodiments, (a) the VH$_A$ region comprises the amino acid sequence of SEQ ID NO: 7, and the VL$_A$ region comprises the amino acid sequence of SEQ ID NO: 8; (b) the VH$_{B1}$ region comprises the amino acid sequence of SEQ ID NO: 41, and the VL$_{B1}$ region comprises the amino acid sequence of SEQ ID NO: 49; and (c) the VH$_{B2}$ region comprises the amino acid sequence of SEQ ID NO: 41, and the VL$_{B2}$ region comprises the amino acid sequence of SEQ ID NO: 49. For example, in some embodiments, the bispecific antigen-binding molecule is an anti-CD3/HER2 bispecific antigen-binding molecule (e.g., an anti-CD3/HER2 1 Fab-IgG TDB, e.g., an anti-CD3/HER2 1 Fab-IgG TDB having a 40G5c CD3 binding domain and two 4D5 N30S.Y55E.H91A.N54E.D98T HER2 binding domains).

In another aspect, the invention features a bispecific antigen-binding molecule comprising a monovalent arm and a bivalent arm, wherein: (a) the monovalent arm comprises a Fab$_A$, wherein the C-terminus of the Fab$_A$ is fused to an N-terminus of a first Fc subunit, and wherein the Fab$_A$ comprises the following HVRs: (i) an HVR-H1 comprising the amino acid sequence of SEQ ID NO: 1, (ii) an HVR-H2 comprising the amino acid sequence of SEQ ID NO: 2, (iii) an HVR-H3 comprising the amino acid sequence of SEQ ID NO: 3, (iv) an HVR-L1 comprising the amino acid sequence of SEQ ID NO: 4, (v) an HVR-L2 comprising the amino acid sequence of SEQ ID NO: 5, and (vi) an HVR-L3 comprising the amino acid sequence of SEQ ID NO: 6; (b) the bivalent arm comprises a Fab$_{B1}$ and a Fab$_{B2}$, wherein the C-terminus of the Fab$_{B2}$ is fused to the N-terminus of the Fab$_{B1}$, and the C-terminus of the Fab$_{B1}$ is fused to an N-terminus of a second Fc subunit, wherein the Fab$_{B1}$ and the Fab$_{B2}$ each comprise the following HVRs: (i) an HVR-H1 comprising the amino acid sequence of SEQ ID NO: 11, (ii) an HVR-H2 comprising the amino acid sequence of SEQ ID NO: 36, (iii) an HVR-H3 comprising the amino acid sequence of SEQ ID NO: 43, (iv) an HVR-L1 comprising the amino acid sequence of SEQ ID NO: 38, (v) an HVR-L2 comprising the amino acid sequence of SEQ ID NO: 29, and (vi) an HVR-L3 comprising the amino acid sequence of SEQ ID NO: 26; and (c) the first Fc subunit is associated with the second Fc subunit to form an Fc domain. In some embodiments, (a) the $Fab_A$ comprises a $VH_A$ region and a $VL_A$ region, wherein the $VH_A$ region comprises an amino acid sequence having at least 95% sequence identity to SEQ ID NO: 7, and the $VL_A$ region comprises an amino acid sequence having at least 95% sequence identity to SEQ ID NO: 8; (b) the $Fab_{B1}$ comprises a $VH_{B1}$ region and a $VL_{B1}$ region, wherein the $VH_{B1}$ region comprises an amino acid sequence having at least 95% sequence identity to SEQ ID NO: 44, and the $VL_{B1}$ region comprises an amino acid sequence having at least 95% sequence identity to SEQ ID NO: 49; and (c) the $Fab_{B2}$ comprises a $VH_{B2}$ region and a $VL_{B2}$ region, wherein the $VH_{B2}$ region comprises an amino acid sequence having at least 95% sequence identity to SEQ ID NO: 44, and the $VL_{B2}$ region comprises an amino acid sequence having at least 95% sequence identity to SEQ ID NO: 49. For example, in some embodiments, (a) the $VH_A$ region comprises the amino acid sequence of SEQ ID NO: 7, and the $VL_A$ region comprises the amino acid sequence of SEQ ID NO: 8; (b) the $VH_{B1}$ region comprises the amino acid sequence of SEQ ID NO: 44, and the $VL_{B1}$ region comprises the amino acid sequence of SEQ ID NO: 49; and (c) the $VH_{B2}$ region comprises the amino acid sequence of SEQ ID NO: 44, and the $VL_{B2}$ region comprises the amino acid sequence of SEQ ID NO: 49. For example, in some embodiments, the bispecific antigen-binding molecule is an anti-CD3/HER2 bispecific antigen-binding molecule (e.g., an anti-CD3/HER2 1 Fab-IgG TDB, e.g., an anti-CD3/HER2 1 Fab-IgG TDB having a 40G5c CD3 binding domain and two 4D5 N30S.Y55E.H91A.N54E.D98T.Y102V HER2 binding domains).

Peptide Linkers Fusing the Second and Third Antigen-Binding Moieties

In some embodiments, a bispecific antigen-binding molecule of the invention features a structure wherein the C-terminus of the third antigen-binding moiety is fused to the N-terminus of the second antigen-binding moiety via a peptide linker. The peptide linker can be 5-20 amino acids in length (e.g., 5-10, 10-15, or 15-20, e.g., 5, 6, 7, 8, 9, 10, 11, 12, 13, 14, 15, 16, 17, 18, 19, or 20 amino acids in length). In some embodiments, the peptide linker is the natural amino acid sequence of the variable heavy chain hinge region (e.g., DKTHT; SEQ ID NO: 50). Alternatively, in some embodiments, the peptide linker includes the $G4SG_2$ linker (SEQ ID NO: 51). In some embodiments, the peptide linker comprises the $G4SG_2$ linker and the hinge region (e.g., SEQ ID NO: 52).

The amino acid sequences of exemplary heavy chain polypeptides comprising the second and third antigen-binding moiety heavy chains, with and without a $G4SG_2$ linker (SEQ ID NO: 51), are provided in Table 2.

TABLE 2

SEQ ID NOs corresponding to polypeptides comprising the Fc domain, the second antigen-binding moiety heavy chain region, and the third antigen-binding moiety heavy chain region of exemplary 1Fab-IgG TDB molecules, including and without a $G_4SG_2$ (SEQ ID NO: 51) linker. The sequences shown below include a hinge sequence as part of the linker peptide fusing the second and third antigen-binding moiety heavy chains.

| | Without $G_4SG_2$ | Including $G_4SG_2$ |
|---|---|---|
| 4D5 Consensus | 55 | 56 |
| 4D5 Wildtype (trastuzumab) | 57 | 58 |

TABLE 2-continued

SEQ ID NOs corresponding to polypeptides comprising the Fc domain, the second antigen-binding moiety heavy chain region, and the third antigen-binding moiety heavy chain region of exemplary 1Fab-IgG TDB molecules, including and without a $G_4SG_2$ (SEQ ID NO: 51) linker. The sequences shown below include a hinge sequence as part of the linker peptide fusing the second and third antigen-binding moiety heavy chains.

| | Without $G_4SG_2$ | Including $G_4SG_2$ |
|---|---|---|
| 4D5 H91A | 59 | 60 |
| 4D5 Y55E.Y102V | 61 | 62 |
| 4D5 D98A.F100A.Y102V | 63 | 64 |
| 4D5 D98T.F100A.Y102V | 65 | 66 |
| 4D5 N30S.N54E.D98T | 67 | 68 |
| 4D5 N30S.H91A.N54E.D98T | 69 | 70 |
| 4D5 H91A.N54E.D98T | 71 | 72 |
| 4D5 N30S.Y55E.N54E.D98T.Y102V | 73 | 74 |
| 4D5 N30S | 75 | 76 |
| 4D5 N54E.D98T | 77 | 78 |
| 4D5 N30S.N54E.D98T.F100A.Y102V | 79 | 80 |
| 4D5 N30S.N54E.D98A.F100A.Y102V | 81 | 82 |
| 4D5 Y55E.H91A.N54E.D98T | 83 | 84 |
| 4D5 Y55E.H91A.N54E.D98T.Y102V | 85 | 86 |
| 4D5 N30S.Y55E.H91A.N54E.D98T | 87 | 88 |
| 4D5 N30S.Y55E.H91A.N54E.D98T.Y102V | 89 | 90 |

In particular, a bispecific antigen-binding molecule of the invention may feature a peptide linker comprising the amino acid sequence of SEQ ID NO: 50. In some embodiments, the antigen-binding molecule comprises an amino acid sequence having at least 95% sequence identity to SEQ ID NO: 55 (e.g., at least 96% sequence identity to SEQ ID NO: 55, at least 97% sequence identity to SEQ ID NO: 55, at least 98% sequence identity to SEQ ID NO: 55, at least 99% sequence identity to SEQ ID NO: 55, or 100% sequence identity to SEQ ID NO: 55). In other instances, the antigen-binding molecule comprises an amino acid sequence having at least 95% sequence identity SEQ ID NO: 59 (e.g., at least 96% sequence identity to SEQ ID NO: 59, at least 97% sequence identity to SEQ ID NO: 59, at least 98% sequence identity to SEQ ID NO: 59, at least 99% sequence identity to SEQ ID NO: 59, or 100% sequence identity to SEQ ID NO: 59). Alternatively, the antigen-binding molecule may comprise an amino acid sequence having at least 95% sequence identity SEQ ID NO: 63 (e.g., at least 96% sequence identity to SEQ ID NO: 63, at least 97% sequence identity to SEQ ID NO: 63, at least 98% sequence identity to SEQ ID NO: 63, at least 99% sequence identity to SEQ ID NO: 63, or 100% sequence identity to SEQ ID NO: 63). In some embodiments, the antigen-binding molecule comprises an amino acid sequence having at least 95% sequence identity SEQ ID NO: 83 (e.g., at least 96% sequence identity to SEQ ID NO: 83, at least 97% sequence identity to SEQ ID NO: 83, at least 98% sequence identity to SEQ ID NO: 83, at least 99% sequence identity to SEQ ID NO: 83, or 100% sequence identity to SEQ ID NO: 83). In other instances, the antigen-binding molecule comprises an amino acid sequence having at least 95% sequence identity SEQ ID NO: 85 (e.g., at least 96% sequence identity to SEQ ID NO: 85, at least 97% sequence identity to SEQ ID NO: 85, at least 98% sequence identity to SEQ ID NO: 85, at least 99% sequence identity to SEQ ID NO: 85, or 100% sequence identity to SEQ ID NO: 85). In some embodiments, the antigen-binding molecule comprises an amino acid sequence having at least 95% sequence identity SEQ ID NO: 87 (e.g., at least 96% sequence identity to SEQ ID NO: 87, at least 97% sequence identity to SEQ ID NO: 87, at least 98% sequence identity to SEQ ID NO: 87, at least 99% sequence identity to SEQ ID NO: 87, or 100% sequence identity to SEQ ID NO: 87). In some embodiments, the antigen-binding molecule comprises an amino acid sequence having at least 95% sequence identity SEQ ID NO: 89 (e.g., at least 96% sequence identity to SEQ ID NO: 89, at least 97% sequence identity to SEQ ID NO: 89, at least 98% sequence identity to SEQ ID NO: 89, at least 99% sequence identity to SEQ ID NO: 89, or 100% sequence identity to SEQ ID NO: 89).

In other instances, the peptide linker comprises the amino acid sequence of SEQ ID NO: 51. The antigen-binding molecule may comprises an amino acid sequence having at least 95% sequence identity to SEQ ID NO: 56 (e.g., at least 96% sequence identity to SEQ ID NO: 56, at least 97% sequence identity to SEQ ID NO: 56, at least 98% sequence identity to SEQ ID NO: 56, at least 99% sequence identity to SEQ ID NO: 56, or 100% sequence identity to SEQ ID NO: 56). In some embodiments, the antigen-binding molecule may comprise an amino acid sequence having at least 95% sequence identity SEQ ID NO: 60 (e.g., at least 96% sequence identity to SEQ ID NO: 60, at least 97% sequence identity to SEQ ID NO: 60, at least 98% sequence identity to SEQ ID NO: 60, at least 99% sequence identity to SEQ ID NO: 60, or 100% sequence identity to SEQ ID NO: 60). In some embodiments, the antigen-binding molecule comprises an amino acid sequence having at least 95% sequence identity SEQ ID NO: 64 (e.g., at least 96% sequence identity to SEQ ID NO: 64, at least 97% sequence identity to SEQ ID NO: 64, at least 98% sequence identity to SEQ ID NO: 64, at least 99% sequence identity to SEQ ID NO: 64, or 100% sequence identity to SEQ ID NO: 64). In some embodiments, the antigen-binding molecule comprises an amino acid sequence having at least 95% sequence identity SEQ ID NO: 84 (e.g., at least 96% sequence identity to SEQ ID NO: 84, at least 97% sequence identity to SEQ ID NO: 84, at least 98% sequence identity to SEQ ID NO: 84, at least 99% sequence identity to SEQ ID NO: 84, or 100% sequence identity to SEQ ID NO: 84). In some embodiments, the antigen-binding molecule comprises an amino acid sequence having at least 95% sequence identity SEQ ID NO: 86 (e.g., at least 96% sequence identity to SEQ ID NO: 86, at least 97% sequence identity to SEQ ID NO: 86, at least 98% sequence identity to SEQ ID NO: 86, at least 99% sequence identity to SEQ ID NO: 86, or 100% sequence identity to SEQ ID NO: 86). In some embodiments, the antigen-binding molecule comprises an amino acid sequence having at least 95% sequence identity SEQ ID NO: 88 (e.g., at least 96% sequence identity to SEQ ID NO: 88, at least 97% sequence identity to SEQ ID NO: 88, at least 98% sequence identity to SEQ ID NO: 88, at least 99% sequence identity to SEQ ID NO: 88, or 100% sequence identity to SEQ ID NO: 88). In some embodiments, the antigen-binding molecule comprises an amino acid sequence having at least 95% sequence identity SEQ ID NO: 90 (e.g., at least 96% sequence identity to SEQ ID NO: 90, at least 97% sequence identity to SEQ ID NO: 90, at least 98% sequence identity to SEQ ID NO: 90, at least 99% sequence identity to SEQ ID NO: 90, or 100% sequence identity to SEQ ID NO: 90).

Fc Domains

Bispecific antigen-binding molecules of the invention may feature an Fc domain. The Fc domain may be an IgG Fc domain (e.g., an $IgG_1$ or $IgG_4$ Fc domain). For example, the Fc domain can be a human Fc domain. In some embodiments, the Fc domain comprises one or more amino acid substitution that reduces binding to an Fc receptor and/or effector function. For example, in some embodiments, the one or more amino acid substitutions that reduces binding to an Fc receptor and/or effector function is at one or more position selected from the group of L234, L235, and P329 (e.g., wherein the first Fc subunit and the second Fc subunit each comprises the amino acid substitutions of L234A, L235A and P329G). The Fc receptor may be, for example, an Fcγ receptor. Thus, the bispecific antigen-binding molecules of the invention can be configured to reduce antibody-dependent cell-mediated cytotoxicity (ADCC).

In some instances, the Fc domain comprises a modification configured to promote the association of the first Fc subunit with the second Fc subunit. "Knob-in-hole" engineering of bispecific antibodies may be utilized to generate a first arm containing a knob and a second arm containing the hole into which the knob of the first arm may bind. The knob of the multispecific antibodies of the invention may be a monovalent arm (e.g., anti-CD3 arm) in one embodiment. Alternatively, the knob of the multispecific antibodies of the invention may be a bivalent arm (e.g., anti-tumor arm). The hole of the multispecific antibodies of the invention may be a monovalent arm (e.g., anti-CD3 arm) in one embodiment. Alternatively, the hole of the multispecific antibodies of the invention may be a bivalent arm (e.g., anti-tumor arm). Bispecific antibodies may also be engineered using immunoglobulin crossover (also known as Fab domain exchange or CrossMab format) technology (see e.g., WO 2009/080253; Schaefer et al., Proc. Natl. Acad. Sci. USA, 108: 11187-11192 (2011)). Bispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); or by using leucine zippers to produce bi-specific antibodies (see, e.g., Kostelny et al., J. Immunol., 148(5):1547-1553 (1992)).

An amino acid residue in the CH3 domain of the second Fc subunit may be replaced with an amino acid residue having a larger side chain volume, thereby generating a protuberance (e.g., a knob) within the CH3 domain of the second Fc subunit which is positionable in a cavity (e.g., a hole) within the CH3 domain of the first Fc subunit, and an amino acid residue in the CH3 domain of the first Fc subunit may be replaced with an amino acid residue having a smaller side chain volume, thereby generating a cavity (e.g., a hole) within the CH3 domain of the first Fc subunit within which the protuberance (e.g., a knob) within the CH3 domain of the second Fc subunit may be positionable. In some embodiments, the CH3 domain of the second Fc subunit comprises the amino acid substitution of T366, and the CH3 domain of the first Fc subunit comprises amino acid substitutions at one, two, or all three of T366, L368, and/or Y407. In some embodiments, the CH3 domain of the second Fc subunit comprises the amino acid substitution of T366W, and the CH3 domain of the first Fc subunit comprises one, two, or all three amino acid substitutions of T366S, L368A, and/or Y407V.

It is expressly contemplated that such bispecific antigen-binding molecules or other antibodies described herein for use in any of the instances enumerated herein may have any of the features, singly or in combination, described in Sections 1-6 below.

1. Antibody Affinity

In certain instances, a bispecific antigen-binding molecule has an equilibrium dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

In one instance, $K_D$ is measured by a radiolabeled antigen binding assay (RIA). In one instance, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (about 23° C.). In a non-adsorbent plate (Nunc #269620), 100 μM or 26 μM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another instance, $K_D$ is measured using a BIACORE® surface plasmon resonance assay. For example, an assay using a BIACORE®-2000 or a BIACORE®-3000 (BIACORE®, Inc., Piscataway, NJ) is performed at 25° C. with immobilized antigen CM5 chips at ~10 response units (RU). In one instance, carboxymethylated dextran biosensor chips (CM5, BIACORE®, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve about 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of about 25 μl/min. Association rates ($k_{on}$) and dissociation rates ($k_{on}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{on}/k_{on}$. See, for example, Chen et al., J. Mol. Biol. 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain instances, a bispecific antigen-binding molecule provided herein is includes one or more antibody fragments. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Plückthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9:129-134 (2003); and Hollinger et al. *Proc. Nat. Acad. Sci. USA* 90: 6444-6448 (1993). Triabodies and tetrabodies are also described in Hudson et al. *Nat. Med.* 9:129-134 (2003).

Single-domain antibodies are antibody fragments comprising all or a portion of the heavy chain variable domain or all or a portion of the light chain variable domain of an antibody. In certain instances, a single-domain antibody is a human single-domain antibody (Domantis, Inc., Waltham, MA; see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain instances, a bispecific antigen-binding molecule provided herein is a chimeric antibody. Certain chimeric antibodies are described, e.g., in U.S. Pat. No. 4,816,567; and Morrison et al. *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain instances, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some instances, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., Proc. Natl. Acad. Sci. USA 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain instances, a bispecific antigen-binding molecule provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Bispecific antigen-binding molecules of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N J, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N J, 2003); Sidhu et al., *J. Mol. Biol.* 338(2): 299-310 (2004); Lee et al., J. *Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Antigen-Binding Molecule Variants

In certain instances, amino acid sequence variants of the bispecific antigen-binding molecules of the invention are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

In certain embodiments, a bispecific antigen-binding molecule of the invention comprises one or more modifications in the VH/VL region and/or CH1/CL region to facilitate correct heavy/light chain pairing. In some embodiments, a bispecific antigen-binding molecule of the invention comprises one or more modifications in the Fc region to facilitate heterodimerization of the two arms of the bispecific antigen-binding molecule. Such modifications in the VH/VL region, CH1/CL region, and/or FC region are described in International Patent Publication No. WO 2016/172485, which is herein incorporated by reference in its entirety.

A. Substitution, Insertion, and Deletion Variants

In certain instances, antigen-binding moiety variants having one or more amino acid substitutions are provided. Sites of interest for substitutional mutagenesis include the HVRs and FRs. Conservative substitutions are shown in Table 3 under the heading of "preferred substitutions." More substantial changes are provided in Table 3 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved Antibody-Dependent Cell-Mediated Cytotoxicity (ADCC) or Complement Dependent Cytotoxicity (CDC).

TABLE 3

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gin;
(3) acidic: Asp, Glu;
(4) basic: His, Lys, Arg;
(5) residues that influence chain orientation: Gly, Pro; or
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity and/or reduced immunogenicity) relative to the parent antibody and/or will have substantially retained certain biological properties of the parent antibody. An exemplary substitutional variant is an affinity matured antibody, which may be conveniently generated, for example, using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001)). In some instances of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain instances, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen-contacting residues in the HVRs. In certain instances of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

B. Glycosylation Variants

In certain instances, antigen-binding molecules of the invention can be altered to increase or decrease the extent to which the antibody is glycosylated. Addition or deletion of glycosylation sites to an antibody of the invention may be conveniently accomplished by altering the amino acid sequence such that one or more glycosylation sites is created or removed.

Where the antigen-binding molecule comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some instances, modifications of the oligosaccharide in an antibody of the invention may be made in order to create antibody variants with certain improved properties.

In one instance, antigen-binding molecule variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, for example, U.S. Publication Nos. US 2003/0157108 and US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); U.S. Pat. Appl. No. US 2003/0157108 A1; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antigen-binding molecule variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

C. Fc region variants In certain instances, one or more amino acid modifications may be introduced into the Fc region of an antibody of the invention, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain instances, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest are described in U.S. Pat. No. 5,500,362 (see, e.g., Hellstrom, I. et al. *Proc. Natl. Acad. Sci. USA* 83:7059-7063 (1986) and Hellstrom, I et al., *Proc. Natl. Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CYTOTOX 96® non-radioactive cytotoxicity assay (Promega, Madison, WI))). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Natl. Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, e.g., Gazzano-Santoro et al., *J. Immunol. Methods* 202:163 (1996); Cragg et al., *Blood.* 101:1045-1052 (2003); and Cragg et al., *Blood.* 103:2738-2743 (2004)). FcRn binding and in vivo clearance/half-life determinations can also be performed using methods known in the art (see, e.g., Petkova et al. *Int'l. Immunol.* 18(12):1759-1769 (2006)).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain instances, an antibody variant comprises an Fc region with one or more amino acid substitutions which improve ADCC, e.g., substitutions at positions 298, 333, and/or 334 of the Fc region (EU numbering of residues).

In some instances, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

D. Cysteine Engineered Antibody Variants

In certain instances, it may be desirable to create cysteine engineered antibodies, e.g., "thioMAbs," in which one or more residues of an antibody are substituted with cysteine residues. In particular instances, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain instances, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

E. Antibody Derivatives

In certain instances, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another instance, conjugates of an antibody and non-proteinaceous moiety that may be selectively heated by exposure to radiation are provided. In one instance, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

F. Immunoconjugates

The invention also provides immunoconjugates comprising bispecific antigen-binding molecule conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one instance, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another instance, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another instance, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron. Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, and SVSB (succinimidyl-(4-vinylsulfone)benzoate) which are commercially available (e.g., from Pierce Biotechnology, Inc., Rockford, IL., U.S.A).

III. Recombinant Methods and Compositions

Bispecific antigen-binding molecules of the invention may be produced using recombinant methods and compositions, for example, as described in U.S. Pat. No. 4,816,567 and in U.S. Publication No. 2013/0078249, which is incorporated herein by reference in its entirety. In one embodiment, isolated nucleic acid (e.g., a polynucleotide) encoding bispecific antigen-binding molecule described herein is provided. Such nucleic acid may encode an amino acid sequence comprising the VL and/or an amino acid sequence comprising a VH of the bispecific antigen-binding molecule (e.g., the light and/or heavy chains of the either arm of the bispecific antigen-binding molecule). In a further embodiment, one or more vectors (e.g., expression vectors) comprising such nucleic acid are provided.

Polynucleotides encoding bispecific antigen-binding molecules of the invention may be expressed as a single polynucleotide molecule or as multiple (e.g., two or more) polynucleotides that are co-expressed. Polypeptides encoded by polynucleotides that are co-expressed may associate through, e.g., disulfide bonds or other means to form a functional bispecific antigen-binding molecule. For example, a light chain portion of an antigen binding moiety may be encoded by a separate polynucleotide from the portion of the bispecific antigen-binding molecule comprising the heavy chain portion of the antigen binding moiety, an Fc domain subunit and optionally another antigen binding moiety. When co-expressed, the heavy chain polypeptides will associate with the light chain polypeptides to form the antigen binding moiety. In another example, the portion of the bispecific antigen-binding molecule comprising one of the two Fc domain subunits and optionally one or more antigen-binding moieties could be encoded by a separate polynucleotide from the portion of the T cell activating bispecific antigen binding molecule comprising the other of the two Fc domain subunits and optionally an antigen binding moiety. When co-expressed, the Fc domain subunits will associate to form the Fc domain.

In certain embodiments, an isolated polynucleotide of the invention encodes a fragment of a bispecific antigen-binding molecule comprising a first and a second antigen-binding moiety, and an Fc domain consisting of two subunits. In one embodiment, an isolated polynucleotide of the invention encodes the first antigen binding moiety and a subunit of the Fc domain. In another embodiment, an isolated polynucleotide of the invention encodes the heavy chain of the second antigen binding moiety and a subunit of the Fc domain. In a more specific embodiment, the isolated polynucleotide encodes a polypeptide, wherein a Fab heavy chain shares a C-terminal peptide bond with an Fc domain subunit. In yet another embodiment, an isolated polynucleotide of the invention encodes the heavy chain of the third antigen-binding moiety, the heavy chain of the second antigen binding moiety, and a subunit of the Fc domain. In some embodiments, the light chains of the second and third antigen-binding moieties are co-expressed and associate with the heavy chain regions to form Fab domains.

In a further embodiment, a host cell comprising such nucleic acid is provided. In one such embodiment, a host cell comprises (e.g., has been transformed with): (1) a vector comprising a nucleic acid that encodes an amino acid sequence comprising at least one VL of the bispecific antigen-binding molecule and an amino acid sequence comprising at least one VH of the bispecific antigen-binding molecule, or (2) a first vector comprising a nucleic acid that encodes an amino acid sequence comprising a VL of the bispecific antigen-binding molecule and a second vector comprising a nucleic acid that encodes an amino acid sequence comprising a VH of the bispecific antigen-binding molecule. In one embodiment, the host cell is eukaryotic, e.g., a Chinese Hamster Ovary (CHO) cell or lymphoid cell. In one embodiment, a method of making a bispecific antigen-binding molecule is provided, wherein the method comprises culturing a host cell comprising a nucleic acid encoding the bispecific antigen-binding molecule, as provided above, under conditions suitable for expression of the antibody, and optionally recovering the antibody from the host cell (or host cell culture medium).

For recombinant production of a bispecific antigen-binding molecule, a polynucleotide encoding a bispecific antigen-binding molecule, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the bispecific antigen-binding molecule).

Suitable host cells for cloning or expression of bispecific antigen-binding molecule-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B.K.C. Lo, ed., Humana Press, Totowa, N J, 2003), pp. 245-254, describing expression of antibody fragments in *E. coli*.) After expression, the antibody may be isolated from the bacterial cell paste in a soluble fraction and can be further purified.

IV. Pharmaceutical Formulations

Therapeutic formulations of the bispecific antigen-binding molecules of the present invention are prepared for storage by mixing the bispecific antigen-binding molecule having the desired degree of purity with optional pharmaceutically acceptable carriers, excipients, or stabilizers in the form of lyophilized formulations or aqueous solutions. For general information concerning formulations, see, e.g., Gilman et al. (eds.) *The Pharmacological Bases of Therapeutics*, 8th Ed., Pergamon Press, 1990; A. Gennaro (ed.), *Remington's Pharmaceutical Sciences*, 18th Edition, Mack Publishing Co., Pennsylvania, 1990; Avis et al. (eds.) *Pharmaceutical Dosage Forms: Parenteral Medications Dekker, New York*, 1993; Lieberman et al. (eds.) *Pharmaceutical Dosage Forms: Tablets Dekker, New York*, 1990; Lieberman et al. (eds.), *Pharmaceutical Dosage Forms: Disperse Systems Dekker, New York*, 1990; and Walters (ed.) Dermatological and Transdermal Formulations (Drugs and the Pharmaceutical Sciences), Vol 119, Marcel Dekker, 2002.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

The formulation herein may also contain more than one active compound, preferably those with complementary activities that do not adversely affect each other. The type and effective amounts of such medicaments depend, for example, on the amount and type of antagonist present in the formulation, and clinical parameters of the subjects.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The formulations to be used for in vivo administration must be sterile. This is readily accomplished by filtration through sterile filtration membranes.

V. Therapeutic Methods

Any of the bispecific antigen-binding molecules of the invention (e.g., bispecific antigen-binding molecules having a monovalent arm capable of specific binding to a first antigen and a bivalent arm capable of specific binding to two second antigens) or compositions thereof may be used in any of the therapeutic methods described herein.

In one aspect, a bispecific antigen-binding molecule for use as a medicament is provided. For example, in some embodiments, the bispecific antigen-binding molecules described herein are for use in treating or delaying progression of a cell proliferative disorder (e.g., cancer) or an autoimmune disorder in a subject in need thereof. In some embodiments, the bispecific antigen-binding molecule of any of the preceding aspects are for use in enhancing immune function in a subject having a cell proliferative disorder (e.g., cancer) or an autoimmune disorder. In certain embodiments, the invention provides bispecific antigen-binding molecule for use in a method of enhancing immune function in an individual having a cell proliferative disorder or an autoimmune disorder comprising administering to the individual an effective of the bispecific antigen-binding molecule to activate effector cells (e.g., T cells, e.g., CD8+ and/or CD4+ T cells), expand (increase) an effector cell population, reduce a population of target cells (e.g., a population of cells expressing a second target cell antigen recognized by a bispecific antigen-binding molecule of the invention), and/or kill a target cell (e.g., target tumor cell).

The invention features use of the bispecific antigen-binding molecule of the invention in the manufacture of a medicament for treating or delaying progression of a disorder, such as a cell proliferative disorder (e.g., a cancer) or an autoimmune disorder. In a further embodiment, the medicament is for use a method of treating a cell proliferative disorder or an autoimmune disorder comprising administering to an individual having a cell proliferative disorder or an autoimmune disorder an effective amount of the medicament. In one such embodiment, the method further comprises administering to the subject an effective amount of at least one additional therapeutic agent, for example, as described below. In a further embodiment, the medicament is for activating effector cells (e.g., T cells, e.g., CD8+ and/or CD4+ T cells), expanding (increasing) an effector cell population, reducing a population of target cells (e.g., a population of cells expressing a second target cell antigen recognized by a bispecific antigen-binding molecule of the invention), and/or killing a target cell (e.g., target tumor cell).

In a further aspect, the invention provides a method of treating or delaying the progression of a disorder in a subject in need thereof, the method comprising administering to the subject the bispecific antigen-binding molecule of any of the preceding aspects. In one embodiment, the method comprises administering to a subject having such a cell proliferative disorder or an autoimmune disorder an effective amount of a bispecific antigen-binding molecule (e.g., a bispecific antigen-binding molecule having an anti-CD3 monovalent arm and an anti-tumor cell antigen bivalent arm). In one such embodiment, the method further comprises administering to the individual an effective amount of at least one additional therapeutic agent, for example, as described below.

In another aspect, the invention provides a method of enhancing immune function in a subject having a disorder, the method comprising administering to the subject the bispecific antigen-binding molecule of any of the preceding aspects (e.g., a bispecific antigen-binding molecule having an anti-CD3 monovalent arm and an anti-tumor cell antigen bivalent arm). In some embodiments, the disorder is a cell proliferative disorder (e.g., cancer) or an autoimmune disorder. In certain embodiments, the method includes administering an effective amount of the bispecific antigen-binding molecule to activate effector cells (e.g., T cells, e.g., CD8+ and/or CD4+ T cells), expand (increase) an effector cell population, reduce a population of target cells (e.g., a population of cells expressing a second target cell antigen recognized by a bispecific antigen-binding molecule of the invention), and/or kill a target cell (e.g., target tumor cell).

In some embodiments, the bispecific antigen-binding molecules provided herein, compositions, and methods of use thereof, are used for the treatment of cancer, such as breast cancer, gastric cancer, colorectal cancer, non-small cell lung cancer, non-Hodgkin's lymphoma (NHL), B cell lymphoma, B cell leukemia, multiple myeloma, renal cancer, prostate cancer, liver cancer, head and neck cancer, melanoma, ovarian cancer, mesothelioma, glioblastoma, germinal-center B-cell-like (GCB) diffuse large B cell lymphoma (DLBCL), activated B cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenström macroglobulinemia (WM), central nervous system lymphoma (CNSL), Burkitt's lymphoma (BL), B cell prolymphocytic leukemia, splenic marginal zone lymphoma, hairy cell leukemia, splenic lymphoma/leukemia, splenic diffuse red pulp small B cell lymphoma, hairy cell leukemia variant, a heavy chain disease, γ heavy chain disease, µ heavy chain disease, plasma cell myeloma, solitary plasmacytoma of bone, extraosseous plasmacytoma, extranodal marginal zone lymphoma of mucosa-associated lymphoid tissue (MALT lymphoma), nodal marginal zone lymphoma, pediatric nodal marginal zone lymphoma, pediatric follicular lymphoma, primary cutaneous follicle centre lymphoma, T cell/histiocyte rich large B cell lymphoma, primary DLBCL of the central nervous system, primary cutaneous DLBCL (leg type), Epstein-Barr virus (EBV)-positive DLBCL of the elderly, DLBCL associated with chronic inflammation, lymphomatoid granulomatosis, primary mediastinal (thymic) large B cell lymphoma, intravascular large B cell lymphoma, anaplastic lymphoma kinase (ALK)-positive large B cell lymphoma, plasmablastic lymphoma, large B cell lymphoma arising in HHV8-associated multicentric Castleman disease, primary effusion lymphoma, large B cell lymphoma, unclassifiable, with features intermediate between diffuse large B-cell lymphoma and Burkitt lymphoma, or large B cell lymphoma, unclassifiable, with features intermediate between diffuse large B-cell lymphoma and classical Hodgkin lymphoma)). In some embodiments, the bispecific antigen-binding molecules provided herein, compositions, and methods of use thereof, are used for the treatment of a HER2-positive cancer (e.g., a HER2-positive breast cancer or a HER2-positive gastric cancer).

The invention further provides combination therapies including administration of a bispecific antigen-binding molecule with one or more additional therapeutic agents (e.g., one, two, three, four, five, or more additional therapeutic agents) administered in parallel or as part of a complex regimen. In one embodiment, a bispecific antigen-binding molecule is co-administered with one or more biological modifiers selected from a BCL-2 inhibitor (e.g., GDC-0199/ABT-199), lenalidomide (REVLIMID®), a PI3K-delta inhibitor (such as idelalisib (ZYDELIG®)), an agonist, e.g., agonist antibody directed against an activating co-stimulatory molecule, e.g., CD40, CD226, CD28, OX40 (e.g., AgonOX), GITR, CD137 (also known as TNFRSF9, 4-1BB, or ILA), CD27 (e.g., CDX-1127), HVEM, or CD127, an antagonist, e.g., antagonist antibody, directed against an inhibitory co-stimulatory molecule, e.g., CTLA-4 (also known as CD152), PD-1, TIM-3, BTLA, VISTA, LAG-3, B7-H3, B7-H4, IDO (e.g., 1-methyl-D-tryptophan (also known as 1-D-MT)), TIGIT, MICA/B, GITR (e.g., TRX518) or arginase, ipilimumab (also known as MDX-010, MDX-101, or YERVOY®), tremelimumab (also known as ticilimumab or CP-675,206, urelumab (also known as BMS-663513), MGA271, an antagonist directed against a TGF-β, e.g., metelimumab (also known as CAT-192), fresolimumab (also known as GC1008), LY2157299k, and an adoptive transfer of a T cell (e.g., a cytotoxic T cell) expressing a chimeric antigen receptor (CAR), e.g., adoptive transfer of a T cell comprising a dominant-negative TGF-β receptor, e.g., a dominant-negative TGF-β type II receptor.

In a particular embodiment, the biological modifier is a PD-1 axis binding antagonist. In some embodiments, the PD-1 axis binding antagonist or additional therapeutic agent is administered prior to or subsequent to the administration of the bispecific antigen-binding molecule. In some embodiments, the PD-1 axis binding antagonist or additional therapeutic agent is administered concurrently with the bispecific antigen-binding molecule. In some embodiments, the PD-1 axis binding antagonist is selected from the group consisting of a PD-L1 binding antagonist (e.g., atezolizumab (MPDL3280A), YW243.55.S70, MDX-1105, MEDI4736 (durvalumab), and MSB0010718C (avelumab)), a PD-1 binding antagonist (e.g., MDX-1106 (nivolumab), MK-3475 (pembrolizumab), CT-011 (pidilizumab), MEDI-0680 (AMP-514), PDR001 (spartalizumab), REGN2810 (cemiplimab), and BGB-108), and a PD-L2 binding antagonist (e.g., an antibody or an immunoadhesin).

Additionally or alternatively, a bispecific antigen-binding molecule of the invention may be co-administered with one or more chemotherapeutic agents (e.g., as part of a method of treating a subject having a cell proliferative disorder, e.g., a cancer).

In a further aspect, the invention provides a method for treating a HER2-positive cancer. In one embodiment, the method comprises administering to an individual having a HER2-positive cancer an effective amount of a bispecific antigen-binding molecule of the invention, such as a 1Fab-IgG TDB molecule having a bivalent anti-HER2 arm and a monovalent anti-CD3 arm. In a particular embodiment, the anti-HER2 arm possesses an acceptable toxicity profile when administered in an effective dose in a patient. In one embodiment, the anti-CD3 arm of 1Fab-IgG TDB molecule with an acceptable toxicity profile is a low affinity anti-CD3 antigen-binding moiety. In one embodiment, the anti-CD3 antigen-binding moiety of the 1Fab-IgG TDB with an acceptable toxicity profile is 40G5c.

In a particular embodiment, the HER2-positive cancer is a HER2-positive breast cancer or HER2-positive gastric cancer. The HER2-positive cancer (e.g., the HER2-positive breast cancer or the HER2-positive gastric cancer) may be characterized by tumor cells that express HER2 at a copy number (e.g., an average copy number) of at least 200,000 per cell (e.g., at least 250,000 HER2 copies per cell, at least 300,000 HER2 copies per cell, at least 400,000 HER2 copies per cell, at least 500,000 HER2 copies per cell, at least 600,000 HER2 copies per cell, at least 700,000 HER2 copies per cell, at least 750,000 HER2 copies per cell, at least 800,000 HER2 copies per cell, at least 900,000 HER2 copies per cell, at least 1,000,000 HER2 copies per cell, at least 1,200,000 HER2 copies per cell, at least 1,500,000 HER2 copies per cell, at least 2,000,000 HER2 copies per cell, at least 2,500,000 HER2 copies per cell, at least 3,000,000 HER2 copies per cell, or more, e.g., from 200,000 to 2,000,000 HER2 copies per cell, from 300,000 to 1,500,000 HER2 copies per cell, from 400,000 to 1,200,000 HER2 copies per cell, or from 500,000 to 1,000,000 HER2 copies per cell, e.g., from 200,000 to 1,000,000 HER2 copies per cell (e.g., from 200,000 to 250,000 HER2 copies per cell, from 250,000 to 300,000 HER2 copies per cell, from 300,000 to 400,000 HER2 copies per cell, from 400,000 to 500,000 HER2 copies per cell, from 500,000 to 750,000 HER2 copies per cell, or from 750,000 to 1,000,000 HER2 copies per cell) or from 1,000,000 to 3,000,000 HER2 copies per cell (e.g., from 1,000,000 to 1,500,000 HER2 copies per cell, from 1,500,000 to 2,000,000 HER2 copies per cell, from 2,000,000 to 2,500,000 HER2 copies per cell, or from 2,500,000 to 3,000,000 HER2 copies per cell).

In one embodiment, an anti-HER2 bispecific antigen-binding molecule is co-administered with one or more additional therapeutic agents that target the HER pathway. In one embodiment, the therapeutic agent that targets the HER pathway is selected from an EGFR inhibitor, a HER2 inhibitor, a HER3 inhibitor, and/or a HER4 inhibitor. In one embodiment, a HER2 TDB (e.g., a 1Fab-IgG TDB) is co-administered with one or more additional therapeutic agents selected from trastuzumab (HERCEPTIN®), T-DM1 (KADCYLA®) and pertuzumab (PERJETA®). In one embodiment, an anti-HER2/CD3 bispecific antigen-binding molecule is co-administered with trastuzumab. In one embodiment, an anti-HER2/CD3 bispecific antigen-binding molecule is co-administered with T-DM1. In one embodiment, an anti-HER2/CD3 bispecific antigen-binding molecule is co-administered with pertuzumab. In one embodiment, an anti-HER2/CD3 bispecific antigen-binding molecule is co-administered with trastuzumab and pertuzumab. In one embodiment, an anti-HER2/CD3 bispecific antigen-binding molecule is co-administered with T-DM1 and pertuzumab.

Such combination therapies noted above encompass combined administration (where two or more therapeutic agents are included in the same or separate formulations), and separate administration, in which case, administration of the bispecific antigen-binding molecule of the invention can occur prior to, simultaneously, and/or following, administration of the additional therapeutic agent or agents. In one embodiment, administration of the anti-CD3 antibody and administration of an additional therapeutic agent occur within about one month, or within about one, two or three weeks, or within about one, two, three, four, five, or six days, of each other.

A bispecific antigen-binding molecule of the invention (and/or any additional therapeutic agent) can be administered by any suitable means, including subcutaneously, intravenously, intramuscularly, topically, orally, transdermally, intraperitoneally, intraorbitally, by implantation, by inhalation, intrathecally, intraventricularly, or intranasally. For example, in some embodiments, the bispecific antigen-binding molecule is administered subcutaneously. In other embodiments, the bispecific antigen-binding molecule is administered intravenously. In some embodiments, a bispecific antigen-binding molecule administered by subcutaneous injection exhibits a less toxic response in a patient than the same bispecific antigen-binding molecule administered by intravenous injection. Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

Bispecific antigen-binding molecules of the invention can be formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. The bispecific antigen-binding molecule need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a bispecific antigen-binding molecule of the invention (when used alone or in combination with one or more other additional therapeutic agents) will depend on the type of disease to be treated, the severity and course of the disease, whether the bispecific antigen-binding molecule is administered for preventive or therapeutic purposes, previous therapy, the patient's clinical history and response to the bispecific antigen-binding molecule, and the discretion of the attending physician. The bispecific antigen-binding molecule is suitably administered to the patient at one time or over a series of treatments.

As a general proposition, the therapeutically effective amount of the bispecific antigen-binding molecule administered to a human will be in the range of about 0.01 to about 100 mg/kg of patient body weight whether by one or more administrations. In some embodiments, the bispecific antigen-binding molecule used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In one embodiment, an bispecific antigen-binding molecule described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the subject. Such doses may be administered intermittently, for example, every week or every three weeks (e.g., such that the patient receives from about two to about twenty, or, for example, about six doses of the anti-CD3 antibody). An initial higher loading dose, followed by one or more lower doses may be administered. The progress of this therapy is easily monitored by conventional techniques and assays. In some embodiments of any of the preceding aspects of the invention, the subject, patient, or individual is a human.

VI. Kits

Provided herein are kits including one or more compositions described herein (e.g., a composition including any one or more of the bispecific antigen-binding molecules described herein and a pharmaceutically acceptable carrier) and a package insert for administering the composition to a subject to treat or delay progression of a disorder (e.g., a cell proliferative disorder (e.g., a cancer, such as breast cancer, gastric cancer, colorectal cancer, non-small cell lung cancer, non-Hodgkin's lymphoma (NHL), B cell lymphoma, B cell leukemia, multiple myeloma, renal cancer, prostate cancer, liver cancer, head and neck cancer, melanoma, ovarian cancer, mesothelioma, glioblastoma, germinal-center B-cell-like (GCB) diffuse large B cell lymphoma (DLBCL), activated B cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenström macroglobulinemia (WM), central nervous system lymphoma (CNSL), Burkitt's lymphoma (BL), B cell prolymphocytic leukemia, splenic marginal zone lymphoma, hairy cell leukemia, splenic lymphoma/leukemia, splenic diffuse red pulp small B cell lymphoma, hairy cell leukemia variant, a heavy chain disease, γ heavy chain disease, μ heavy chain disease, plasma cell myeloma, solitary plasmacytoma of bone, extraosseous plasmacytoma, extranodal marginal zone lymphoma of mucosa-associated lymphoid tissue (MALT lymphoma), nodal marginal zone lymphoma, pediatric nodal marginal zone lymphoma, pediatric follicular lymphoma, primary cutaneous follicle centre lymphoma, T cell/histiocyte rich large B cell lymphoma, primary DLBCL of the central nervous system, primary cutaneous DLBCL (leg type), Epstein-Barr virus (EBV)-positive DLBCL of the elderly, DLBCL associated with chronic inflammation, lymphomatoid granulomatosis, primary mediastinal (thymic) large B cell lymphoma, intravascular large B cell lymphoma, anaplastic lymphoma kinase (ALK)-positive large B cell lymphoma, plasmablastic lymphoma, large B cell lymphoma arising in HHV8-associated multicentric Castleman disease, primary effusion lymphoma, large B cell lymphoma, unclassifiable, with features intermediate between diffuse large B-cell lymphoma and Burkitt lymphoma, or large B cell lymphoma, unclassifiable, with features intermediate between diffuse large B-cell lymphoma and classical Hodgkin lymphoma)). In some embodiments, the cancer is a HER2-positive cancer (e.g., a HER2-positive breast cancer or a HER2-positive gastric cancer). Additionally or alternatively, the kit may include a package insert for administering the composition to a subject to treat or delay progression of an autoimmune disorder.

Examples

The following are examples of methods and compositions of the invention. It is understood that various other embodiments may be practiced, given the general description provided above.

Example 1. Materials and Methods

Gene Synthesis
Fab
Genes encoding variants of anti-HER2 (4D5-8; Carter et al., *Proc. Natl. Acad. Sci. USA*. 1992, 89: 4285-4289) Fabs were obtained by gene synthesis of light chain and heavy chain variable domains. The anti-HER2.4D5 Fab and variants were produced in 30 mL scale in Expi293T™ cells and purified in batch using anti-Flag affinity resin. After a 3×PBS wash step, Fabs were eluted with 50 mM phosphoric acid (pH 3.0), neutralized with 20×PBS (pH 11.0), and filtered. All Fabs were ≥95% pure and verified by mass spectrometry.
IgG TDB & 1Fab-IgG TDB
Knob (anti-HER2.N297G.knob (4D5-8 and variants); Kelley and O'Connell, Biochemistry 1993, 32: 6828-6835) and hole (anti-CD3.N297G.hole (40G5c, unless otherwise specified)) half-antibodies were generated as previously described (Dillon et al., MAbs 2017, 9: 213-230). For 1Fab-IgG TDB constructs, the coding region for anti-HER2 Fab (E1-T225) directly preceded the coding region of the anti-HER2.knob sequence and was synthesized with or without a G4SGG linker (SEQ ID NO: 51) between them.
Luciferase Fusions of 1Fab-IgG TDB
The mature protein sequence for luciferase (AAG54095.1) K18-D185 was fused C-terminally to the anti-HER2.hu4D5 light chain. Anti-HER2.hu4D5 Fab with and without the luciferase light chain fusion produced similar binding kinetics to HER2 using a BIACORE® T200 (GE Healthcare) and method described below.
Antibody Expression and Purification
IgG TDB, 1Fab-IgG TDB, and Luciferase fusions of 1Fab-IgG TDB were produced as follows. Half-antibodies anti-HER2.hu4D5.knob and variants and anti-CD3.40G5c.hole were produced in CHO cells at ≥1 L scale and purified by MAbSelect SuRe (GE Healthcare). Bispecific IgG TDB, 1Fab-IgG TDB, or 1Fab-IgG TDB Luciferase fusion assembly from half-antibodies was performed as described in Junttila et al., *Cancer Res.* 2014, 74: 5561-5571; Spiess et al., *Nat. Biotechnol.* 2013, 31: 753-758.
HER2 Western Blot Analysis
Cell lysates were generated using Cell Signaling Technology lysis buffer. Protein was quantitated using BCA assay reagents (Pierce Cat. Nos. 23228 and 23224). 40 µg protein was loaded onto SDS-PAGE gels and a HER2 antibody (Dako Cat. No. A0485) was used for detection.

Immunohistochemistry (IHC)

Immunohistochemistry for HER2 was performed on five-μm formalin-fixed, paraffin-embedded tissue samples and tissue microarray (TMA) samples with anti-Her-2/neu (Ventana Medical Systems, clone 4B5, Tuscan, AZ) rabbit monoclonal primary antibody using the Ventana Ultraview-Benchmark system with Ventana DAB detection. Staining results were scored as 0, 1+, 2+, or 3+ using ASCO-CAP recommended clinical HER2 scoring guidelines.

Fluorescence In-Situ Hybridization (FISH)

Probes

A commercially available, FDA approved HER2 FISH probe (PathVysion, Abbott Molecular) was used by Core Diagnostics for the analysis of the cell line TMA. The PathVysion HER-2 DNA Probe cocktail consists of two labeled DNA probes. The LSI HER2 probe that spans the entire HER2 gene is labeled in SpectrumOrange. The CEP17 probe is labeled in SpectrumGreen and hybridizes to the alpha satellite DNA located at the centromere of chromosome 17 (17p11.1-q11.1). Inclusion of the CEP17 probe allows for the relative copy number of the HER2 gene to be determined.

Assay

Five-μm thick FFPE sections from the TMA block were subjected to FISH analysis as described previously with modifications. Following overnight incubation at 56° C., the slides were de-paraffinized in three washes of CitroSolv for five minutes each, dehydrated by two alcohol washes and air-dried. Subsequently, the FFPE sections were incubated in a Pretreatment reagent (Abbott Molecular, IL) for 30 minutes at 80° C. and were then treated with Protease II (Abbott Molecular, IL) prior to additional washes in water and a series of ethanol. Dried slides were then co-denatured at 76° C. for six minutes with the probes and were hybridized overnight at 37° C. (ThermoBrite; Abbott Molecular). Post-hybridization washes and counter-staining were done in a manner similar to those previously described.

The sections were viewed using fluorescence microscopes equipped with computer-driven imaging systems (BioView Duet, BioView Ltd.). A minimum of 50 non-overlapping tumor cells from each sample were enumerated for HER2 and CEP17 hybridization signals. The current HER2 scoring criteria and guidelines were used for the analysis of the slides. A cell line was considered FISH-positive if it had a HER2-to-CEP17 ratio of two or more or had an average HER2 copy number of more than six signals per nuclei in cells with a HER2-to-CEP17 ratio of less than two. Samples with a HER2-to-CEP17 ratio of less than two and an average HER2 copy number of less than four signals per nuclei were considered as negative and samples with a HER2-to-CEP17 ratio of less than two and an average HER2 copy number between four to six signals per nuclei were considered as equivocal.

Cellular HER2 Binding Assays

Cellular binding of Luciferase fusions of 1Fab-IgGs—Direct binding assay: Cells (SKBR3: 40,000 per well, MCF7: 200,000 per well) were plated into 96 flat-bottom white sterile tissue culture treated plates (Thermo Scientific; Cat #136101) and allowed to adhere overnight. Cells were then washed with binding buffer (PBS+3% BSA+0.05% sodium azide; pH 7.2), and varying concentrations (0.002 nM-100 nM) of TDB luciferase fusion proteins in binding buffer were added to each well. Plates were then incubated at 4° C. for four hours and subsequently washed three times with binding buffer. After the final wash, 20 μl binding buffer containing 50 μl of the luciferase substrate (New England Biolab, Cat #E3300L) was added to each well. Luminescence values were read on Perkin Elmer Envision Plate Reader. The binding data was fit using the GraphPad Prism model, "One Site-Specific Binding" to determine the binding affinity of the antibody.

Cellular Binding of Luciferase Fusions of 1Fab-IgGs—Competition Binding Assay:

Cells were plated and washed as described above. To measure competitive binding, a fixed concentration of a TDB luciferase fusion protein (15 nM 4D5-WT or 50 nM 4D5-H91A) was mixed with increasing concentrations of TDB (0.007 nM-400 nM) in binding buffer and added to the cells. Plates were incubated for four hours at 4° C., washed, and read as described above. The binding data was fit using the GraphPad Prism model, "One Site-Fit Ki" to determine the binding affinity of the antibody.

Cellular Binding by Flow Cytometry

MCF7 and SKBR3 cells were plated at 100,000 cells per well in 96-well U bottom plates in 50 μL of FACS Buffer (1% BSA, 2 mM EDTA in PBS). Test articles were serially diluted 1:5 in FACS buffer starting at either 50 μg/mL or 10 μg/mL and incubated with cells on ice for 30 minutes. Cells were washed twice with FACS buffer and resuspended in 100 μL Alexa 647 Goat Anti-Human IgG, Fcγ Fragment (Jackson ImmunoResearch No. 109-606-098), at a 1:200 dilution, in FACS buffer and incubated on ice for 30 minutes. Cells were resuspended in 100 μL FACS Buffer containing propidium iodide (PI; eBioscience #00-6990-50) at a 1:100 dilution and analyzed on BD FACSCaliber.

Blood Cell Fractionation

Peripheral blood mononuclear cells (PBMC) were separated from the blood of healthy volunteers using lymphocyte separation medium (MP Biomedicals). $CD8^+$ cells were extracted from PBMC using human $CD8^+$ Isolation Kit (Miltenyi Biotec No. 130-094-156) by negative selection.

T Cell Activation

All antibodies for flow cytometry cell staining were obtained from BD Biosciences (San Jose, CA). Human PBMC and target cells (10:1 ratio) were incubated in the presence of test article for 24 hours in flat-bottom 96 well plate (BD). After incubation, cells were transferred to a new V-bottom 96 well plate. Cells were stained with anti-CD8-FITC, anti-CD69-PE, and anti-CD25-APC. CD69 and CD25 surface expression was detected on CD8+ T cells by flow cytometry. The percentage of CD8+CD69+CD25+ was reported as T cell activation. To determine HER2-independent T cell activation, Jurkat-Dual NF-κB/IRF reporter cells (Invivogen Cat #jktd-isnf) were incubated at 37° C. with TDB or OKT CD3 antibody for 24 hours. 10 μL of supernatant was removed from each well and added to a white, clear bottom 96 well plate. 100 μL of Quantiluc solution (Invivogen) was added to the harvested supernatants and plates were read on Perkin Elmer Envision plate reader.

In Vitro Apoptosis

Target cells were plated at 10,000 cells per well in culture media into a clear-bottom 96 black well plate (Corning No. 3904) and placed in 37° C., 5% $CO_2$ incubator overnight. The test article, 50,000 purified $CD8^+$ cells, and a 1:1000 dilution of Caspase 3/7 reagent (Essen No. 4440) were added to pre-plated cells and placed into the Incucyte zoom. Images were collected every four hours over 40 hours and analyzed for number of apoptotic events per $mm^2$.

Cell Viability

Cells were grown to confluence in RPMI supplemented with 10% FBS, penicillin (100 U/mL), streptavidin (100 μg/mL), and L-Glutamate (0.2 mM). Cells were dissociated with PBS based cell dissociation media and plated in black, clear-bottomed 96-well plates at density of 10,000 cells per well. On day four, media was discarded and plates were washed twice with PBS. 100 μL CELLTITER-GLO® Luminescent Cell Viability reagent (Promega Cat. No. G7570) was added and plates were read on luminometer as described in the instructions.

Breast Cancer Cell Proliferation

CD8+ cells were used as effectors in a 3:1 effector:target ratio. Breast cancer cell proliferation/viability was detected using the CELLTITER-GLO® Luminescent Cell Viability Assay (Promega). For the assay, $15 \times 10^3$ cells per well were plated in 96-well plates and incubated overnight for cell attachment before treatments.

In Vivo Efficacy

Female NOD scid gamma (NSG) mice were obtained from The Jackson Laboratory. Human PBMC were used as effector cells in the mice. PBMC were purified from the blood of healthy donors using the Lymphocyte Separation Medium (MP Biomedical, LLC, Salon, Ohio) and cryopreserved at −80° C. Prior to transferring into mice PBMCs were thawed and cultured overnight in 10% FBS containing RPMI medium at 37° C., 5% $CO_2$. PBMCs were inoculated into mice intraperitoneally, one day after tumor cell inoculation at a concentration of $10 \times 10^6$ cells per mouse, in a volume of 100 μL of Hank's balanced salt solution (HBSS) buffer. To evaluate efficacy in treatment of HER2 amplified breast cancer, animals were inoculated with $3 \times 10^6$ KPL-4 tumor cells in HBSS/MATRIGEL® via subcutaneous administration in the right thoracic mammary fat pad. To evaluate activity in treatment of low HER2-expressing tumors, animals were subcutaneously inoculated with $5 \times 10^6$ HT55 tumor cells in HBSS. Single dose treatments were administered intravenously at day 0 as indicated in the figure legends.

Cynomolgus Monkey Safety and Pharmacokinetic (PK) Study

Eleven female cynomolgus monkeys (*Macaca fascicularis*; ages and weights at the initiation of dosing ranging from 24-60 months and 2-5 kg) were randomly assigned to three groups. Animals received vehicle control (N=3) or anti-HER2-CD3 4D4-H91A 1Fab-IgG TDB at 3 mg/kg (N=3), or TDB at 20 mg/kg (N=5) via one-hour intravenous infusion at a volume of two mL/kg/hour. Animals were monitored twice daily for any abnormalities and signs of pain or distress. Additional endpoints included food consumption, body weights, physical examinations, body temperature, respiration rate, and heart rate.

PK Analysis

Cynomolgus monkey blood was collected at various times throughout the study to assess the pharmacokinetics. Blood was allowed to clot at room temperature for at least 30 minutes. Samples were centrifuged at about 1500-2000×g at 2-8° C. within one hour of collection. Serum was collected and stored at −60° C. to −80° C. until shipped for analysis. Serum PK samples were analyzed by GRIP ELISA (Yang et al., *Journal of Immunological Methods* 2008, 335: 8-20). Serum concentration-time profiles were used to estimate the following PK parameters using non-compartmental analysis (WinNonlin, version 5.2.1; Pharsight Corporation, Mountain View, CA): total drug exposure defined as area under the serum concentration-time curve (AUC), antibody clearance (CL), and observed maximum serum concentration (Cmax). Each animal was analyzed separately, and results for each dose group were summarized as mean±standard deviation (SD).

Clinical Pathology

At least twice during the predose phase and on study days 2 and 8 blood was collected into tubes containing the anticoagulant sodium citrate for coagulation tests or potassium EDTA for hematology tests.

BIACORE®

Binding kinetics of the anti-HER2 Fabs or anti-HER2/CD3 T cell dependent bispecific (TDB) antibodies were measured using surface plasmon resonance on a BIACORE® T200 or 8K instrument (GE Healthcare). All kinetics experiments were performed at a flow rate of 30 μL/minutes at 37° C., and with a running buffer of 10 mM HEPES, pH 7.2, 150 mM NaCl, 0.05% Tween 20, and 1 mM EDTA (HBS-EP Buffer). Human HER2 extracellular domain (ECD; Sino Biologicals 10004-H08H or Novus Biologicals NBP1-94702) or Cynomolgus monkey HER2 ECD was immobilized on a CM5 sensor chip via amine-based coupling. For human HER2 ECD, a 3-fold concentration series of anti-HER2 Fabs or TDBs ranging from 0.27 to 200 nM was used to analyze binding. For cynomolgus monkey HER2 ECD, a 1.5-fold concentration series of anti-HER2 Fabs ranging from 87.8 to 1000 nM was used to analyze binding. Sensorgrams for binding of HER2 were recorded using an injection time of 180 seconds followed by 300 seconds of dissociation time and regeneration of the surface with 50 mM HCl. All sensorgrams observed for antigen binding to antibodies were analyzed using a 1:1 *Langmuir* binding, with the exception of 4D5 Fab variants binding to cynomolgus monkey HER2, which used a steady state binding model to calculate the kinetics and binding constants. Due to the requirement of high Fab concentrations to measure weak affinities to cynomolgus monkey HER2, all Fab variants were buffer exchanged into HBS-EP buffer prior to the experiment in order to prevent buffer effects and ensure accurate measurements. The mass of all 4D5 variants was verified by mass spectrometry.

Example 2. Her2 Affinity of the Anti-Her2/Cd3 Igg Tdb has a Direct Effect on Killing Activity, but not on Selectivity to Her2-Overexpressing Cells Anti-HER2/CD3 bispecific antibodies that are monovalent for each binding arm have been shown to have robust activity in HER2-amplified in vitro and in vivo breast cancer models. However, this IgG TDB format also retains low level activity against cell lines expressing low levels of HER2, similar to normal HER2-positive human epithelial cells. It is desirable to increase the selectivity of anti-HER2/CD3 TDB to HER2 amplified cells in order to minimize the risk of on-target off-tumor activity and thereby increase the therapeutic index of the HER2 targeting TDB. Initially, the impact of HER2 affinity on selectivity of the IgG TDB to HER2 amplified cells was investigated. Multiple variants of anti-HER2 4D5 with monovalent binding affinities as Fabs ranging from 0.3 to 213 nM (Table 4) were generated. For all variants, the main driver for reduced affinity was the increase in (i.e., faster) dissociation rate ($k_d$), whereas the association rate ($k_a$) remained unaltered.

TABLE 4

Monovalent binding affinities of 4D5 variants.

| Anti-HER2 (4D5) Fab | $k_a$ (1/Ms, 1E+5) | $k_d$ (1/s, 1E−3) | $K_D$ (nM) | $K_D$ Ratio (Variant/WT) |
|---|---|---|---|---|
| WT (trastuzumab) | 8.74 ± 1.74 | 0.25 ± 0.03 | 0.30 ± 0.01 | 1.0 |
| Y102V | 9.28 ± 0.34 | 0.30 ± 0.02 | 0.32 ± 0.03 | 1.1 |
| Y55E.Y102V | 5.83 ± 1.04 | 1.43 ± 0.10 | 2.60 ± 0.34 | 8.7 |
| Y55E.D98A.F100A.Y102V | 11.5 ± 3.34 | 15.6 ± 2.58 | 14.0 ± 2.08 | 47 |
| D98A.F100A.Y102V | 10.1 ± 1.47 | 22.8 ± 2.12 | 22.7 ± 2.07 | 76 |
| H91A | 7.07 ± 2.43 | 33.6 ± 6.54 | 49.3 ± 8.57 | 164 |
| Y55E.H91A | 5.10 ± 0.20 | 87.5 ± 3.60 | 172 ± 13.2 | 573 |
| Y100aA | 4.61 ± 1.27 | 91.9 ± 11.2 | 213 ± 81.8 | 710 |
| N30A.H91A | 5.75 ± 0.56 | 201 ± 19.1 | 353 ± 62.7 | 1177 |

For the primary selectivity test, SKBR3 and MCF7 were used as model cell lines. SKBR3 is a HER2-amplified breast cancer cell line, whereas MCF7 is breast cancer cell line expressing low levels of HER2 (FIG. 1), similar to levels detected in non-cancerous cells, such as cultured cardiomyocytes (Junttila et al. *Cancer Res.* 74(19): 5561-5571, 2014). The cell membrane copy number of HER2 in SKBR3 and MCF7 cells has been reported as $2 \times 10^6$ per cell and $1.5 \times 10^4$ per cell, respectively (Aguilar et al. *Oncogene* 18(44): 6050-6062, 1999). Decreasing HER2 binding affinity gradually reduced the killing activity of the anti-HER2 IgG TDB on both SKBR3 and MCF7 cell lines (FIGS. 2A-2F). Killing activity was practically abolished with IgG TDBs having an affinity to HER2 of 49 nM or higher. Similar levels of activity decrease were observed in SKBR3 and MCF7 cells. In summary, monovalent HER2 affinity plays a key role in the activity of the anti-HER2/CD3 IgG TDB but did not affect selectivity to HER2-overexpressing cells.

Figure 3:
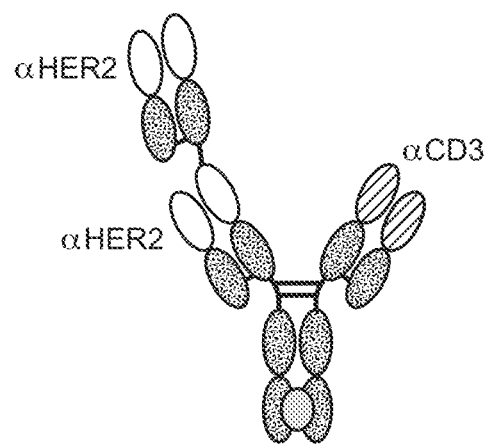
FIG. 3 is a schematic drawing of a representative trivalent antibody of the 1Fab-IgG TDB format. The antibody features a bivalent arm with two anti-HER2 binding moieties and a monovalent arm with one anti-CD3 binding moiety.
Figure 4A:
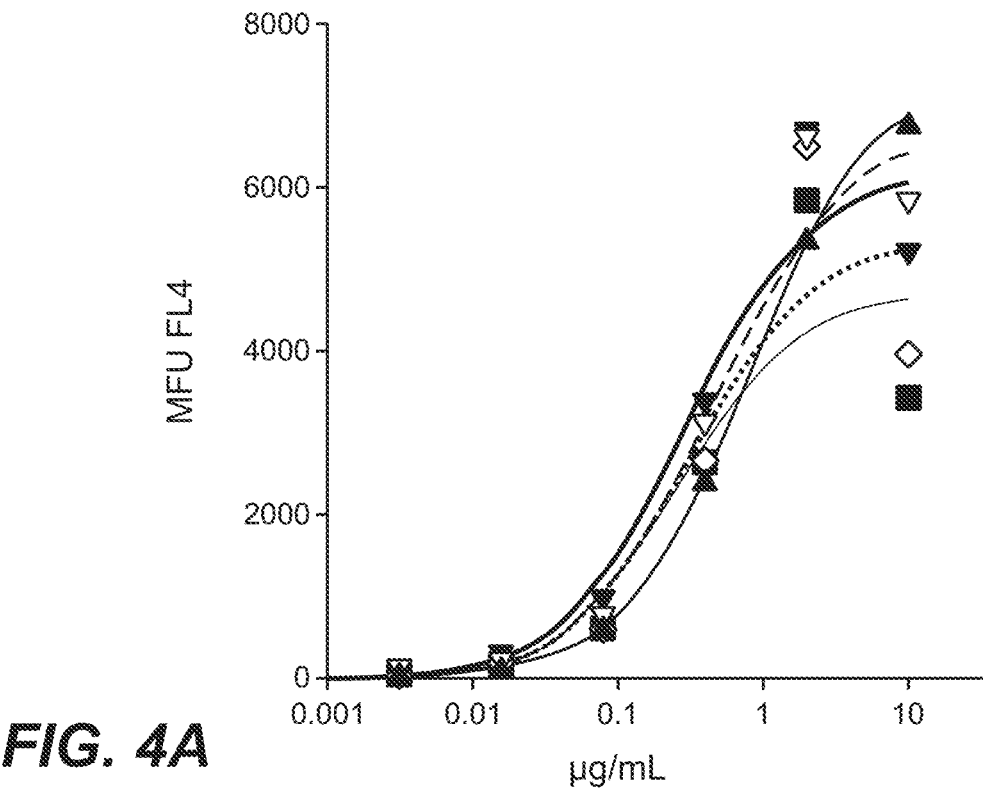
FIG. 4A is a graph showing dose response curves quantifying binding of various 1Fab-IgG TDB antibodies, relative to the wild-type 4D5 IgG TDB antibody to SKBR3, as quantified by flow cytometry. Solid downward-pointing triangles represent the wildtype 4D5 IgG TDB antibody (trastuzumab); solid squares represent the 4D5 antibody variant, H91A-IgG TDB; solid upward-pointing triangles represent the 4D5 antibody variant, D98A.F100A.Y102V-IgG TDB; open downward-pointing triangles represent the 4D5 antibody variant, Y102V-IgG TDB; and open diamonds represent the 4D5 antibody variant, Y55E.Y102V-IgG TDB.
Figure 4B:
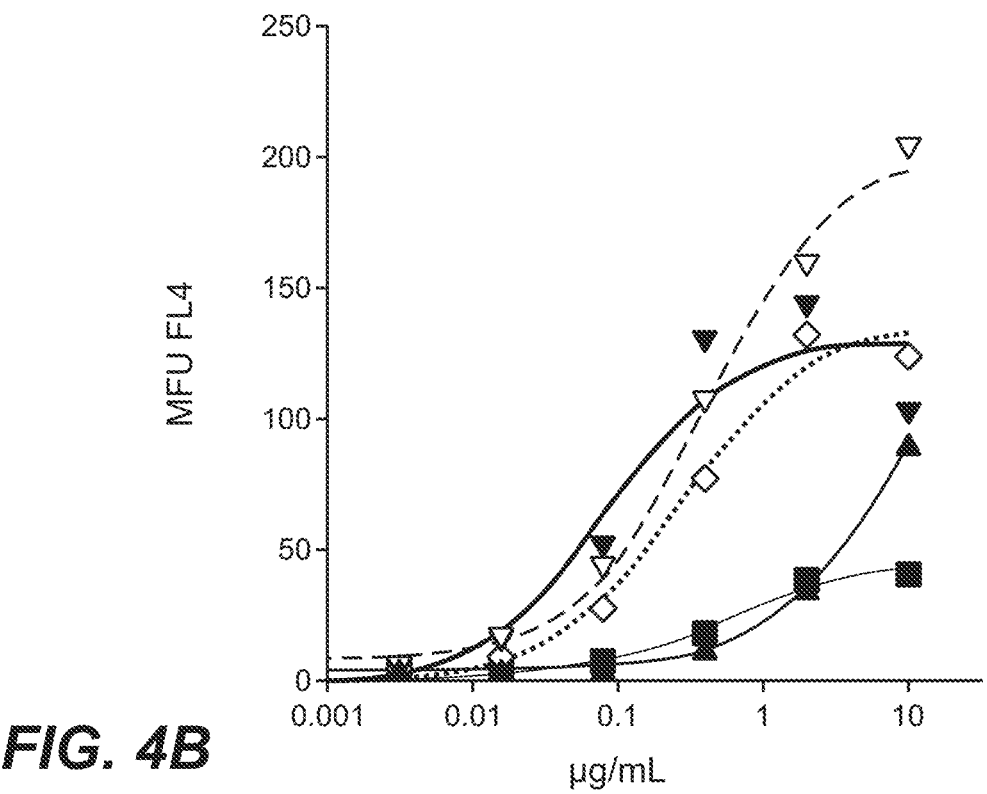
FIG. 4B is a graph showing dose response curves quantifying binding of various 1Fab-IgG TDB antibodies, relative to the wild-type 4D5 IgG TDB antibody, to MCF7, as quantified by flow cytometry. Solid downward-pointing triangles represent the wildtype 4D5 IgG TDB antibody (trastuzumab); solid squares represent the 4D5 antibody variant, H91A-IgG TDB; solid upward-pointing triangles represent the 4D5 antibody variant, D98A.F100A.Y102V-IgG TDB; open downward-pointing triangles represent the 4D5 antibody variant, Y102V-IgG TDB; and open diamonds represent the 4D5 antibody variant, Y55E.Y102V-IgG TDB.
Figure 5A:
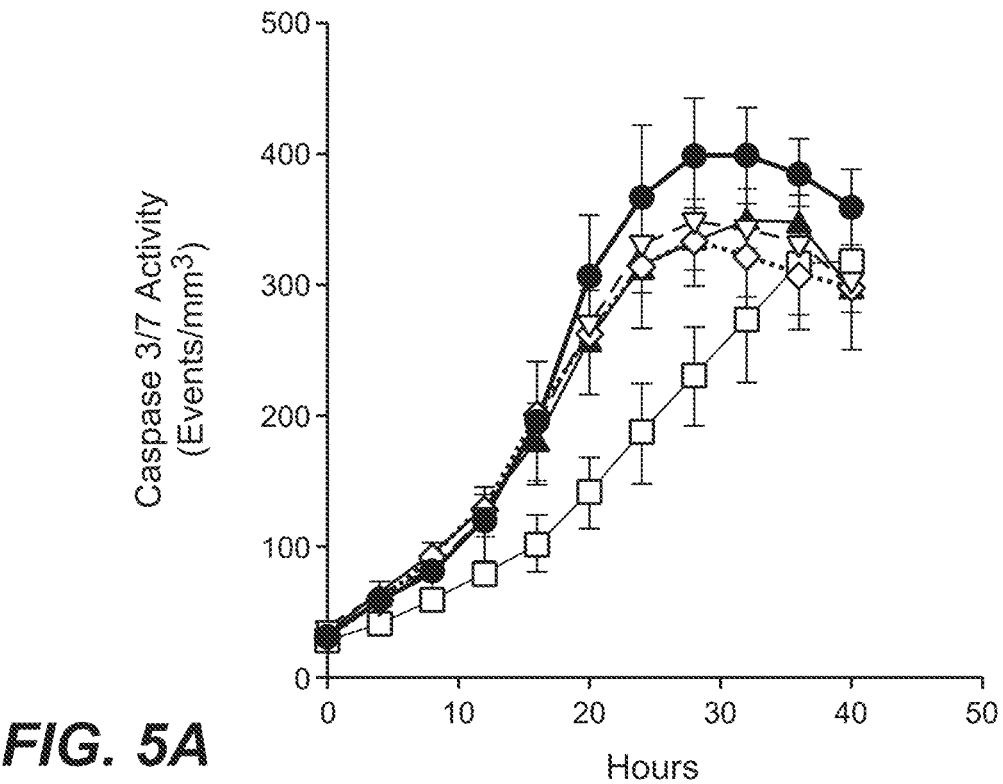
FIG. 5A is a graph showing induction of apoptosis in SKBR3 cells as a result of various 1Fab-IgG TDB antibodies, relative to the wild-type 4D5 IgG TDB antibody, as quantified by caspase 3/7 activity over time. Solid dots represent the wildtype 4D5 IgG TDB antibody (trastuzumab); open squares represent the 4D5 antibody variant, H91A-IgG TDB; solid triangles represent the 4D5 antibody variant, D98A.F100A.Y102V-IgG TDB; open triangles represent the 4D5 antibody variant, Y102V-IgG TDB; and open diamonds represent the 4D5 antibody variant, Y55E.Y102V-IgG TDB. Data are represented as mean±standard deviation.
Figure 5B:
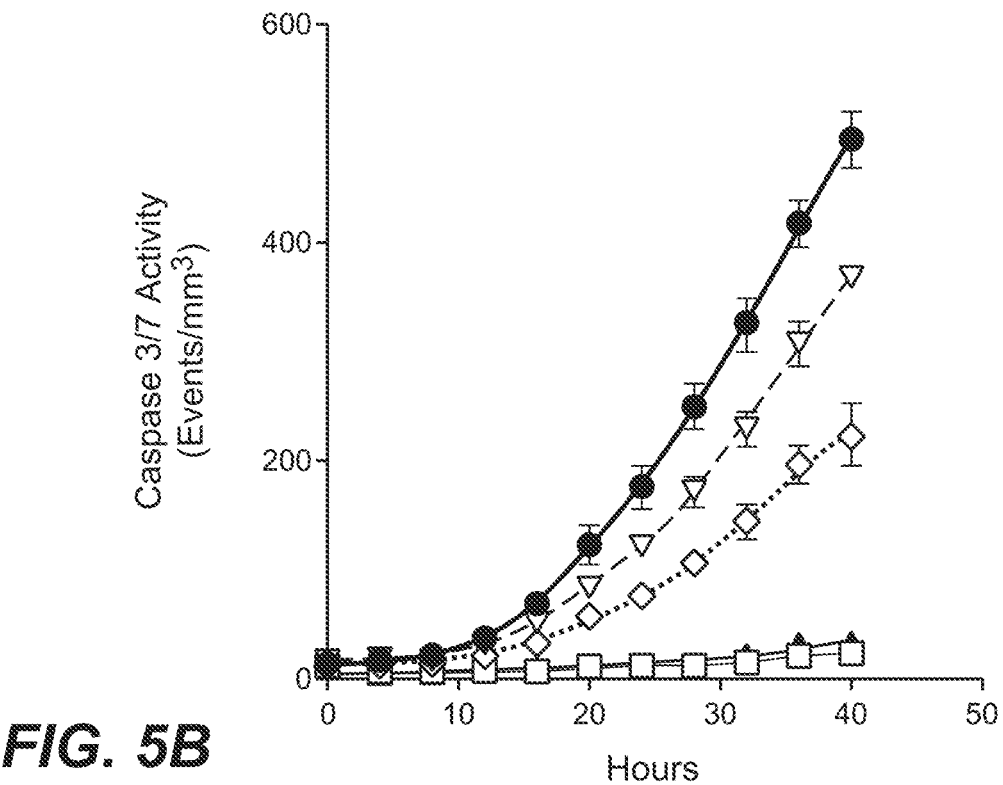
FIG. 5B is a graph showing induction of apoptosis in MCF7 cells as a result of various 1Fab-IgG TDB antibodies, relative to the wild-type 4D5 IgG TDB antibody, as quantified by caspase 3/7 activity over time. Solid dots represent the wildtype 4D5 IgG TDB antibody (trastuzumab); open squares represent the 4D5 antibody variant, H91A-IgG TDB; solid triangles represent the 4D5 antibody variant, D98A.F100A.Y102V-IgG TDB; open triangles represent the 4D5 antibody variant, Y102V-IgG TDB; and open diamonds represent the 4D5 antibody variant, Y55E.Y102V-IgG TDB. Data are represented as mean±standard deviation.
Figure 6A:
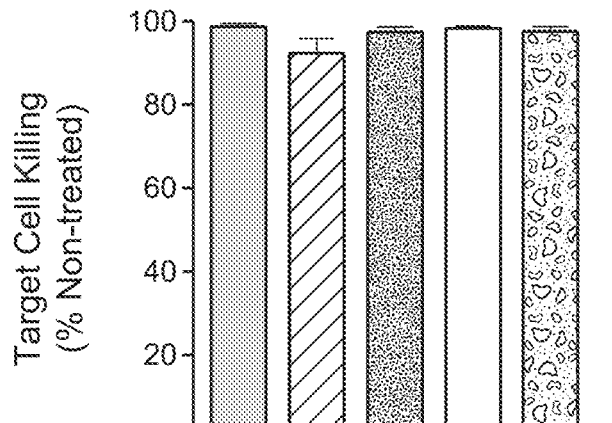
FIG. 6A is a graph showing cytotoxicity in SKBR3 cells in response to incubation with 50 ng/mL of various 1Fab-IgG TDB antibodies, relative to the wild-type 4D5 IgG TDB antibody, as measured by a CELLTITER-GLO® assay. The first bar (on the left) represents the wildtype 4D5 TDB antibody (trastuzumab); the second bar represents the 4D5 antibody variant, H91A-IgG TDB; the third bar represents the 4D5 antibody variant, D98A.F100A.Y102V-IgG TDB; the fourth bar represents the 4D5 antibody variant, Y102V-IgG TDB; and the fifth bar (on the right) represents the 4D5 antibody variant, Y55E.Y102V-IgG TDB. Data are represented as mean±standard deviation.
Figure 6B:
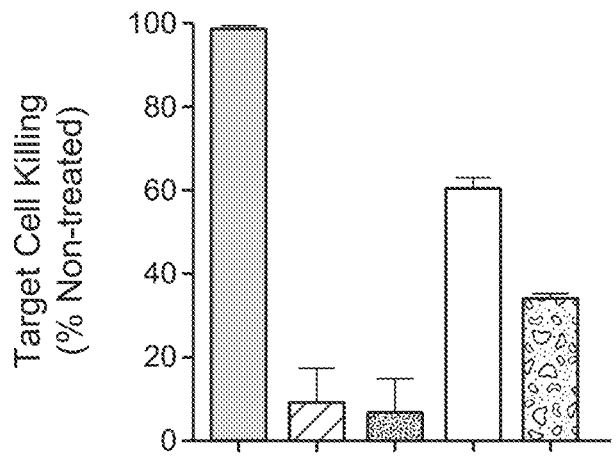
FIG. 6B is a graph showing cytotoxicity in MCF7 cells in response to incubation with 50 ng/mL of various 1Fab-IgG TDB antibodies, relative to the wild-type 4D5 IgG TDB antibody, as measured by a CELLTITER-GLO® assay. The first bar (on the left) represents the wildtype 4D5 TDB antibody (trastuzumab); the second bar represents the 4D5 antibody variant, H91A-IgG TDB; the third bar represents the 4D5 antibody variant, D98A.F100A.Y102V-IgG TDB; the fourth bar represents the 4D5 antibody variant, Y102V-IgG TDB; and the fifth bar (on the right) represents the 4D5 antibody variant, Y55E.Y102V-IgG TDB. Data are represented as mean±standard deviation.
Figure 6C:
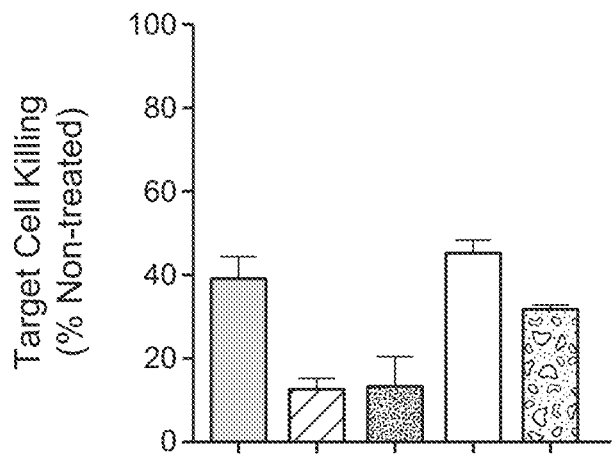
FIG. 6C is a graph showing cytotoxicity in MCF7 cells in response to incubation with 50 µg/mL of various 1Fab-IgG TDB antibodies, relative to the wild-type 4D5 IgG TDB antibody, as measured by a CELLTITER-GLO® assay. The first bar (on the left) represents the wildtype 4D5 TDB antibody (trastuzumab); the second bar represents the 4D5 antibody variant, H91A-IgG TDB; the third bar represents the 4D5 antibody variant, D98A.F100A.Y102V-IgG TDB; the fourth bar represents the 4D5 antibody variant, Y102V-IgG TDB; and the fifth bar (on the right) represents the 4D5 antibody variant, Y55E.Y102V-IgG TDB. Data are represented as mean±standard deviation.
Figure 7A:
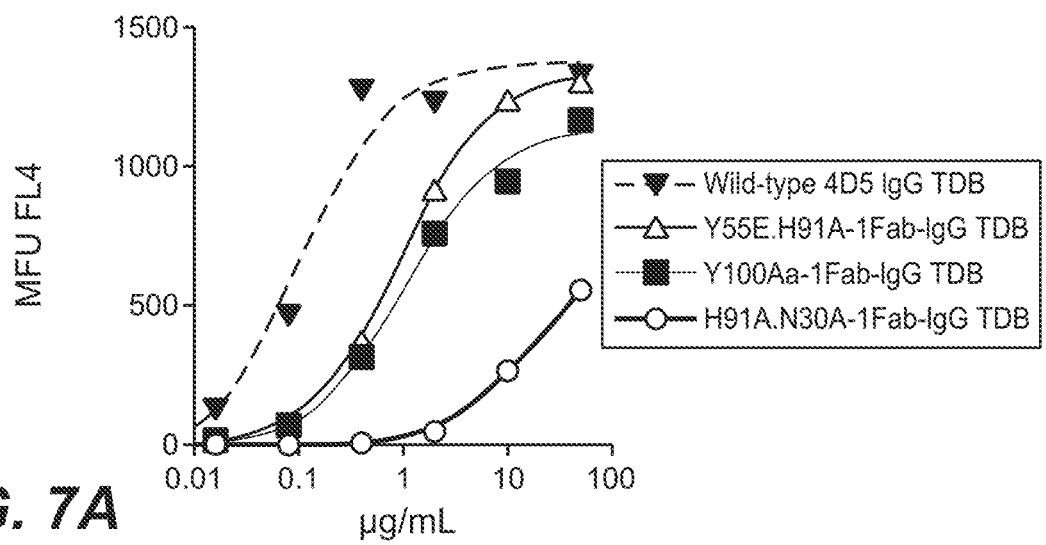
FIG. 7A is a graph showing dose response curves quantifying the binding of various 1Fab-IgG TDB antibodies to SKBR3 cells, relative to the wild-type 4D5 IgG TDB antibody (trastuzumab; solid triangles), as quantified by flow cytometry. Open triangles represent the 4D5 antibody variant, Y55E.H91A-1Fab-IgG TDB; squares represent the 4D5 antibody variant, Y100Aa-1Fab-IgG TDB; and circles represent the 4D5 antibody variant, H91A.N30A-1Fab-IgG TDB.
Figure 7B:
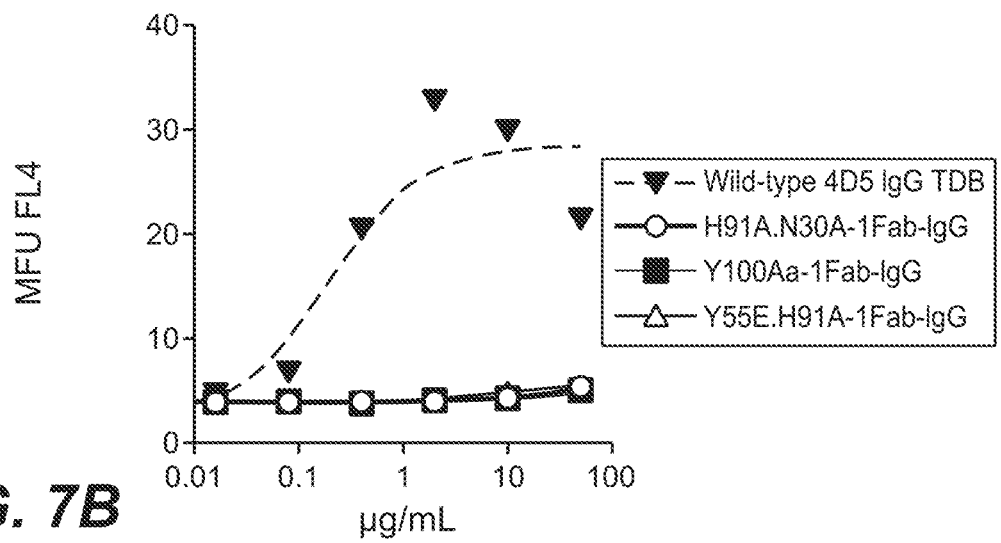
FIG. 7B is a graph showing dose response curves quantifying the binding of various 1Fab-IgG TDB antibodies to MCF7 cells, relative to the wild-type 4D5 IgG TDB antibody (trastuzumab; solid triangles), as quantified by flow cytometry. Open triangles represent the 4D5 antibody variant, Y55E.H91A-1Fab-IgG TDB; squares represent the 4D5 antibody variant, Y100Aa-1Fab-IgG TDB; and circles represent the 4D5 antibody variant, H91A.N30A-1Fab-IgG TDB.
Figure 8:
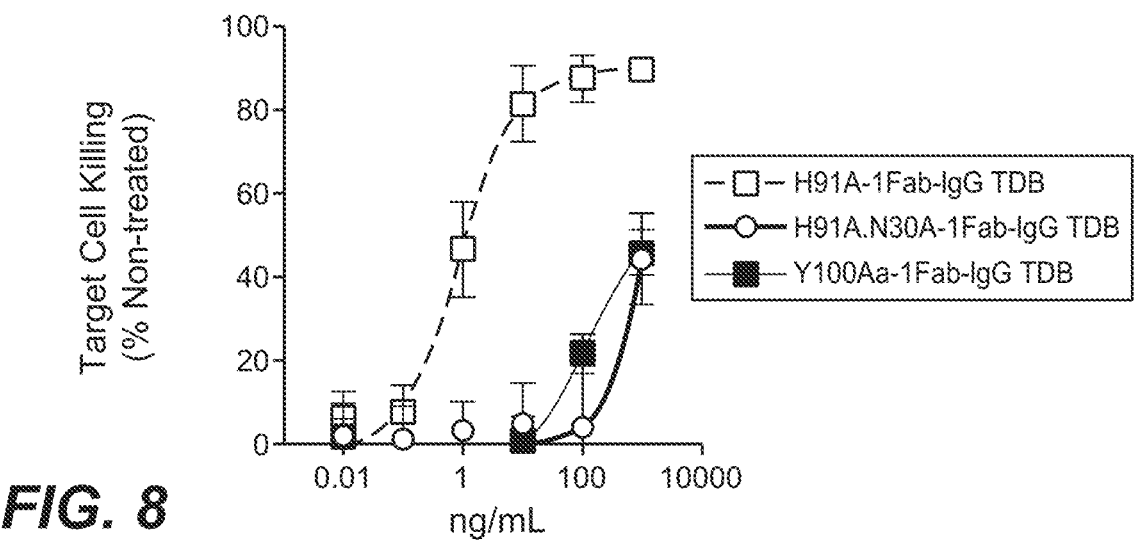
FIG. 8 is a graph showing dose response curves quantifying the cytotoxicity of various 1Fab-IgG TDB antibodies to SKBR3 cells, as measured by a CELLTITER-GLO® assay. Open squares represent the 4D5 antibody variant, H91A-1Fab-IgG TDB; solid squares represent the 4D5 antibody variant, Y100Aa-1Fab-IgG TDB; and circles represent the 4D5 antibody variant, H91A.N30A-1Fab-IgG TDB. Data are represented as mean±standard deviation.

Example 3. Characterizing the Effect of Bivalent Low Affinity Her2 Binding on Selectivity for Her2 Overexpressing Cells Antibodies having bivalent HER2 binding and monovalent CD3 binding (1Fab-IgG TDB format) were constructed based on monovalent 4D5 affinity variants (FIG. 3). 1Fab-IgG TDBs were tested for cellular binding to SKBR3 cells (FIGS. 4A and 7A) and to MCF7 cells (FIGS. 4B and 7B) and for ability to mediate apoptosis (FIGS. 5A and 5B) and killing (FIGS. 6A-6C and 8) of SKBR3 and MCF7 cells. Multiple 4D5 1 Fab-IgG TDB variants demonstrated similar binding to SKBR3 and MCF7 cells compared to a control IgG TDB with a monovalent high affinity HER2 arm based on wild-type 4D5 (trastuzumab; FIGS. 4A and 4B). Y55E.H91A, Y100aA, or N30A.H91A substitutions (monovalent KDS of 172, 213, and 353 nM, respectively) resulted in substantially reduced cellular binding in the 1Fab-IgG TDB format compared to the monovalent high-affinity HER2 IgG TDB format (FIGS. 7A and 7B). Lower binding was reflected in substantially reduced killing of SKBR3 cells (FIG. 8). Y102V and Y55E.Y102V substitutions (monovalent $K_D$ 0.3 and 2.6 nM, respectively) in the 1Fab-IgG TDB format resulted in similar binding to both SKBR3 and MCF7 cell lines compared to control IgG TDB (FIGS. 4A and 4B). Consistent with cellular binding, Y102V and Y55E.Y102V 1Fab-IgG TDB variants demonstrated substantial potency in killing of low HER2-expressing MCF7 cells, suggesting that these modifications did not improve selectivity to HER2 overexpressing cells (FIGS. 5A, 5B, 6B, and 6C).

Two 4D5 variants, D98A.F100A.Y102V and H91A (monovalent $K_D$ 23 and 49 nM, respectively), retained high cellular binding to SKBR3 cells, while demonstrating only minimal binding to MCF7 cells (FIGS. 4A, 4B, 5A, and 5B). This cellular binding was reflected in killing activity. In particular, the D98A.F100A.Y102V and H91A 1Fab-IgG TDB variants induced potent apoptosis and killing of SKBR3 cells but were unable to mediate killing of low HER2-expressing MCF7 cells despite very high concentrations (50 ng/mL to 50 µg/mL). In vitro activity of monovalent high HER2 affinity HER2-IgG TDB has been reported to saturate at ~10 ng/mL concentration (Junttila et al. *Cancer Res.* 74(19): 5561-5571, 2014). These results suggest that the enhanced avidity of the 1Fab-IgG TDB, relative to conventional antibodies, can enable enhanced selectivity to HER2-overexpressing cells. The window for monovalent affinity ($K_D$) resulting in increased selectivity was in the 20-50 nM range, measured as Fabs. Smaller reduction in affinity does not improve selectivity and larger reduction in affinity significantly compromises the potency of the TDB.

Figure 9:
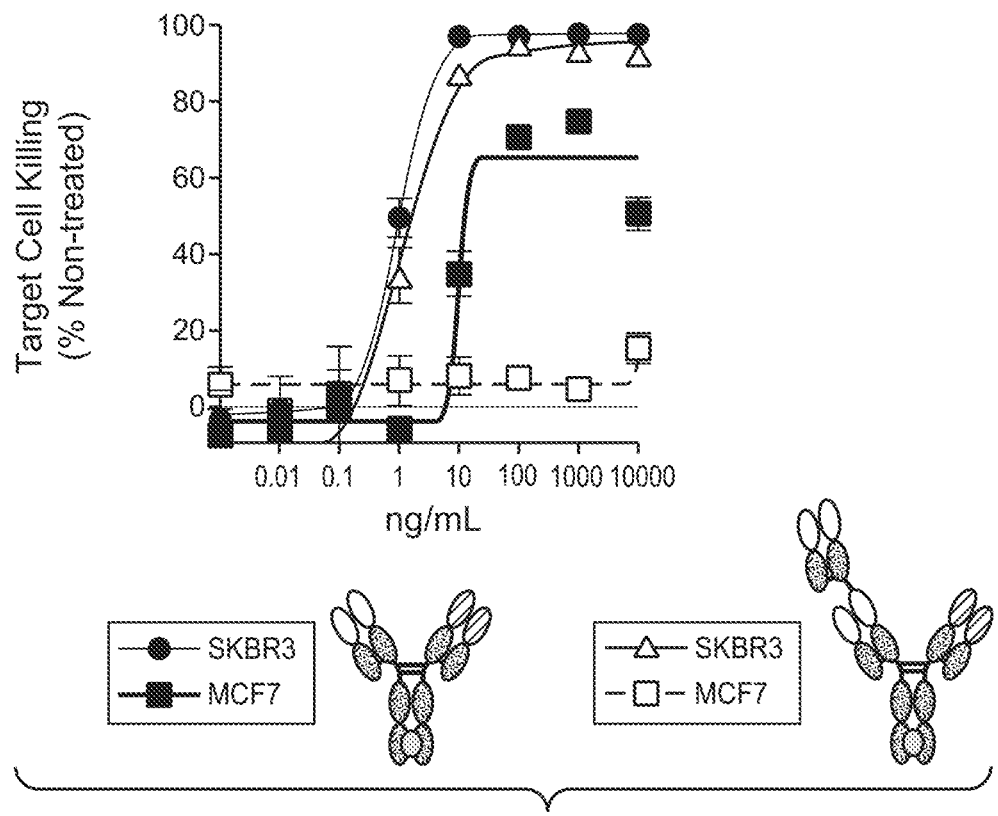
FIG. 9 is a graph showing dose response curves comparing the cytotoxicity of 4D5 IgG TDB antibodies relative to 4D5 H91A-1Fab-IgG TDB antibodies. Cytotoxicity induced by 4D5 IgG TDB antibodies in SKBR3 cells and MCF7 cells are represented by solid circles and solid squares, respectively. Cytotoxicity induced by 4D5 H91A-1Fab-IgG TDB antibodies in SKBR3 cells and MCF7 cells are represented by open triangles and open squares, respectively. Data are represented as mean±standard deviation.
Figure 10:
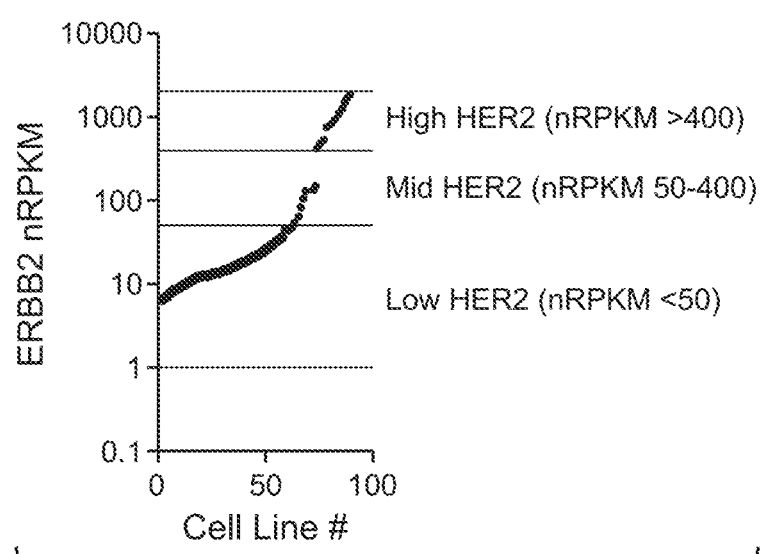
FIG. 10 is a graph showing results of an RNA-seq analysis of ErbB2 RNA expression in 90 breast cancer cell lines. Cell lines were classified as low ErbB2 expressing, medium ErbB2 expressing, and high ErbB2 expressing cell lines.
Figure 11A:
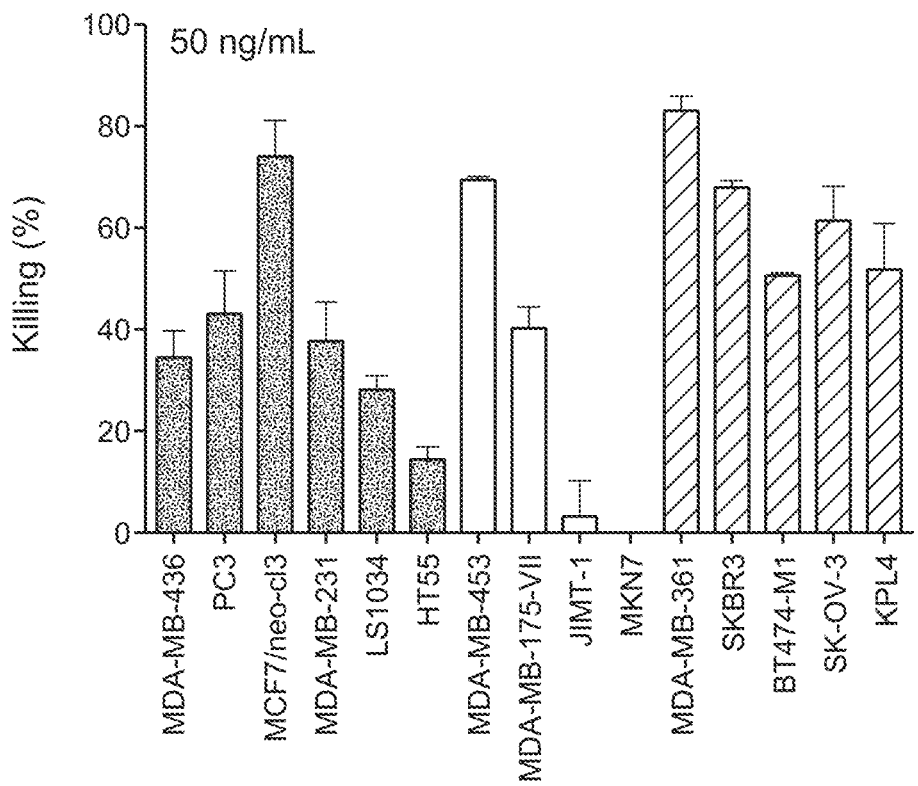
FIG. 11A is a graph showing cytotoxicity of 4D5 IgG TDB antibodies at a concentration of 50 ng/mL on low ErbB2 expressing cell lines (MDA-MB-436, PC3, MCF7/neo-cl3, MDA-MB-231, LS1034, and HT55), medium ErbB2 expressing cell lines (MDA-MB-453, MDA-MB-175-VII, JIMT-1, and MKN7), and high Erb2 expressing cell lines (MDA-MB-361, SKBR3, BT474-M1, SK-OV-3, and KPL4). Data are represented as mean±standard deviation.
Figure 11B:
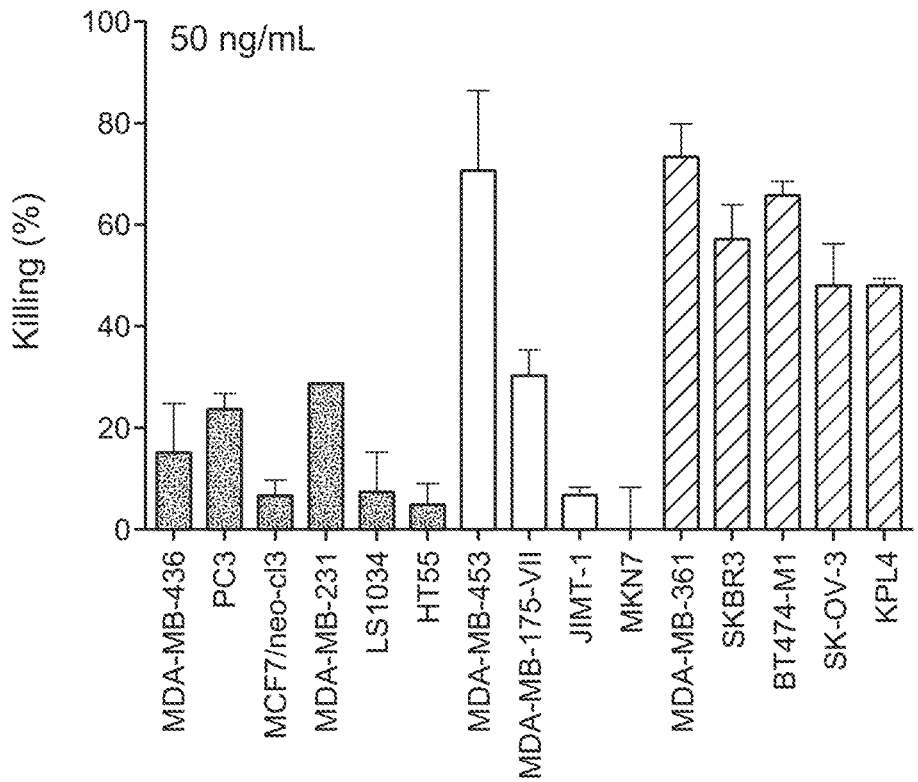
FIG. 11B is a graph showing cytotoxicity of 4D5 IgG TDB antibodies at a concentration of 50 µg/mL on low ErbB2 expressing cell lines (MDA-MB-436, PC3, MCF7/neo-cl3, MDA-MB-231, LS1034, and HT55), medium ErbB2 expressing cell lines (MDA-MB-453, MDA-MB-175-VII, JIMT-1, and MKN7), and high Erb2 expressing cell lines (MDA-MB-361, SKBR3, BT474-M1, SK-OV-3, and KPL4). Data are represented as mean±standard deviation.
Figure 11C:
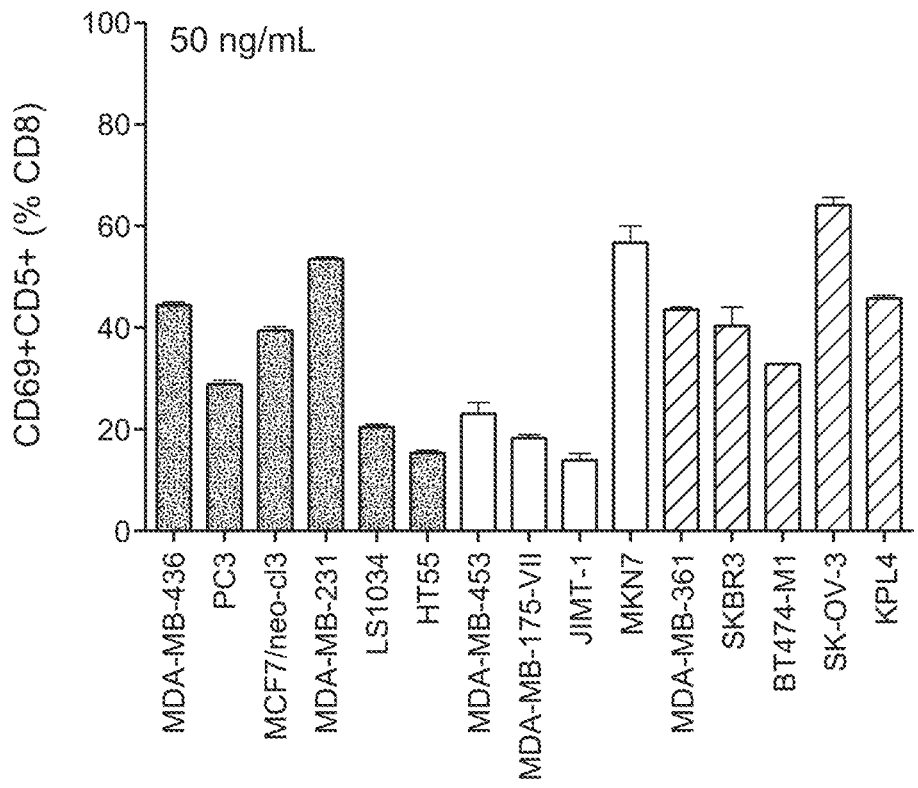
FIG. 11C is a graph showing the effect of 4D5 TDB antibodies at a concentration of 50 ng/mL on activation of human CD8+ T cells cultured with low ErbB2 expressing cell lines (MDA-MB-436, PC3, MCF7/neo-cl3, MDA-MB-231, LS1034, and HT55), medium ErbB2 expressing cell lines (MDA-MB-453, MDA-MB-175-VII, JIMT-1, and MKN7), and high Erb2 expressing cell lines (MDA-MB-361, SKBR3, BT474-M1, SK-OV-3, and KPL4). T cell activation was measured by dual expression of CD69 and CD45. Data are represented as mean±standard deviation.
Figure 11D:
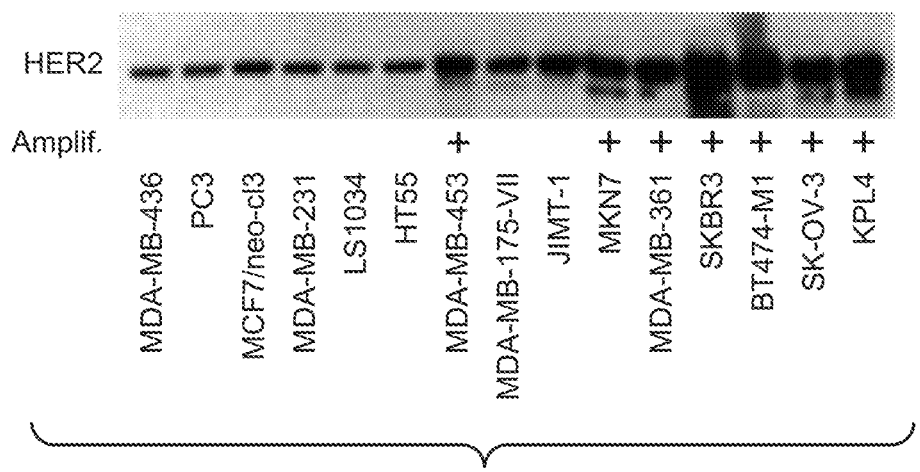
FIG. 11D is an immunoblot showing HER2 protein expression by each of the cells lines represented in FIGS. 11A-11C.
Figure 12A:
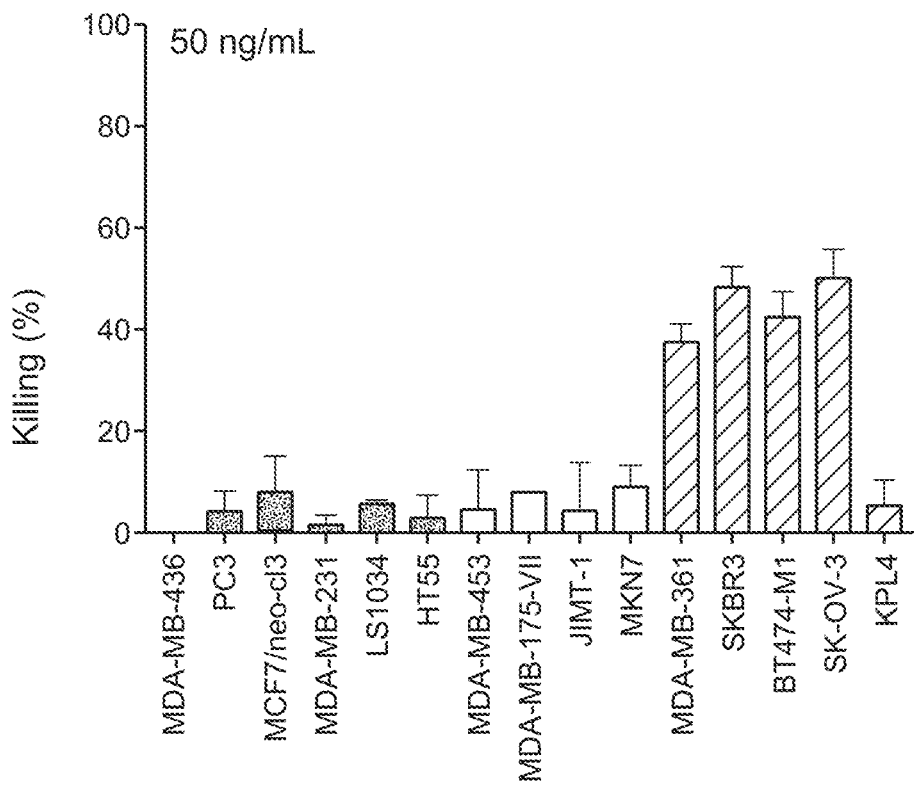
FIG. 12A is a graph showing cytotoxicity of 4D5 H91A-1Fab-IgG TDB antibodies at a concentration of 50 ng/mL on low ErbB2 expressing cell lines (MDA-MB-436, PC3, MCF7/neo-cl3, MDA-MB-231, LS1034, and HT55), medium ErbB2 expressing cell lines (MDA-MB-453, MDA-MB-175-VII, JIMT-1, and MKN7), and high Erb2 expressing cell lines (MDA-MB-361, SKBR3, BT474-M1, SK-OV-3, and KPL4). Data are represented as mean±standard deviation.
Figure 12B:
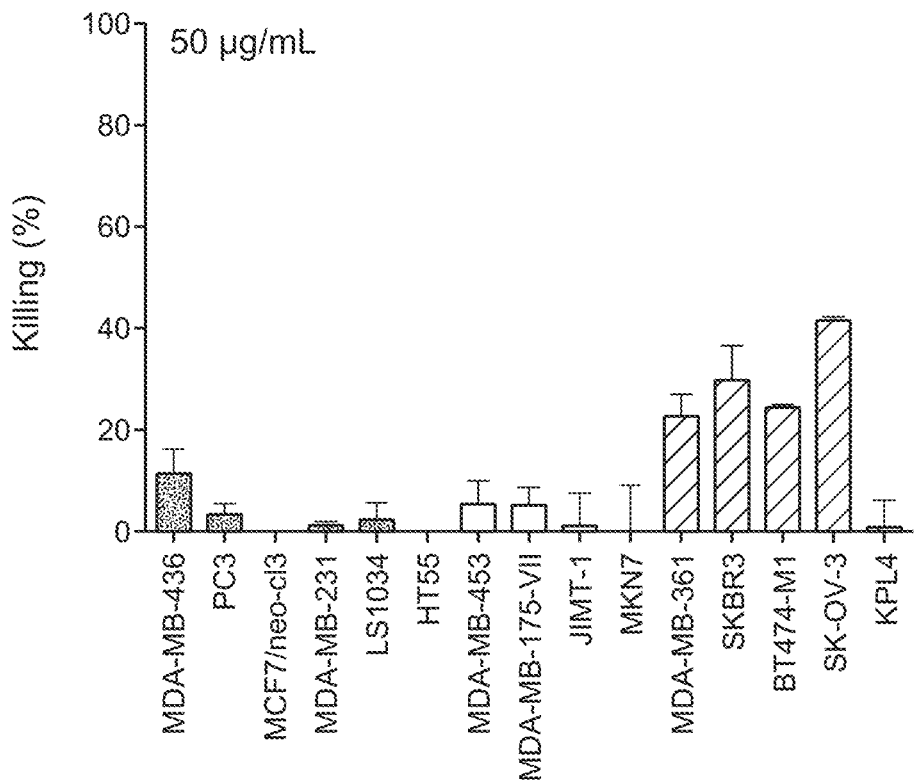
FIG. 12B is a graph showing cytotoxicity of 4D5 H91A-1Fab-IgG TDB1Fab-IgG TDB antibodies at a concentration of 50 μg/mL on low ErbB2 expressing cell lines (MDA-MB-436, PC3, MCF7/neo-cl3, MDA-MB-231, LS1034, and HT55), medium ErbB2 expressing cell lines (MDA-MB-453, MDA-MB-175-VII, JIMT-1, and MKN7), and high Erb2 expressing cell lines (MDA-MB-361, SKBR3, BT474-M1, SK-OV-3, and KPL4). Data are represented as mean±standard deviation.
Figure 12C:
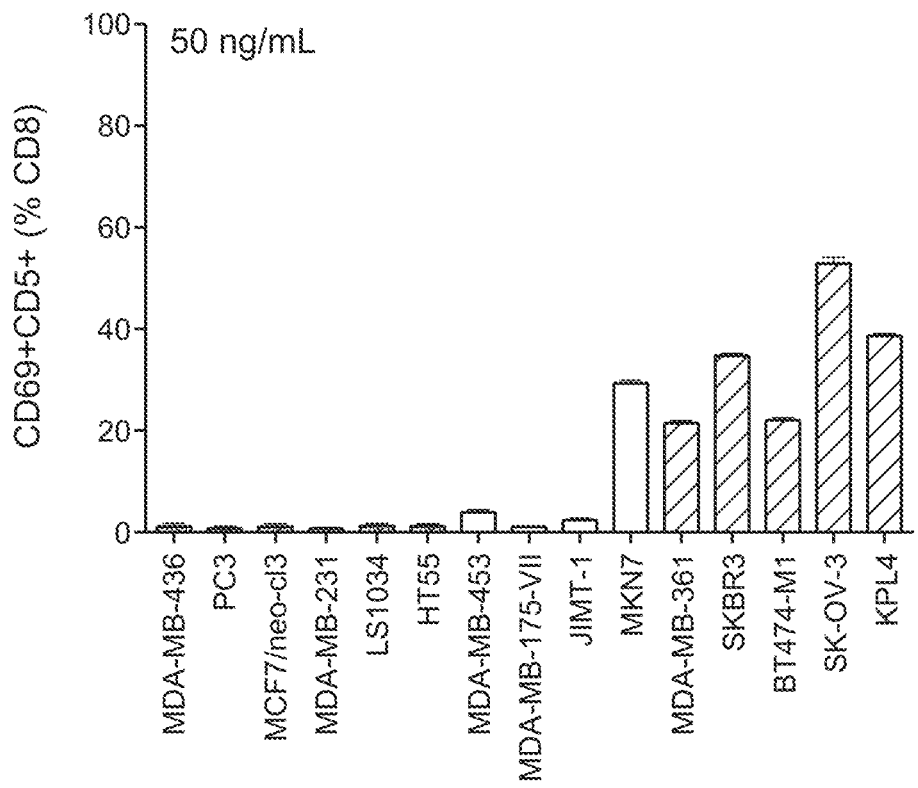
FIG. 12C is a graph showing the effect of 4D5 H91A-1Fab-IgG TDB antibodies at a concentration of 50 ng/mL on activation of human CD8+ T cells cultured with low ErbB2 expressing cell lines (MDA-MB-436, PC3, MCF7/neo-cl3, MDA-MB-231, LS1034, and HT55), medium ErbB2 expressing cell lines (MDA-MB-453, MDA-MB-175-VII, JIMT-1, and MKN7), and high Erb2 expressing cell lines (MDA-MB-361, SKBR3, BT474-M1, SK-OV-3, and KPL4). T cell activation was measured by dual expression of CD69 and CD45. Data are represented as mean±standard deviation.
Figure 12D:
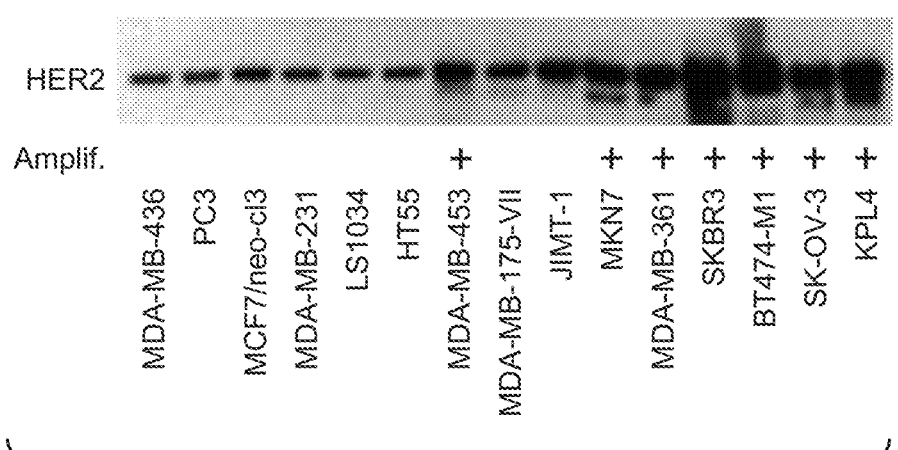
FIG. 12D is an immunoblot showing HER2 protein expression by each of the cells lines represented in FIGS. 12A-12C.

Example 4. Characterizing Enhanced Selectivity of the 1Fab-Igg Tdb Format for Her2 Overexpressing Cells The H91A-1Fab-IgG TDB variant of 4D5 was selected to further analyze in vitro activity. A dose response study demonstrated that 4D5 H91A-1Fab-IgG TDB activity on SKBR3 was nearly identical compared to monovalent high HER2-affinity IgG TDB (FIG. 9; $EC_{50}$ 6.9 and 6.3 µM, respectively). In contrast to IgG TDB, no activity was seen on any dose level of 1Fab-IgG TDB against MCF7 cells (FIG. 9). 90 breast cancer cell lines were arbitrarily split to high (>400 normalized reads per kilobase of transcript length per million mapped read (nRPKM)), medium (50-400 nRPKM), and low (<50 nRPKM). HER2-expressing cells based on HER2-RNA expression reported in Klijn 2015 (FIG. 10; Klijn et al. *Nat. Biotechnol.* 33(3): 306-312, 2015). Selectivity studies were extended to 15 cell lines with variable HER2 expression levels. At a high dose level (50 ng/mL), no clear correlation was seen between T cell activation and HER2 expression for the monovalent high HER2 affinity IgG TDB (FIGS. 11A-11D). In striking contrast, T cell activation was induced only in the cell lines with the highest HER2 expression level when H91A affinity variant 1Fab-IgG TDB was tested (FIGS. 12A-12D). Similarly, target cell killing was limited to high HER2-expressing cell lines with the 1Fab-IgG TDB molecule, whereas the high HER2 affinity IgG TDB was broadly active also in inducing killing of the low HER2-expressing cells when used at high dose levels (FIGS. 11A-11D and 12A-12D). A 50 ng/mL dose of control IgG TDB induced T cell activation and killing of low HER2-expressing cells, while a 50 µg/ml 1Fab-IgG TDB did not impact viability of low HER2-expressing cells. Therefore, the improvement in selectivity of 1Fab-IgG TDB molecules relative to control IgG TDB to HER2 was calculated to be ≥1000-fold.

The activity was further tested in human non-cancer cell lines derived from lung, skin, and breast tissues. Low level HER2 expression was confirmed in all tested non-cancerous cells by flow cytometry. Table 5 shows a characterization of these cells and binding of IgG TDBs and 1Fab-IgG TDB.

TABLE 5

Binding to low HER2-expressing human non-cancer cells.

| Cell Line | Tissue Source | HER2 MFI* | IgG TDB $EC_{50}$ | IgG TDB MED** | 1Fab-IgG TDB MED** |
|---|---|---|---|---|---|
| MRC-5 | Normal lung | 74 | No activity | No activity | No activity |
| HBL-100 | Epithelial | 60 | 2 ng/mL | 5 ng/mL | No activity |
| BEAS-2B | Normal lung | 33 | No activity | No activity | No activity |
| Hs 888.Sk | Normal skin | 35 | 7 ng/mL | 50 ng/mL | No activity |
| hTERT-HME1 | Normal breast + hTERT | 9 | 32 ng/mL | 50 ng/mL | No activity |
| Kd | Normal fibroblast lip | 46 | No activity | No activity | No activity |
| HMEC-1 | Microvascular endothelial foreskins | 15 | No activity | 50 ng/mL | No activity |

*MFI = Mean fluorescence intensity
**MED = Minimal efficacious dose level

Figure 13:
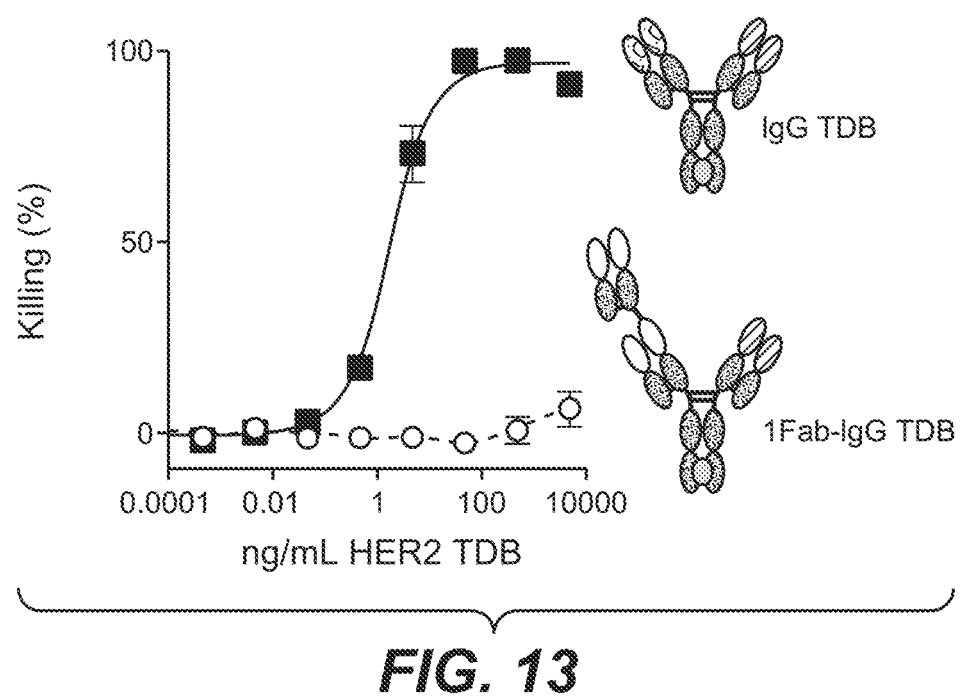
FIG. 13 is a graph showing dose response curves quantifying the cytotoxicity of 4D5 H91A-IgG TDB antibodies (squares) and 4D5 H91A-1Fab-IgG TDB antibodies (circles) on HBL-100 cells.
Figure 14A:
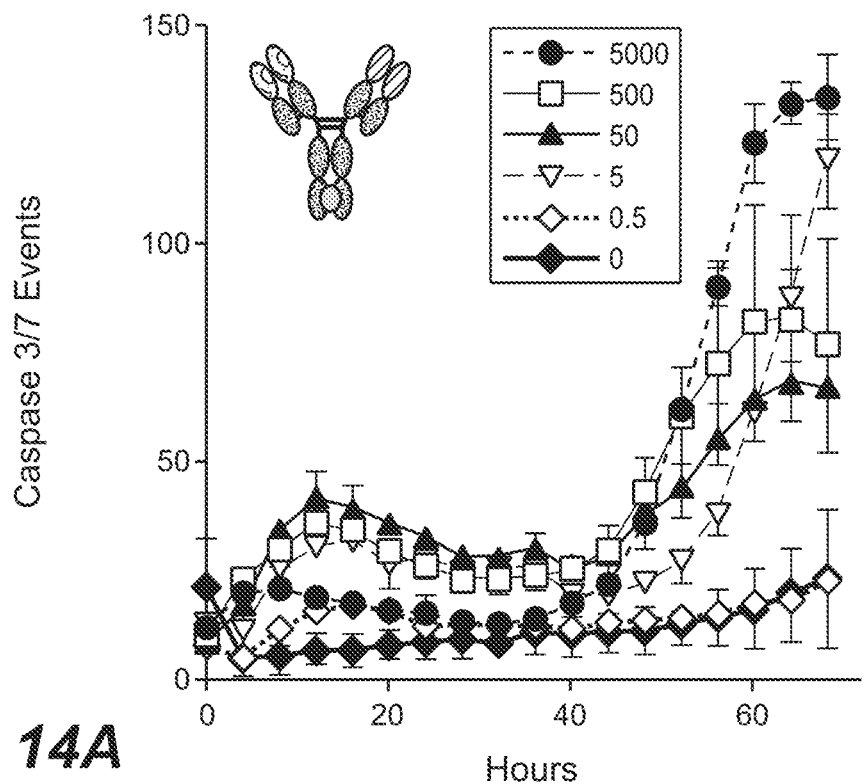
FIG. 14A is a graph showing dose response curves quantifying the cytotoxicity of various concentrations of 4D5 H91A-IgG TDB antibodies on HBL-100 cells over time. Solid circles represent a dose of 5,000 ng/mL 4D5 H91A-IgG TDB, open squares represent a dose of 500 ng/mL 4D5 H91A-IgG TDB, solid upward-pointing triangles represent a dose of 50 ng/mL 4D5 H91A-IgG TDB, open downward-pointing triangles represent a dose of 5 ng/mL 4D5 H91A-IgG TDB, open diamonds represent a dose of 0.5 ng/mL 4D5 H91A-IgG TDB, and solid diamonds represent an untreated control.
Figure 14B:
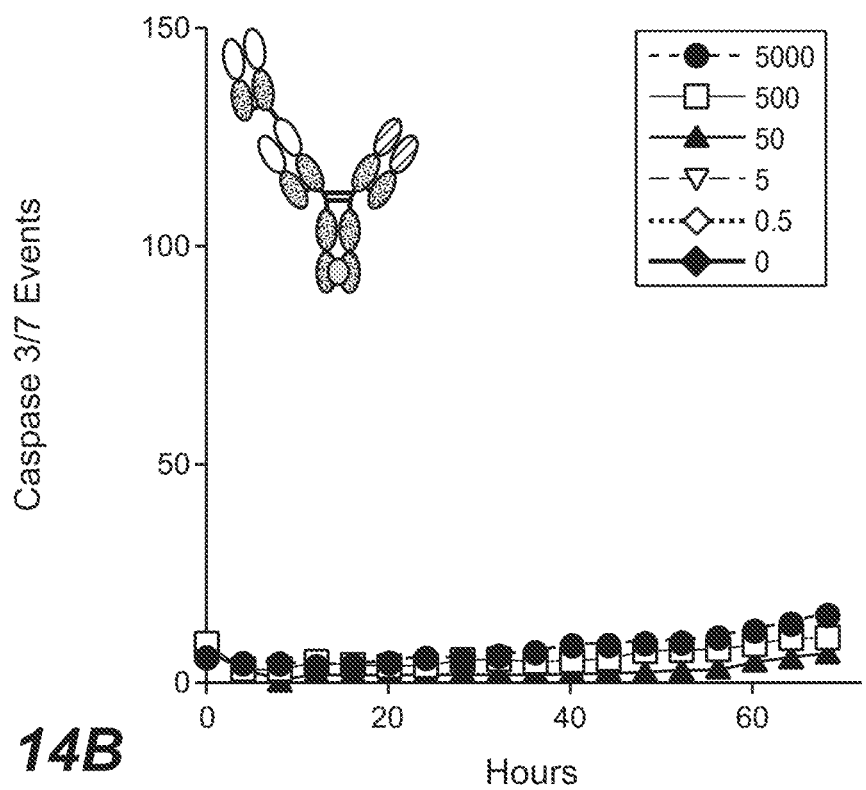
FIG. 14B is a graph showing dose response curves quantifying the cytotoxicity of various concentrations of 4D5 H91A-1Fab-IgG TDB antibodies on HBL-100 cells over time. Solid circles represent a dose of 5,000 ng/mL 4D5 H91A-1Fab-IgG TDB, open squares represent a dose of 500 ng/mL 4D5 H91A-1Fab-IgG TDB, solid upward-pointing triangles represent a dose of 50 ng/mL 4D5 H91A-1Fab-IgG TDB, open downward-pointing triangles represent a dose of 5 ng/mL 4D5 H91A-1Fab-IgG TDB, open diamonds represent a dose of 0.5 ng/mL 4D5 H91A-1Fab-IgG TDB, and solid diamonds represent an untreated control.

H91A affinity variant 1Fab-IgG TDB demonstrated no apoptotic activity against any of the 8 tested cells at concentrations ≤5 µg/mL. A representative comparison of dose-response curves between 1Fab-IgG TDB and IgG TDB cultured with HBL-100 cells shows that H91A-IgG TDB potently kills low HER2-expressing HBL-100 cells, in contrast to H91A-1Fab-IgG TDB (FIG. 13). Kinetic assays confirm the dose-dependence of H91A-IgG TDB on HBL-100 killing over time and further demonstrate that H91A-1Fab-IgG TDB-induced killing is minimal over the course of 70 hours (FIGS. 14A and 14B). These results demonstrate that in vitro potency of the 1Fab-IgG TDB is similar to monovalent high HER2-affinity IgG TDB in killing of high HER2-expressing cell lines. However, 1Fab-IgG TDB had no detectable activity on any tested low HER2-expressing cell lines, suggesting that it is selective to HER2-overexpressing cells.

Figure 15A:
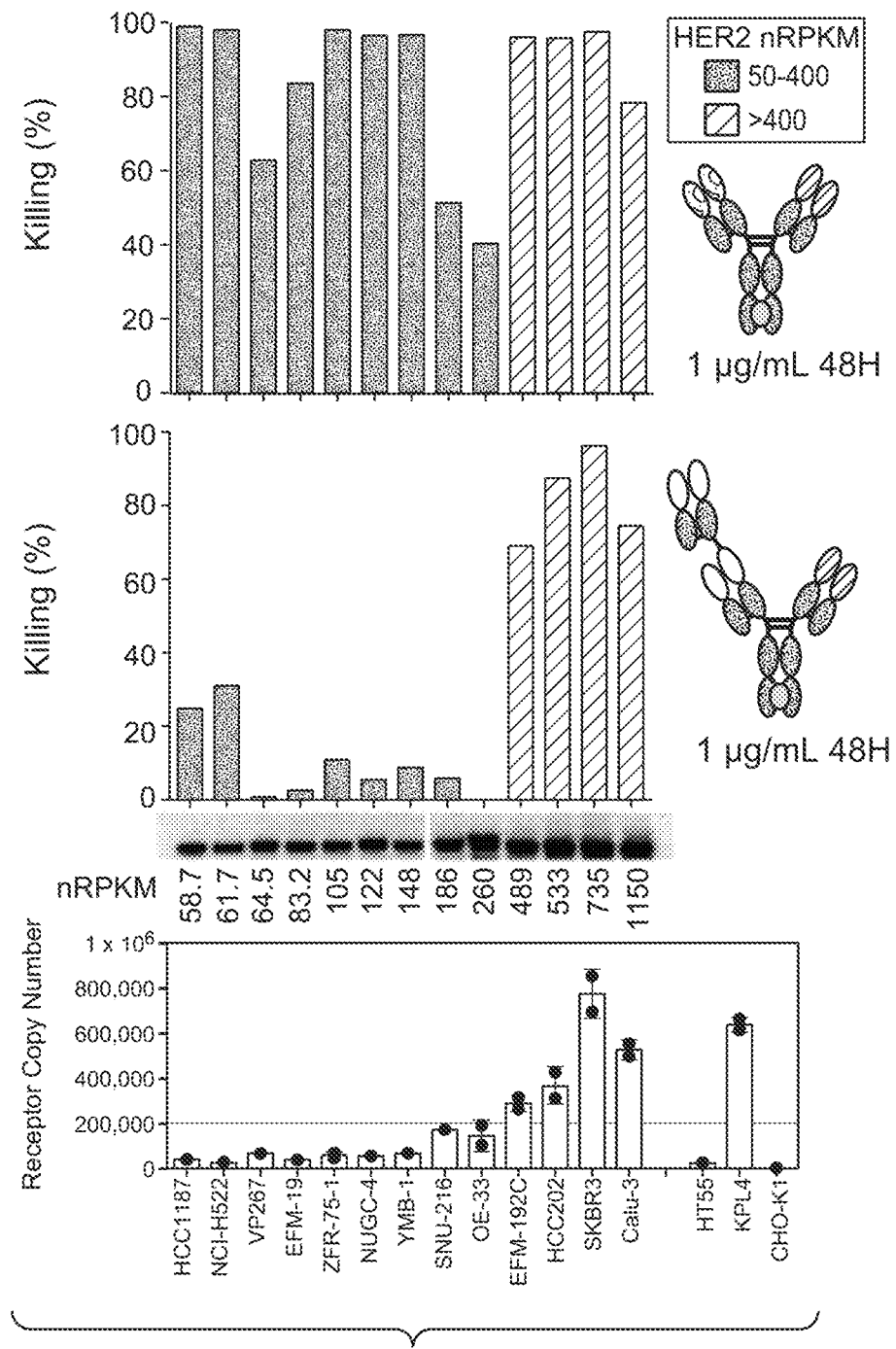
FIG. 15A is a set of graphs showing the effect of killing of 4D5 H91A-IgG TDB and 4D5 H91A-1Fab-IgG TDB on cell lines expressing increasing amounts of HER2, from left to right, as shown by the underlying immunoblot and bar graph.

The threshold of HER2 expression level that is required for activity of H91A affinity variant 1Fab-IgG TDB was then investigated. Upon incubation of 1Fab-IgG TDB with 13 target cell lines having various HER2 expression profiles, killing was observed in target cells expressing HER2 at a copy number of greater than 200,000 HER2 molecules per cell (FIG. 15A). In particular, robust killing activity was detected in all cell lines expressing HER2 RNA ≥489 nRPKM (i.e., cell lines expressing HER2 at a copy number ≥290,579). Minimal activity was detected in all cell lines that expressed HER2 RNA ≤260 nRPKM (i.e., cell lines expressing HER2 at a copy number ≤146,208). HER2 copy number for each cell line was quantified by FACS using Quantum-Alexa647 MESF beads, and results are summarized in Table 6, below.

TABLE 6

HER2 copy number of various cell lines tested for 1Fab-IgG TDB killing

| Cell Line | Mean HER2 Copy Number | Standard Deviation | % Standard Deviation |
|---|---|---|---|
| HCC1187 | 38,436 | 3,238 | 8% |
| NCI-H522 | 26,954 | 198 | 1% |
| VP267 | 70,761 | 7,515 | 11% |
| EFM-19 | 38,479 | 51 | 0% |

TABLE 6-continued

HER2 copy number of various cell lines tested for 1Fab-IgG TDB killing

| Cell Line | Mean HER2 Copy Number | Standard Deviation | % Standard Deviation |
|---|---|---|---|
| ZFR-75-1 | 58,337 | 18,222 | 31% |
| NUGC-4 | 59,298 | 3,020 | 5% |
| YMB-1 | 69,655 | 964 | 1% |
| SNU-216 | 175,357 | 1,819 | 1% |
| OE-33 | 146,208 | 68,969 | 47% |
| EFM-192C | 290,579 | 34,503 | 12% |
| HCC202 | 368,513 | 82,560 | 22% |
| SKBR3 | 774,501 | 109,335 | 14% |
| Calu-3 | 525,657 | 42,062 | 8% |
| HT55 | 26,337 | 1,157 | 4% |
| KPL4 | 636,978 | 31,743 | 5% |
| CHO-K1 | 0 | 0 | 0% |

Figure 15B:
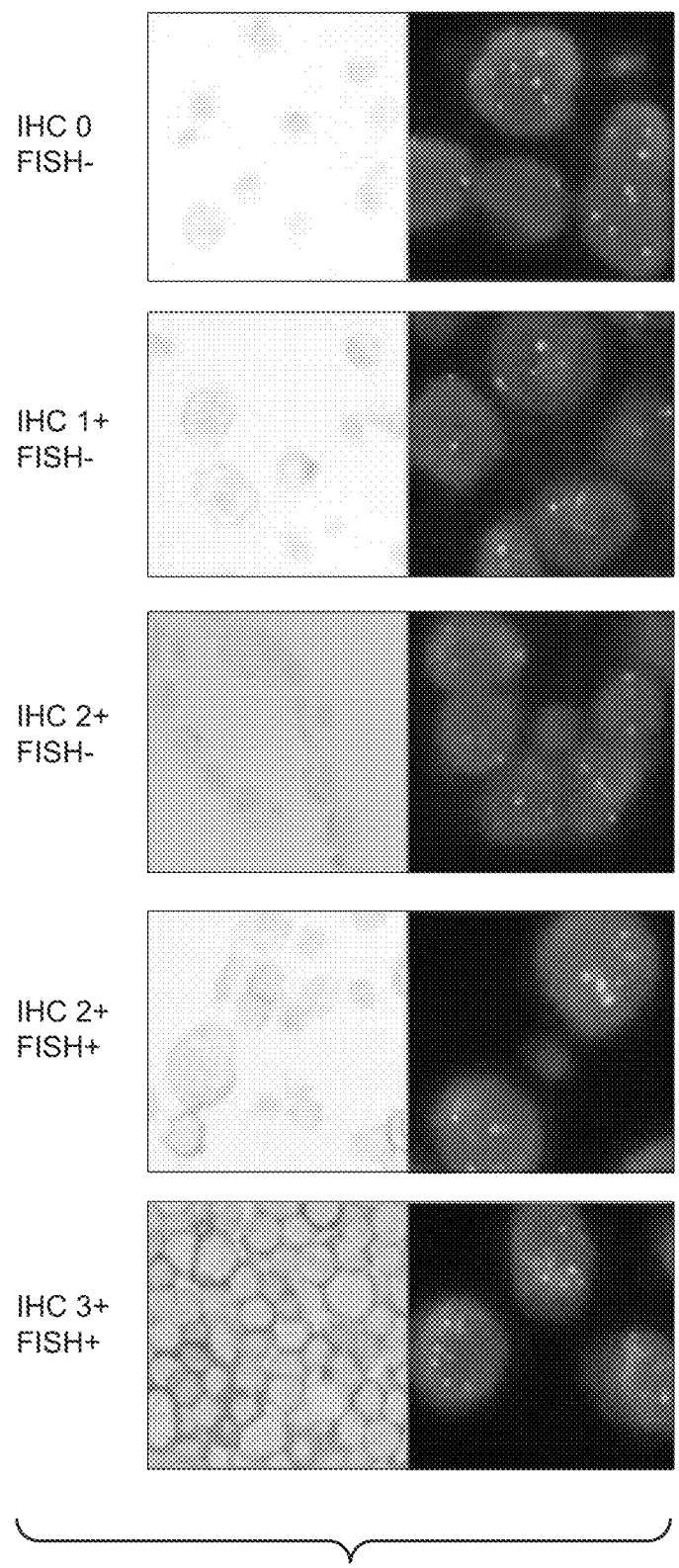
FIG. 15B is a series of photomicrographs showing the results of IHC and FISH detection assays of relative HER2 expression.
Figure 15C:
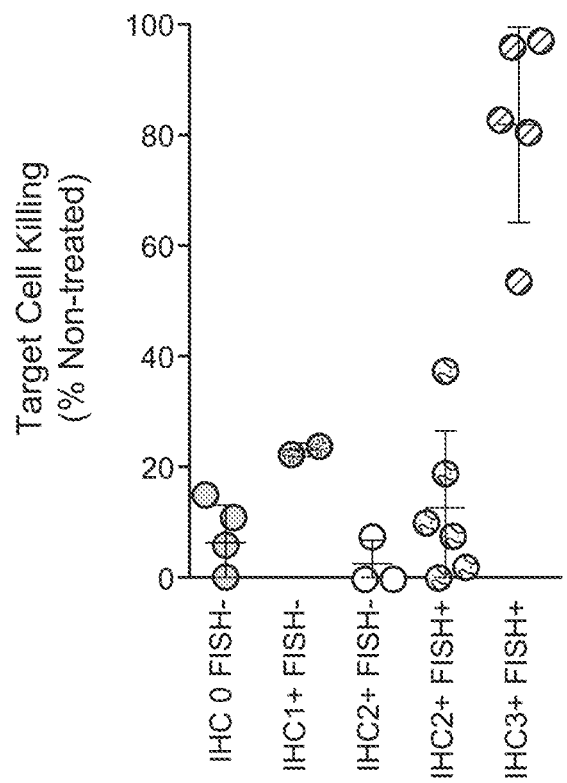
FIG. 15C is a graph showing killing of cells characterized in FIG. 15B by 4D5 H91A-1Fab-IgG TDB.

The activity was further benchmarked to HER2 diagnostic tests that are clinically validated and used for patient selection. Out of 20 cell tested cell lines, substantial killing activity was seen only in IHC 3+, FISH+ cell lines using the H91A affinity variant 1Fab-IgG TDB (FIGS. 15B and 15C).

Figure 16:
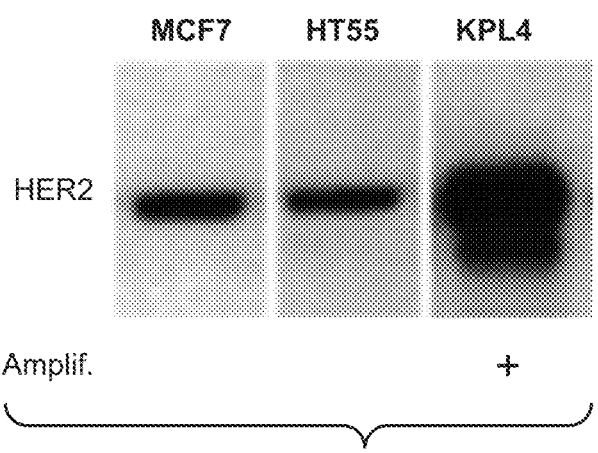
FIG. 16 is an immunoblot showing HER2 protein expression in MCF7 cells, HT55 cells, and HER2-amplified KPL4 cells.
Figure 17:
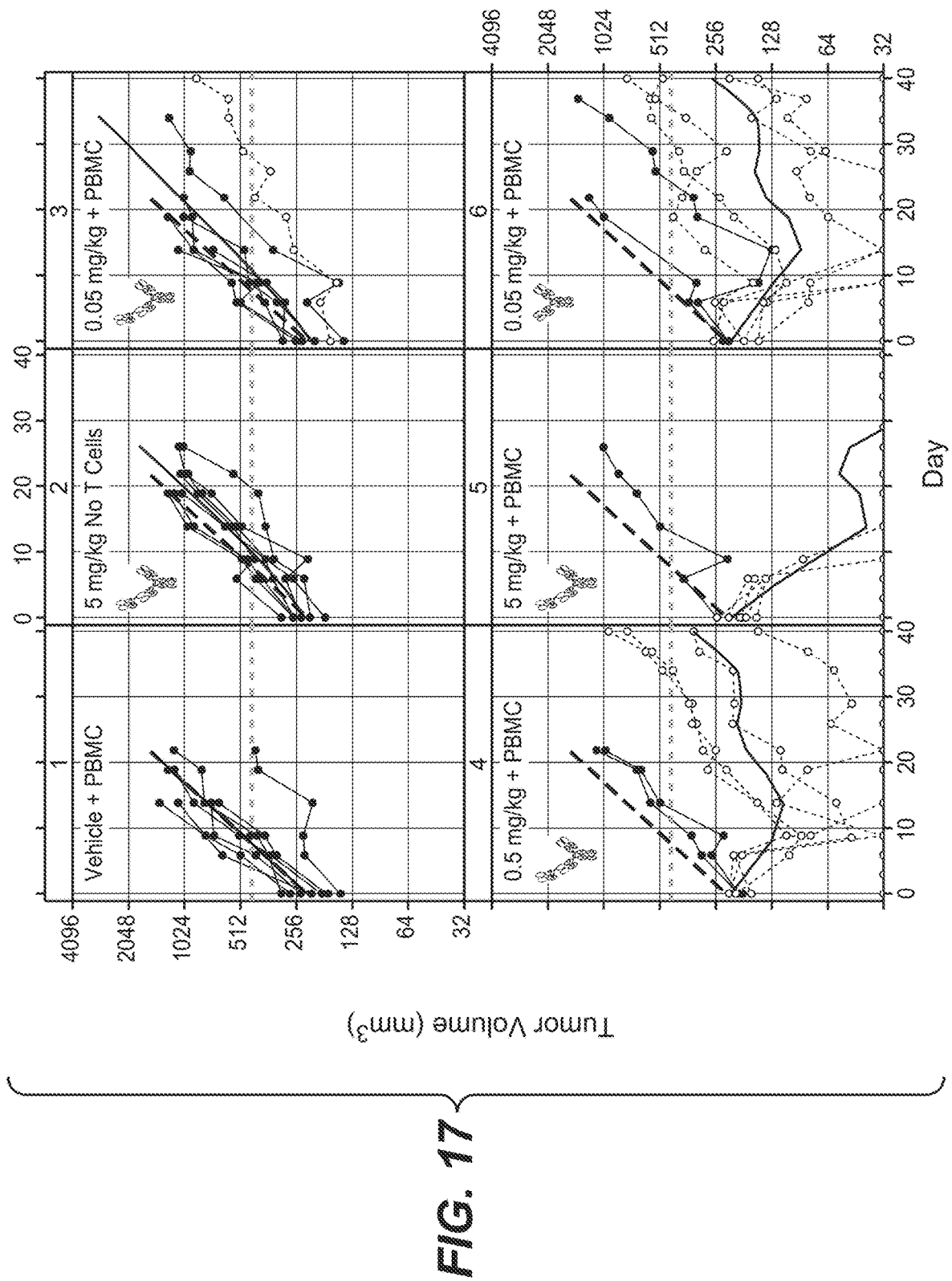
FIG. 17 is a trellis plot showing KPL4 tumor volume over the course of treatment with various doses of 4D5 H91A-1Fab-IgG TDB antibodies or wildtype 4D5 TDB antibodies in mice supplemented with human PBMCs. Mice with established KPL4 tumors received a single intravenous dose at day 0 at indicated doses. Each panel in the trellis depicts one dose group, as indicated by the panel header. Bold, solid black lines represent the fitted tumor volume for each dose group. Dashed bold lines represent the fitted tumor volume for the control group, which received the histidine buffer vehicle. Dashed lines with open circles represent individual animals. Solid lines with solid dots represent animals that were removed from the study. Dashed horizontal gray lines mark a tumor volume of 500 mm$^3$.
Figure 18:
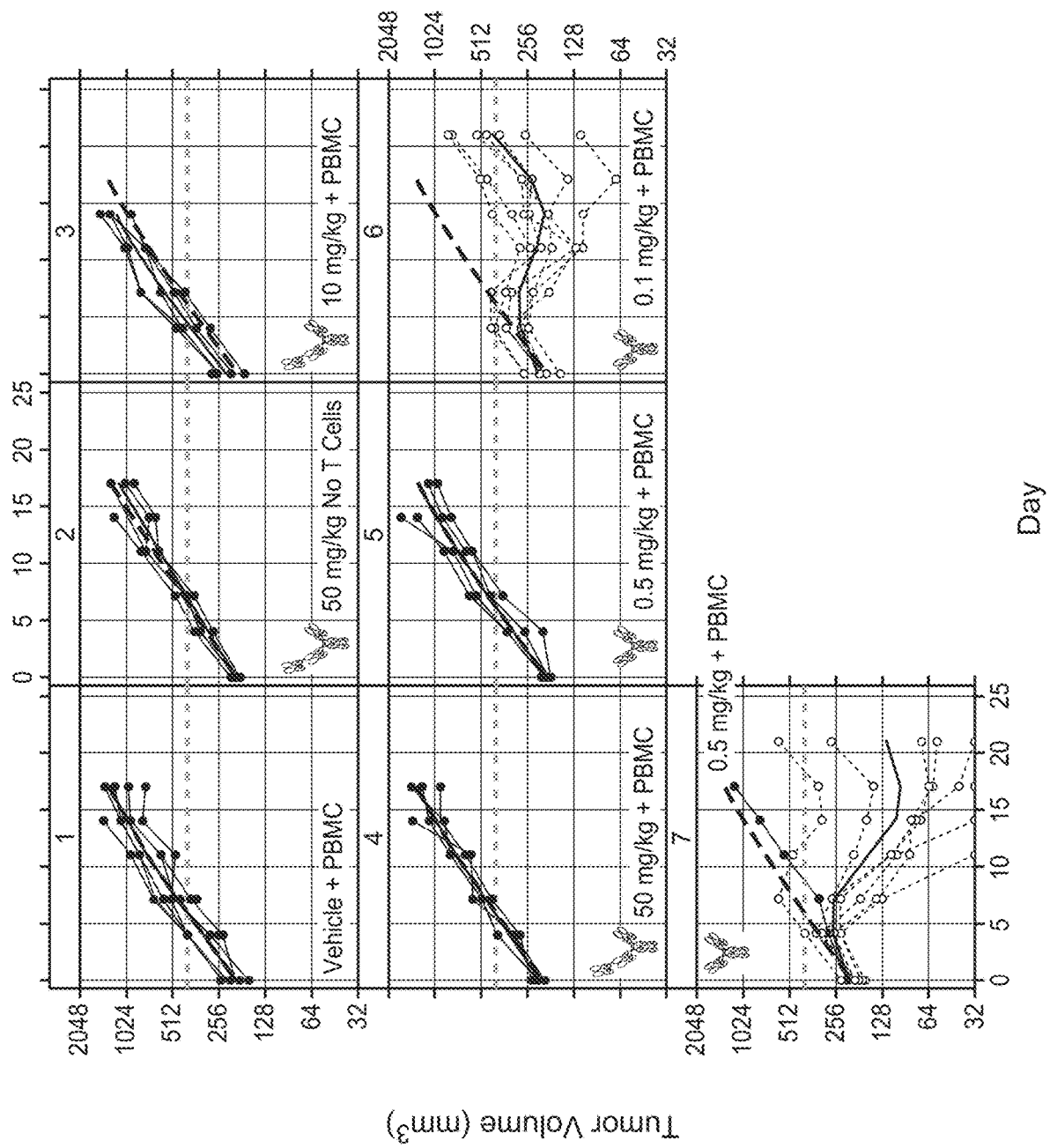
FIG. 18 is a trellis plot showing HT55 tumor volume over the course of treatment with various doses of 4D5 H91A-1Fab-IgG TDB antibodies or wildtype 4D5 IgG TDB antibodies in mice supplemented with human PBMCs. Mice with established HT55 tumors received a single intravenous dose at day 0 at indicated doses. Each panel in the trellis depicts one dose group, as indicated by the panel header. Bold, solid black lines represent the fitted tumor volume for each dose group. Dashed bold lines represent the fitted tumor volume for the control group, which received the histidine buffer vehicle. Dashed lines with open circles represent individual animals. Solid lines with solid dots represent animals that were removed from the study. Dashed horizontal gray lines mark a tumor volume of 500 mm$^3$.

Example 5. Assessing In Vivo Selectivity of 1Fab-Igg Tdb for Her2 Overexpressing Tumors In vivo activity of the H91A affinity variant 1Fab-IgG TDB was evaluated. NSG mice supplemented with human PBMC were grafted with HER2-amplified KPL4 tumors or HT55 tumors, which expressed a similar level of HER2 as MCF7 cells (FIG. 16). The H91A-1Fab-IgG TDB induced dose regressions in response to a single 0.5-5 mg/kg dose (FIG. 17), whereas the monovalent high HER2 affinity IgG TDB induced regressions at 0.05 mg/kg dose, indicating that the 1Fab-IgG TDB is about 10-fold less active in vivo. As expected based on the in vitro results, less activity was detected in treatment of HT55 tumors (FIG. 18). Monovalent high HER2 affinity IgG TDB induced HT55 tumor regressions at single 0.1 mg/kg dose. The H91A-1Fab-IgG TDB did not have any anti-tumor activity in the treatment of HT55 tumors at doses ≤50 mg/kg. These results demonstrated that both molecules were highly potent in treatment of HER2 amplified tumors and provide support for a positive therapeutic index based on HER2 expression level in HER2 amplified cancer. The H91A-1Fab-IgG TDB HER2 TDB demonstrated ≥100-fold in vivo selectivity to HER2 amplified tumors compared to tumors that express normal, low levels of HER2 (e.g., similar to normal human tissues).

Example 6. Adjusting HER2 Affinity for Enhanced Selectivity

Figure 19:
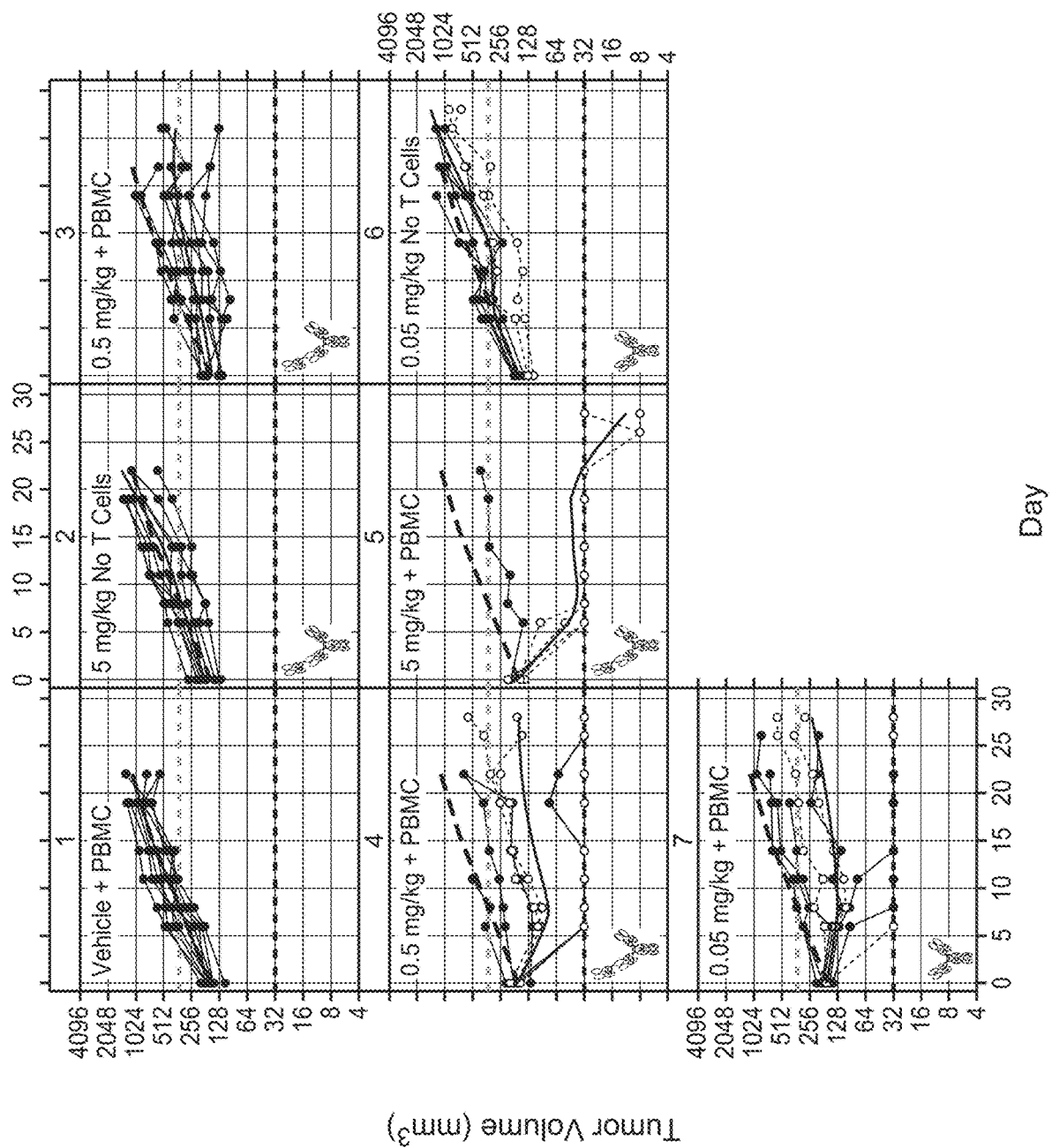
FIG. 19 is a trellis plot showing KPL4 tumor volume over the course of treatment with various doses of 4D5 D98A.F100A.Y102V-1Fab-IgG TDB antibodies or wildtype 4D5 IgG TDB antibodies in mice supplemented with human PBMCs. Mice with established KPL4 tumors received a single intravenous dose at day 0 at indicated doses. Each panel in the trellis depicts one dose group, as indicated by the panel header. Bold, solid black lines represent the fitted tumor volume for each dose group. Dashed bold lines represent the fitted tumor volume for the control group, which received the histidine buffer vehicle. Dashed lines with open circles represent individual animals. Solid lines with solid dots represent animals that were removed from the study. Dashed horizontal red lines mark a tumor volume of 500 mm$^3$.
Figure 20:
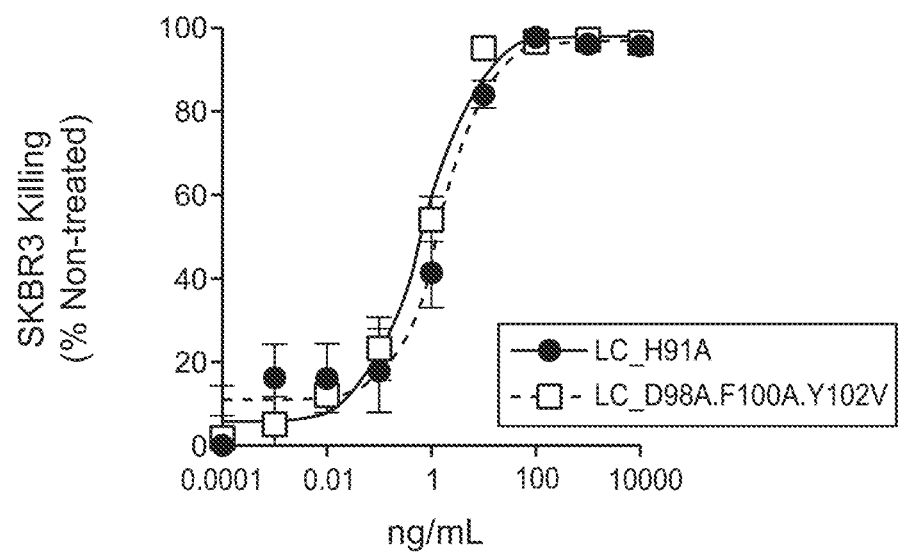
FIG. 20 is a graph showing dose response curves quantifying the cytotoxicity of 4D5 H91A-1Fab-IgG TDB antibodies (solid circles) and 4D5 D98A.F100A.Y102V-1Fab-IgG TDB antibodies (open squares) on SKBR3 cells. Data are represented as mean±standard deviation.
Figure 21A:
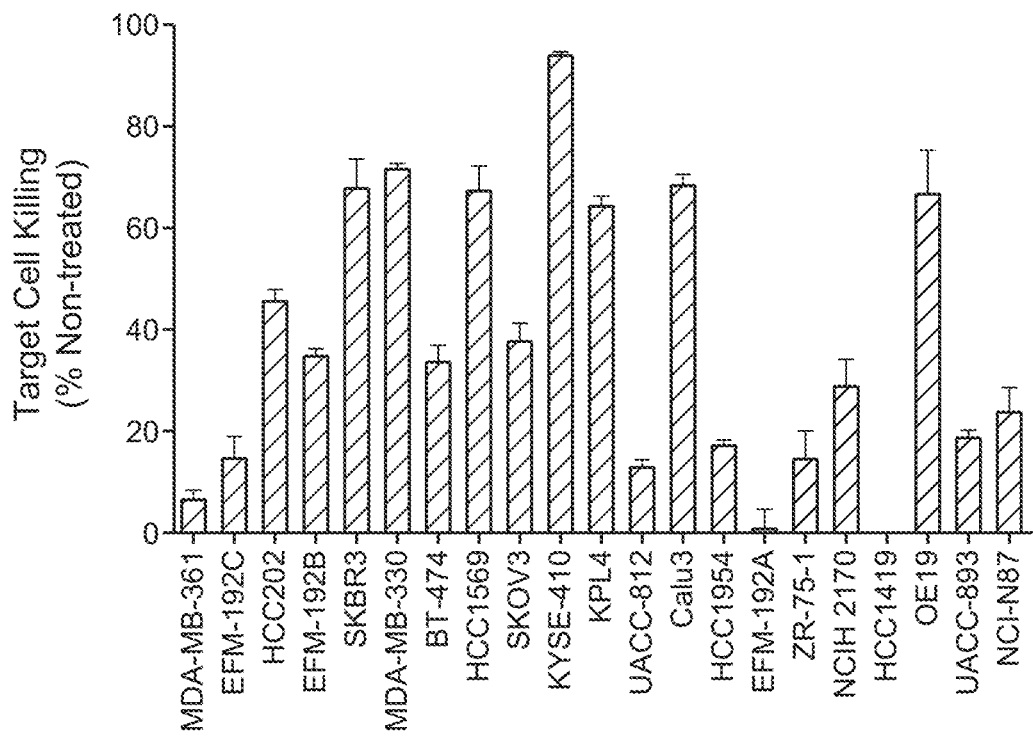
FIG. 21A is a graph showing killing by 4D5 H91A-1Fab-IgG TDB antibodies of high HER2-expressing cell lines (n=20). High HER2-expressing cell lines are characterized by high expression of Erb2 RNA. Data are represented as mean±standard deviation.
Figure 21B:
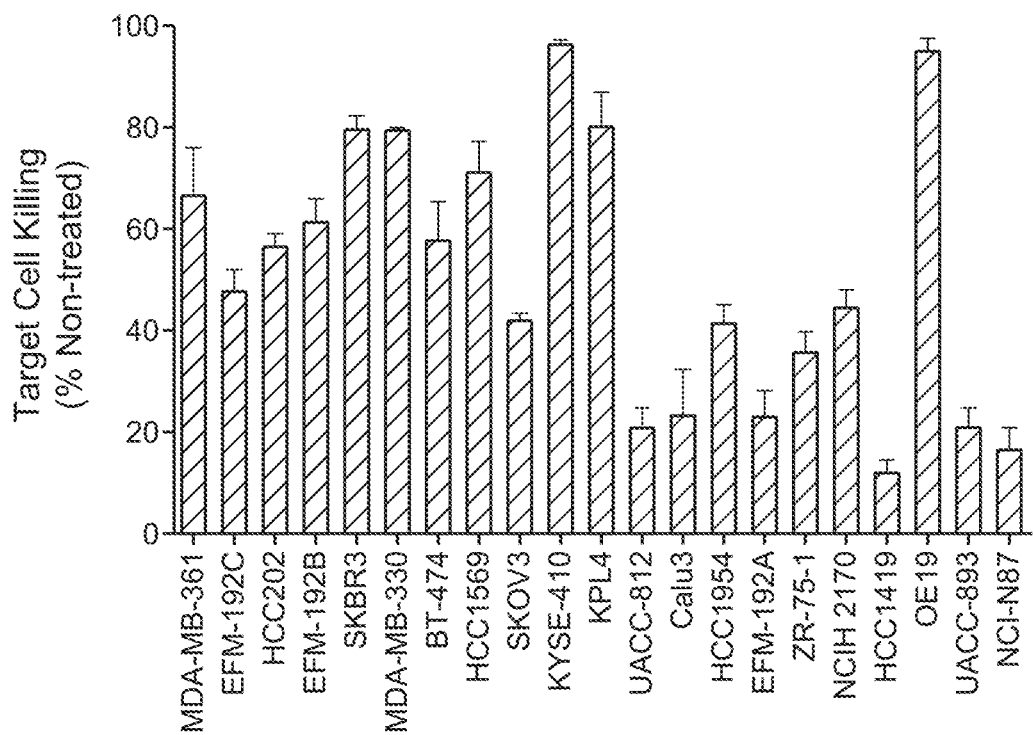
FIG. 21B is a graph showing killing by 4D5 D98A.F100A.Y102V-1Fab-IgG TDB antibodies of high HER2-expressing cell lines (n=20). High HER2-expressing cell lines are characterized by high expression of Erb2 RNA. Data are represented as mean±standard deviation.
Figure 22:
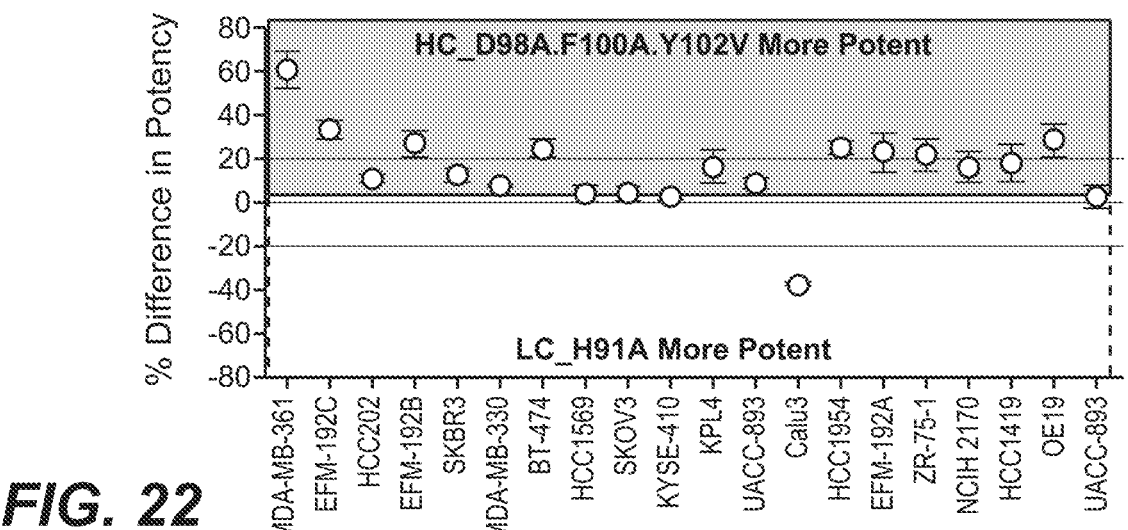
FIG. 22 is a graph showing the relative potency of killing of high HER2-expressing cell lines by 4D5 D98A.F100.Y102V-1Fab-IgG TDB antibodies relative to 4D5 H91A-1Fab-IgG TDB antibodies. Data are derived from FIGS. 20A and 20B.
Figure 24:
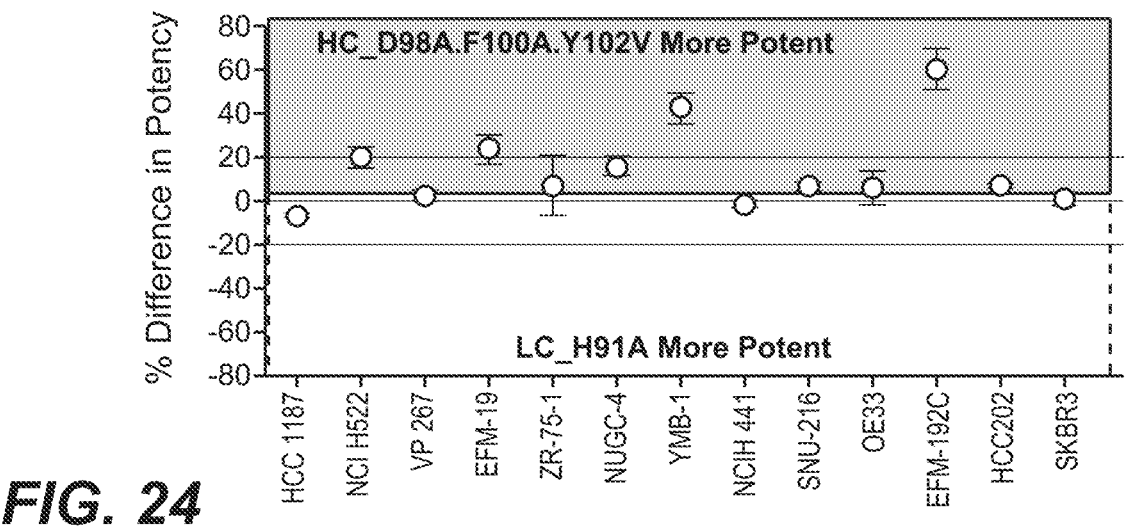
FIG. 24 is a graph showing the relative potency of killing of medium HER2-expressing cell lines by 4D5 D98A.F100.Y102V-1Fab-IgG TDB antibodies relative to 4D5 H91A-1Fab-IgG TDB antibodies. Data are derived from FIGS. 22A and 22B.
Figure 26:
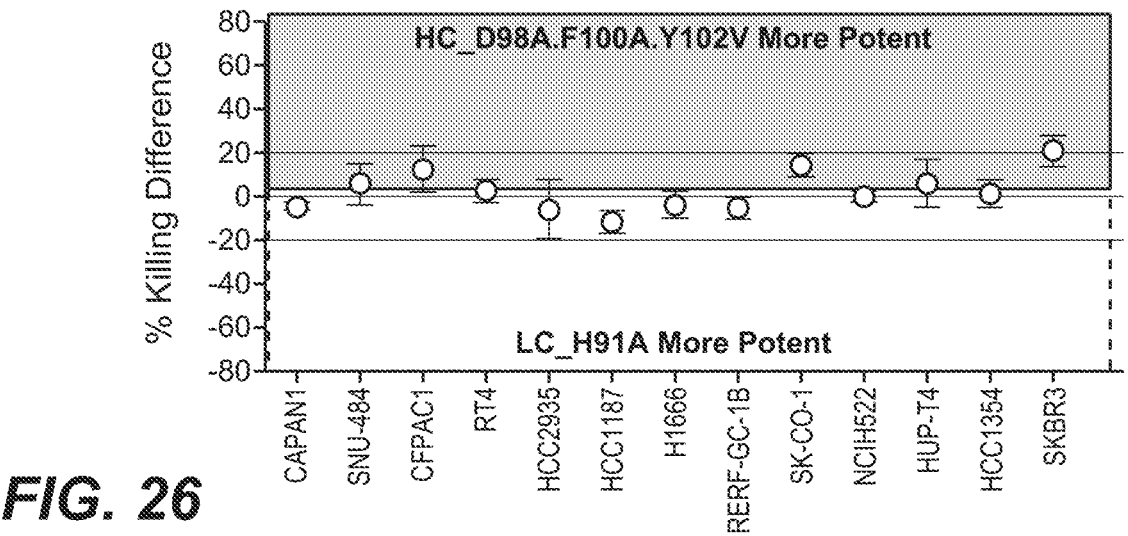
FIG. 26 is a graph showing the relative potency of killing of low HER2-expressing cell lines by 4D5 D98A.F100.Y102V-1Fab-IgG TDB antibodies relative to 4D5 H91A-1Fab-IgG TDB antibodies. Data are derived from FIGS. 24A and 24B.
Figure 23A:
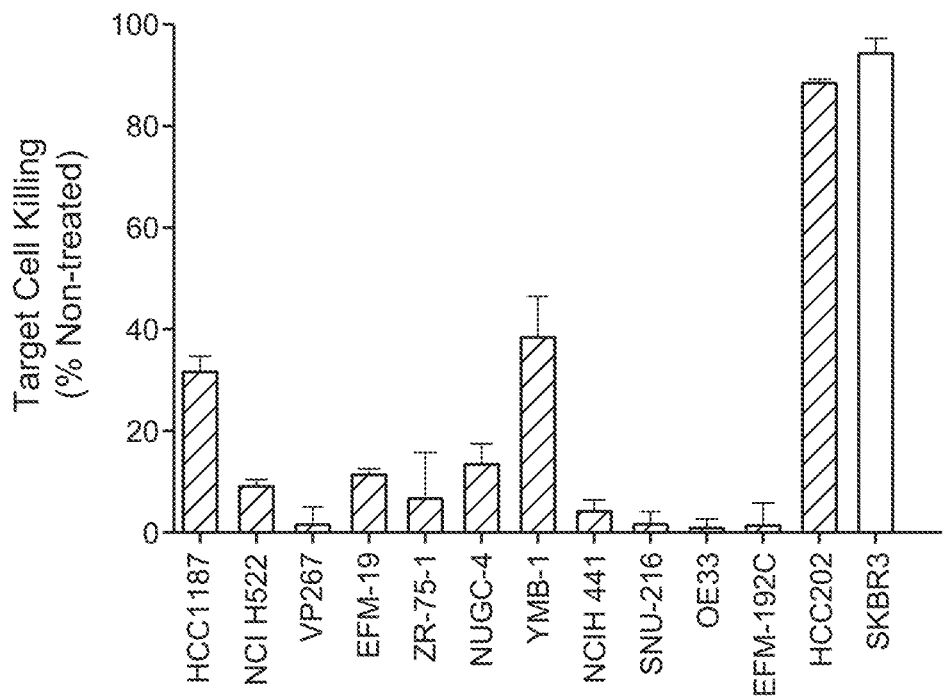
FIG. 23A is a graph showing killing by 4D5 H91A-1Fab-IgG TDB antibodies of medium HER2-expressing cell lines (n=12). Killing of SKBR3 cells is provided as a positive control. Medium HER2-expressing cell lines are characterized by medium expression of Erb2 RNA. Data are represented as mean±standard deviation.
Figure 23B:
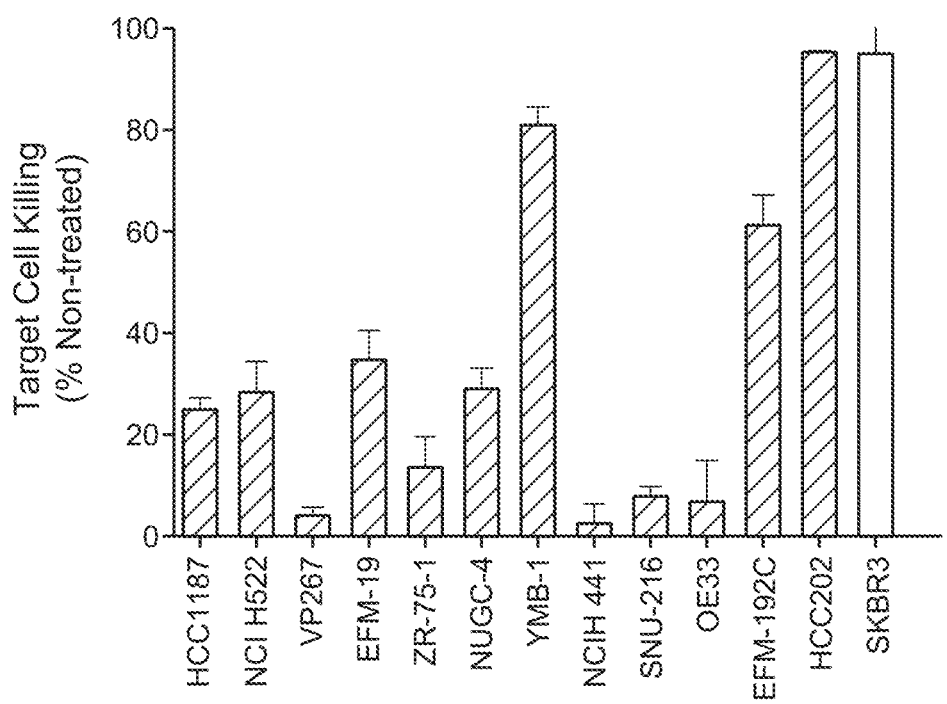
FIG. 23B is a graph showing killing by 4D5 D98A.F100A.Y102V-1Fab-IgG TDB antibodies of medium HER2-expressing cell lines (n=12). Killing of SKBR3 cells is provided as a positive control. Medium HER2-expressing cell lines are characterized by medium expression of Erb2 RNA. Data are represented as mean±standard deviation.
Figure 25A:
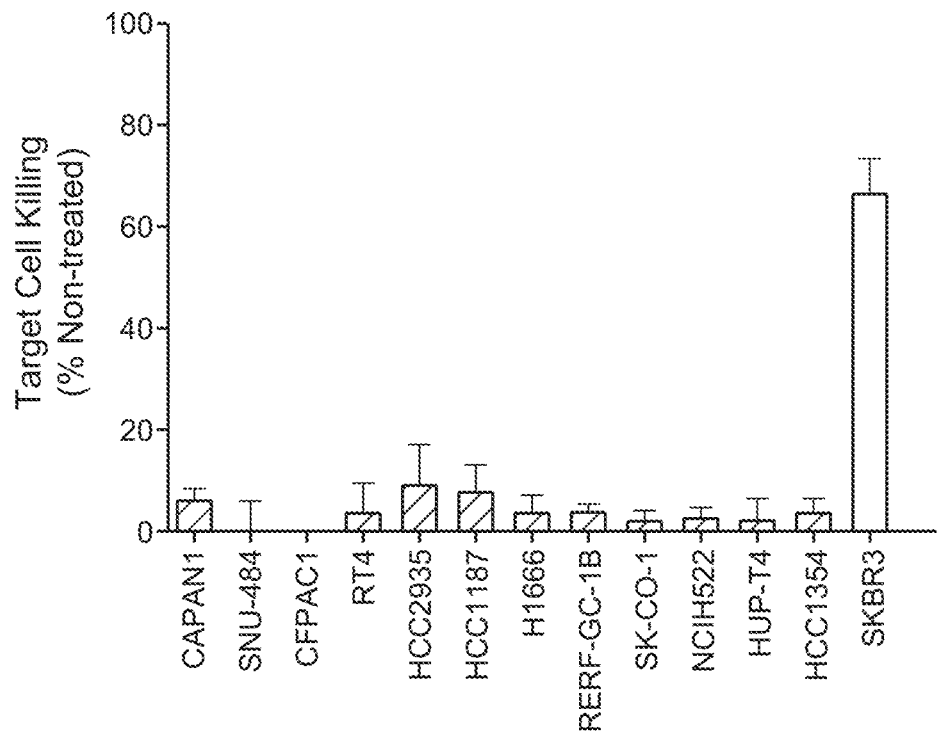
FIG. 25A is a graph showing killing by 4D5 H91A-1Fab-IgG TDB antibodies of low HER2-expressing cell lines (n=12). Killing of SKBR3 cells is provided as a positive control. Low HER2-expressing cell lines are characterized by low expression of Erb2 RNA. Data are represented as mean±standard deviation.
Figure 25B:
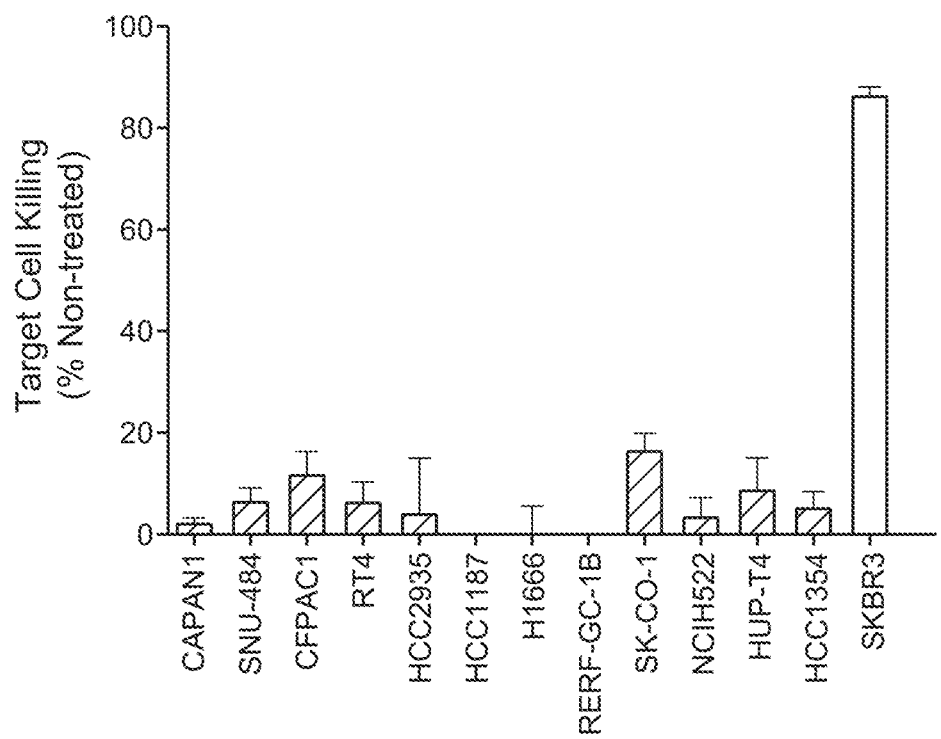
FIG. 25B is a graph showing killing by 4D5 D98A.F100A.Y102V-1Fab-IgG TDB antibodies of low HER2-expressing cell lines (n=12). Killing of SKBR3 cells is provided as a positive control. Low HER2-expressing cell lines are characterized by low expression of Erb2 RNA. Data are represented as mean±standard deviation.

Two 4D5 variants, D98A.F100A.Y102V and H91A (monovalent $K_D$ 23 and 49 nM, respectively), which demonstrated improved selectivity in 1Fab-IgG TDB format, were selected for extended characterization to identify optimal affinity to achieve maximal selectivity to HER2-overexpressing cells. In an in vitro dose response assay against SKBR3 cells, D98A.F100A.Y102V and H91A variants demonstrated near identical activity (FIG. 20). Both molecules demonstrated robust anti-tumor activity on 0.5 mg/kg doses in treatment of HER2 amplified KPL4 tumor xenografts (FIGS. 17 and 19). In vitro activity assays were extended by treating multiple cell lines expressing high, medium, or low levels of HER2 with a high concentration (50 ng/mL) of 1Fab-IgG TDB variants, H91A-1FabIg (FIGS. 21A, 23A, and 25A) and D98A.F100A.Y102V (FIGS. 21B, 23B, and 25B). Responses of the cell lines were generally similar to both molecules. However, a clear trend was observed in which potency of the D98A.F100A.Y102V variant was higher compared to H91A variant (FIGS. 22, 24, and 26). As this trend was detectable in low HER2-expressing cells, it was determined that the H91A substitution in the 4D5 HVR that binds HER2 with monovalent $K_D$ of 49 nM resulted in maximal selectivity to HER2-overexpressing cells.

Example 7. Characterizing the Effect of Linker Sequence Length

Figure 27A:
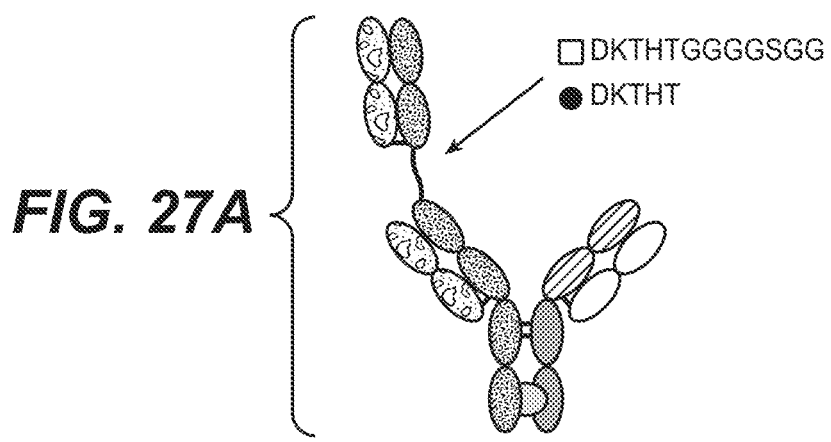
FIG. 27A is a schematic drawing showing the position and sequences of the two peptide linkers tested in FIG. 27B. Each peptide linker fuses the C-terminus of the constant heavy chain (CH) region of the distal Fab to the N-terminus of the variable heavy chain (VH) region of the proximal Fab. DKTHTGGGGSGG (SEQ ID NO: 52) is represented by open squares, and DKTHT (SEQ ID NO: 50) is represented by solid circles, in FIG. 27B.
Figure 27B:
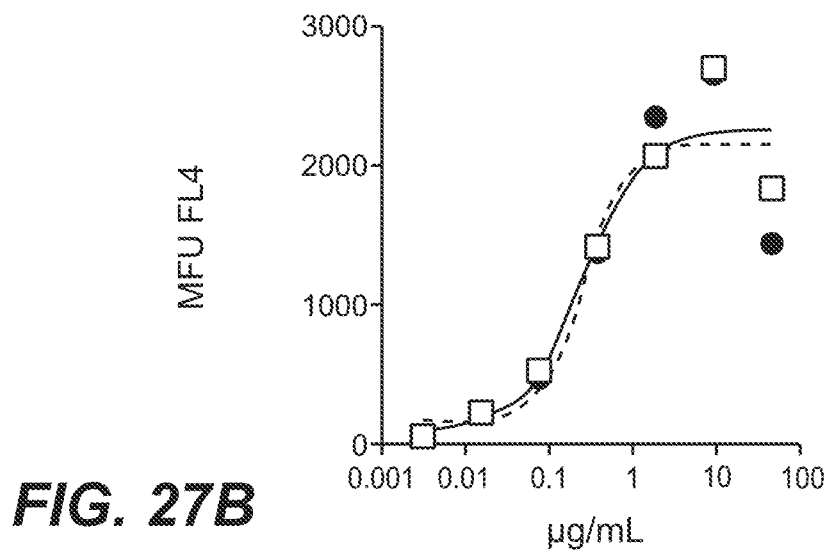
FIG. 27B is a graph showing dose response curves quantifying the binding to MCF7 cells of 4D5 H91A-1Fab-IgG TDB antibodies having the DKTHTGGGGSGG linker (SEQ ID NO: 52; open squares), relative to 4D5 H91A-1Fab-IgG TDB antibodies having the DKTHT linker (SEQ ID NO: 50; solid circles). Data are represented as mean±standard deviation.
Figure 27C:
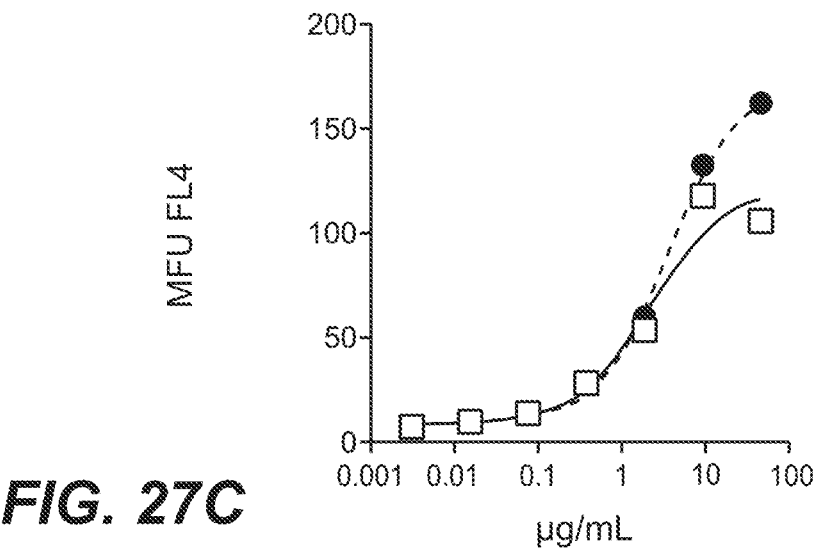
FIG. 27C is a graph showing dose response curves quantifying the killing of SKBR3 cells by 4D5 H91A-1Fab-IgG TDB antibodies having the DKTHTGGGGSGG linker (SEQ ID NO: 52; open squares), relative to 4D5 H91A-1Fab-IgG TDB antibodies having the DKTHT linker (SEQ ID NO: 50; solid circles). Data are represented as mean±standard deviation.

To quantify the effect of the length of the linker sequence fusing the anti-HER2 Fabs in the heavy chain bivalent HER2 binding and activity, two linker sequences were tested (FIG. 27A). All 1Fab-IgG TDB molecules in previous experiments included the extended linker sequence (DKTHTGGGGSGG, SEQ ID NO: 52) including therewithin the natural DKTHT sequence (SEQ ID NO: 50) derived from the upper IgG$_1$ hinge of the distal Fab, followed by a GGGGSGG extension (SEQ ID NO: 51). The extended linker sequence was compared to a 1Fab-IgG TDB molecule having a linker of the natural DKTHT sequence (SEQ ID NO: 50). The impact of the linkers was tested using H91A-1Fab-IgG TDB. No difference in binding to SKBR3 or MCF7 cells was observed (FIGS. 27B and 27C). In vitro dose response in SKBR3 killing, as well as broader cell line activity screen, demonstrated near identical activity between the variants. The natural linker variant performed similarly in treatment of KPL4 and HT55 tumor xenografts, relative to the extended linker. These data suggest that anti-HER2 1 Fab-IgG TDB having monovalent affinities for HER2 ranging from $K_D$ 23 nM to 49 nM exhibit favorable activity profiles. In these studies, maximal selectivity to HER2-overexpressing cells was achieved using the H91A 4D5 variant ($K_D$ 49 nM).

Example 8. T Cell-Independent Anti-Signaling Effect of Trastuzumab is Attenuated in 1Fab-IgG TDB Molecule with Bivalent Low Affinity Binding to HER2

Figure 28A:
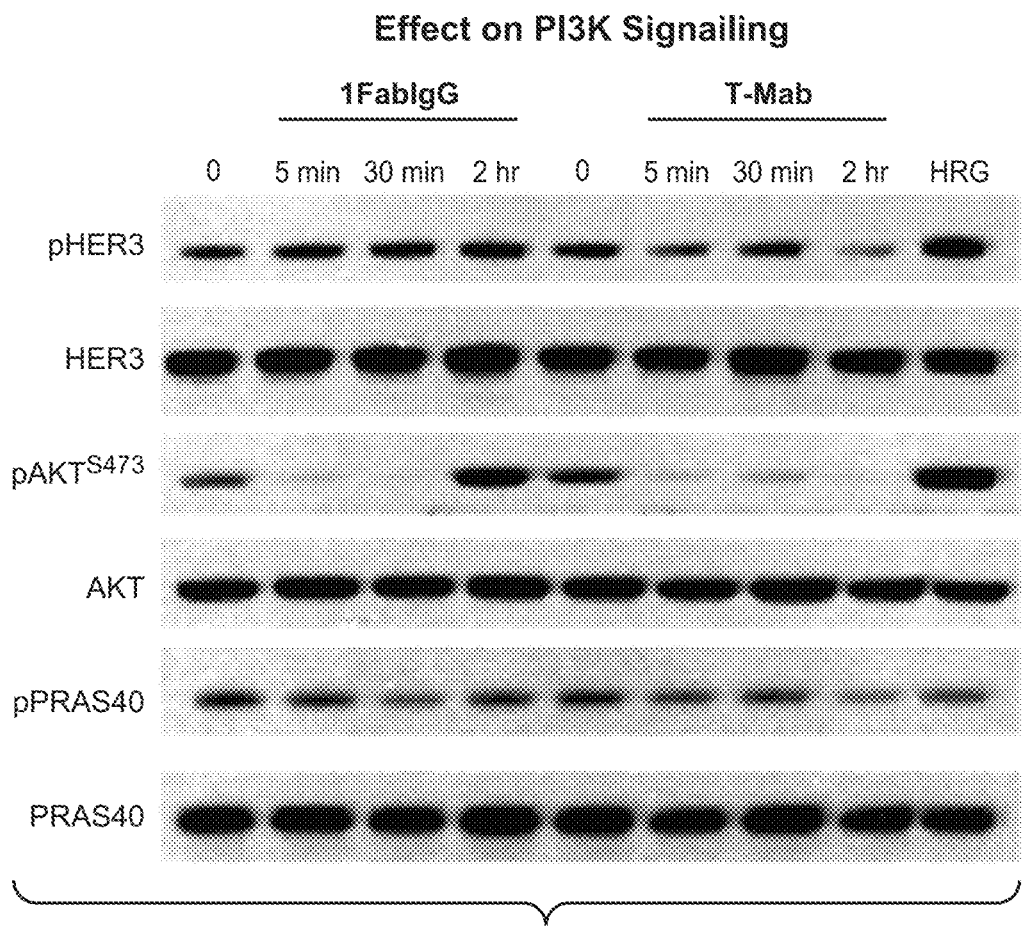
FIG. 28A is a series of immunoblots showing the effect of anti-HER2-CD3 1 Fab-IgG on the expression of pAKT$^{S473}$ and pHER3 by SKBR3 cells over time.
Figure 28B:
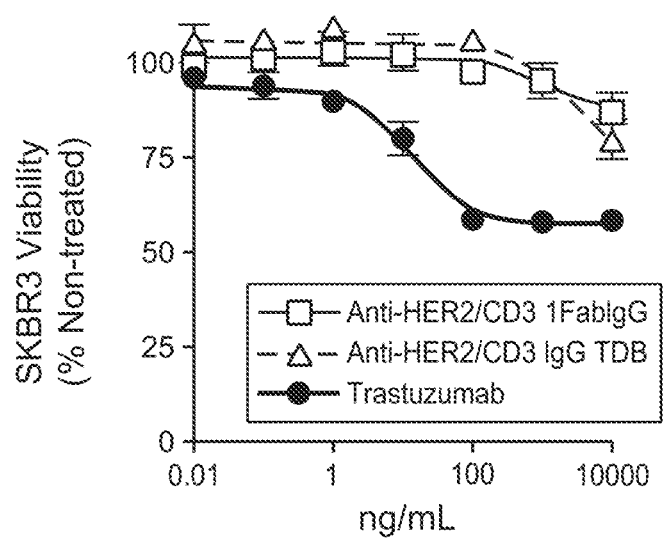
FIG. 28B is a graph showing dose response curves quantifying the viability of SKBR3 cells in response to treatment with anti-HER2-CD3 1 Fab-IgG, anti-HER2-CD3 IgG TDB, and Trastuzumab.
Figure 29A:
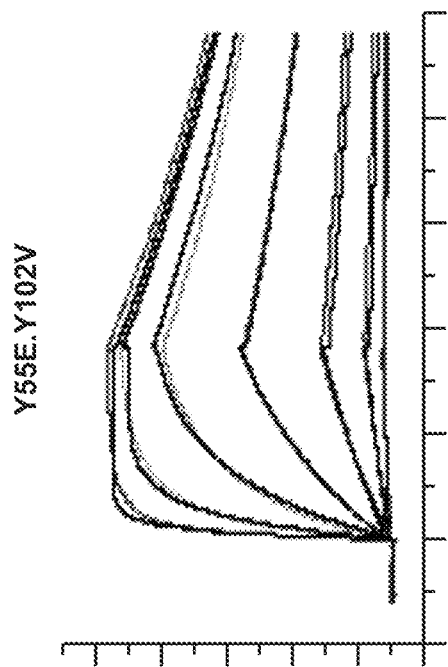
FIG. 29A is a sensorgram showing binding kinetics of the wildtype 4D5 Fab to directly immobilized human HER2 (extracellular domain; Novus Biologicals), as measured using BIACORE® surface plasmon resonance. The wildtype 4D5 Fab samples ranged in concentrations of 0.27 nM to 200 nm, in 3-fold dilutions.
Figure 29B:
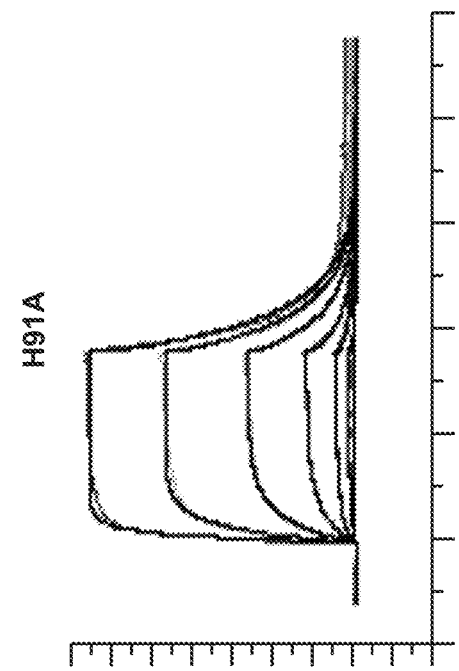
FIG. 29B is a sensorgram showing binding kinetics of the 4D5 Y55E.Y102V-Fab to directly immobilized human HER2 (extracellular domain; Novus Biologicals), as measured using BIACORE® surface plasmon resonance. The 4D5 Y55E.Y102V-Fab samples ranged in concentrations of 0.27 nM to 200 nm, in 3-fold dilutions.
Figure 29C:
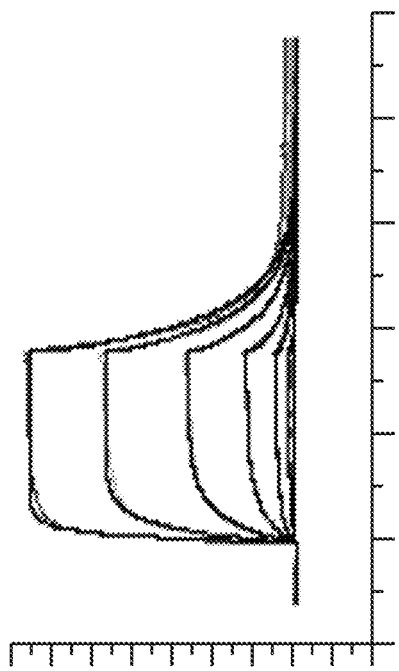
FIG. 29C is a sensorgram showing binding kinetics of the 4D5 D98A.F100A.Y102V-Fab to directly immobilized human HER2 (extracellular domain; Novus Biologicals), as measured using BIACORE® surface plasmon resonance. The 4D5 D98A.F100A.Y102V-Fab samples ranged in concentrations of 0.27 nM to 200 nm, in 3-fold dilutions.
Figure 29D:
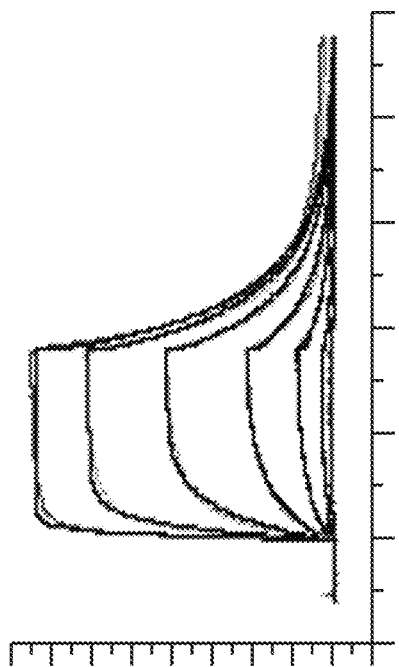
FIG. 29D is a sensorgram showing binding kinetics of the 4D5 H91A-Fab to directly immobilized human HER2 (extracellular domain; Novus Biologicals), as measured using BIACORE® surface plasmon resonance. The 4D5 H91A-Fab samples ranged in concentrations of 0.27 nM to 200 nm, in 3-fold dilutions.

Binding of trastuzumab to overexpressed HER2 in HER2 amplified cancer cells results in robust interference of constitutive ligand independent PI3K signaling initiated by the deregulated HER2-HER3 complex (Junttila et al. *Cancer Res.* 74(19): 5561-5571, 2014). The 1Fab-IgG TDB molecule binds to HER2 in bivalent form. In vitro treatment of SKBR3 cells with incubation with 1Fab-IgG TDB resulted in transient non-durable reduction of pAKT, without detectable effect on HER3 phosphorylation (FIG. 28A). In addition, neither monovalent high HER2 affinity IgG TDB, nor bivalent low HER2 affinity 1Fab-IgG TDB substantially affected the proliferation/viability of SKBR3 cells (FIG. 28B). In summary, bivalent low affinity binding to HER2 does not inhibit proliferation of HER2-amplified cells.

Example 9. Combining 4D5 Antibody Variants with Liability Fix Variants

Figure 30A:
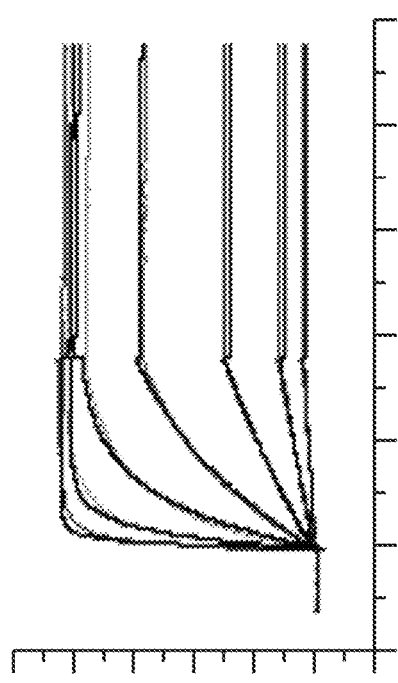
FIG. 30A is a sensorgram showing binding kinetics of the 4D5 N30S-Fab to directly immobilized human HER2 (extracellular domain; Novus Biologicals), as measured using BIACORE® surface plasmon resonance. The 4D5 N30S-Fab samples ranged in concentrations of 0.27 nM to 200 nm, in 3-fold dilutions.
Figure 30B:
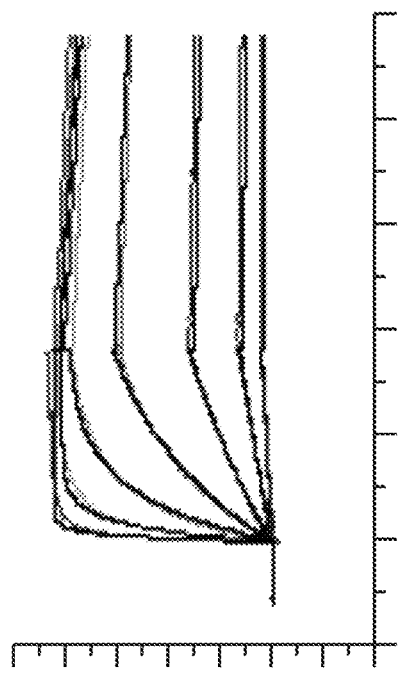
FIG. 30B is a sensorgram showing binding kinetics of the 4D5 N54E.D98T-Fab to directly immobilized human HER2 (extracellular domain; Novus Biologicals), as measured using BIACORE® surface plasmon resonance. The 4D5 N54E.D98T-Fab samples ranged in concentrations of 0.27 nM to 200 nm, in 3-fold dilutions.
Figure 30C:
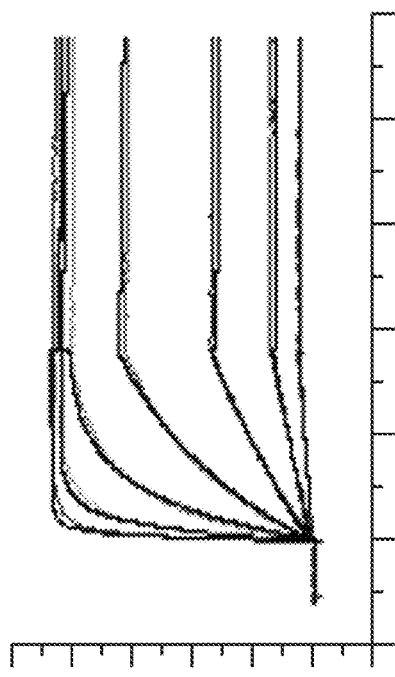
FIG. 30C is a sensorgram showing binding kinetics of the 4D5 N30S.N54E.D98T-Fab to directly immobilized human HER2 (extracellular domain; Novus Biologicals), as measured using BIACORE® surface plasmon resonance. The 4D5 N30S.N54E.D98T-Fab samples ranged in concentrations of 0.27 nM to 200 nm, in 3-fold dilutions.
Figure 31A:
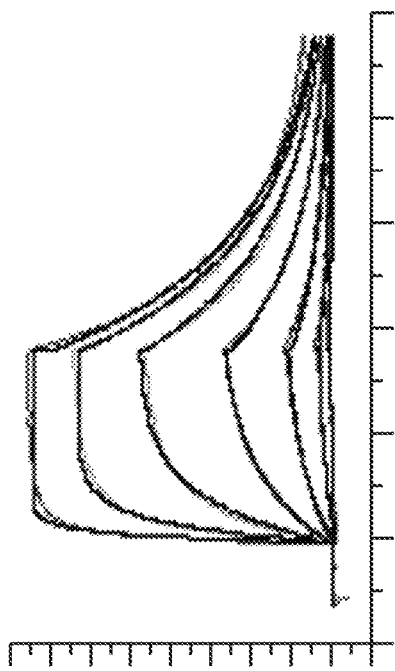
FIG. 31A is a sensorgram showing binding kinetics of the 4D5 N30S.Y55E.N54E.D98T.Y102V-Fab to directly immobilized human HER2 (extracellular domain; Novus Biologicals), as measured using BIACORE® surface plasmon resonance. The 4D5 N30S.Y55E.N54E.D98T.Y102V-Fab samples ranged in concentrations of 0.27 nM to 200 nm, in 3-fold dilutions.
Figure 31B:
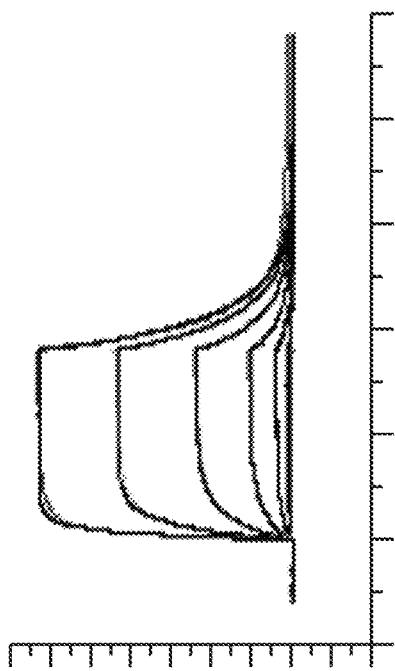
FIG. 31B is a sensorgram showing binding kinetics of the 4D5 N30S.N54E.D98T.F100A.Y102V-Fab to directly immobilized human HER2 (extracellular domain; Novus Biologicals), as measured using BIACORE® surface plasmon resonance. The 4D5 N30S.N54E.D98T.F100A.Y102V-Fab samples ranged in concentrations of 0.27 nM to 200 nm, in 3-fold dilutions.
Figure 31C:
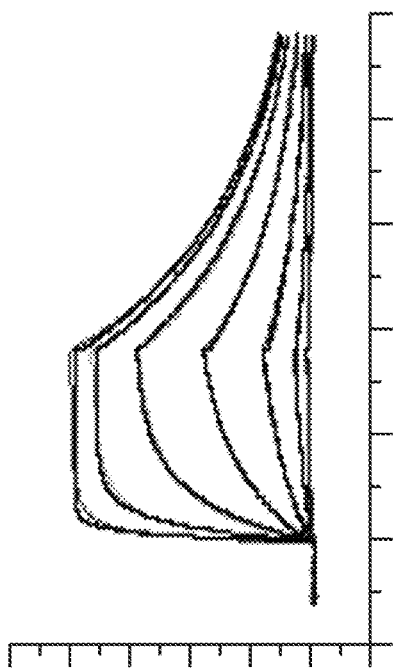
FIG. 31C is a sensorgram showing binding kinetics of the 4D5 N30S.H91A.N54E.D98T-Fab to directly immobilized human HER2 (extracellular domain; Novus Biologicals), as measured using BIACORE® surface plasmon resonance. The 4D5 N30S.H91A.N54E.D98T-Fab samples ranged in concentrations of 0.27 nM to 200 nm, in 3-fold dilutions.
Figures 32E, 32F, 32G, 32H:
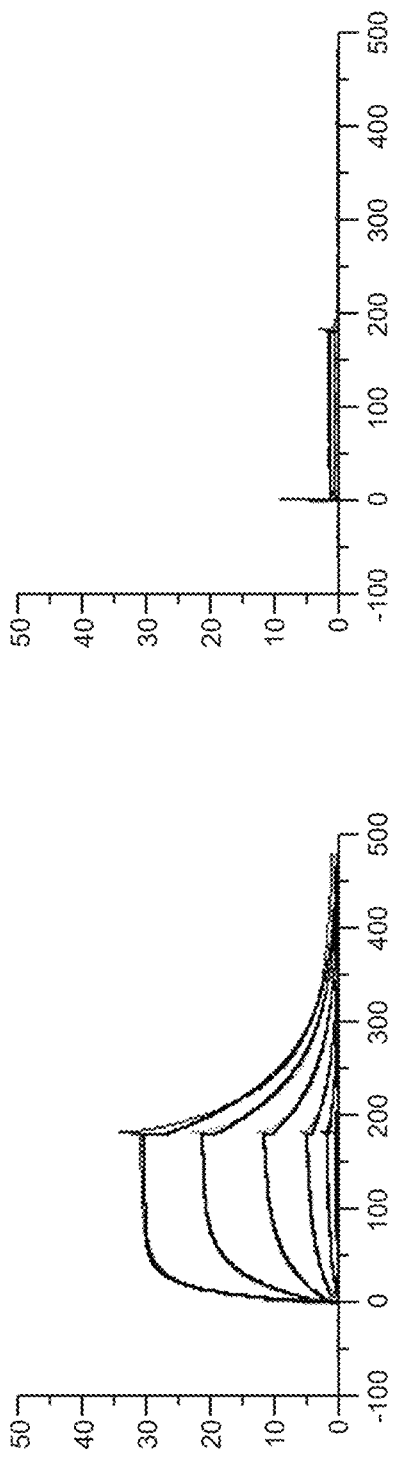
Figure 32I:
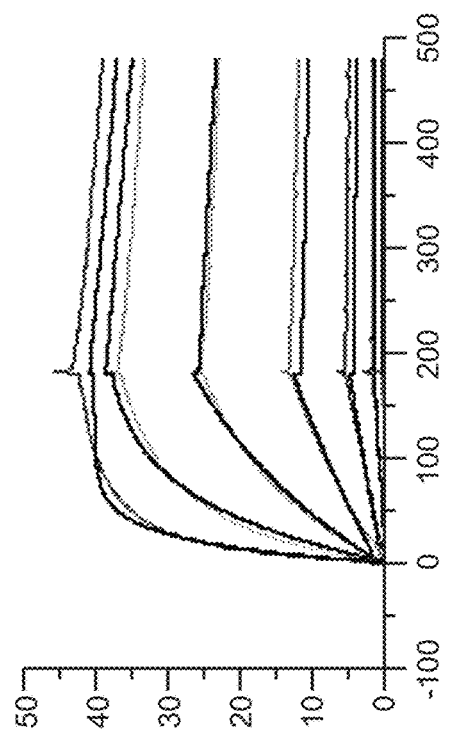
Figure 32J:
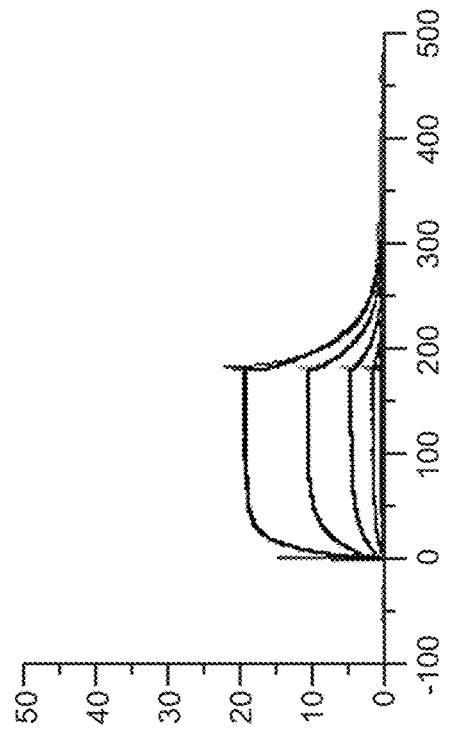
Figure 32K:
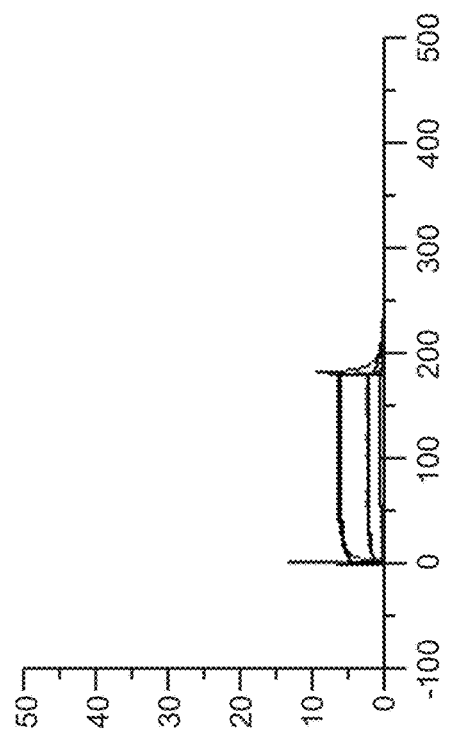

To enhance stability of 4D5 antibody affinity variants, liability fixes were introduced. To reduce deamidation, 4D5 light chain residue N30 was substituted with a serine residue (N30S), and 4D5 heavy chain residue N54 was substituted with a glutamic acid residue (N54E). To reduce isomerization, 4D5 heavy chain residue D98 was substituted with an alanine residue (D98A) and/or a threonine residue (D98T). Binding affinities of the wildtype 4D5 Fab and affinity variants thereof (4D5 Y55E.Y102V-Fab, 4D5 D98A.F100A.Y102V-Fab, and 4D5 H91A-Fab; FIGS. 29A-29D); liability fix variants (4D5 N30S-Fab, 4D5 N54E.D98T-Fab, and N30S.N54E.D98T-Fab; FIGS. 30A-30C); and affinity variants with liability fixes (4D5 N30S.Y55E.N54E.D98T.Y102V-Fab, 4D5 N30S.N54E.D98A.F100A.Y102V-Fab, and 4D5 H91A.N30S.N54E.D98T-Fab; FIGS. 31A-31C) were quantified by BIACORE®.

4D5 affinity variants having liability fixes were generated and characterized. The molecular weights (MW; Daltons) of each 4D5 Fab variant was measured by mass spectrometry and the degree of aggregation was quantified by size exclusion chromatography (SEC). Results are shown in Table 7, below. The observed difference in MW between observed and expected values was linked to C-terminal lysine clipping.

TABLE 7

Results of mass spectrometry and SEC experiments.

| 4D5 Fab | Observed MW | Expected MW | Delta MW | % Monomer |
|---|---|---|---|---|
| WT | 48,605 | 48,773 | −128 | 99.11 |
| H91A | 48,539 | 48,667 | −128 | 97.89 |
| Y55E.Y102V | 48,507 | 48,635 | −128 | 96.28 |
| D98A.F100A.Y102V | 48,421 | 48,549 | −128 | 99.28 |
| D98T.F100A.Y102V | 48,451 | 48,579 | −128 | 98.71 |
| N30S.N54E.D98T | 48,579 | 48,707 | −128 | 98.69 |
| N30S.H91A.N54E.D98T | 48,513 | 48,641 | −128 | 98.86 |
| H91A.N54E.D98T | 48,540 | 48,668 | −128 | 99.03 |
| N30S.Y55E.N54E.D98T.Y102V | 48,442 | 48,570 | −128 | 99.65 |
| N30S | 48,578 | 48,706 | −128 | 95.13 |
| N54E.D98T | 48,606 | 48,734 | −128 | 97.16 |
| N30S.N54E.D98A.F100A.Y102V | 48,409 | 48,537 | −128 | 97.24 |

TABLE 7-continued

Results of mass spectrometry and SEC experiments.

| 4D5 Fab | Observed MW | Expected MW | Delta MW | % Monomer |
|---|---|---|---|---|
| N30S.N54E.D98T.F100A.Y102V | 48,439 | 48,567 | −128 | 98.67 |

Variants of 4D5 affinity variants were formatted into IgG TDB antibodies by associating a monovalent 4D5 arm with an anti-CD3 (40G5c N297G) arm (see, e.g., U.S. Publication No. 2015/095392, which is incorporated herein by reference in its entirety). The antibodies were tested for binding to human HER2 by BIACORE®. Results are shown in FIGS. 32A-32K and summarized in Table 8, below.

TABLE 8

Binding characteristics of 4D5 IgG TDB antibodies to human HER2.

| Anti-HER2 Variant (IgG TDB) | $k_a$ (1/Ms) | $k_d$ (1/s) | $K_D$ (nM) Hu HER2 | $K_D$ Ratio (Variant/WT) | Rmax (RU) | Chi$^2$ (RU$^2$) |
|---|---|---|---|---|---|---|
| H91A.D98A.F100A.Y102V | — | — | — | — | — | — |
| Y55E.H91A.D98A.F100A.Y102V | — | — | — | — | — | — |
| Y55E.H91A.Y102V | — | — | — | — | — | — |
| WT | 3.20E+05 | 2.75E−04 | 0.86 | 1 | 42.4 | 6.02 |
| Y102V | 2.59E+05 | 3.27E−04 | 1.26 | 1.5 | 41.2 | 4.58 |
| Y55E.Y102V | 1.82E+05 | 1.30E−03 | 7.15 | 8.3 | 36.7 | 2.93 |
| Y55E.D98A.F100A.Y102V | 2.65E+05 | 1.12E−02 | 42.1 | 48.8 | 33.1 | 4.11 |
| D98A.F100A.Y102V | 3.12E+05 | 1.51E−02 | 48.5 | 56.3 | 32.8 | 6.24 |
| H91A | 2.37E+05 | 2.17E−02 | 91.6 | 106.3 | 28.6 | 2.28 |
| H91A.Y102V | 2.61E+05 | 3.17E−02 | 121 | 140.4 | 25.4 | 2.07 |
| Y55E.H91A | 1.55E+05 | 4.67E−02 | 301 | 349.2 | 12.2 | 2.26 |

No binding was detected in H91A.D98T.F100A.Y102V-IgG TDB, Y55E.H91A.D98A.F100A.Y102V-IgG TDB, or Y55E.H91A.Y102V-IgG TDB variants. In general, lower $K_D$ values (stronger binding affinities) were largely associated with slower off-rates. In the IgG TDB format, about two-fold weaker affinity was observed compared to the Fab format (Tables 9 and 10). However, when a $K_D$ ratio is used, wherein the $K_D$ of a 4D5 variant is divided by the $K_D$ of a 4D5 wildtype, the result is a relatively consistent value of 100-200 for the H91A variant in either the IgG TDB or Fab format.

affinity and kinetics were most desirable in the H91A variant, elimination of possible molecular liabilities in this variant was undertaken. Liabilities included light chain position N(30)T in HVR-L1 and heavy chain positions N(54)G in HVR-H2 and D(98)G in HVR-H3. The objective was to prevent possible D(98)G isomerization and possible N(30)T and N(54)G deamidation. Initially, rational design was used to screen the variants. However, combining weak affinity variants with high affinity variants did not yield predictive affinity, and even combinations of two or three variants yielded unpredictable results, as illustrated in FIG. 38. For example, Y55E typically weakened affinity 3.5- to 20-fold, but in one case yielded a small increase in affinity. H91A weakened affinity from 91 to 163-fold and Y102V either increased affinity or did not change affinity. Therefore, a small matrix was tested using N30S.N54E.D98A/T to fix the molecular liabilities. N30S was used to prevent possible deamidation in the HVR-L1 and had little-to-no effect on affinity. N54E.D98T increased affinity to 0.07 nM, so affinity weakening mutations were required to achieve a $K_D$ of about 50 nM. Through the use of the affinity mutations Y55E, H91A, and/or Y102V, in addition to the liability fixes, two variants having similar kinetics to H91A were identified (Table 10). 4D5 N30S.Y55E.H91A.HC-N54E.D98T-Fab features fixes in all three liabilities, while 4D5 Y55E.H91A.HC-N54E.D98T.Y102V-Fab features two liability fixed residues, and both have KDs of about 50 nM.

TABLE 9

Binding characteristics of liability fixed 4D5 Fab molecules to human HER2.

| 4D5 Fab | $k_a$ (1/Ms) | $k_d$ (1/s) | $K_D$ (nM) | $K_D$ ratio (Variant/WT) | $R_{max}$ (RU) | $X^2$ (RU$^2$) |
|---|---|---|---|---|---|---|
| N30S.N54E.D98T | 1.07E+6 | 6.18E−5 | 0.06 | 0.23 | 42.1 | 0.681 |
| N54E.D98T | 9.62E+5 | 6.89E−5 | 0.07 | 0.29 | 40.9 | 0.722 |
| WT | 1.02E+6 | 2.54E−4 | 0.25 | 1 | 43 | 0.544 |
| N30S | 1.05E+6 | 2.82E−4 | 0.27 | 1.07 | 41.2 | 0.656 |
| Y55E.Y102V | 6.60E+5 | 1.46E−3 | 2.21 | 8.84 | 42.3 | 0.555 |
| H91A.N54E.D98T | 7.82E+5 | 5.02E−3 | 6.42 | 25.7 | 39.6 | 0.185 |
| N30S.H91A.N54E.D98T | 8.22E+5 | 6.55E−3 | 7.97 | 31.9 | 39.7 | 0.15 |
| N30S.N54E.D98T.F100A.Y102V | 7.39E+5 | 6.76E−3 | 9.15 | 36.6 | 38.3 | 0.185 |
| N30S.N54E.D98A.F100A.Y102V | 7.58E+5 | 9.58E−3 | 12.6 | 50.4 | 37.2 | 0.235 |
| D98T.F100A.Y102V | 1.14E+6 | 1.47E−2 | 12.9 | 51.6 | 38.9 | 0.212 |
| D98A.F100A.Y102V | 1.14E+6 | 2.37E−2 | 20.7 | 82.8 | 37.7 | 0.319 |
| H91A | 6.63E+5 | 2.82E−2 | 42.6 | 170 | 36 | 0.281 |
| Y55E.H91A.N54E.D98T.Y102V | 6.42E+5 | 3.18E−2 | 49.5 | 198 | 35.8 | 0.113 |

A panel of 4D5 variants in Fab format was generated to obtain a range of affinities for screening in either IgG TDB (Table 9) or 1Fab-IgG TDB format (Table 10). Because the Another variant, 4D5 N30S.Y55E.H91A.N54E.D98T.Y102V-Fab exhibited a consistently slightly faster off-rate and had a $K_D$ of 70 nM.

TABLE 10

Binding characteristics of liability fixed 4D5 Fab molecules to human HER2.

| 4D5 Fab | $k_a$ (1/Ms, E+5) | $k_d$ (1/s, E−3) | $K_D$ (nM) | $K_D$ ratio (Variant/WT) |
|---|---|---|---|---|
| WT | 8.74 ± 1.74 | 0.25 ± 0.03 | 0.30 ± 0.01 | 1.0 |
| N30S.Y55E.H91A.N54E.D98T | 6.76 ± 1.41 | 32.8 ± 4.07 | 49.2 ± 5.06 | 164 |
| H91A | 7.07 ± 2.43 | 33.6 ± 6.54 | 49.3 ± 8.57 | 164 |
| Y55E.H91A.N54E.D98T.Y102V | 5.98 ± 0.18 | 32.2 ± 1.45 | 54.0 ± 2.51 | 180 |
| N30S.Y55E.H91A.N54E.D98T.Y102V | 6.34 ± 0.33 | 44.0 ± 1.97 | 69.8 ± 6.95 | 233 |
| Y55E.H91A.N54E.D98T | 1.85 ± 0.49 | 22.7 ± 3.25 | 126 ± 18.0 | 420 |

As shown in Table 11, monovalent affinity of wildtype 4D5 Fab to cynomolgus monkey HER2 (3.3 nM) was roughly 10-fold weaker than to human HER2 (0.3 nM). The 4D5 H91A-Fab affinity variant and the liability fixed variants exhibit monovalent affinities greater than 300 nM to cynomolgus monkey HER2 (Table 12). However, the ratio of $K_D$ to the cynomolgus HER2 protein of the cynomolgus monkey variant 4D5 H91A-Fab and 4D5 wildtype was roughly 100-200, within a similar range of that observed in the human format.

TABLE 11

Binding characteristics of liability fixed 4D5 Fab molecules to cynomolgus monkey HER2.

| 4D5 Fab | $K_D$ (nM) | $K_D$ ratio (Variant/WT) | Cyno $K_D$ (nM) | Human $K_D$ (nM) | Cyno/ Human $K_D$ |
|---|---|---|---|---|---|
| WT | 3.35 | 1 | 3.35 | 0.30 | 11.2 |
| H91A | 334 | 100 | 325 | 49.3 | 6.77 |
| Y55E.H91A.N54E.D98T | ≥770 | 230 | ≥728 | 126 | ≥6.11 |
| Y55E.H91A.N54E.D98T.Y102V | ≥710 | 212 | ≥692 | 54.0 | ≥13.1 |
| N30S.Y55E.H91A.N54E.D98T | 420 | 125 | 400 | 49.2 | 8.54 |
| N30S.Y55E.H91A.N54E.D98T.Y102V | 452 | 134 | 429 | 69.8 | 6.48 |

Example 10. Characterizing 4D5 Liability Fixed Affinity Variants

Figure 33A:
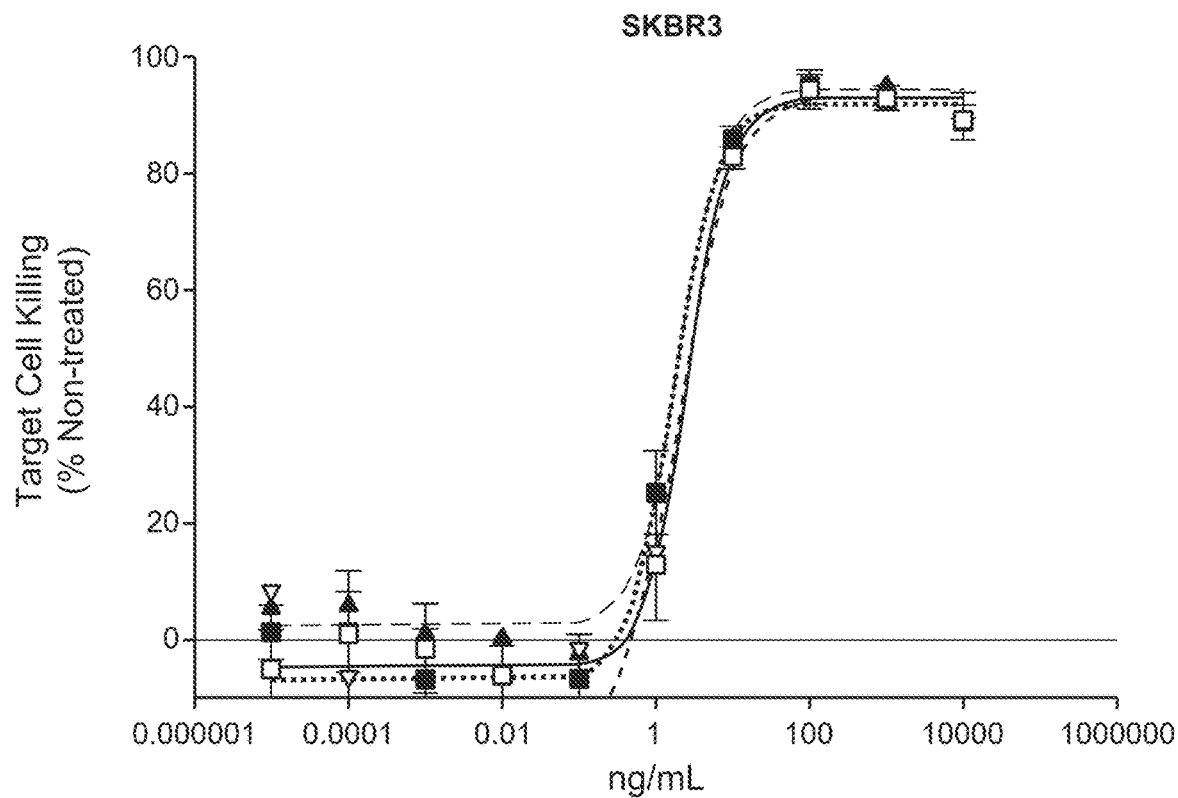
FIG. 33A is a graph showing dose response curves quantifying the killing of SKBR3 cells by 4D5 Y55E.H91A.N54E.D98T.Y102V-1Fab-IgG TDB (lot 1) antibodies (open squares); 4D5 Y55E.H91A.N54E.D98T-1Fab-IgG TDB antibodies (solid squares); 4D5 Y55E.H91A.N54E.D98T.Y102V-1Fab-IgG TDB (lot 2) antibodies (open downward-facing triangles); or 4D5 H91A-1Fab-IgG TDB antibodies (solid upward-facing triangles).
Figure 33B:
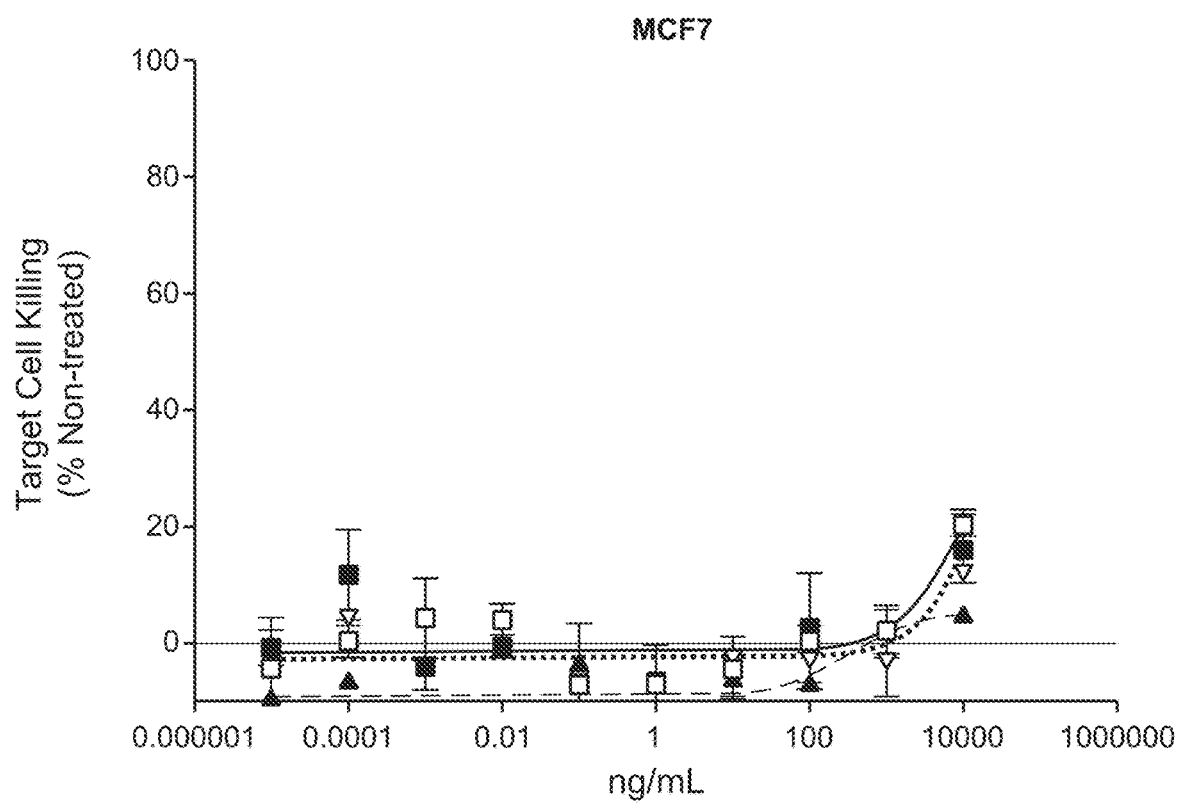
FIG. 33B is a graph showing dose response curves quantifying the killing of MCF7 cells by 4D5 Y55E.H91A.N54E.D98T.Y102V-1Fab-IgG TDB (lot 1) antibodies (open squares); 4D5 Y55E.H91A.N54E.D98T-1Fab-IgG TDB antibodies (solid squares); 4D5 Y55E.H91A.N54E.D98T.Y102V-1Fab-IgG TDB (lot 2) antibodies (open downward-facing triangles); or 4D5 H91A-1Fab-IgG TDB antibodies (solid upward-facing triangles).

Several 4D5 liability fixed affinity variants were selected for further characterization. Y55E.H91A.N54E.D98T and Y55E.H91A.N54E.D98T.Y102V variants were formatted into a 1Fab-IgG TDB antibody having a natural (short) linker (hinge; DKTHT, SEQ ID NO: 50) and compared to H91A-1Fab-IgG TDB in a dose response assay to quantify killing of SKBR3 (FIG. 33A) or MCF7 (FIG. 33B) target cells. Each well was seeded with 1.5×10⁴ SKBR3 or MCF7 target cells and co-cultured with PMBC-derived CD8⁺ effector cells at a 1:3 effector:target ratio. Results are summarized in Table 12, below.

TABLE 12

SKBR3 target cell killing by selected 4D5 1Fab-IgG TDB variants

| 4D5 1Fab-IgG TDB | SKBR3 $IC_{50}$ (ng/mL) | MCF7 $IC_{50}$ (ng/mL) |
|---|---|---|
| Y55E.H91A.N54E.D98T.Y102V | 2.61 | >1,000 |
| Y55E.H91A.N54E.D98T | 1.63 | >1,000 |
| Y55E.H91A.N54E.D98T.Y102V | 1.83 | >1,000 |
| H91A | 2.01 | >1,000 |

Figure 34A:
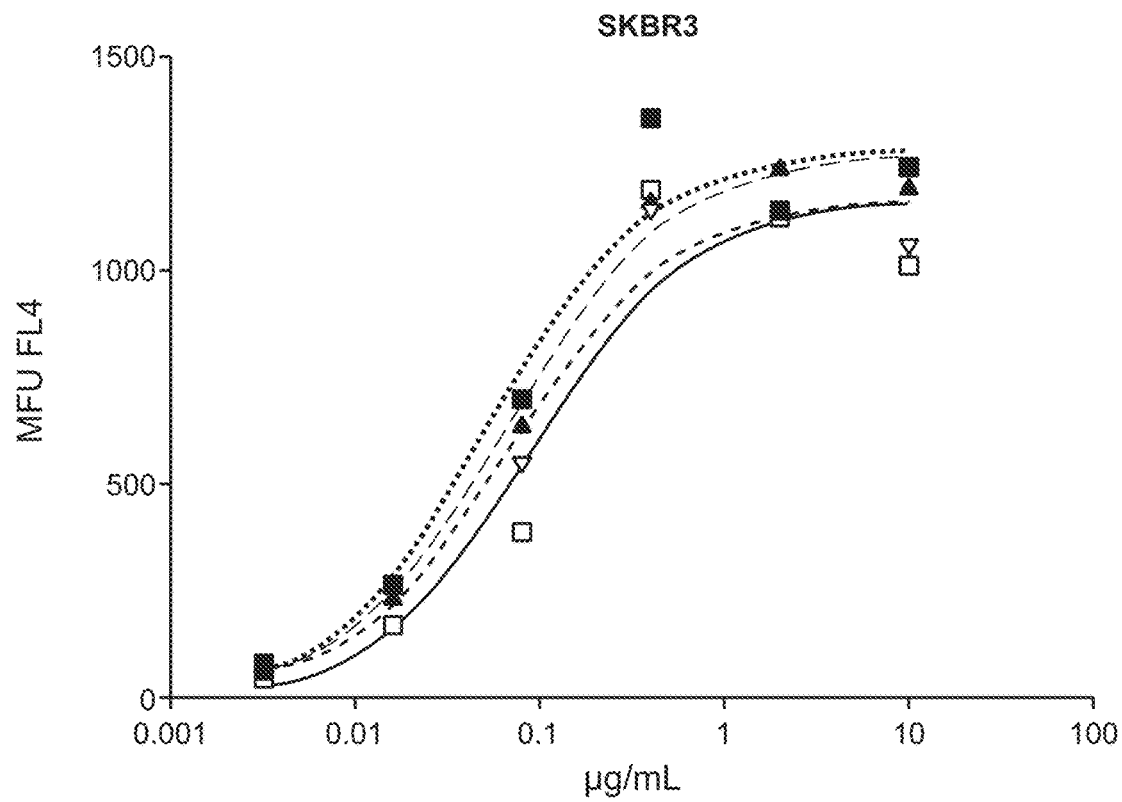
FIG. 34A is a graph showing dose response curves quantifying binding of various 1Fab-IgG TDB variants to SKBR8 cells, as measured by flow cytometry. Open squares represent 4D5 Y55E.H91A.N54E.D98T.Y102V-1Fab-IgG TDB (lot 1) antibodies; solid squares represent 4D5 Y55E.H91A.N54E.D98T-1Fab-IgG TDB antibodies; open downward-facing triangles represent 4D5 Y55E.H91A.N54E.D98T.Y102V-1Fab-IgG TDB (lot 2) antibodies; and solid upward-facing triangles represent 4D5 H91A-1Fab-IgG TDB antibodies.
Figure 34B:
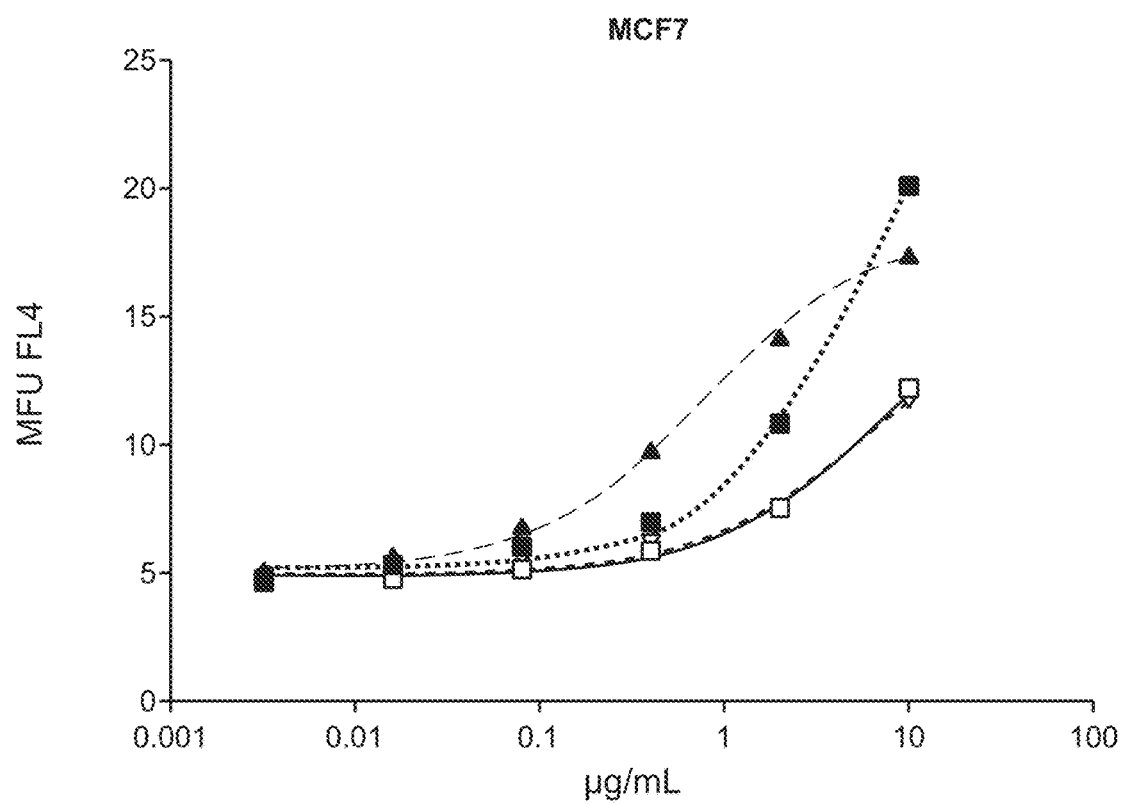
FIG. 34B is a graph showing dose response curves quantifying binding of various 1Fab-IgG TDB variants to MCF7 cells, as measured by flow cytometry. Open squares represent 4D5 Y55E.H91A.N54E.D98T.Y102V-1Fab-IgG TDB (lot 1) antibodies; solid squares represent 4D5 Y55E.H91A.N54E.D98T-1Fab-IgG TDB antibodies; open downward-facing triangles represent 4D5 Y55E.H91A.N54E.D98T.Y102V-1Fab-IgG TDB (lot 2) antibodies; and solid upward-facing triangles represent 4D5 H91A-1Fab-IgG TDB antibodies.

The binding of 4D5 Y55E.H91A.N54E.D98T-1Fab-IgG TDB and 4D5 Y55E.H91A.N54E.D98T.Y102V antibodies to SKBR3 cells (FIG. 34A) and MCF7 cells (FIG. 34B) was also characterized by flow cytometry. In general, 4D5 Y55E.H91A.N54E.D98T.Y102V-1Fab-IgG TDB were similar to 4D5 H91A-1Fab-IgG TDB in terms of cytotoxicity and binding to SKBR3 cells and MCF7 cells.

Example 11. Cellular Binding Affinity

To understand the contribution of bivalent HER2 engagement, or avidity, to cell-based affinity in greater detail, the apparent affinities of the 4D5-WT 1Fab-IgG TDB and 4D5-H91A 1Fab-IgG TDB molecules to SKBR3, MCF7, and cells transfected to express cynomolgus monkey HER2 at levels comparable to MCF7 was determined (Table 13). Despite the 164-fold difference between 4D5 and the affinity attenuated 4D5-H91A variant as monovalent Fab, the cell-based binding affinities of the 1Fab-IgG molecules to SKBR3 cells were comparable, as determined by direct cell binding or competition binding assays. The apparent affinity of 4D5-H91A 1Fab-IgG TDB for HER2 expressed on SKBR3 cells was in the range of 1.5-5 nM, which is ~10-fold higher compared to its monovalent Fab affinity measured by BIACORE®. This result suggests that the low monovalent Fab affinity can be compensated by avidity that is mediated by bivalent binding to HER2 in a cellular context. In contrast, 4D5-H91A 1Fab-IgG TDB did not demonstrate substantial binding to MCF7 or cyno HER2-expressing cells ($K_D$>100 nM for both in direct cell binding and no binding detected in competition binding), suggesting that the lower HER2 copy number on these cells is not sufficient for bivalent HER2 engagement. Results are summarized in Table 13.

TABLE 13

Binding affinity of the 1Fab-IgG TDBs for cynomolgus monkey HER2.

| | $K_D$ (nM) | | |
|---|---|---|---|
| 1Fab IgG | SKBR3 | MCF7 | CHO-cynoHER2 High |
| WT | 3.26 ± 1.22 | 11.57 ± 5.91 | 1.51 ± 0.15 |
| H91A | 5.02 ± 1.96 | >100 | >100 |

TABLE 13-continued

Binding affinity of the 1Fab-IgG TDBs for cynomolgus monkey HER2.

| 1Fab IgG | $K_D$ (nM) | | |
|---|---|---|---|
| | SKBR3 | MCF7 | CHO-cynoHER2 High |
| N30S.Y55E.H91A.<br>N54E.D98T | 5.08 ± 1.22 | >100 | >100 |

Figure 37:
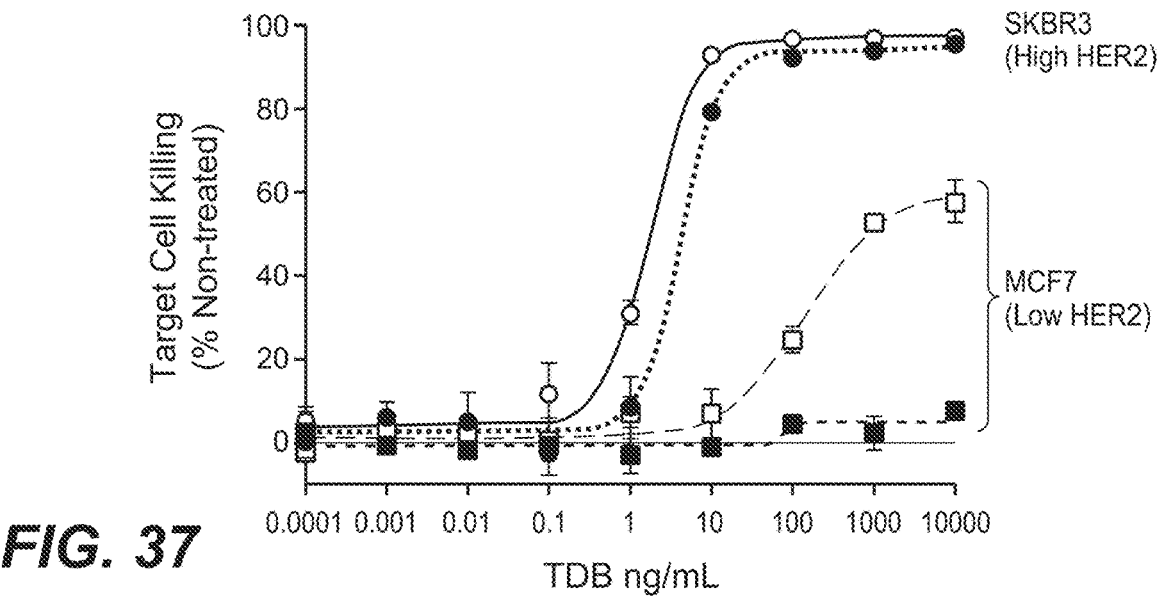
FIG. 37 is a graph showing dose response curves quantifying killing of SKBR3 target cells by 38E4v1 4D5-H91A 1Fab-IgG TDB (open circles); SKBR3 target cells by 40G5c 4D5-H91A 1Fab-IgG TDB (solid circles); MCF7 target cells by 38E4v1 4D5-H91A 1Fab-IgG TDB (open squares); and MCF7 target cells by 40G5c 4D5-H91A 1Fab-IgG TDB (closed squares).

The effect of CD3 binding affinity on TDB-mediated target cell killing was also assessed. 4D5-H91A 1Fab-IgG TDB having the low-affinity 40G5c anti-CD3 arm ("40G5c 4D5-H91A 1Fab-IgG TDB"; CD3 $K_D$ ~50 nM) was compared to an analogous 4D5-H91A 1Fab-IgG TDB having a high-affinity 38E4v1 anti-CD3 arm ("38E4v1 4D5-H91A 1Fab-IgG TDB"; CD3 $K_D$ ~1 nM). In an in vitro cell killing assay using the high-HER2-expressing target cell line SKBR3, 40G5c 4D5-H91A 1Fab-IgG TDB exhibited similar potency in target cell killing as 38E4v1 4D5-H91A 1Fab-IgG TDB (FIG. 37). In contrast, in an analogous assay using the low-HER2-expressing target cell line MCF7, 38E4v1 4D5-H91A 1Fab-IgG TDB was substantially more potent in target cell killing than 40G5c 4D5-H91A 1Fab-IgG TDB, which exhibited very little cell-killing ability. These results, summarized in Table 14, below, show that low anti-CD3 binding dramatically enhances the ability of 4D5-H91A 1Fab-IgG TDB to selectively kill cells that express high levels of HER2.

TABLE 14

Effect of CD3 binding affinity on 4D5-H91A 1Fab-IgG TDB-mediated target cell killing

| Anti-CD3 clone | Cell Line | $IC_{50}$ (ng/mL) | $IC_{50}$ (pM) |
|---|---|---|---|
| 40G5c (low-affinity) | MCF7 | >1,000 | >1,000 |
| 40G5c (low-affinity) | SKBR3 | 4.2 | 28 |
| 38E4v1 (high-affinity) | MCF7 | 150 | 970 |
| 38E4v1 (high-affinity) | SKBR3 | 11 | 1.8 |

Figure 38A:
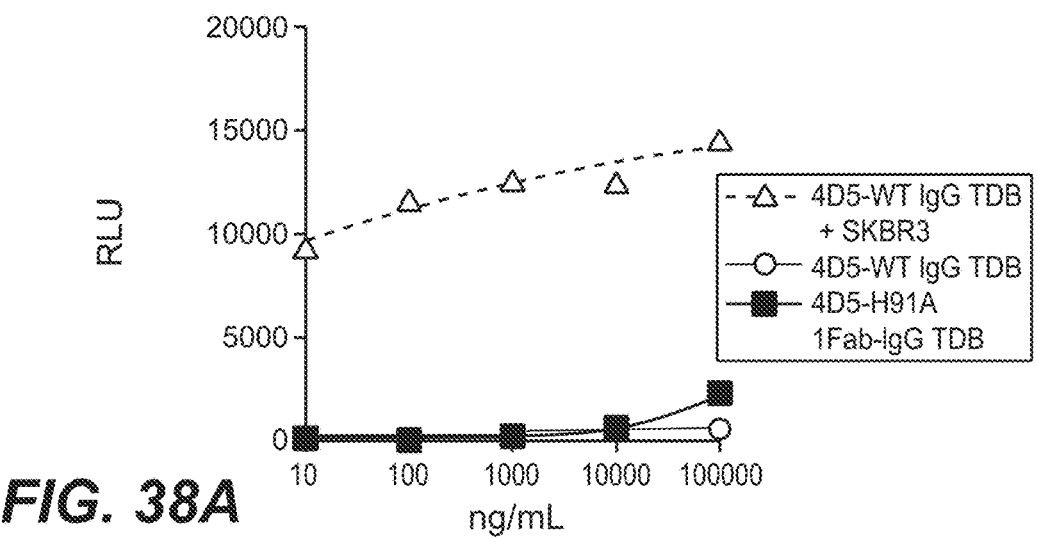
FIG. 38A is a graph showing level of 4D5 H91A 1Fab-IgG TDB and 4D5 IgG TDB-induced HER2 independent T cell activation as tested in the presence and absence of HER2 expressing cells.
Figure 38B:
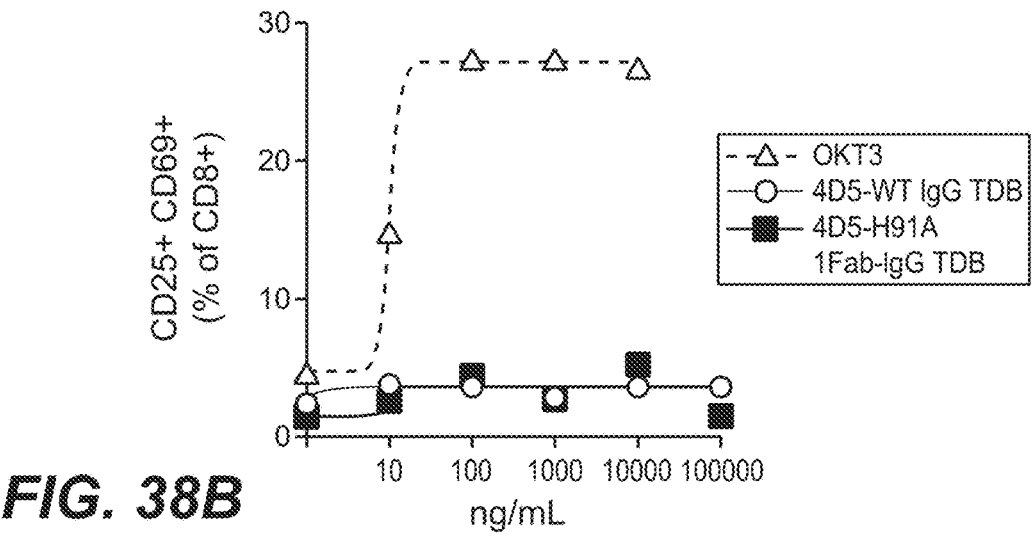
FIG. 38B is a graph showing level of 4D5 H91A 1Fab-IgG TDB and 4D5 IgG TDB-induced HER2 independent T cell activation as tested in the presence and absence of bivalent anti-CD3 OKT3.

Example 12. High Dose of 4D5-H91A 1Fab-IgG TDB does not Result in HER2-Independent T Cell Activation FcγR binding has been attenuated in TDBs by N297G substitution in the Fc-region. To confirm that TDBs do not induce target-independent T cell activation at high concentration, a Jurkat reporter cell line was used (FIG. 38A). A robust signal was detected when reporter cells were stimulated with TDB in the presence of HER2 expressing cells. Neither 4D5-WT IgG TDB nor 4D5 H91A 1Fab-IgG TDB activated T cells in the absence of HER2. High levels of TDB were spiked into human PBMC (FIG. 38B). Bivalent anti-CD3 (OKT-3) induced T cell activation at 10 ng/ml concentration, whereas no T cell activation was detected at 100 µg/ml concentration, indicating that neither TDB format induces HER2-independent T cell activation at high concentrations.

Figure 38C:
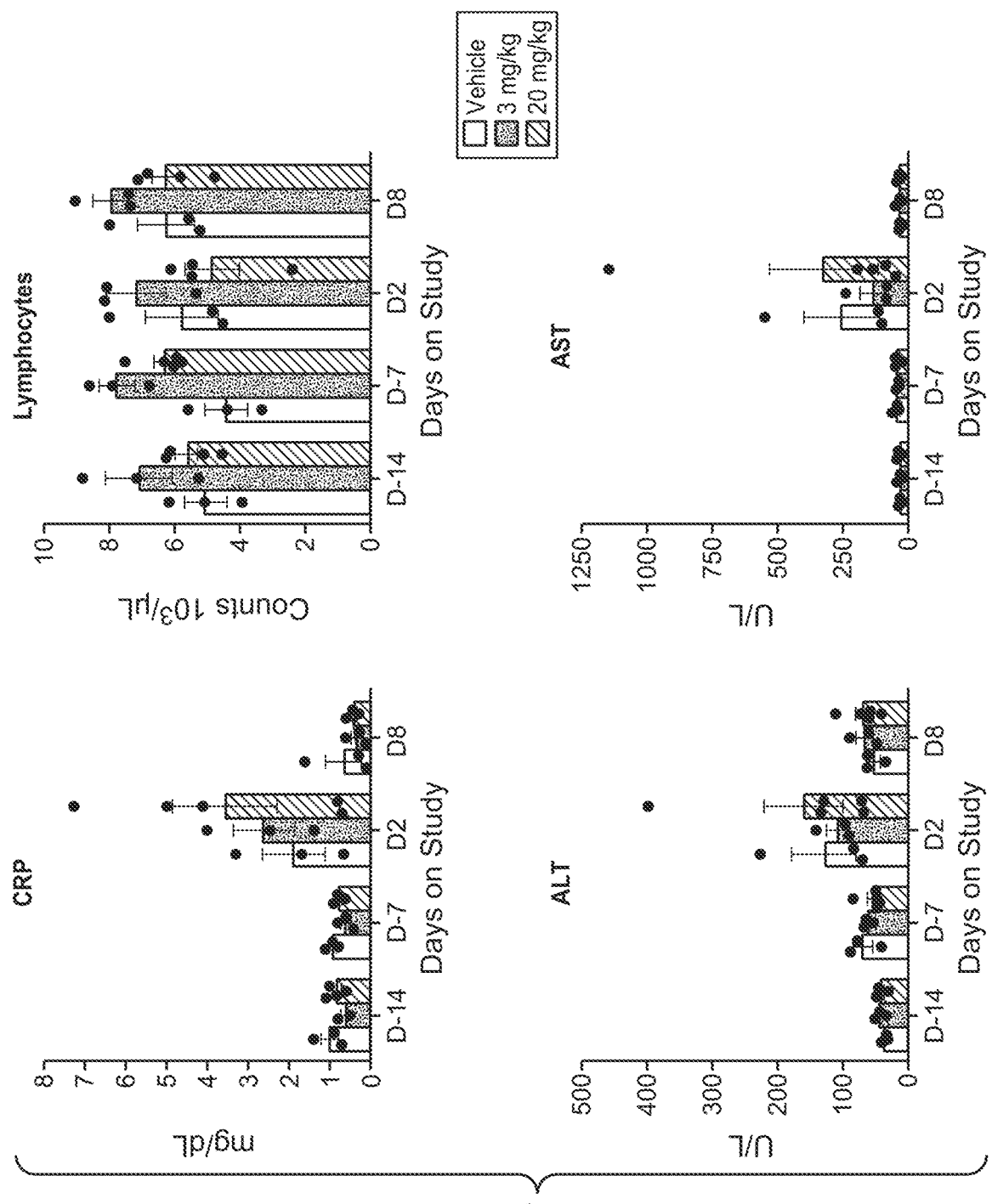
FIG. 38C is a series of graphs showing blood markers for inflammation (C-reactive protein; CRP), T cell activation (lymphocyte margination), and liver damage (alanine and aspartate aminotransferases; ALT and AST) as measured two days and eight days after dosing cynomolgus monkeys with H91A 1Fab-IgG TDB or vehicle control.

Example 13. 4D5-H91A 1Fab-IgG TDB has Limited Pharmacological Activity and is Well-Tolerated in Cynomolgus Monkey Cynomolgus monkey (cyno) tissues express low levels of HER2, similar to human normal tissues. 4D5-H91A 1Fab-IgG TDB does not substantially bind or induce apoptosis of cells that express low-to-moderate levels of cyno-HER2 (Table 13). To test the tolerability of 4D5-H91A 1Fab-IgG TDB, a single dose tolerability study was designed to study the pharmacodynamic activity (PD) and pharmacokinetics (PK) in cynomolgus monkey. Female monkeys were dosed with slow intravenous infusion at 3 mg/kg (N=3) and 20 mg/kg (N=5) dose level. Tolerability/PK/PD readouts included clinical observations, clinical chemistry, hematology, cytokines, and PK. Histopathology was not included in the analysis. No or minimal test article-related changes were detected in clinical observations (body weight, heart rate, temperature, respiration rate). Typical TDB-associated pharmacological and clinical pathology responses (Bargou et al., Science 2008, 321: 974-977; Lutterbuese et al., Proc. Nat. Acad. Sci. 2010, 107(28): 12605-12610) were strikingly absent (FIG. 38C). C-reactive protein (CRP; an acute phase reactant and a marker for inflammation) levels remained at the background level. No lymphocyte margination, elevation of liver enzymes (alanine and aspartate aminotransferases; ALT and AST) or elevation of peripheral blood cytokines (not shown) were detected, despite the high TDB dose. Taken together, 4D5-H91A 1Fab-IgG TDB was well tolerated at high dose level and demonstrated limited pharmacological activity in cyno.

Figure 38D:
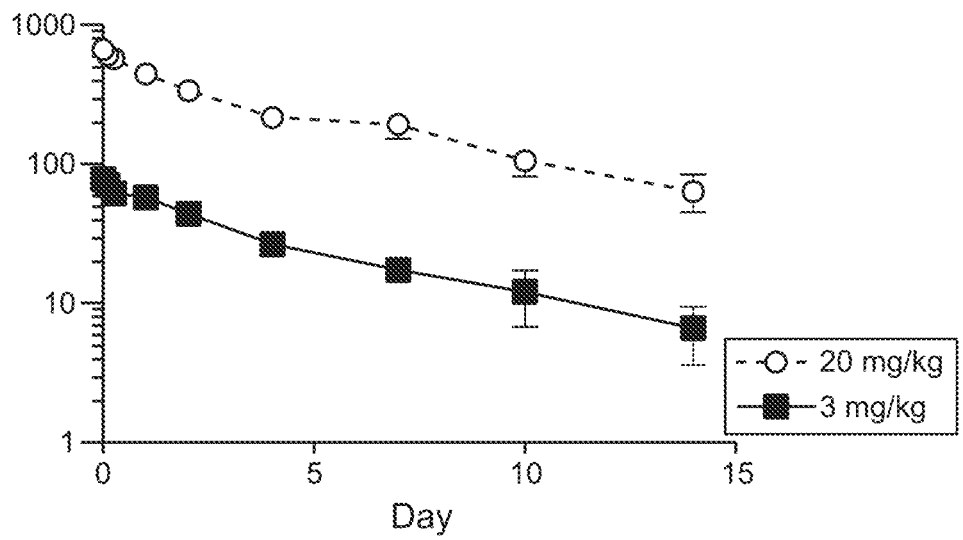
FIG. 38D is a graph and summary table showing PK parameters as detected by ELISA from cynomolgus monkeys dosed with H91A 1Fab-IgG TDB at 20 mg/kg and 3 mg/kg doses.
Figure 38E:
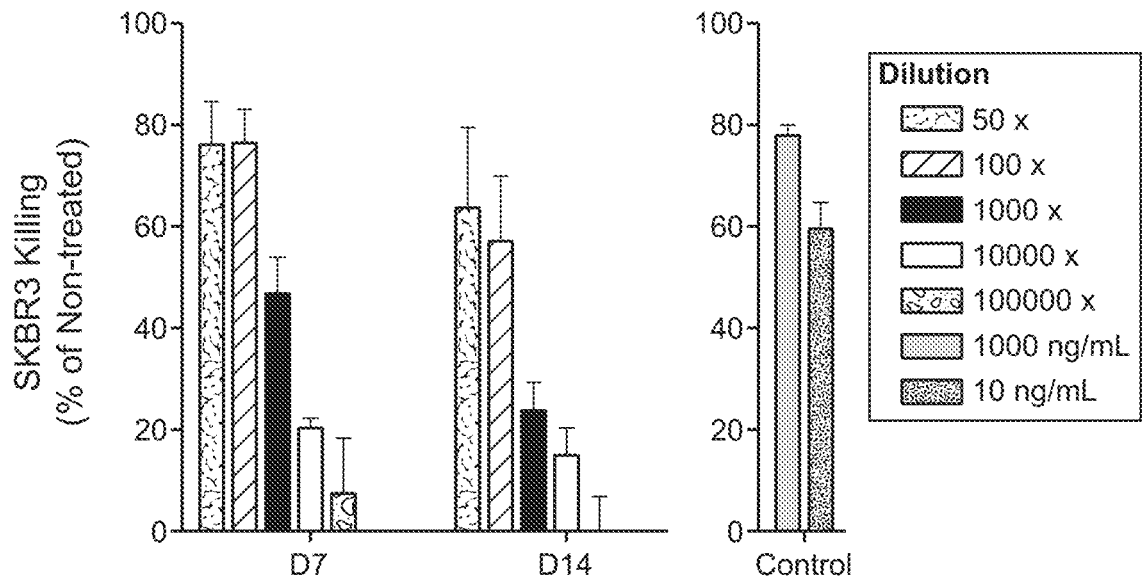
FIG. 38E is a graph showing H91A 1Fab-IgG TDB cynomolgus serum levels at 7 days and 14 days after dosing and subjected to healthy donor PBMC and SKBR3 cells for 24 hours using indicated dilutions. Parallel experiments were carried out using dilutions of fresh 4D5-H91A 1Fab-IgG TDB (Control).
Figure 39:
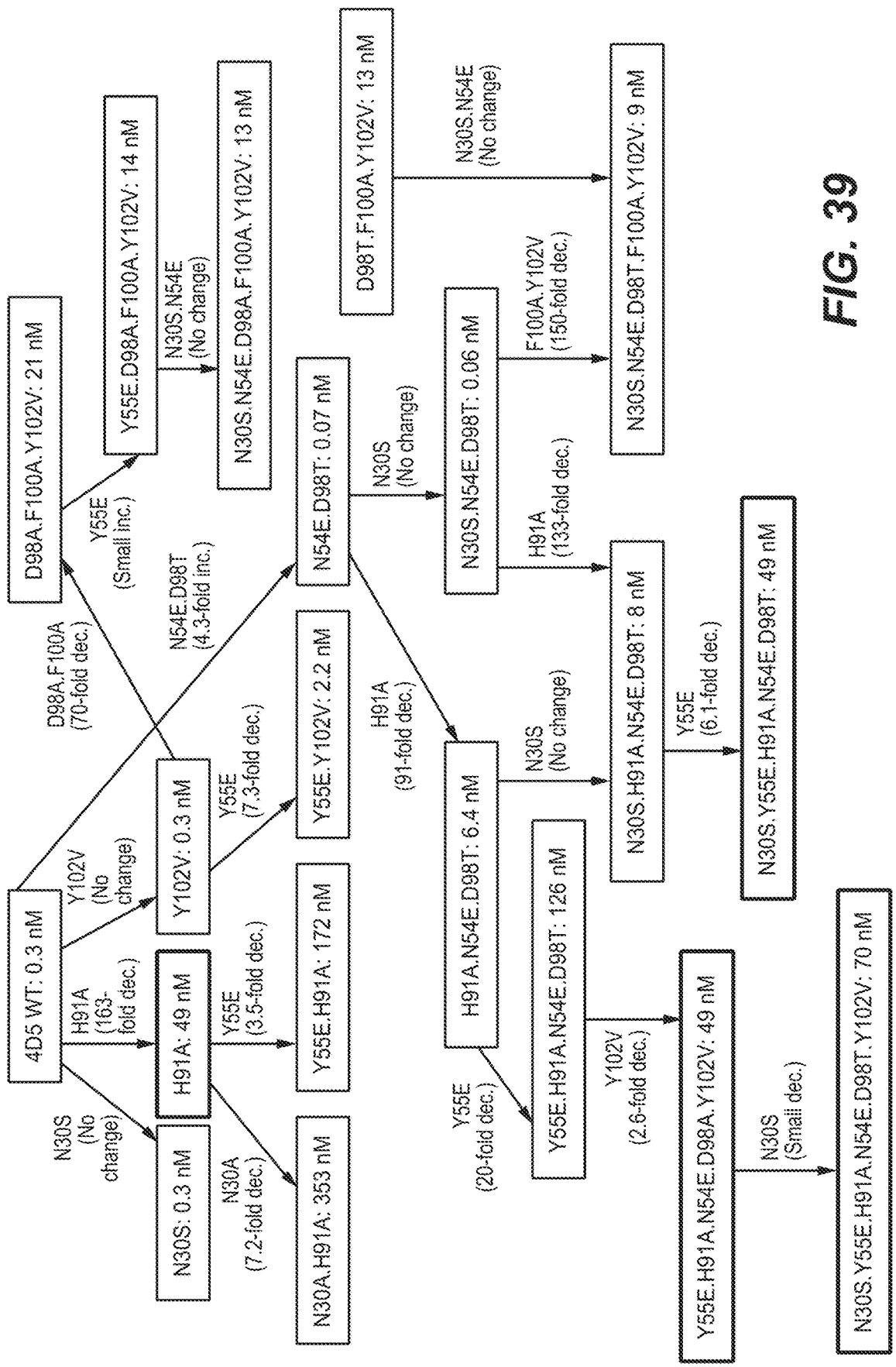
FIG. 39 is a diagram showing the effect of various amino acid substitutions on the binding affinity of 4D5 anti-HER2 Fab variants.

TDB exposure was confirmed for both dose levels tested and PK characteristics normal (FIG. 38D). Exposures were close to dose-proportional and maintained until the last evaluated time point (14 days). To confirm that the TDB is not inactivated in cyno, aliquots of serum were recovered from samples harvested 7 days and 14 days after dose with 20 mg/kg of the TDB, and serum dilutions were used to mediate killing of SKBR3 cells in vitro using healthy donor human T cells (FIG. 38E). Measured TDB serum concentrations in undiluted samples were 193 and 65 µg/mL for day-7 and day-14 samples, respectively. 100-fold dilution of serum 14 days after dosing induced similar level of SKBR3 killing, compared to maximal activity achieved in parallel killing assay using fresh TDB at high (1 µg/ml) concentration, which typically is sufficient to saturate activity. Together, this data suggests that the low HER2 expression in normal cyno tissues is not sufficient to trigger T cell activation or off-tumor T cell activity on normal tissues that express low levels of HER2.

What is claimed is:

1. A bispecific antigen-binding molecule that specifically binds CD3 and HER2 comprising a monovalent arm and a bivalent arm, wherein:
   (a) the monovalent arm comprises a $Fab_A$ that specifically binds CD3, wherein the C-terminus of the $Fab_A$ is fused to an N-terminus of a first Fc subunit, and wherein the $Fab_A$ comprises the following HVRs:
      (i) an HVR-H1 comprising the amino acid sequence of SEQ ID NO: 1,
      (ii) an HVR-H2 comprising the amino acid sequence of SEQ ID NO: 2,
      (iii) an HVR-H3 comprising the amino acid sequence of SEQ ID NO: 3,
      (iv) an HVR-L1 comprising the amino acid sequence of SEQ ID NO: 4,
      (v) an HVR-L2 comprising the amino acid sequence of SEQ ID NO: 5, and
      (vi) an HVR-L3 comprising the amino acid sequence of SEQ ID NO: 6;
   (b) the bivalent arm comprises a $Fab_{B1}$ and a $Fab_{B2}$ that each specifically binds HER2, wherein the C-terminus of the $Fab_{B2}$ is fused to the N-terminus of the $Fab_{B1}$, and the C-terminus of the $Fab_{B1}$ is fused to an N-terminus of a second Fc subunit, wherein the $Fab_{B1}$ and the $Fab_{B2}$ each comprise the following HVRs:
      (i) an HVR-H1 comprising the amino acid sequence of SEQ ID NO: 11,
      (ii) an HVR-H2 comprising the amino acid sequence of SEQ ID NO: 36,
      (iii) an HVR-H3 comprising the amino acid sequence of SEQ ID NO: 37,
      (iv) an HVR-L1 comprising the amino acid sequence of SEQ ID NO: 38,
      (v) an HVR-L2 comprising the amino acid sequence of SEQ ID NO: 29, and
      (vi) an HVR-L3 comprising the amino acid sequence of SEQ ID NO: 26; and
   (c) the first Fc subunit is associated with the second Fc subunit to form an Fc domain.

2. The bispecific antigen-binding molecule of claim 1, wherein:
   (a) the $Fab_A$ comprises a $VH_A$ region and a $VL_A$ region, wherein the $VH_A$ region comprises an amino acid sequence having at least 95% sequence identity to SEQ ID NO: 7, and the $VL_A$ region comprises an amino acid sequence having at least 95% sequence identity to SEQ ID NO: 8;
   (b) the $Fab_{B1}$ comprises a $VH_{B1}$ region and a $VL_{B1}$ region, wherein the $VH_{B1}$ region comprises an amino acid sequence having at least 95% sequence identity to SEQ ID NO: 41, and the $VL_{B1}$ region comprises an amino acid sequence having at least 95% sequence identity to SEQ ID NO: 49; and
   (c) the $Fab_{B2}$ comprises a $VH_{B2}$ region and a $VL_{B2}$ region, wherein the $VH_{B2}$ region comprises an amino acid sequence having at least 95% sequence identity to SEQ ID NO: 41, and the $VL_{B2}$ region comprises an amino acid sequence having at least 95% sequence identity to SEQ ID NO: 49.

3. The bispecific antigen-binding molecule of claim 2, wherein:
   (a) the $VH_A$ region comprises the amino acid sequence of SEQ ID NO: 7, and the $VL_A$ region comprises the amino acid sequence of SEQ ID NO: 8;
   (b) the $VH_{B1}$ region comprises the amino acid sequence of SEQ ID NO: 41, and the $VL_{B1}$ region comprises the amino acid sequence of SEQ ID NO: 49; and
   (c) the $VH_{B2}$ region comprises the amino acid sequence of SEQ ID NO: 41, and the $VL_{B2}$ region comprises the amino acid sequence of SEQ ID NO: 49.

4. A bispecific antigen-binding molecule that specifically binds CD3 and HER2 comprising a monovalent arm and a bivalent arm, wherein:
   (a) the monovalent arm comprises a $Fab_A$ that specifically binds CD3, wherein the C-terminus of the $Fab_A$ is fused to an N-terminus of a first Fc subunit, and wherein the $Fab_A$ comprises the following HVRs:
      (i) an HVR-H1 comprising the amino acid sequence of SEQ ID NO: 1,
      (ii) an HVR-H2 comprising the amino acid sequence of SEQ ID NO: 2,
      (iii) an HVR-H3 comprising the amino acid sequence of SEQ ID NO: 3,
      (iv) an HVR-L1 comprising the amino acid sequence of SEQ ID NO: 4,
      (v) an HVR-L2 comprising the amino acid sequence of SEQ ID NO: 5, and
      (vi) an HVR-L3 comprising the amino acid sequence of SEQ ID NO: 6;
   (b) the bivalent arm comprises a $Fab_{B1}$ and a $Fab_{B2}$ that each specifically binds HER2, wherein the C-terminus of the $Fab_{B2}$ is fused to the N-terminus of the $Fab_{B1}$, and the C-terminus of the $Fab_{B1}$ is fused to an N-terminus of a second Fc subunit, wherein the $Fab_{B1}$ and the $Fab_{B2}$ each comprise the following HVRs:
      (i) an HVR-H1 comprising the amino acid sequence of SEQ ID NO: 11,
      (ii) an HVR-H2 comprising the amino acid sequence of SEQ ID NO: 19,
      (iii) an HVR-H3 comprising the amino acid sequence of SEQ ID NO: 20,
      (iv) an HVR-L1 comprising the amino acid sequence of SEQ ID NO: 21,
      (v) an HVR-L2 comprising the amino acid sequence of SEQ ID NO: 22, and
      (vi) an HVR-L3 comprising the amino acid sequence of SEQ ID NO: 26; and
   (c) the first Fc subunit is associated with the second Fc subunit to form an Fc domain.

5. The bispecific antigen-binding molecule of claim 4, wherein:
   (a) the $Fab_A$ comprises a $VH_A$ region and a $VL_A$ region, wherein the $VH_A$ region comprises an amino acid sequence having at least 95% sequence identity to SEQ ID NO: 7, and the $VL_A$ region comprises an amino acid sequence having at least 95% sequence identity to SEQ ID NO: 8;
   (b) the $Fab_{B1}$ comprises a $VH_{B1}$ region and a $VL_{B1}$ region, wherein the $VH_{B1}$ region comprises an amino acid sequence having at least 95% sequence identity to SEQ ID NO: 24, and the $VL_{B1}$ region comprises an amino acid sequence having at least 95% sequence identity to SEQ ID NO: 27; and
   (c) the $Fab_{B2}$ comprises a $VH_{B2}$ region and a $VL_{B2}$ region, wherein the $VH_{B2}$ region comprises an amino acid sequence having at least 95% sequence identity to SEQ ID NO: 24, and the $VL_{B2}$ region comprises an amino acid sequence having at least 95% sequence identity to SEQ ID NO: 27.

6. The bispecific antigen-binding molecule of claim 5, wherein:
   (a) the VH$_A$ region comprises the amino acid sequence of SEQ ID NO: 7, and the VL$_A$ region comprises the amino acid sequence of SEQ ID NO: 8;
   (b) the VH$_{B1}$ region comprises the amino acid sequence of SEQ ID NO: 24, and the VL$_{B1}$ region comprises the amino acid sequence of SEQ ID NO: 27; and
   (c) the VH$_{B2}$ region comprises the amino acid sequence of SEQ ID NO: 24, and the VL$_{B2}$ region comprises the amino acid sequence of SEQ ID NO: 27.

7. A bispecific antigen-binding molecule that specifically binds CD3 and HER2 comprising a monovalent arm and a bivalent arm, wherein:
   (a) the monovalent arm comprises a Fab$_A$ that specifically binds CD3, wherein the C-terminus of the Fab$_A$ is fused to an N-terminus of a first Fc subunit, and wherein the Fab$_A$ comprises the following HVRs:
      (i) an HVR-H1 comprising the amino acid sequence of SEQ ID NO: 1,
      (ii) an HVR-H2 comprising the amino acid sequence of SEQ ID NO: 2,
      (iii) an HVR-H3 comprising the amino acid sequence of SEQ ID NO: 3,
      (iv) an HVR-L1 comprising the amino acid sequence of SEQ ID NO: 4,
      (v) an HVR-L2 comprising the amino acid sequence of SEQ ID NO: 5, and
      (vi) an HVR-L3 comprising the amino acid sequence of SEQ ID NO: 6;
   (b) the bivalent arm comprises a Fab$_{B1}$ and a Fab$_{B2}$ that each specifically binds HER2, wherein the C-terminus of the Fab$_{B2}$ is fused to the N-terminus of the Fab$_{B1}$, and the C-terminus of the Fab$_{B1}$ is fused to an N-terminus of a second Fc subunit, wherein the Fab$_{B1}$ and the Fab$_{B2}$ each comprise the following HVRs:
      (i) an HVR-H1 comprising the amino acid sequence of SEQ ID NO: 11,
      (ii) an HVR-H2 comprising the amino acid sequence of SEQ ID NO: 19,
      (iii) an HVR-H3 comprising the amino acid sequence of SEQ ID NO: 32,
      (iv) an HVR-L1 comprising the amino acid sequence of SEQ ID NO: 21,
      (v) an HVR-L2 comprising the amino acid sequence of SEQ ID NO: 22, and
      (vi) an HVR-L3 comprising the amino acid sequence of SEQ ID NO: 23; and
   (c) the first Fc subunit is associated with the second Fc subunit to form an Fc domain.

8. The bispecific antigen-binding molecule of claim 7, wherein:
   (a) the Fab$_A$ comprises a VH$_A$ region and a VL$_A$ region, wherein the VH$_A$ region comprises an amino acid sequence having at least 95% sequence identity to SEQ ID NO: 7, and the VL$_A$ region comprises an amino acid sequence having at least 95% sequence identity to SEQ ID NO: 8;
   (b) the Fab$_{B1}$ comprises a VH$_{B1}$ region and a VL$_{B1}$ region, wherein the VH$_{B1}$ region comprises an amino acid sequence having at least 95% sequence identity to SEQ ID NO: 33, and the VL$_{B1}$ region comprises an amino acid sequence having at least 95% sequence identity to SEQ ID NO: 25; and
   (c) the Fab$_{B2}$ comprises a VH$_{B2}$ region and a VL$_{B2}$ region, wherein the VH$_{B2}$ region comprises an amino acid sequence having at least 95% sequence identity to SEQ ID NO: 33, and the VL$_{B2}$ region comprises an amino acid sequence having at least 95% sequence identity to SEQ ID NO: 25.

9. The bispecific antigen-binding molecule of claim 8, wherein:
   (a) the VH$_A$ region comprises the amino acid sequence of SEQ ID NO: 7, and the VL$_A$ region comprises the amino acid sequence of SEQ ID NO: 8;
   (b) the VH$_{B1}$ region comprises the amino acid sequence of SEQ ID NO: 33, and the VL$_{B1}$ region comprises the amino acid sequence of SEQ ID NO: 25; and
   (c) the VH$_{B2}$ region comprises the amino acid sequence of SEQ ID NO: 33, and the VL$_{B2}$ region comprises the amino acid sequence of SEQ ID NO: 25.

10. A bispecific antigen-binding molecule that specifically binds CD3 and HER2 comprising a monovalent arm and a bivalent arm, wherein:
   (a) the monovalent arm comprises a Fab$_A$ that specifically binds CD3, wherein the C-terminus of the Fab$_A$ is fused to an N-terminus of a first Fc subunit, and wherein the Fab$_A$ comprises the following HVRs:
      (i) an HVR-H1 comprising the amino acid sequence of SEQ ID NO: 1,
      (ii) an HVR-H2 comprising the amino acid sequence of SEQ ID NO: 2,
      (iii) an HVR-H3 comprising the amino acid sequence of SEQ ID NO: 3,
      (iv) an HVR-L1 comprising the amino acid sequence of SEQ ID NO: 4,
      (v) an HVR-L2 comprising the amino acid sequence of SEQ ID NO: 5, and
      (vi) an HVR-L3 comprising the amino acid sequence of SEQ ID NO: 6;
   (b) the bivalent arm comprises a Fab$_{B1}$ and a Fab$_{B2}$ that each specifically binds HER2, wherein the C-terminus of the Fab$_{B2}$ is fused to the N-terminus of the Fab$_{B1}$, and the C-terminus of the Fab$_{B1}$ is fused to an N-terminus of a second Fc subunit, wherein the Fab$_{B1}$ and the Fab$_{B2}$ each comprise the following HVRs:
      (i) an HVR-H1 comprising the amino acid sequence of SEQ ID NO: 11,
      (ii) an HVR-H2 comprising the amino acid sequence of SEQ ID NO: 36,
      (iii) an HVR-H3 comprising the amino acid sequence of SEQ ID NO: 43,
      (iv) an HVR-L1 comprising the amino acid sequence of SEQ ID NO: 21,
      (v) an HVR-L2 comprising the amino acid sequence of SEQ ID NO: 29, and
      (vi) an HVR-L3 comprising the amino acid sequence of SEQ ID NO: 26; and
   (c) the first Fc subunit is associated with the second Fc subunit to form an Fc domain.

11. The bispecific antigen-binding molecule of claim 10, wherein:
   (a) the Fab$_A$ comprises a VH$_A$ region and a VL$_A$ region, wherein the VH$_A$ region comprises an amino acid sequence having at least 95% sequence identity to SEQ ID NO: 7, and the VL$_A$ region comprises an amino acid sequence having at least 95% sequence identity to SEQ ID NO: 8;
   (b) the Fab$_{B1}$ comprises a VH$_{B1}$ region and a VL$_{B1}$ region, wherein the VH$_{B1}$ region comprises an amino acid sequence having at least 95% sequence identity to SEQ ID NO: 44, and the VL$_{B1}$ region comprises an amino acid sequence having at least 95% sequence identity to SEQ ID NO: 48; and (c) the Fab$_{B2}$ comprises a VH$_{B2}$ region and a VL$_{B2}$ region, wherein the VH$_{B2}$ region comprises an amino acid sequence having at least 95% sequence identity to SEQ ID NO: 44, and the VL$_{B2}$ region comprises an amino acid sequence having at least 95% sequence identity to SEQ ID NO: 48.

12. The bispecific antigen-binding molecule of claim 11, wherein:
   (a) the VH$_A$ region comprises the amino acid sequence of SEQ ID NO: 7, and the VL$_A$ region comprises the amino acid sequence of SEQ ID NO: 8;
   (b) the VH$_{B1}$ region comprises the amino acid sequence of SEQ ID NO: 44, and the VL$_{B1}$ region comprises the amino acid sequence of SEQ ID NO: 48; and
   (c) the VH$_{B2}$ region comprises the amino acid sequence of SEQ ID NO: 44, and the VL$_{B2}$ region comprises the amino acid sequence of SEQ ID NO: 48.

13. An immunoconjugate comprising the bispecific antigen-binding molecule of claim 1 and a cytotoxic agent.

14. An immunoconjugate comprising the bispecific antigen-binding molecule of claim 4 and a cytotoxic agent.

15. An immunoconjugate comprising the bispecific antigen-binding molecule of claim 7 and a cytotoxic agent.

16. An immunoconjugate comprising the bispecific antigen-binding molecule of claim 10 and a cytotoxic agent.

17. A composition comprising the bispecific antigen-binding molecule of claim 1 and a pharmaceutically acceptable carrier, excipient, or diluent.

18. A composition comprising the bispecific antigen-binding molecule of claim 4 and a pharmaceutically acceptable carrier, excipient, or diluent.

19. A composition comprising the bispecific antigen-binding molecule of claim 7 and a pharmaceutically acceptable carrier, excipient, or diluent.

20. A composition comprising the bispecific antigen-binding molecule of claim 10 and a pharmaceutically acceptable carrier, excipient, or diluent.

21. A kit comprising:
   (a) the composition of claim 17; and
   (b) a package insert comprising instructions for administering the composition to a subject to treat or delay progression of a HER2-positive cancer.

22. A kit comprising:
   (a) the composition of claim 18; and
   (b) a package insert comprising instructions for administering the composition to a subject to treat or delay progression of a HER2-positive cancer.

23. A kit comprising:
   (a) the composition of claim 19; and
   (b) a package insert comprising instructions for administering the composition to a subject to treat or delay progression of a HER2-positive cancer.

24. A kit comprising:
   (a) the composition of claim 20; and
   (b) a package insert comprising instructions for administering the composition to a subject to treat or delay progression of a HER2-positive cancer.

* * * * *